United States Patent
Lücking et al.

(10) Patent No.: US 9,133,171 B2
(45) Date of Patent: Sep. 15, 2015

(54) DISUBSTITUTED 5-FLUORO PYRIMIDINE DERIVATIVES CONTAINING A SULFOXIMINE GROUP

(75) Inventors: Ulrich Lücking, Berlin (DE); Dirk Kosemund, Berlin (DE); Arne Scholz, Berlin (DE); Philip Lienau, Berlin (DE); Gerhard Siemeister, Berlin (DE); Ulf Bömer, Glienicke (DE); Rolf Bohlmann, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/345,353

(22) PCT Filed: Sep. 13, 2012

(86) PCT No.: PCT/EP2012/067962
§ 371 (c)(1),
(2), (4) Date: Jun. 25, 2014

(87) PCT Pub. No.: WO2013/037894
PCT Pub. Date: Mar. 21, 2013

(65) Prior Publication Data
US 2015/0005329 A1 Jan. 1, 2015

(30) Foreign Application Priority Data
Sep. 16, 2011 (EP) .................... 11181602

(51) Int. Cl.
*A61K 31/506* (2006.01)
*C07D 405/04* (2006.01)
*C07D 239/42* (2006.01)
*C07C 381/10* (2006.01)
*A61K 31/505* (2006.01)

(52) U.S. Cl.
CPC ............ *C07D 405/04* (2013.01); *A61K 31/505* (2013.01); *A61K 31/506* (2013.01); *C07C 381/10* (2013.01); *C07D 239/42* (2013.01)

(58) Field of Classification Search
CPC ............................ C07D 405/04; A61K 31/506
See application file for complete search history.

(56) References Cited

U.S. PATENT DOCUMENTS

| | | | |
|---|---|---|---|
| 7,291,616 B2 | 11/2007 | Bhatt et al. | |
| 7,618,968 B2 | 11/2009 | Bhatt et al. | |
| 2003/0153570 A1 | 8/2003 | Bhatt et al. | |
| 2005/0176743 A1 | 8/2005 | Luecking et al. | |
| 2008/0064700 A1 | 3/2008 | Bhatt et al. | |
| 2014/0315906 A1* | 10/2014 | Lucking et al. ............ | 514/245 |

FOREIGN PATENT DOCUMENTS

| | | |
|---|---|---|
| EP | 2179991 A1 | 4/2010 |
| WO | 01/25220 A1 | 4/2001 |
| WO | 02/066481 A1 | 8/2002 |
| WO | 03/037346 A1 | 5/2003 |
| WO | 2004/009562 A1 | 1/2004 |
| WO | 2004/072063 A1 | 8/2004 |
| WO | 2008/025556 A1 | 3/2008 |
| WO | 2008/079933 A2 | 7/2008 |
| WO | WO 2008079918 A1 * | 7/2008 |
| WO | 2008/109943 A1 | 9/2008 |
| WO | 2008/129070 A1 | 10/2008 |
| WO | 2008/129071 A1 | 10/2008 |
| WO | 2008/129080 A1 | 10/2008 |
| WO | 2009/032861 A1 | 3/2009 |
| WO | 2010/009155 A2 | 1/2010 |
| WO | 2011/012661 A1 | 2/2011 |
| WO | 2011/046970 A1 | 4/2011 |

OTHER PUBLICATIONS

G. Romano et al., 7 Cell Cycle, 3664-3668 (2008).*
G. De Falco et al., 1 Cancer Biology & Therapy, 342-347 (2002).*
Cho et al., "Cycling through transcription Posttranslational modifications of P-TEFb regulate transcription elongation," Cell Cycle, May 1, 2010, 9(9):1697-1705.
He et al., "A La-Related Protein Modulates 7SK snRNP Integrity to Suppress P-TEFb-Dependent Transcriptional Elongation and Tumorigenesis," Molecular Cell, Mar. 14, 2008, 29:588-599.
Yang et al., "Recruitment of P-TEFb for Stimulation of Transcriptional Elongation by the Bromodomain Protein Brd4," Molecular Cell, Aug. 19, 2005, 19:535-545.
Zhou et al., "The Yin and Yang of P-TEFb Regulation: Implications for Human Immunodeficiency Virus Gene Expression and Global Control of Cell Growth and Differentiation," Microbiology and Molecular Biology Reviews, Sep. 2006, 70(3):646-659.
Wang et al., "Cyclin-dependent kinase 9: a key transcriptional regulator and potential drug target in oncology, virology and cardiology," Trends in Pharmacological Sciences, 2008, 29(6):302-313.
Bark-Jones et al., "EBV EBNA 2 stimulates CDK9-dependent transcription and RNA polymerase II phosphorylation on serine 5," Oncogene, 2006, 25:1775-1785.
Zhou et al., "Tax Interacts with P-TEFb in a Novel Manner to Stimulate Human T-Lymphotropic Virus Type 1 Transcription," Journal of Virology, May 2006, 80(10):4781-4791.

(Continued)

*Primary Examiner* — Alexander R Pagano

(57) ABSTRACT

The present invention relates to disubstituted 5-fluoro pyrimidine derivatives containing a sulfoximine group of general formula (I) as described and defined herein, and methods for their preparation, their use for the treatment and/or prophylaxis of disorders, in particular of hyper-proliferative disorders and/or virally induced infectious diseases and/or of cardiovascular diseases. The invention further relates to intermediate compounds useful in the preparation of said compounds of general formula (I).

(I)

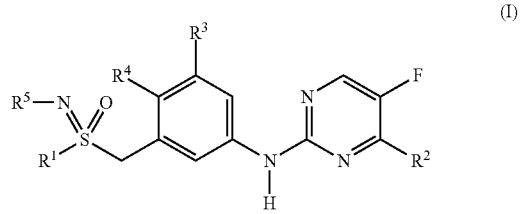

13 Claims, No Drawings

(56) References Cited

OTHER PUBLICATIONS

Dey et al., "HEXIM1 and the Control of Transcription Elongation From Cancer and Inflammation to AIDS and Cardiac Hypertrophy," Cell Cycle, Aug. 1, 2007, 6(15):1856-1863.

Wang et al., "Discovery and Characterization of 2-Anilino-4-(Thiazol-5-yl)Pyrimidine Transcriptional CDK Inhibitors as Anticancer Agents," Chemistry & Biology, Oct. 29, 2010, 17:1111-1121.

Payton et al., "Deregulation of Cyclin E2 expression and associated kinase activity in primary breast tumors," Oncogene, 2002, 21:8529-8534.

Huang et al., "An Integrated Bioinformatics Approach Identifies Elevated Cyclin E2 Expression and E2F Activity as Distinct Features of Tamoxifen Resistant Breast Tumors," PLoS One, Jul. 2011, 6(7):1-11, e22274.

Hunt et al., "Cyclin E as a prognostic and predictive marker in breast cancer," Seminars in Cancer Biology, 2005, 15:319-326.

* cited by examiner

DISUBSTITUTED 5-FLUORO PYRIMIDINE DERIVATIVES CONTAINING A SULFOXIMINE GROUP

The present invention relates to disubstituted 5-fluoro pyrimidine derivatives containing a sulfoximine group of general formula (I) as described and defined herein, and methods for their preparation, their use for the treatment and/or prophylaxis of disorders, in particular of hyper-proliferative disorders and/or virally induced infectious diseases and/or of cardiovascular diseases. The invention further relates to intermediate compounds useful in the preparation of said compounds of general formula (I).

The family of cyclin-dependent kinase (CDK) proteins consists of members that are key regulators of the cell division cycle (cell cycle CDK's), that are involved in regulation of gene transcription (transcriptional CDK's), and of members with other functions. CDKs require for activation the association with a regulatory cyclin subunit. The cell cycle CDKs CDK1/cyclin B, CDK2/cyclin A, CDK2/cyclinE, CDK4/cyclinD, and CDK6/cyclinD get activated in a sequential order to drive a cell into and through the cell division cycle. The transcriptional CDKs CDK9/cyclin T and CDK7/cyclin H regulate the activity of RNApolymerase II via phosphorylation of the carboxy-terminal domain (CTD). Positive transcription factor b (P-TEFb) is a heterodimer of CDK9 and one of four cyclin partners, cyclin T1, cyclin K, cyclin T2a or T2b.

Whereas CDK9 (NCBI GenBank Gene ID 1025) is exclusively involved in transcriptional regulation, CDK7 in addition participates in cell cycle regulation as CDK-activating kinase (CAK).

Transcription of genes by RNA polymerase II is initiated by assembly of the pre-initiation complex at the promoter region and phosphorylation of Ser 5 and Ser 7 of the CTD by CDK7/cyclin H. For a major fraction of genes RNA polymerase II stops mRNA transcription after it moved 20-40 nucleotides along the DNA template. This promoter-proximal pausing of RNA polymerase II is mediated by negative elongation factors and is recognized as a major control mechanism to regulate expression of rapidly induced genes in response to a variety of stimuli (Cho et al., Cell Cycle 2010, 9, 1697). P-TEFb is crucially involved in overcoming promoter-proximal pausing of RNA polymerase II and transition into a productive elongation state by phosphorylation of Ser 2 of the CTD as well as by phosphorylation and inactivation of negative elongation factors.

Activity of P-TEFb itself is regulated by several mechanisms. About half of cellular P-TEFb exists in an inactive complex with 7SK small nuclear RNA (7SK snRNA), La-related protein 7 (LARP7/PIP7S) and hexamethylene bis-acetamide inducible proteins 1/2 (HEXIM1/2, He et al., Mol. Cell. 2008, 29, 588). The remaining half of P-TEFb exists in an active complex containing the bromodomain protein Brd4 (Yang et al., Mol. Cell. 2005, 19, 535). Brd4 recruits P-TEFb through interaction with acetylated histones to chromatin areas primed for gene transcription. Through alternately interacting with its positive and negative regulators, P-TEFb is maintained in a functional equilibrium: P-TEFb bound to the 7SK snRNA complex represents a reservoir from which active P-TEFb can be released on demand of cellular transcription and cell proliferation (Zhou & Yik, Microbiol. Mol. Biol. Rev. 2006, 70, 646).

Furthermore, the activity of P-TEFb is regulated by post-translational modifications including phosphorylation/de-phosphorylation, ubiquitination, and acetylation (reviewed in Cho et al., Cell Cycle 2010, 9, 1697).

Deregulated activity of CDK9 kinase activity of the P-TEFb heterodimer is associated with a variety of human pathological settings such as hyper-proliferative diseases (e.g. cancer), virally induced infectious diseases or cardiovascular diseases.

Cancer is regarded as a hyper-proliferative disorder mediated by a disbalance of proliferation and cell death (apoptosis). High levels of anti-apoptotic Bcl-2-family proteins are found in various human tumors and account for prolonged survival of tumor cells and therapy resistance Inhibition of P-TEFb kinase activity was shown to reduce transcriptional activity of RNA polymerase II leading to a decline of short-lived anti-apoptotic proteins, especially Mcl-1 and XIAP, reinstalling the ability of tumor cells to undergo apoptosis. A number of other proteins associated with the transformed tumor phenotype (such as Myc, NF-kB responsive gene transcripts, mitotic kinases) are either short-lived proteins or are encoded by short-lived transcripts which are sensitive to reduced RNA polymerase II activity mediated by P-TEFb inhibition (reviewed in Wang & Fischer, Trends Pharmacol. Sci. 2008, 29, 302).

Many viruses rely on the transcriptional machinery of the host cell for the transcription of their own genome. In case of HIV-1 RNA polymerase II gets recruited to the promoter region within the viral LTR's. The viral transcription activator (Tat) protein binds to nascent viral transcripts and overcomes promoter-proximal RNA polymerase II pausing by recruitment of P-TEFb which in turn promotes transcriptional elongation. Furthermore, the Tat protein increases the fraction of active P-TEFb by replacement of the P-TEFb inhibitory proteins HEXIM1/2 within the 7SK snRNA complex. Recent data have shown that inhibition of the kinase activity of P-TEFb is sufficient to block HIV-1 replication at kinase inhibitor concentrations that are not cytotoxic to the host cells (reviewed in Wang & Fischer, Trends Pharmacol. Sci. 2008, 29, 302). Similarly, recruitment of P-TEFb by viral proteins has been reported for other viruses such as B-cell cancer-associated Epstein-Barr virus, where the nuclear antigen EBNA2 protein interacts with P-TEFb (Bark-Jones et al., Oncogene 2006, 25, 1775), and the human T-lymphotrophic virus type 1 (HTLV-1), where the transcriptional activator Tax recruits P-TEFb (Zhou et al., J. Virol. 2006, 80, 4781).

Cardiac hypertrophy, the heart's adaptive response to mechanical overload and pressure (hemodynamic stress e.g. hypertension, myocardial infarction), can lead, on a long term, to heart failure and death. Cardiac hypertrophy was shown to be associated with increased transcriptional activity and RNA polymerase II CTD phosphorylation in cardiac muscle cells. P-TEFb was found to be activated by dissociation from the inactive 7SK snRNA/HEXIM1/2 complex. These findings suggest pharmacological inhibition of P-TEFb kinase activity as a therapeutic approach to treat cardiac hypertrophy (reviewed in Dey et al., Cell Cycle 2007, 6, 1856).

In summary, multiple lines of evidence suggest that selective inhibition of the CDK9 kinase activity of the P-TEFb heterodimer (=CDK9 and one of four cyclin partners, cyclin T1, cyclin K, cyclin T2a or T2b) represents an innovative approach for the treatment of diseases such as cancer, viral diseases, and/or diseases of the heart. CDK9 belongs to a family of at least 13 closely related kinases of which the subgroup of the cell cycle CDK's fulfills multiple roles in regulation of cell proliferation. Thus, co-inhibition of cell cycle CDK's (e.g. CDK1/cyclin B, CDK2/cyclin A, CDK2/cyclinE, CDK4/cyclinD, CDK6/cyclinD) and of CDK9, is expected to impact normal proliferating tissues such as intestinal mucosa, lymphatic and hematopoietic organs, and reproductive organs. To maximize the therapeutic margin of CDK9 kinase inhibitors, molecules with high selectivity towards CDK9 are therefore required.

CDK inhibitors in general as well as CDK9 inhibitors are described in a number of different publications:

WO2008129070 and WO2008129071 both describe 2,4 disubstituted aminopyrimidines as CDK inhibitors in general. It is also asserted that some of these compounds may act as selective CDK9 inhibitors (WO2008129070) and as CDK5 inhibitors (WO2008129071), respectively, but no specific CDK9 $IC_{50}$ (WO2008129070) or CDK5 $IC_{50}$ (WO2008129071) data is presented.

WO2008129080 discloses 4,6 disubstituted aminopyrimidines and demonstrates that these compounds show an inhibitory effect on the protein kinase activity of various protein kinases, such as CDK1, CDK2, CDK4, CDK5, CDK6 and CDK9, with a preference for CDK9 inhibition (example 80).

EP1218360 B1 describes triazin derivatives as kinase inhibitors, but does not disclose potent or selective CDK9 inhibitors.

WO2008079933 discloses aminopyridine and aminopyrimidine derivatives and their use as CDK1, CDK2, CDK3, CDK4, CDK5, CDK6, CDK7, CDK8 or CDK9 inhibitors.

WO2011012661 describes aminopyridine derivatives useful as CDK inhibitors.

Wang et al. (Chemistry & Biology 2010, 17, 1111-1121) describe 2-anilino-4-(thiazol-5-yl)pyrimidine transcriptional CDK inhibitors, which show anticancer activity in animal models.

WO2004009562 discloses substituted triazine kinase inhibitors. For selected compounds CDK1 and CDK 4 test data, but no CDK9 data is presented.

WO2004072063 describes heteroaryl (pyrimidine, triazine) substituted pyrroles as inhibitors of protein kinases such as ERK2, GSK3, PKA or CDK2.

WO2010009155 discloses triazine and pyrimidine derivatives as inhibitors of histone deacetylase and/or cyclin dependent kinases (CDKs). For selected compounds CDK2 test data is described.

WO2003037346 (corresponding to U.S. Pat. No. 7,618,968B2, U.S. Pat. No. 7,291,616B2, US2008064700A1, US2003153570A1) relates to aryl triazines and uses thereof, including to inhibit lysophosphatidic acid acyltransferase beta (LPAAT-beta) activity and/or proliferation of cells such as tumor cells.

WO2008025556 describes carbamoyl sulfoximides having a pyrimidine core, which are useful as kinase inhibitors. No CDK9 data is presented.

WO2002066481 describes pyrimidine derivatives as cyclin dependent kinase inhibitors CDK9 is not mentioned and no CDK9 data is presented.

WO2008109943 concerns phenyl aminopyri(mi)dine compounds and their use as kinase inhibitors, in particular as JAK2 kinase inhibitors. The specific examples focus on compounds having a pyrimidine core.

WO2009032861 describes substituted pyrimidinyl amines as JNK kinase inhibitors. The specific examples focus on compounds having a pyrimidine core.

WO2011046970 concerns amino-pyrimidine compounds as inhibitors of TBKL and/or IKK epsilon. The specific examples focus on compounds having a pyrimidine core.

Despite the fact that various inhibitors of CDK's are known, there remains a need for selective CDK9 inhibitors to be used for the treatment of diseases such as hyper-proliferative diseases, viral diseases, and/or diseases of the heart, which offer one or more advantages over the compounds known from prior art, such as: improved activity and/or efficacy,

- beneficial kinase selectivity profile according to the respective therapeutic need,
- improved side effect profile, such as fewer undesired side effects,
- lower intensity of side effects, or reduced (cyto)toxicity,
- improved physicochemical properties, such as solubility in water and body fluids,
- improved pharmacokinetic properties, allowing e.g. for dose reduction or an easier dosing scheme,
- and/or easier drug substance manufacturing e.g. by shorter synthetic routes or easier purification.

A particular object of the invention is to provide CDK9 kinase inhibitors which, compared to the compounds known from prior art, show an increased selectivity for CDK9/Cyclin T1 as compared to CDK2/Cyclin E.

Another object of the invention is to provide CDK9 kinase inhibitors which show an increased potency to inhibit CDK9 activity (demonstrated by a lower $IC_{50}$ value for CDK9/Cyc T1) compared to the compounds known from prior art.

Another object of the invention is to provide CDK9 kinase inhibitors which show an increased potency to inhibit CDK9 activity at high ATP concentrations compared to the compounds known from prior art.

Another object of the invention is to provide CDK9 kinase inhibitors, which show an improved anti-proliferative activity in certain tumor cell lines such as HeLa compared to the compounds known from prior art.

Further, it is also an object of the present invention to provide CDK9 kinase inhibitors, which, compared to the compounds known from prior art, are highly selective for CDK9/Cyclin T1 as compared to CDK2/Cyclin E, and/or which show an increased potency to inhibit CDK9 activity (demonstrated by a lower 1050 value for CDK9/Cyc T1) and/or which show an improved anti-proliferative activity in certain tumor cell lines such as HeLa and/or which show an increased potency to inhibit CDK9 activity at high ATP concentrations compared to the compounds known from prior art.

The present invention relates to compounds of general formula (I)

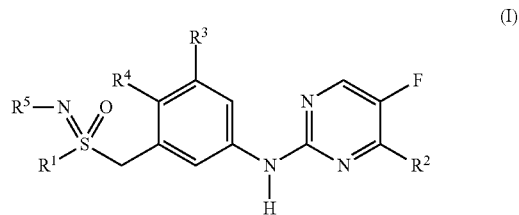

wherein
$R^1$ represents a group selected from $C_1$-$C_6$-alkyl-, $C_3$-$C_7$-cycloalkyl heterocyclyl-, phenyl, heteroraryl, phenyl-$C_1$-$C_3$-alkyl- or heteroaryl-$C_1$-$C_3$-alkyl-,
  wherein said group is optionally substituted with one or two or three substituents, identically or differently, selected from the group of hydroxy, cyano, halogen, halo-$C_1$-$C_3$-alkyl-, $C_1$-$C_6$-alkoxy-, $C_1$-$C_3$-fluoroalkoxy-, amino, alkylamino-, dialkylamino-, acetylamino-, N-methyl-N-acetylamino-, cyclic amines;

$R^2$ represents a group selected from

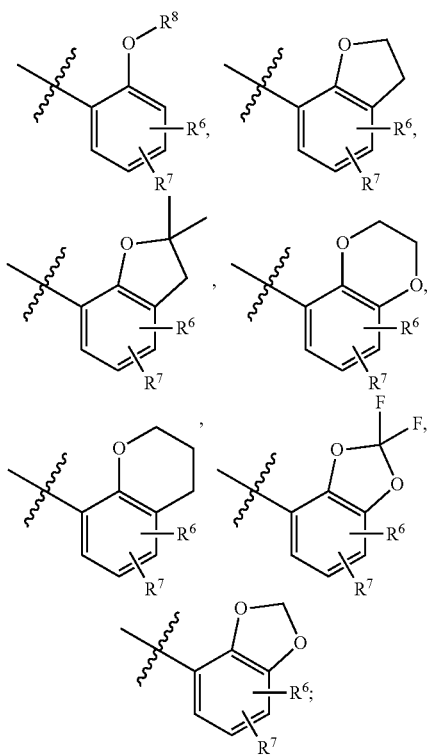

$R^3$, $R^4$ represent, independently from each other, a group selected from a hydrogen atom, halogen atom, cyano, —$SF_5$, $C_1$-$C_3$-alkyl-, $C_1$-$C_3$-alkoxy-, halo-$C_1$-$C_3$-alkyl-, $C_1$-$C_3$-fluoroalkoxy-;

$R^5$ represents a group selected from a hydrogen atom, cyano, —C(O)$R^9$, —C(O)O$R^9$, —S(O)$_2R^9$, —C(O)N$R^{10}R^{11}$, $C_1$-$C_6$-alkyl-, $C_3$-$C_7$-cycloalkyl-, heterocyclyl-, phenyl, heteroaryl
wherein said $C_1$-$C_6$-alkyl, $C_3$-$C_7$-cycloalkyl heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^6$, $R^7$ represent, independently from each other, a group selected from a hydrogen atom, halogen atom, cyano, $C_1$-$C_3$-alkyl-, $C_1$-$C_3$-alkoxy-, halo-$C_1$-$C_3$-alkyl-, $C_1$-$C_3$-fluoroalkoxy-;

$R^8$ represents a group selected from
a) a $C_1$-$C_6$-alkyl group, which is optionally substituted with one or two or three substituents, identically or differently, selected from the group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl heterocyclyl-, phenyl, heteroaryl,
wherein said $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

b) a $C_3$-$C_6$-alkenyl group, which is optionally substituted with one or two or three substituents, identically or differently, selected from the group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl heterocyclyl-, phenyl, heteroaryl,
wherein said $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

c) a $C_3$-$C_6$-alkynyl group, which is optionally substituted with one or two or three substituents, identically or differently, selected from the group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl heterocyclyl-, phenyl, heteroaryl,
wherein said $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

d) a $C_3$-$C_7$-cycloalkyl- group, which is optionally substituted with one or two or three substituents, identically or differently, selected from the group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-;

e) a heterocyclyl-group, which is optionally substituted with one or two or three substituents, identically or differently, selected from the group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-;

f) a phenyl group, which is optionally substituted with one or two or three substituents, identically or differently, selected from the group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

g) a heteroaryl group, which is optionally substituted with one or two or three substituents, identically or differently, selected from the group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

h) a phenyl-$C_1$-$C_3$-alkyl- group, which phenyl group is optionally substituted with one or two or three substituents, identically or differently, selected from the group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

i) a heteroaryl-$C_1$-$C_3$-alkyl- group, which heteroaryl group is optionally substituted with one or two or three substituents, identically or differently, selected from the group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

j) a $C_3$-$C_6$-cycloalkyl-$C_1$-$C_3$-alkyl- group, which $C_3$-$C_6$-cycloalkyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;

k) a heterocyclyl-$C_1$-$C_3$-alkyl- group, which heterocyclyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;

l) phenyl-cyclopropyl- group, which phenyl group is optionally substituted with one or two or three substituents, identically or differently, selected from the group of halogen, hydroxy, $NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

m) a heteroaryl-cyclopropyl- group, which heteroaryl group is optionally substituted with one or two or three substituents, identically or differently, selected from the group of halogen, hydroxy, $NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

$R^9$ represents a group selected from $C_1$-$C_6$-alkyl-, $C_3$-$C_7$-cycloalkyl-, heterocyclyl-, phenyl, benzyl or heteroaryl wherein said group is optionally substituted with one, two or three substituents, identically or differently, selected from halogen, hydroxy, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^{10}$, $R^{11}$ represent, independently from each other, a group selected from hydrogen, $C_1$-$C_6$-alkyl-, $C_3$-$C_7$-cycloalkyl-, heterocyclyl-, phenyl or heteroaryl wherein said $C_1$-$C_6$-alkyl, $C_3$-$C_7$-cycloalkyl-, heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

or their enantiomers, diastereomers, salts, solvates or salts of solvates.

Compounds according to the invention are the compounds of the formula (I) and the salts, solvates and solvates of the salts thereof, the compounds of the hereinafter recited formula which are encompassed by formula (I) and the salts, solvates and solvates of the salts thereof, and the compounds which are encompassed by formula (I) and are mentioned hereinafter as exemplary embodiments and the salts, solvates and solvates of the salts thereof, where the compounds which are encompassed by formula (I) and are mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

If the compounds according to the invention can be in tautomeric forms, the present invention encompasses all tautomeric forms.

Further, the compounds of the present invention can exist in free form, e.g. as a free base, or as a free acid, or as a zwitterion, or can exist in the form of a salt. Said salt may be any salt, either an organic or inorganic addition salt, particularly any physiologically acceptable organic or inorganic addition salt, customarily used in pharmacy.

Salts which are preferred for the purposes of the present invention are physiologically acceptable salts of the compounds according to the invention. However, salts which are not suitable for pharmaceutical applications per se, but which, for example, can be used for the isolation or purification of the compounds according to the invention, are also comprised.

The term "physiologically acceptable salt" refers to a relatively non-toxic, inorganic or organic acid addition salt of a compound of the present invention, for example, see S. M. Berge, et al. "Pharmaceutical Salts," J. Pharm. Sci. 1977, 66, 1-19.

Physiologically acceptable salts of the compounds according to the invention encompass acid addition salts of mineral acids, carboxylic acids and sulfonic acids, for example salts of hydrochloric acid, hydrobromic acid, hydroiodic, sulfuric acid, bisulfuric acid, phosphoric acid, nitric acid or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Physiologically acceptable salts of the compounds according to the invention also comprise salts of conventional bases, such as, by way of example and by preference, alkali metal salts (for example sodium and potassium salts), alkaline earth metal salts (for example calcium and magnesium salts) and ammonium salts derived from ammonia or organic amines with 1 to 16 C atoms, such as, by way of example and by preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methylglucamine, dimethylglucamine, ethylglucamine, 1,6-hexadiamine, glucosamine, sarcosine, serinol, tris(hydroxymethyl)aminomethane, aminopropane diol, Sovak base, and 1-amino-2,3,4-butanetriol. Additionally, basic nitrogen containing groups may be quaternised with such agents as lower alkylhalides such as methyl-, ethyl-, propyl-, and butylchlorides, -bromides and -iodides; dialkylsulfates like dimethyl-, diethyl-, dibutyl- and diamylsulfates, long chain halides such as decyl-, lauryl-, myristyl- and stearylchlorides, -bromides and -iodides, aralkylhalides like benzyl- and phenethylbromides and others.

The present invention includes all possible salts of the compounds of the present invention as single salts, or as any mixture of said salts, in any ratio.

Solvates is the term used for the purposes of the invention for those forms of the compounds according to the invention which form a complex with solvent molecules by coordination in the solid or liquid state. Hydrates are a special form of solvates in which the coordination takes place with water. Hydrates are preferred as solvates within the scope of the present invention.

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulfur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

In addition, the present invention also encompasses prodrugs of the compounds according to the invention. The term "prodrugs" encompasses compounds which themselves may be biologically active or inactive, but are converted (for example by metabolism or hydrolysis) to compounds according to the invention during their residence time in the body.

For the purposes of the present invention, the substituents have the following meaning, unless otherwise specified:

The term "halogen", "halogen atom" or "halo" represents fluorine, chlorine, bromine and iodine, particularly chlorine or fluorine, preferably fluorine atoms.

The term "alkyl" represents a linear or branched alkyl radical having the number of carbon atoms specifically indicated, e.g. $C_1$-$C_6$ one, two, three, four, five or six carbon atoms, e.g. methyl, ethyl, n-propyl-, isopropyl, n-butyl, tert-butyl, pentyl, isopentyl, hexyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl. Preferably, the alkyl group has 1, 2 or 3 carbon atoms ("$C_1$-$C_3$-alkyl"), methyl, ethyl, n-propyl or isopropyl.

The term "$C_2$-$C_6$-alkenyl" is to be understood as preferably meaning a linear or branched, monovalent hydrocarbon group, which contains one double bond, and which has 2 to 6 carbon atoms ("$C_2$-$C_6$-alkenyl").

The term "$C_2$-$C_6$-alkynyl" is to be understood as preferably meaning a linear, monovalent hydrocarbon group which contains one triple bond, and which contains 2 to 6 carbon atoms.

The term "$C_3$-$C_7$-cycloalkyl" is to be understood as preferably meaning a saturated, monovalent, monocyclic hydrocarbon ring which contains 3, 4, 5, 6 or 7 carbon atoms. Said $C_3$-$C_7$-cycloalkyl group is for example, a monocyclic hydrocarbon ring, e.g. a cyclopropyl, cyclobutyl, cyclopentyl, cyclohexyl or cycloheptyl group. Said cycloalkyl ring can optionally contain one or more double bonds e.g. cycloalkenyl, such as a cyclopropenyl, cyclobutenyl, cyclopentenyl, cyclohexenyl or cycloheptenyl group, wherein the bond between said ring with the rest of the molecule may be to any carbon atom of said ring, be it saturated or unsaturated.

The term "$C_3$-$C_6$-cycloalkyl" is to be understood as preferably meaning a saturated, monovalent, monocyclic hydrocarbon ring which contains 3, 4, 5 or 6 carbon atoms. In particular said $C_3$-$C_6$-cycloalkyl group is a monocyclic hydrocarbon ring such as a cyclopropyl, cyclobutyl, cyclopentyl or cyclohexyl group.

The term "$C_3$-$C_6$-cycloalkyl-$C_1$-$C_3$-alkyl-" group is to be understood as preferably meaning a $C_3$-$C_6$-cycloalkyl group as defined supra, in which one of the hydrogen atoms is replaced by a $C_1$-$C_3$-alkyl group, as defined supra, that links the $C_3$-$C_6$-cycloalkyl-$C_1$-$C_3$-alkyl- group to the molecule. Particularly, the "$C_3$-$C_6$-cycloalkyl-$C_1$-$C_3$-alkyl-" is a "$C_3$-$C_6$-cycloalkyl-$C_1$-$C_2$-alkyl-", preferably it is a "$C_3$-$C_6$-cycloalkyl-methyl-" group.

The term "heterocyclyl" is to be understood as meaning a saturated or partially unsaturated, monovalent, mono- or bicyclic hydrocarbon ring which contains 3, 4, 5, 6, 7, 8 or 9 carbon atoms and further containing 1, 2 or 3 heteroatom-containing groups selected from oxygen, sulfur, nitrogen. Particularly, the term "heterocyclyl" is to be understood as meaning a "4- to 10-membered heterocyclic ring".

The term "a 4- to 10-membered heterocyclic ring" is to be understood as meaning a saturated or partially unsaturated, monovalent, mono- or bicyclic hydrocarbon ring which contains 3, 4, 5, 6, 7, 8 or 9 carbon atoms, and further containing 1, 2 or 3 heteroatom-containing groups selected from oxygen, sulfur, nitrogen. Said heterocyclic ring is for example, a monocyclic heterocyclic ring such as an oxetanyl, azetidinyl, tetrahydrofuranyl, pyrrolidinyl, 1,3-dioxolanyl, imidazolidinyl, pyrazolidinyl, oxazolidinyl, isoxazolidinyl, 1,4-dioxanyl, pyrrolinyl, tetrahydropyranyl, piperidinyl, morpholinyl, 1,3-dithianyl, thiomorpholinyl, piperazinyl, or chinuclidinyl group. Optionally, said heterocyclic ring can contain one or more double bonds, e.g. 4H-pyranyl, 2H-pyranyl, 2,5-dihydro-1H-pyrrolyl, 1,3-dioxolyl, 4H-1,3,4-thiadiazinyl, 2,5-dihydrofuranyl, 2,3-dihydrofuranyl, 2,5-dihydrothienyl, 2,3-dihydrothienyl, 4,5-dihydrooxazolyl, 4,5-dihydroisoxazolyl, or 4H-1,4-thiazinyl group, or, it may be benzo fused.

Particularly, the term "heterocyclyl" is to be understood as being a heterocyclic ring which contains 3, 4 or 5 carbon atoms, and 1, 2 or 3 of the above-mentioned heteroatom-containing groups (a "4- to 7-membered heterocyclic ring"), more particularly said ring can contain 4 or 5 carbon atoms, and 1, 2 or 3 of the above-mentioned heteroatom-containing groups (a "5- to 7-membered heterocyclic ring"), more particularly said heterocyclic ring is a "6-membered heterocyclic ring", which is to be understood as containing 4 carbon atoms and 2 of the above-mentioned heteroatom-containing groups or 5 carbon atoms and one of the above-mentioned heteroatom-containing groups, preferably 4 carbon atoms and 2 of the above-mentioned heteroatom-containing groups.

The term "heterocyclyl-$C_1$-$C_3$-alkyl-" group is to be understood as preferably meaning a heterocyclyl, preferably a 4- to 7-membered heterocyclic ring, more preferably a 5- to 7-membered heterocyclic ring, each as defined supra, in which one of the hydrogen atoms is replaced by a $C_1$-$C_3$-alkyl group, as defined supra, that links the heterocyclyl-$C_1$-$C_3$-alkyl- group to the molecule. Particularly, the "heterocyclyl-$C_1$-$C_3$-alkyl-" is a "heterocyclyl-$C_1$-$C_2$-alkyl-", preferably it is a heterocyclyl-methyl- group.

The term "$C_1$-$C_6$-alkoxy-" is to be understood as preferably meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy, sec-butoxy, pentyloxy, iso-pentyloxy, n-hexyloxy group, or an isomer thereof. Particularly, the "$C_1$-$C_6$-alkoxy-" group is a "$C_1$-$C_4$-alkoxy-", a "$C_1$-$C_3$-alkoxy-", a methoxy, ethoxy, or propoxy group, preferably a methoxy, ethoxy or propoxy group.

The term "$C_1$-$C_3$-fluoroalkoxy-" is to be understood as preferably meaning a linear or branched, saturated, monovalent, $C_1$-$C_3$-alkoxy- group, as defined supra, in which one or more of the hydrogen atoms is replaced, identically or differently, by one or more fluoro atoms. Said $C_1$-$C_3$-fluoroalkoxy- group is, for example a 1,1-difluoromethoxy-, a 1,1,1-trifluoromethoxy-, a 2-fluoroethoxy-, a 3-fluoropropoxy-, a 2,2,2-trifluoroethoxy-, a 3,3,3-trifluoropropoxy- particularly a "$C_1$-$C_2$-fluoroalkoxy-" group.

The term "alkylamino-" is to be understood as preferably meaning an alkylamino group with a linear or branched alkyl group as defined supra. ($C_1$-$C_3$)-alkylamino- for example means a monoalkylamino group with 1, 2 oder 3 carbon atoms, ($C_1$-$C_6$)-alkylamino- with 1, 2, 3, 4, 5 or 6 carbon atoms. The term "alkylamino-" comprises for example methylamino-, ethylamino-, n-propylamino-, isopropylamino-, tert.-butylamino-, n-pentylamino- or n-hexylamino-.

The term "dialkylamino-" is to be understood as preferably meaning an alkylamino group having two linear or branched alkyl groups as defined supra, which are independent from each other. ($C_1$-$C_3$)-dialkylamino- for example represents a dialkylamino group with two alkyl groups each of them having 1 to 3 carbon atoms per alkyl group. The term "dialkylamino-" comprises for example: N,N-Dimethylamino-, N,N-Diethylamino-, N-Ethyl-N-methylamino-, N-Methyl-N-n-propylamino-, N-Isopropyl-N-n-propylamino-, N-t-Butyl-N-methylamino-, N-Ethyl-N-n-pentylamino- and N-n-Hexyl-N-methylamino-.

The term "cyclic amine" is to be understood as preferably meaning a cyclic amine group. Suitable cyclic amines are especially azetidine, pyrrolidine, piperidine, piperazine, 1-methylpiperazine, morpholine, thiomorpholine, which could be optionally substituted by one or two methyl groups.

The term "halo-$C_1$-$C_3$-alkyl-" is to be understood as preferably meaning a linear or branched, saturated, monovalent hydrocarbon group in which the term "$C_1$-$C_3$-alkyl" is defined supra, and in which one or more hydrogen atoms is replaced by a halogen atom, identically or differently, i.e. one halogen atom being independent from another. Particularly, said halogen atom is fluorine. Said halo-$C_1$-$C_3$-alkyl- group is, for example, a halo-$C_1$-$C_2$-alkyl- group, —$CF_3$, —$CHF_2$, —$CH_2F$, —$CF_2CF_3$, or —$CH_2CF_3$, preferably it is —$CF_3$.

The term "phenyl-$C_1$-$C_3$-alkyl-" is to be understood as preferably meaning a phenyl group, in which one of the hydrogen atoms is replaced by a $C_1$-$C_3$-alkyl group, as defined supra, that links the phenyl-$C_1$-$C_3$-alkyl-group to the molecule. Particularly, the "phenyl-$C_1$-$C_3$-alkyl-" is a phenyl-$C_1$-$C_2$-alkyl-, preferably a benzyl- group.

The term "heteroaryl" is to be understood as preferably meaning a monovalent, aromatic ring system having 5, 6, 7, 8, 9, 10, 11, 12, 13 or 14 ring atoms (a "5- to 14-membered heteroaryl" group), particularly 5 (a "5-membered heteroaryl") or 6 (a "6-membered heteroaryl") or 9 (a "9-membered heteroaryl") or 10 ring atoms (a "10-membered heteroaryl"), and which contains at least one heteroatom which may be identical or different, said heteroatom being such as oxygen, nitrogen or sulfur, and can be monocyclic, bicyclic, or tricyclic, and in addition in each case can be benzo-condensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, tetrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, or oxepinyl, etc.

Preferably, heteroaryl is selected from monocyclic heteroaryl, 5-membered heteroaryl or 6-membered heteroaryl.

The term "5-membered heteroaryl" is understood as preferably meaning a monovalent, aromatic ring system having 5 ring atoms and which contains at least one heteroatom which may be identical or different, said heteroatom being such as oxygen, nitrogen or sulfur. Particularly, "5 membered heteroaryl" is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, tetrazolyl.

The term "6-membered heteroaryl" is understood as preferably meaning a monovalent, aromatic ring system having 6 ring atoms and which contains at least one heteroatom which may be identical or different, said heteroatom being such as oxygen, nitrogen or sulfur. Particularly, "6 membered heteroaryl" is selected from pyridyl, pyridazinyl, pyrimidinyl, pyrazinyl, triazinyl.

The term "heteroaryl-$C_1$-$C_3$-alkyl-" is to be understood as preferably meaning a heteroaryl, a 5-membered heteroaryl or a 6-membered heteroaryl group, each as defined supra, in which one of the hydrogen atoms is replaced by a $C_1$-$C_3$-alkyl group, as defined supra, that links the heteroaryl-$C_1$-$C_3$-alkyl-group to the molecule. Particularly, the "heteroaryl-$C_1$-$C_3$-alkyl-" is a heteroaryl-$C_1$-$C_2$-alkyl-, a pyridinyl-$C_1$-$C_3$-alkyl, a pyridinylmethyl-, a pyridinylethyl-, a pyridinylpropyl-, a pyrimidinyl-$C_1$-$C_3$-alkyl-, a pyrimidinylmethyl-, a pyrimidinylethyl-, a pyrimidinylpropyl-, preferable a pyridinylmethyl- or a pyridinylethyl- or a pyrimidinylethyl- or a pyrimidinylpropyl- group.

The term "$C_1$-$C_6$", as used throughout this text, e.g. in the context of the definition of "$C_1$-$C_6$-alkyl", "$C_1$-$C_6$-alkoxy" is to be understood as meaning an alkyl group having a finite number of carbon atoms of 1 to 6, i.e. 1, 2, 3, 4, 5 or 6 carbon atoms. It is to be understood further that said term "$C_1$-$C_6$" is to be interpreted as any sub-range comprised therein, e.g. $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, $C_5$-$C_6$.

Similarly, as used herein, the term "$C_1$-$C_3$", as used throughout this text, e.g. in the context of the definition of "$C_1$-$C_3$-alkyl", "$C_1$-$C_3$-alkoxy" or "$C_1$-$C_3$-fluoroalkoxy" is to be understood as meaning an alkyl group having a finite number of carbon atoms of 1 to 3, i.e. 1, 2 or 3 carbon atoms. It is to be understood further that said term "$C_1$-$C_3$" is to be interpreted as any sub-range comprised therein, e.g. $C_1$-$C_3$, $C_1$-$C_2$, $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_3$-$C_5$, $C_3$-$C_4$, $C_4$-$C_6$, $C_4$-$C_5$, $C_5$-$C_6$.

Further, as used herein, the term "$C_3$-$C_7$", as used throughout this text, e.g. in the context of the definition of "$C_3$-$C_7$-cycloalkyl", is to be understood as meaning a cycloalkyl group having a finite number of carbon atoms of 3 to 7, i.e. 3, 4, 5, 6 or 7 carbon atoms, particularly 3, 4, 5 or 6 carbon atoms. It is to be understood further that said term "$C_3$-$C_7$" is to be interpreted as any sub-range comprised therein, e.g. $C_3$-$C_7$, $C_3$-$C_6$, $C_3$-$C_5$, $C_3$-$C_4$, $C_4$-$C_7$, $C_4$-$C_6$, $C_4$-$C_5$, $C_5$-$C_7$, $C_5$-$C_6$, $C_6$-$C_7$.

A symbol  at a bond denotes the linkage site in the molecule.

As used herein, the term "one or more times", e.g. in the definition of the substituents of the compounds of the general formulae of the present invention, is understood as meaning one, two, three, four or five times, particularly one, two, three or four times, more particularly one, two or three times, even more particularly one or two times.

Where the plural form of the word compounds, salts, hydrates, solvates and the like, is used herein, this is taken to mean also a single compound, salt, isomer, hydrate, solvate or the like.

The present invention relates to compounds of general formula (I), wherein $R^1$ represents a group selected from $C_1$-$C_6$-alkyl-, $C_3$-$C_7$-cycloalkyl-, heterocyclyl-, phenyl, heteroraryl, phenyl-$C_1$-$C_3$-alkyl- or heteroaryl-$C_1$-$C_3$-alkyl-,
  wherein said group is optionally substituted with one or two or three substituents, identically or differently, selected from the group of hydroxy, cyano, halogen, halo-$C_1$-$C_3$-alkyl-, $C_1$-$C_6$-alkoxy-, $C_1$-$C_3$-fluoroalkoxy-, amino, alkylamino-, dialkylamino-, acetylamino-, N-methyl-N-acetylamino-, cyclic amines;

$R^2$ represents a group selected from

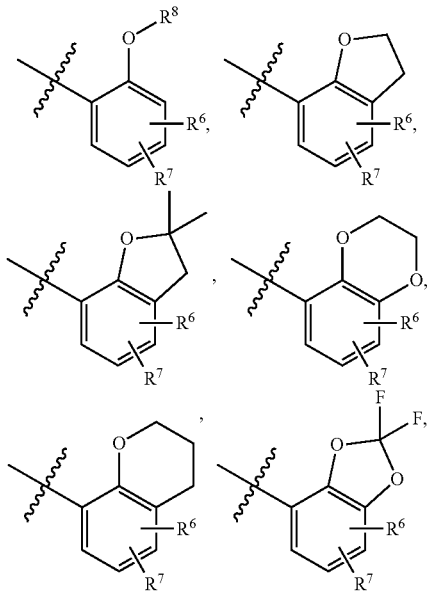

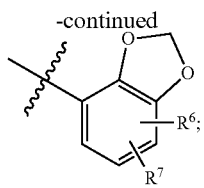

$R^3$, $R^4$ represent, independently from each other, a group selected from a hydrogen atom, fluoro atom, chloro atom, cyano, $C_1$-$C_3$-alkyl-, $C_1$-$C_3$-alkoxy-, halo-$C_1$-$C_3$-alkyl-, $C_1$-$C_3$-fluoroalkoxy-;

$R^5$ represents a group selected from a hydrogen atom, cyano, —C(O)$R^9$, —C(O)O$R^9$, —S(O)$_2$$R^9$, —C(O)N$R^{10}$$R^{11}$, $C_1$-$C_6$-alkyl-, $C_3$-$C_7$-cycloalkyl-, heterocyclyl-, phenyl, heteroaryl
  wherein said $C_1$-$C_6$-alkyl, $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^6$, $R^7$ represent, independently from each other, a group selected from a hydrogen atom, fluoro atom, chloro atom, cyano, $C_1$-$C_3$-alkyl-, $C_1$-$C_3$-alkoxy-, halo-$C_1$-$C_3$-alkyl-, $C_1$-$C_3$-fluoroalkoxy-;

$R^8$ represents a group selected from
  a) a $C_1$-$C_6$-alkyl group, which is optionally substituted with one or two or three substituents, identically or differently, selected from the group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl heterocyclyl-, phenyl, heteroaryl,
    wherein said $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-;
  b) a $C_3$-$C_7$-cycloalkyl- group, which is optionally substituted with one or two or three substituents, identically or differently, selected from the group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-;
  c) a heterocyclyl-group, which is optionally substituted with one or two or three substituents, identically or differently, selected from the group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-;
  d) a phenyl group, which is optionally substituted with one or two or three substituents, identically or differently, selected from the group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

e) a heteroaryl group, which is optionally substituted with one or two or three substituents, identically or differently, selected from the group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

f) a phenyl-$C_1$-$C_3$-alkyl- group, which phenyl group is optionally substituted with one or two or three substituents, identically or differently, selected from the group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

g) a heteroaryl-$C_1$-$C_3$-alkyl- group, which heteroaryl group is optionally substituted with group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

h) a $C_3$-$C_6$-cycloalkyl-$C_1$-$C_3$-alkyl- group, which $C_3$-$C_6$-cycloalkyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;

i) a heterocyclyl-$C_1$-$C_3$-alkyl- group, which heterocyclyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;

j) phenyl-cyclopropyl- group, which phenyl group is optionally substituted with one or two or three substituents, identically or differently, selected from the group of halogen, hydroxy, $NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

k) a heteroaryl-cyclopropyl- group, which heteroaryl group is optionally substituted with one or two or three substituents, identically or differently, selected from the group of halogen, hydroxy, $NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

$R^9$ represents a group selected from $C_1$-$C_6$-alkyl-, $C_3$-$C_7$-cycloalkyl-, heterocyclyl-, phenyl, benzyl or heteroaryl wherein said group is optionally substituted with one, two or three substituents, identically or differently, selected from halogen, hydroxy, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^{10}$, $R^{11}$ represent, independently from each other, a group selected from hydrogen, $C_1$-$C_6$-alkyl-, $C_3$-$C_7$-cycloalkyl-, heterocyclyl-, phenyl or heteroaryl wherein said $C_1$-$C_6$-alkyl, $C_3$-$C_7$-cycloalkyl-, heterocyclyl-, phenyl or heteroaryl group is optionally substituted with one or two or three substituents, identically or differently, selected from halogen, hydroxy, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

or their salts, solvates or salts of solvates.

The present invention relates to compounds of general formula (I)

wherein
$R^1$ represents a group selected from $C_1$-$C_6$-alkyl- or $C_3$-$C_7$-cycloalkyl-,
  wherein said group is optionally substituted with one or two or three substituents, identically or differently, selected from the group of hydroxy, cyano, halogen, halo-$C_1$-$C_3$-alkyl-, $C_1$-$C_6$-alkoxy-, $C_1$-$C_3$-fluoroalkoxy-, amino, alkylamino-, dialkylamino-, acetylamino-, N-methyl-N-acetylamino-, cyclic amines;

$R^2$ represents a group selected from

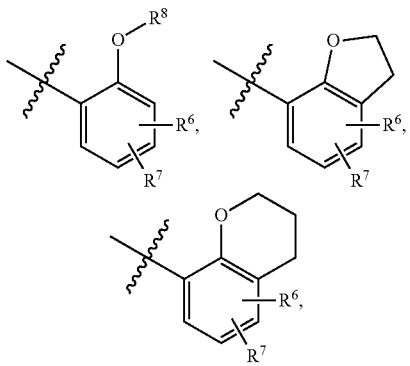

$R^3$, $R^4$ represent, independently from each other, a group selected from a hydrogen atom, halogen atom, —$SF_5$, $C_1$-$C_3$-alkyl-, $C_1$-$C_3$-alkoxy- or halo-$C_1$-$C_3$-alkyl-, $R^5$ represents a group selected from a hydrogen atom, cyano, —C(O)O$R^9$ or —C(O)N$R^{10}R^{11}$, $R^6$, $R^7$ represent, independently from each other, a group selected from a hydrogen atom or a halogen atom, $R^8$ represents a group selected from a) a $C_1$-$C_5$-alkyl group, which is optionally substituted with one or two or three substituents, identically or differently, selected from the group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_3$-$C_7$-cycloalkyl-, heterocyclyl-, phenyl, heteroaryl,
  wherein said $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

b) a phenyl-$C_1$-$C_2$-alkyl- group, which phenyl group is optionally substituted with one or two or three substituents, identically or differently, selected from the group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

$R^9$ represents a group selected from $C_1$-$C_5$-alkyl-, $C_3$-$C_6$-cycloalkyl-, heterocyclyl-, phenyl, benzyl or heteroaryl wherein said group is optionally substituted with one, two or three substituents, identically or differently, selected from halogen, hydroxy, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^{10}$, $R^{11}$ represent, independently from each other, a group selected from hydrogen, $C_1$-$C_5$-alkyl-, $C_3$-$C_6$-cycloalkyl-, heterocyclyl-, phenyl or heteroaryl wherein said $C_1$-$C_6$- alkyl, $C_3$-$C_7$-cycloalkyl-, heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

or their enantiomers, diastereomers, salts, solvates or salts of solvates.

The present invention relates to compounds of general formula (I), wherein $R^1$ represents a group selected from $C_1$-$C_6$-alkyl-, $C_3$-$C_5$-cycloalkyl-, wherein said group is optionally substituted with one or two substituents, identically or differently, selected from the group of hydroxy, $C_1$-$C_2$-alkoxy-, halo-$C_1$-$C_2$-alkyl-, $C_1$-$C_2$-fluoroalkoxy-;

$R^2$ represents a group selected from

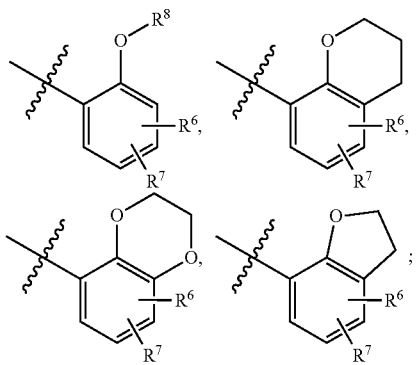

$R^3$ represents a hydrogen atom or fluoro atom;
$R^4$ represents a hydrogen atom or a fluoro atom;
$R^5$ represents a group selected from a hydrogen atom, cyano, —C(O)O$R^9$, —C(O)N$R^{10}R^{11}$;
$R^6$, $R^7$ represent, independently from each other, a group selected from a hydrogen atom, fluoro atom, chloro atom;
$R^8$ represents a group selected from
  a) a $C_1$-$C_6$-alkyl group, which is optionally substituted with one or two or three substituents, identically or differently, selected from halogen, hydroxy, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_3$-$C_7$-cycloalkyl heterocyclyl-, phenyl, heteroaryl,
    wherein said $C_3$-$C_7$-cycloalkyl-, heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, dialkylamino-, acetylamino-, N-methyl-N-acetylamino-, cyclic amines, halo-$C_1$-$C_3$-alkyl-, $C_1$-$C_3$-fluoroalkoxy-;
  b) a phenyl-$C_1$-$C_3$-alkyl- group, which phenyl group is optionally substituted with one or two or three substituents, identically or differently, selected from the group of halogen, hydroxy, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
  c) a heteroaryl-$C_1$-$C_3$-alkyl- group, which heteroaryl group is optionally substituted with one or two or three substituents, identically or differently, selected from the group of halogen, hydroxy, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
  d) a $C_3$-$C_6$-cycloalkyl-$C_1$-$C_3$-alkyl- group, which $C_3$-$C_6$-cycloalkyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;
  e) a heterocyclyl-$C_1$-$C_3$-alkyl- group, which heterocyclyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;
  f) phenyl-cyclopropyl- group, which phenyl group is optionally substituted with one or two or three substituents, identically or differently, selected from the group of halogen, hydroxy, —$NH_2$, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
  g) a heteroaryl-cyclopropyl- group, which heteroaryl group is optionally substituted with one or two or three substituents, identically or differently, selected from the group of halogen, hydroxy, —$NH_2$, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

$R^9$ represents a $C_1$-$C_3$-alkyl group;
$R^{10}R^{11}$ represent, independently from each other, a group selected from hydrogen, $C_1$-$C_2$-alkyl-;

or their salts, solvates or salts of solvates.

The present invention relates to compounds of general formula (I), wherein $R^1$ represents a group selected from $C_1$-$C_6$-alkyl-, $C_3$-$C_5$-cycloalkyl-, wherein said group is optionally substituted with one or two substituents, identically or differently, selected from the group of $C_1$-$C_2$-alkoxy-, halo-$C_1$-$C_2$-alkyl-, $C_1$-$C_2$-fluoroalkoxy-;

$R^2$ represents a group selected from

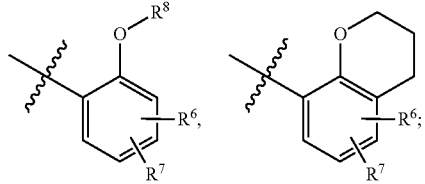

$R^3$ represents a hydrogen atom or fluoro atom;
$R^4$ represents a hydrogen atom or a fluoro atom;
$R^5$ represents a group selected from a hydrogen atom, cyano, —C(O)O$R^9$, —C(O)N$R^{10}R^{11}$;
$R^6$, $R^7$ represent, independently from each other, a group selected from a hydrogen atom, fluoro atom;
$R^8$ represents a group selected from
  a) a $C_1$-$C_3$-alkyl group, which is optionally substituted with one or two or three substituents, identically or differently, selected from halogen, cyano, halo-$C_1$-$C_3$-alkyl-;
  b) a phenyl-$C_1$-$C_3$-alkyl- group, which phenyl group is optionally substituted with one or two or three substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-;

c) a heteroaryl-$C_1$-$C_3$-alkyl- group, which heteroaryl group is optionally substituted with one or two substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-;
d) a $C_3$-$C_6$-cycloalkyl-$C_1$-$C_3$-alkyl- group, which $C_3$-$C_6$-cycloalkyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;
e) a heterocyclyl-$C_1$-$C_3$-alkyl- group, which heterocyclyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;
f) phenyl-cyclopropyl- group, which phenyl group is optionally substituted with one or two or three substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-;
g) a heteroaryl-cyclopropyl- group, which heteroaryl group is optionally substituted with one or two or three substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-;

$R^9$ represents a $C_1$-$C_3$-alkyl group;
$R^{10}R^{11}$ represent, independently from each other, a group selected from hydrogen, $C_1$-$C_2$-alkyl-;
or their salts, solvates or salts of solvates.

The present invention relates to compounds of general formula (I)
wherein
$R^1$ represents a group selected from $C_1$-$C_3$-alkyl- or cyclopropyl-,
$R^2$ represents a group selected from

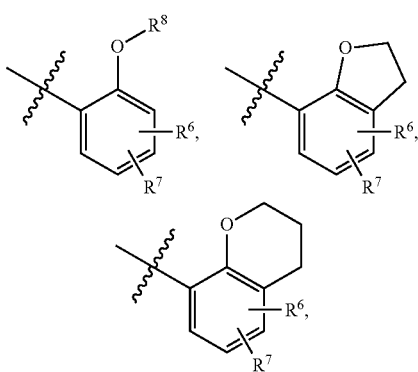

$R^3$, $R^4$ represent, independently from each other, a group selected from a hydrogen atom, a fluoro, a chloro or a bromo atom, —$SF_5$, $C_1$-$C_3$-alkyl-, $C_1$-$C_2$-alkoxy- or —$CF_3$,
$R^5$ represents a group selected from a hydrogen atom, cyano, —C(O)OR$^9$ or —C(O)NR$^{10}$R$^{11}$, $R^6$, $R^7$ represent, independently from each other, a group selected from a hydrogen atom or a fluoro atom,
$R^8$ represents a group selected from
  a) a $C_1$-$C_3$-alkyl group, which is optionally substituted with fluorine,
  b) a phenyl-$C_1$-$C_2$-alkyl- group, which phenyl group is optionally substituted with halogen $R^9$ represents a $C_1$-$C_6$-alkyl-, which is optionally substituted with $C_1$-$C_3$-alkoxy,
$R^{10}$, $R^{11}$ represent, independently from each other, hydrogen or a $C_1$-$C_6$-alkyl-,
or their enantiomers, diastereomers, salts, solvates or salts of solvates.

The present invention relates to compounds of general formula (I), wherein
$R^1$ represents a $C_1$-$C_3$-alkyl- or cyclopropyl group;
$R^2$ represents a group selected from

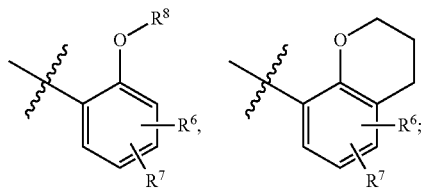

$R^3$ represents a hydrogen atom or fluoro atom;
$R^4$ represents a hydrogen atom or fluoro atom;
$R^5$ represents a group selected from a hydrogen atom, cyano, —C(O)OR$^9$, —C(O)NR$^{10}$R$^{11}$;
$R^6$, $R^7$ represent, independently from each other, a group selected from a hydrogen atom, fluoro atom;
$R^8$ represents a group selected from
  a) a $C_1$-$C_3$-alkyl group;
  b) a phenyl-$C_1$-$C_3$-alkyl-group, which phenyl group is optionally substituted with one or two substituents, identically or differently, selected from the group of halogen;
$R^9$ represents a $C_1$-$C_2$-alkyl group;
$R^{10}$, $R^{11}$ represent, independently from each other, a group selected from hydrogen, $C_1$-$C_2$-alkyl-;
or their salts, solvates or salts of solvates.

The present invention relates to compounds of general formula (I), wherein
$R^1$ represents a group selected from $C_1$-$C_3$-alkyl-;
$R^2$ represents a group selected from

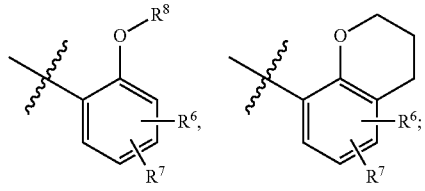

$R^3$ represents a group selected from a hydrogen atom, fluoro atom;
$R^4$ represents a group selected from a hydrogen atom;
$R^5$ represents a group selected from a hydrogen atom, cyano, —C(O)OR$^9$, —C(O)NR$^{10}$R$^{11}$;
$R^6$, $R^7$ represent, independently from each other, a group selected from a hydrogen atom, fluoro atom;
$R^8$ represents a group selected from
  a) a $C_1$-$C_2$-alkyl group;
  b) a phenyl-$C_1$-$C_2$-alkyl- group;
$R^9$ represents a $C_1$-$C_2$-alkyl group;
$R^{10}$, $R^{11}$ represent, independently from each other, a group selected from hydrogen, $C_1$-$C_2$-alkyl-; or their salts, solvates or salts of solvates.

The present invention relates to compounds of general formula (I), wherein $R^1$ represents a methyl group;
$R^2$ represents a group selected from

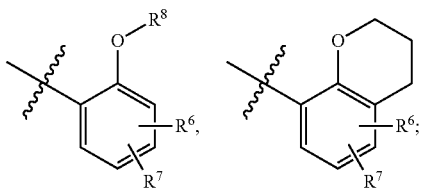

$R^3$ represents a group selected from a hydrogen atom, fluoro atom;
$R^4$ represents a group selected from a hydrogen atom;
$R^5$ represents a group selected from a hydrogen atom, cyano, —C(O)O$R^9$, —C(O)N$R^{10}R^{11}$;
$R^6$, $R^7$ represent, independently from each other, a group selected from a hydrogen atom, fluoro atom;
$R^8$ represents a group selected from
  a) a methyl group;
  b) a benzyl group;
$R^9$ represents an ethyl group;
$R^{10}$ represents a hydrogen atom;
$R^{11}$ represents a methyl group;
or their salts, solvates or salts of solvates.

The present invention relates to compounds of general formula (I), wherein
$R^1$ represents a methyl group;
$R^2$ represents a group selected from 4-fluoro-2-methoxyphenyl-, 2-(benzyloxy)-4-fluorophenyl-, 3,4-dihydro-2H-chromen-8-yl-;
$R^3$ represents a group selected from a hydrogen atom, fluoro atom;
$R^4$ represents a group selected from a hydrogen atom;
$R^5$ represents a group selected from a hydrogen atom, cyano, —C(O)O$R^9$, —C(O)N$R^{10}R^{11}$;
$R^9$ represents an ethyl group;
$R^{10}$ represents a hydrogen atom;
$R^{11}$ represents a methyl group;
or their salts, solvates or salts of solvates.

In another embodiment the invention relates to compounds of formula (I), in which $R^1$ represents a group selected from $C_1$-$C_6$-alkyl-, $C_3$-$C_7$-cycloalkyl heterocyclyl-, phenyl, heteroaryl, phenyl-$C_1$-$C_3$-alkyl- or heteroaryl-$C_1$-$C_3$-alkyl-,
  wherein said group is optionally substituted with one or two or three substituents, identically or differently, selected from the group of hydroxy, cyano, halogen, halo-$C_1$-$C_3$-alkyl-, $C_1$-$C_6$-alkoxy-, $C_1$-$C_3$-fluoroalkoxy-, amino, alkylamino-, dialkylamino-, acetylamino-, N-methyl-N-acetylamino-, cyclic amines;

In another embodiment the invention relates to compounds of formula (I), in which $R^1$ represents a $C_1$-$C_6$-alkyl-, a $C_3$-$C_7$-cycloalkyl-, a heterocyclyl-, a phenyl, a heteroaryl, a phenyl-$C_1$-$C_3$-alkyl- or a heteroaryl-$C_1$-$C_3$-alkyl- group,
  wherein said group is optionally substituted with one or two or three substituents, identically or differently, selected from the group of hydroxy, cyano, halogen, halo-$C_1$-$C_3$-alkyl-, $C_1$-$C_6$-alkoxy-, $C_1$-$C_3$-fluoroalkoxy-, amino, alkylamino-, dialkylamino-, acetylamino-, N-methyl-N-acetylamino-, cyclic amines.

In another embodiment the invention relates to compounds of formula (I), in which $R^1$ represents a $C_1$-$C_3$-alkyl-, a $C_3$-$C_5$-cycloalkyl-, a 4- to 7-membered heterocyclic ring, a phenyl, a heteroaryl, a phenyl-$C_1$-$C_2$-alkyl- or a heteroaryl-$C_1$-$C_2$-alkyl- group,
  wherein said group is optionally substituted with one or two or three substituents, identically or differently, selected from the group of hydroxy, cyano, halogen, halo-$C_1$-$C_2$-alkyl-, $C_1$-$C_3$-alkoxy-, $C_1$-$C_2$-fluoroalkoxy-, amino, alkylamino-, dialkylamino-, acetylamino-, N-methyl-N-acetylamino-, cyclic amines.

In another embodiment the invention relates to compounds of formula (I), in which $R^1$ represents a phenyl or a heteroaryl group,
  wherein said group is optionally substituted with one or two or three substituents, identically or differently, selected from the group of hydroxy, cyano, halogen, halo-$C_1$-$C_2$-alkyl-, $C_1$-$C_3$-alkoxy-, $C_1$-$C_2$-fluoroalkoxy-, amino, alkylamino-, dialkylamino-, acetylamino-, N-methyl-N-acetylamino-, cyclic amines.

In another embodiment the invention relates to compounds of formula (I), in which $R^1$ represents a group selected from $C_1$-$C_6$-alkyl- or $C_3$-$C_7$-cycloalkyl-,
  wherein said group is optionally substituted with one or two or three substituents, identically or differently, selected from the group of hydroxy, cyano, halogen, halo-$C_1$-$C_3$-alkyl-, $C_1$-$C_6$-alkoxy-, $C_1$-$C_3$-fluoroalkoxy-, amino, alkylamino-, dialkylamino-, acetylamino-, N-methyl-N-acetylamino-, cyclic amines.

In another embodiment the invention relates to compounds of formula (I), in which $R^1$ represents a group selected from $C_1$-$C_3$-alkyl- or cyclopropyl-.

In another embodiment the invention relates to compounds of formula (I), in which $R^1$ represents a group selected from methyl, ethyl, propan-2-yl, cyclopropyl, tert-butyl, cyclopentyl, cyclohexyl or phenyl,
  wherein said group is optionally substituted with one substituent selected from the group of hydroxyl or methoxy.

In another embodiment the invention relates to compounds of formula (I), in which $R^1$ represents a group selected from methyl, ethyl, propan-2-yl, cyclopropyl, or phenyl;
  wherein said group is optionally substituted with one substituent selected from the group of hydroxyl or methoxy.

In another embodiment the invention relates to compounds of formula (I), in which $R^1$ represents a $C_1$-$C_3$-alkyl- or a heterocyclyl group.

In another embodiment the invention relates to compounds of formula (I), in which $R^1$ represents a $C_1$-$C_3$-alkyl- or a cyclopropyl group.

In a preferred embodiment the invention relates to compounds of formula (I), in which $R^1$ represents a group selected from methyl or cyclopropyl.

In another preferred embodiment the invention relates to compounds of formula (I), in which $R^1$ represents a $C_1$-$C_3$-alkyl- group.

In a particularly preferred embodiment the invention relates to compounds of formula (I), in which $R^1$ represents a methyl group.

In another preferred embodiment the invention relates to compounds of formula (I), in which $R^1$ represents a cyclopropyl group.

In another embodiment the invention relates to compounds of formula (I), in which $R^1$ represents a $C_3$-$C_5$-cycloalkyl- group.

In another embodiment the invention relates to compounds of formula (I), in which $R^2$ represents a group selected from

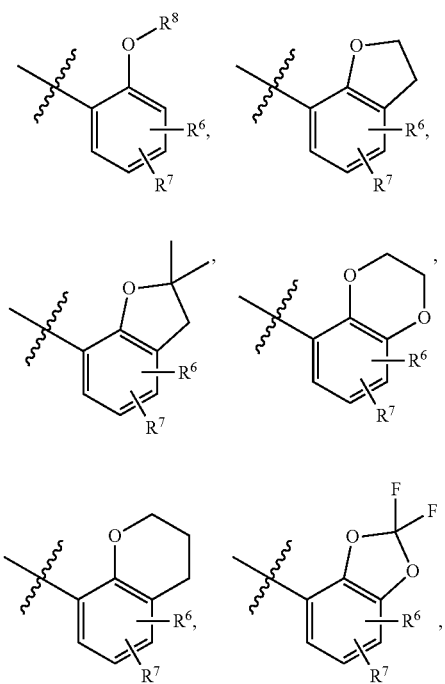

In another embodiment the invention relates to compounds of formula (I), in which $R^2$ represents a group selected from

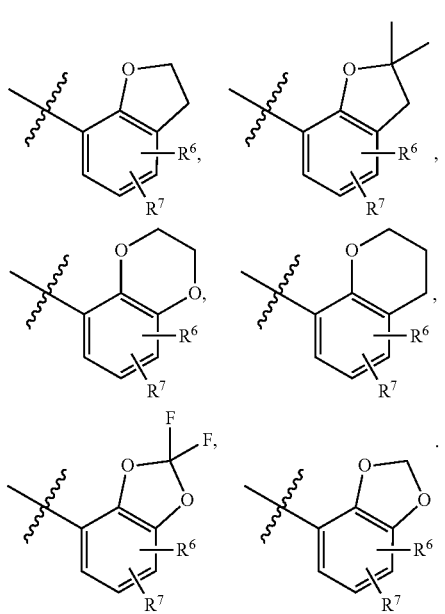

In another embodiment the invention relates to compounds of formula (I), in which $R^2$ represents

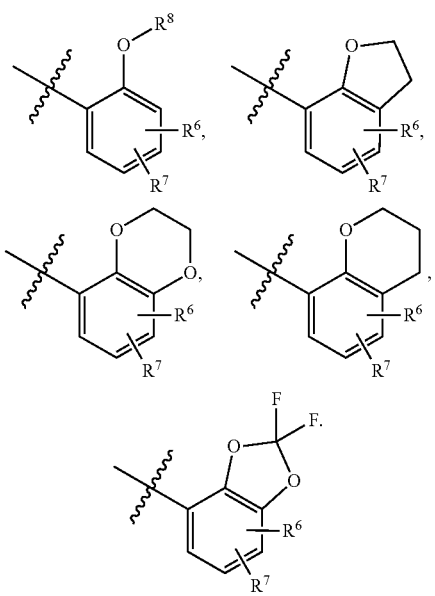

In another embodiment the invention relates to compounds of formula (I), in which $R^2$ represents

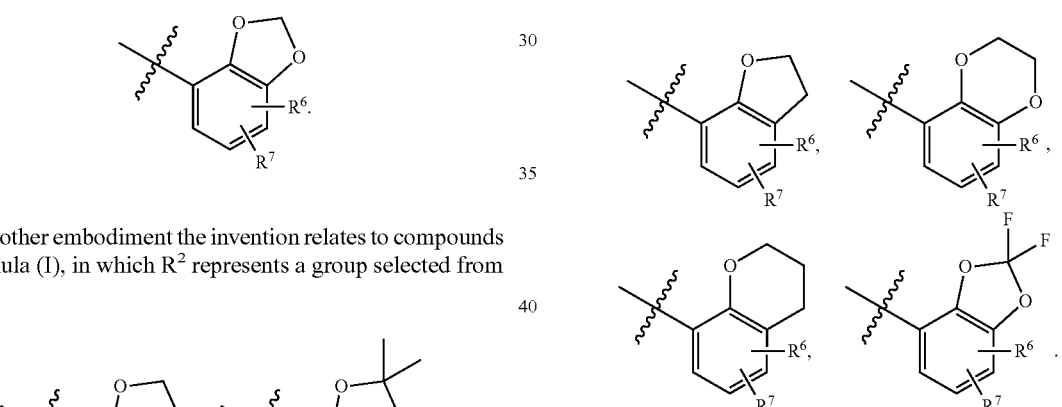

In another embodiment the invention relates to compounds of formula (I), in which $R^2$ represents

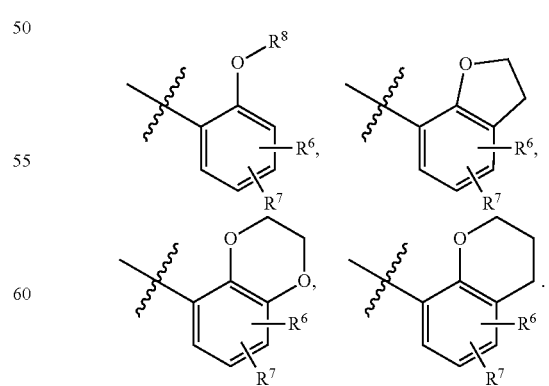

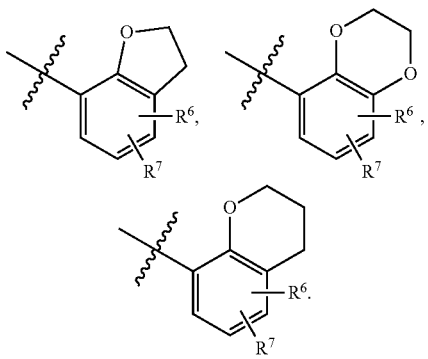

In another embodiment the invention relates to compounds of formula (I), in which R² represents a group selected from

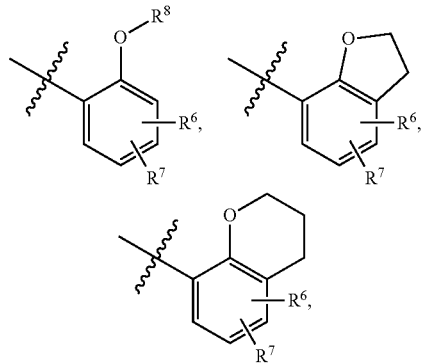

In another embodiment the invention relates to compounds of formula (I), in which R² represents a group selected from

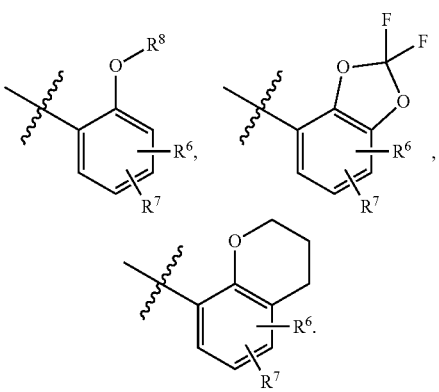

In another embodiment the invention relates to compounds of formula (I), in which R² represents a group selected from

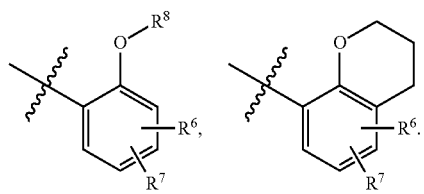

In another embodiment the invention relates to compounds of formula (I), in which R² represents

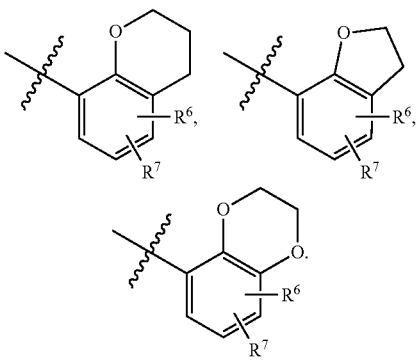

In a preferred embodiment the invention relates to compounds of formula (I), in which R² represents

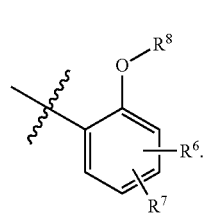

In another embodiment the invention relates to compounds of formula (I), in which R² represents a group selected from 4,5-difluoro-2-methoxyphenyl-; 3,4-difluoro-2-methoxyphenyl-, 4-fluoro-2-methoxyphenyl-, 2-(benzyloxy)-4-fluorophenyl-, 5-fluoro-2-methoxyphenyl-, 2-[(4-fluorobenzyl)oxy]phenyl-, 2-[(3-fluorobenzyl)oxy]phenyl-, 2-[(2-chlorobenzyl)oxy]phenyl-, 2-[(3-chlorobenzyl)oxy]phenyl-, 5-fluoro-2-[(2-fluorobenzyl)oxy]phenyl-, 5-fluoro-2-[(3-fluorobenzyl)oxy]phenyl-, 4-chloro-2-methoxyphenyl-, 3,4-dihydro-2H-chromen-8-yl-.

In another embodiment the invention relates to compounds of formula (I), in which R² represents a group selected from 4,5-difluoro-2-methoxyphenyl-; 4-fluoro-2-methoxyphenyl-, 2-(benzyloxy)-4-fluorophenyl-, 2-[(4-fluorobenzyl)oxy]phenyl-, 2-[(3-fluorobenzyl)oxy]phenyl-, 2-[(3-chlorobenzyl)oxy]phenyl-, 5-fluoro-2-[(3-fluorobenzyl)oxy]phenyl-, 3,4-dihydro-2H-chromen-8-yl-.

In another embodiment the invention relates to compounds of formula (I), in which R² represents a group selected from 4,5-difluoro-2-methoxyphenyl-; 4-fluoro-2-methoxyphenyl-, 2-(benzyloxy)-4-fluorophenyl-, 2-[(4-fluorobenzyl)oxy]phenyl-, 2-[(3-fluorobenzyl)oxy]phenyl-, 5-fluoro-2-[(3-fluorobenzyl)oxy]phenyl-, 3,4-dihydro-2H-chromen-8-yl-.

In another embodiment the invention relates to compounds of formula (I), in which R² represents a group selected from 4-fluoro-2-methoxyphenyl-, 2-(benzyloxy)-4-fluorophenyl-, 2-[(3-fluorobenzyl)oxy]phenyl-, 5-fluoro-2-[(3-fluorobenzyl)oxy]phenyl-, 3,4-dihydro-2H-chromen-8-yl-.

In another embodiment the invention relates to compounds of formula (I), in which R² represents a group selected from 4-fluoro-2-methoxyphenyl-, 2-(benzyloxy)-4-fluorophenyl-, 3,4-dihydro-2H-chromen-8-yl-.

In another embodiment the invention relates to compounds of formula (I), in which R² represents a group selected from 4-fluoro-2-methoxyphenyl- or 2-(benzyloxy)-4-fluorophenyl-, 3,4-dihydro-2H-chromen-8-yl-.

In a preferred embodiment the invention relates to compounds of formula (I), in which $R^2$ represents a 4-fluoro-2-methoxyphenyl- group.

In a preferred embodiment the invention relates to compounds of formula (I), in which $R^2$ represents a 3,4-dihydro-2H-chromen-8-yl- group.

In another embodiment the invention relates to compounds of formula (I), in which $R^3$ and $R^4$ represent, independently from each other, a group selected from a hydrogen atom, halogen atom, cyano, —$SF_5$, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^3$ represents a group selected from a halogen atom, cyano, —$SF_5$, $C_1$-$C_3$-alkyl-, $C_1$-$C_3$-alkoxy-, halo-$C_1$-$C_3$-alkyl-, $C_1$-$C_3$-fluoroalkoxy- and $R^4$ represents hydrogen.

In another embodiment the invention relates to compounds of formula (I), in which $R^3$ and $R^4$ represent, independently from each other, a group selected from a hydrogen atom, halogen atom, —$SF_5$, $C_1$-$C_3$-alkyl-, $C_1$-$C_3$-alkoxy- or halo-$C_1$-$C_3$-alkyl-.

In another embodiment the invention relates to compounds of formula (I), in which $R^3$ and $R^4$ represent, independently from each other, a group selected from a hydrogen atom, a fluoro, a chloro or a bromo atom, —$SF_5$, $C_1$-$C_3$-alkyl-, $C_1$-$C_2$-alkoxy- or —$CF_3$.

In another embodiment the invention relates to compounds of formula (I), in which $R^3$ represents a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^3$ represents a group selected from a hydrogen atom, fluoro atom, chloro atom, $C_1$-$C_2$-alkyl-, $C_1$-$C_2$-alkoxy-, halo-$C_1$-$C_2$-alkyl-, $C_1$-$C_2$-fluoroalkoxy-.

In another embodiment the invention relates to compounds of formula (I), in which $R^3$ represents a group selected from a hydrogen, a fluoro or a chloro atom.

In another embodiment the invention relates to compounds of formula (I), in which $R^3$ represents a fluoro or a chloro atom.

In another embodiment the invention relates to compounds of formula (I), in which $R^3$ represents a group selected from a hydrogen atom, a fluoro, a chloro or a bromo atom, —$SF_5$, $C_1$-$C_3$-alkyl-, $C_1$-$C_2$-alkoxy- or —$CF_3$.

In another embodiment the invention relates to compounds of formula (I), in which $R^3$ represents a group selected from a hydrogen atom or a fluoro atom.

In another embodiment the invention relates to compounds of formula (I), in which $R^3$ represents a hydrogen atom.

In a preferred embodiment the invention relates to compounds of formula (I), in which $R^3$ represents a fluoro atom.

In another embodiment the invention relates to compounds of formula (I), in which $R^4$ represents a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^4$ represents a group selected from a hydrogen atom, fluoro atom, chloro atom, $C_1$-$C_2$-alkyl-, $C_1$-$C_2$-alkoxy-, halo-$C_1$-$C_2$-alkyl-, $C_1$-$C_2$-fluoroalkoxy-.

In another embodiment the invention relates to compounds of formula (I), in which $R^4$ represents a group selected from a hydrogen, a fluoro or a chloro atom.

In another embodiment the invention relates to compounds of formula (I), in which $R^4$ represents a fluoro or a chloro atom.

In another embodiment the invention relates to compounds of formula (I), in which $R^4$ represents a group selected from a hydrogen atom or fluoro atom.

In a preferred embodiment the invention relates to compounds of formula (I), in which $R^4$ represents a hydrogen atom.

In a preferred embodiment the invention relates to compounds of formula (I), in which $R^4$ represents a fluoro atom.

In a particularly preferred embodiment the invention relates to compounds of formula (I), in which $R^3$ represents a fluoro atom and $R^4$ represents a hydrogen atom.

In another preferred embodiment the invention relates to compounds of formula (I), in which $R^3$ represents a hydrogen atom and $R^4$ represents a fluoro atom.

In another embodiment the invention relates to compounds of formula (I), in which $R^5$ represents a group selected from a hydrogen atom, cyano, —$C(O)R^9$, —$C(O)OR^9$, —$S(O)_2R^9$, —$C(O)NR^{10}R^{11}$, $C_1$-$C_6$-alkyl-, $C_3$-$C_7$-cycloalkyl-, heterocyclyl-, phenyl, heteroaryl wherein said $C_1$-$C_6$-alkyl, $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^5$ represents a group selected from a hydrogen atom, cyano, —$C(O)R^9$, —$C(O)OR^9$, —$S(O)_2R^9$, —$C(O)NR^{10}R^{11}$, methyl-.

In another embodiment the invention relates to compounds of formula (I), in which $R^5$ represents a group selected from cyano, —$C(O)R^9$, —$C(O)OR^9$, —$S(O)_2R^9$, —$C(O)NR^{10}R^{11}$, methyl-.

In another embodiment the invention relates to compounds of formula (I), in which $R^5$ represents a group selected from a hydrogen atom, cyano, —$C(O)OR^9$, $C(O)NR^{10}R^{11}$.

In another embodiment the invention relates to compounds of formula (I), in which $R^5$ represents a group selected from cyano, —$C(O)OR^9$, $C(O)NR^{10}R^{11}$.

In another embodiment the invention relates to compounds of formula (I), in which $R^5$ represents a group selected from a hydrogen atom, cyano or —$C(O)OR^9$.

In another embodiment the invention relates to compounds of formula (I), in which $R^5$ represents a group selected from cyano or —$C(O)OR^9$.

In another embodiment the invention relates to compounds of formula (I), in which $R^5$ represents a group selected from a hydrogen atom or a cyano group.

In another embodiment the invention relates to compounds of formula (I), in which $R^5$ represents a group selected from cyano, —$S(O)_2R^9$, —$C(O)NR^{10}R^{11}$.

In another embodiment the invention relates to compounds of formula (I), in which $R^5$ represents a group selected from a hydrogen atom or —$C(O)OR^9$.

In another embodiment the invention relates to compounds of formula (I), in which $R^5$ represents a hydrogen atom.

In another embodiment the invention relates to compounds of formula (I), in which $R^5$ represents —$C(O)OR^9$.

In another embodiment the invention relates to compounds of formula (I), in which $R^5$ represents —$C(O)NR^{10}R^{11}$.

In another preferred embodiment the invention relates to compounds of formula (I), in which $R^5$ represents a cyano group.

In another preferred embodiment the invention relates to compounds of formula (I), in which $R^5$ represents a hydrogen atom.

In another embodiment the invention relates to compounds of formula (I), in which $R^6$ and $R^7$ represent, independently from each other, a group selected from a hydrogen atom, halogen atom, cyano, $C_1$-$C_3$-alkyl-, $C_1$-$C_3$-alkoxy-, halo-$C_1$-$C_3$-alkyl- or $C_1$-$C_3$-fluoroalkoxy-.

In another embodiment the invention relates to compounds of formula (I), in which $R^6$ and $R^7$ represent, independently from each other, a group selected from a hydrogen atom or a halogen atom, In another embodiment the invention relates to compounds of formula (I), in which $R^6$ and $R^7$ represent, independently from each other, a group selected from a hydrogen atom or a fluoro atom, In another embodiment the invention relates to compounds of formula (I), in which $R^6$ represents a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^6$ represents a group selected from a hydrogen atom, fluoro atom, chloro atom, $C_1$-$C_2$-alkyl-, $C_1$-$C_2$-alkoxy-, halo-$C_1$-$C_2$-alkyl-, $C_1$-$C_2$-fluoroalkoxy-.

In another embodiment the invention relates to compounds of formula (I), in which $R^6$ represents a group selected from a hydrogen atom, fluoro atom, chloro atom.

In another embodiment the invention relates to compounds of formula (I), in which $R^6$ represents a hydrogen atom.

In another embodiment the invention relates to compounds of formula (I), in which $R^6$ represents a fluoro atom.

In a preferred embodiment the invention relates to compounds of formula (I), in which $R^6$ is in para position to the 5-fluoropyrimidinyl and represents a fluoro atom.

In another embodiment the invention relates to compounds of formula (I), in which $R^7$ represents a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^7$ represents a group selected from a hydrogen atom, fluoro atom, chloro atom, $C_1$-$C_2$-alkyl-, $C_1$-$C_2$-alkoxy-, halo-$C_1$-$C_2$-alkyl-, $C_1$-$C_2$-fluoroalkoxy-.

In another embodiment the invention relates to compounds of formula (I), in which $R^7$ represents a group selected from a hydrogen atom, fluoro atom, chloro atom.

In another embodiment the invention relates to compounds of formula (I), in which $R^7$ represents a hydrogen atom.

In a preferred embodiment the invention relates to compounds of formula (I), in which $R^6$ represents a fluoro atom and $R^7$ represents a hydrogen atom.

In another embodiment the invention relates to compounds of formula (I), in which $R^6$ is in para position to the 5-fluoropyrimidinyl and represents a fluoro atom and in which $R^7$ represents a hydrogen atom.

In another embodiment the invention relates to compounds of formula (I), in which $R^8$ represents a $C_1$-$C_6$-alkyl group, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, $C_3$-$C_7$-heterocyclyl-, phenyl, heteroaryl,
wherein said $C_3$-$C_7$-cycloalkyl-, $C_3$-$C_7$-heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^8$ represents a $C_1$-$C_3$-alkyl group, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_2$-alkyl-, $C_1$-$C_2$-fluoroalkoxy-, $C_1$-$C_2$-alkoxy-, $C_2$-$C_3$-alkenyl-, $C_2$-$C_3$-alkynyl-, $C_4$-$C_6$-cycloalkyl-, $C_3$-$C_7$-heterocyclyl-, phenyl, heteroaryl,
wherein said $C_4$-$C_6$-cycloalkyl-, $C_3$-$C_7$-heterocyclyl-, phenyl or heteroaryl group is optionally substituted with one, two or three substituents, identically or differently, selected from halogen, hydroxy, $C_1$-$C_2$-alkyl-, $C_1$-$C_2$-alkoxy-, —$NH_2$, alkylamino-, dialkylamino-, acetylamino-, N-methyl-N-acetylamino-, cyclic amines, halo-$C_1$-$C_2$-alkyl-, $C_1$-$C_2$-fluoroalkoxy-.

In another embodiment the invention relates to compounds of formula (I), in which $R^8$ represents a $C_1$-$C_6$-alkyl- group, which is optionally substituted with one or two or three substituents, identically or differently, selected from the group of halogen atom, $C_1$-$C_3$-alkyl-, $C_3$-$C_6$-cycloalkyl-, $C_3$-$C_6$-heterocyclyl-, phenyl, heteroaryl, wherein said $C_3$-$C_6$-cycloalkyl-, $C_3$-$C_6$-heterocyclyl-, phenyl- or heteroaryl group is optionally substituted with one substituent selected from halogen.

In another embodiment the invention relates to compounds of formula (I), in which $R^8$ represents a $C_1$-$C_6$-alkyl group, which is optionally substituted with one or two or three substituents, identically or differently, selected from the group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, heterocyclyl-, phenyl, heteroaryl,
wherein said $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^8$ represents a $C_1$-$C_5$-alkyl group, which is optionally substituted with one or two or three substituents, identically or differently, selected from the group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_3$-$C_7$-cycloalkyl heterocyclyl-, phenyl, heteroaryl,
wherein said $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^8$ represents a $C_1$-$C_3$-alkyl group, which is optionally substituted with fluorine.

In another embodiment the invention relates to compounds of formula (I), in which $R^8$ represents a $C_1$-$C_3$-alkyl group, which is optionally substituted with one or two or three substituents, identically or differently, selected from halogen, cyano, halo-$C_1$-$C_3$-alkyl-.

In another embodiment the invention relates to compounds of formula (I), in which $R^8$ represents a $C_1$-$C_3$-alkyl- group, which is substituted with one or two or three substituents, identically or differently, selected from the group of a halogen atom.

In another embodiment the invention relates to compounds of formula (I), in which $R^8$ represents a $C_1$-$C_3$-alkyl- group, which is substituted with one or two or three substituents, identically or differently, selected from the group of a chloro or fluoro atom.

In another embodiment the invention relates to compounds of formula (I), in which $R^8$ represents a $C_1$-$C_3$-alkyl- group, which is substituted with one or two or three substituents selected from the group of a fluoro atom.

In another embodiment the invention relates to compounds of formula (I), in which $R^8$ represents a group selected from —$CH_2CH_2CF_3$, —$CH_2CH_2CF_2CF_3$.

In another embodiment the invention relates to compounds of formula (I), in which $R^8$ represents a group selected from methyl, ($^2H_3$)methyl.

In a preferred embodiment the invention relates to compounds of formula (I), in which $R^8$ represents a methyl group.

In another embodiment the invention relates to compounds of formula (I), in which $R^8$ represents a $C_3$-$C_6$-alkenyl group, which is optionally substituted with one or two or three substituents, identically or differently, selected from the group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, heterocyclyl-, phenyl, heteroaryl,
wherein said $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, amino, alkylamino-, dialkylamino-, acetylamino-, In another embodiment the invention relates to compounds of formula (I), in which $R^8$ represents a $C_3$-$C_6$-alkynyl group, which is optionally substituted with one or two or three substituents, identically or differently, selected from the group of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, heterocyclyl-, phenyl, heteroaryl,
wherein said $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^8$ represents a $C_5$-$C_6$-cycloalkyl- group, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-.

In another embodiment the invention relates to compounds of formula (I), in which $R^8$ represents a $C_5$-$C_6$-cycloalkyl- group, which is optionally substituted with one or two or three substituents, identically or differently, selected from the group of fluoro, chloro, hydroxy, —$NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-, $C_2$-$C_3$-alkenyl-, $C_2$-$C_3$-alkynyl-.

In another embodiment the invention relates to compounds of formula (I), in which $R^8$ represents a cyclopentyl or cyclohexyl group, which is optionally substituted with one or two or three substituents, identically or differently, selected from the group of fluoro, chloro, hydroxy, —$NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-, $C_2$-$C_3$-alkenyl-, $C_2$-$C_3$-alkynyl-.

In another embodiment the invention relates to compounds of formula (I), in which $R^8$ represents a cyclohexyl or cyclopentyl group.

In another embodiment the invention relates to compounds of formula (I), in which $R^8$ represents a $C_3$-$C_6$-cycloalkyl-$C_1$-$C_3$-alkyl- group, which $C_3$-$C_6$-cycloalkyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^8$ represents a $C_3$-$C_6$-cycloalkyl-$CH_2$— group, which $C_3$-$C_6$-cycloalkyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^8$ represents a cyclohexyl-$CH_2$— or cyclopentyl-$CH_2$— or cyclobutyl-$CH_2$— group, which cyclohexyl or cyclopentyl or cyclobutyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-.

In a preferred embodiment the invention relates to compounds of formula (I), in which $R^8$ represents a cyclohexyl-$CH_2$— or cyclopentyl-$CH_2$— group, which cyclohexyl or cyclopentyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^8$ represents a heterocyclyl-$C_1$-$C_3$-alkyl- group, which heterocyclyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^8$ represents a heterocyclyl-methyl-group, which heterocyclyl group is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^8$ represents a 4- to 7-membered heterocyclic ring, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-.

In another embodiment the invention relates to compounds of formula (I), in which $R^8$ represents a 4- to 7-membered heterocyclic ring, which is optionally substituted with one or two or three substituents, identically or differently, selected from the group of halogen, hydroxy, —NH$_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-, $C_2$-$C_3$-alkenyl-, $C_2$-$C_3$-alkynyl-.

In another embodiment the invention relates to compounds of formula (I), in which $R^8$ represents a phenyl group, which is optionally substituted with one or two or three substituents, identically or differently, selected from the group of halogen, hydroxy, —NH$_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^8$ represents a phenyl group, which is optionally substituted with one or two or three substituents, identically or differently, selected from the group of halogen, hydroxy, —NH$_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I), in which $R^8$ represents a heteroaryl group, which is optionally substituted with one or two or three substituents, identically or differently, selected from the group of halogen, hydroxy, —NH$_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^8$ represents a heteroaryl group, which is optionally substituted with one or two or three substituents, identically or differently, selected from the group of halogen, hydroxy, —NH$_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I), in which $R^8$ represents a phenyl-$C_1$-$C_2$-alkyl- group, which phenyl group is optionally substituted with one or two or three substituents, identically or differently, selected from the group of halogen, hydroxy, NH$_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^8$ represents a phenyl-$C_1$-$C_2$-alkyl- group, which phenyl group is optionally substituted with one or two or three substituents, identically or differently, selected from the group of halogen, hydroxy, NH$_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In a preferred embodiment the invention relates to compounds of formula (I), in which $R^8$ represents a phenyl-$C_1$-$C_2$-alkyl- group, which phenyl group is optionally substituted with halogen.

In a preferred embodiment the invention relates to compounds of formula (I), in which $R^8$ represents a phenyl-$C_1$-$C_3$-alkyl- group, which phenyl group is optionally substituted with one or two or three substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^8$ represents a benzyl group, which phenyl group is optionally substituted with one or two or three substituents, identically or differently, selected from the group of halogen, hydroxy, NH$_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In a preferred embodiment the invention relates to compounds of formula (I), in which $R^8$ represents a benzyl group, which phenyl group is optionally substituted with one or two or three substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^8$ represents a benzyl group, which phenyl group is optionally substituted with one or two or three substituents, identically or differently, selected from the group of a fluoro atom or a methyl group.

In another embodiment the invention relates to compounds of formula (I), in which $R^8$ represents a benzyl group, which phenyl group is optionally substituted with one or two substituents, identically or differently, selected from the group of a fluoro or a chloro atom.

In another embodiment the invention relates to compounds of formula (I), in which $R^8$ represents a benzyl group, which phenyl group is optionally substituted with one or two fluoro atom.

In another embodiment the invention relates to compounds of formula (I), in which $R^8$ represents a benzyl, a 4-fluorobenzyl, a 4-chlorobenzyl, a 3-fluorobenzyl or a 3-chlorobenzyl group.

In another embodiment the invention relates to compounds of formula (I), in which $R^8$ represents a group selected from $C_1$-$C_3$-alkyl or benzyl.

In another embodiment the invention relates to compounds of formula (I), in which $R^8$ represents a group selected from methyl or benzyl.

In a preferred embodiment the invention relates to compounds of formula (I), in which $R^8$ represents a benzyl group.

In another embodiment the invention relates to compounds of formula (I), in which $R^8$ represents a phenyl-cyclopropyl- group, which phenyl group is optionally substituted with one or two or three substituents, identically or differently, selected from the group of halogen, hydroxy, NH$_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^8$ represents a phenyl-cyclopropyl- group, which phenyl group is optionally substituted with one or two or three substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^8$ represents a phenyl-cyclopropyl- group, which phenyl group is optionally substituted with one or two or three substituents, identically or differently, selected from the group of a fluoro atom, a methyl group.

In another embodiment the invention relates to compounds of formula (I), in which $R^8$ represents a heteroaryl-$C_1$-$C_2$-alkyl- group, which heteroaryl group is optionally substituted with one or two or three substituents, identically or differently, selected from the group of halogen, hydroxy, NH$_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^8$ represents a heteroaryl-$C_1$-$C_2$-alkyl-, which heteroaryl group is optionally substituted with one or two or three substituents, identically or differently, selected from the group of halogen, hydroxy, $NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In a preferred embodiment the invention relates to compounds of formula (I), in which $R^8$ represents a heteroaryl-$C_1$-$C_3$-alkyl- group, which heteroaryl group is optionally substituted with one or two substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^8$ represents a pyridyl-$C_1$-$C_2$-alkyl-group, which pyridyl group is optionally substituted with one or two or three substituents, identically or differently, selected from the group of halogen, hydroxy, $NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I), in which $R^8$ represents a pyridyl-methyl-group, which pyridyl group is optionally substituted with one or two or three substituents, identically or differently, selected from the group of halogen, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I), in which $R^8$ represents a heteroaryl-cyclopropyl- group, which heteroaryl group is optionally substituted with one or two or three substituents, identically or differently, selected from the group of halogen, hydroxy, $NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^8$ represents a heteroaryl-cyclopropyl- group, which heteroaryl group is optionally substituted with one or two or three substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^8$ represents a pyridyl-cyclopropyl-group, which pyridyl group is optionally substituted with one or two or three substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^9$ represents a group selected from $C_1$-$C_6$-alkyl-, $C_3$-$C_7$-cycloalkyl heterocyclyl-, phenyl, benzyl or heteroaryl,
  wherein said group is optionally substituted with one, two or three substituents, identically or differently, selected from halogen, hydroxy, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^9$ represents a group selected from $C_1$-$C_5$-alkyl-, $C_3$-$C_6$-cycloalkyl-, heterocyclyl-, phenyl, benzyl or heteroaryl
  wherein said group is optionally substituted with one, two or three substituents, identically or differently, selected from halogen, hydroxy, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^9$ represents a group selected from $C_1$-$C_6$-alkyl-.

In another embodiment the invention relates to compounds of formula (I), in which $R^9$ represents a group selected from $C_1$-$C_3$-alkyl- which is optionally substituted with $C_1$-$C_3$-alkoxy.

In another embodiment the invention relates to compounds of formula (I), in which $R^{10}$ and $R^{11}$ represent, independently from each other, a group selected from hydrogen, $C_1$-$C_5$-alkyl-, $C_3$-$C_6$-cycloalkyl-, heterocyclyl-, phenyl or heteroaryl wherein said $C_1$-$C_6$-alkyl, $C_3$-$C_7$-cycloalkyl heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^{10}$ and $R^{11}$ represent, independently from each other, hydrogen or a $C_1$-$C_6$-alkyl-.

In another embodiment the invention relates to compounds of formula (I), in which $R^{10}$ represents a group selected from hydrogen, $C_1$-$C_6$-alkyl-, $C_3$-$C_7$-cycloalkyl-, heterocyclyl-, phenyl or heteroaryl
  wherein said $C_1$-$C_6$-alkyl, $C_3$-$C_7$-cycloalkyl-, heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^{10}$ represents a group selected from hydrogen, $C_1$-$C_6$-alkyl-.

In another embodiment the invention relates to compounds of formula (I), in which $R^{10}$ represents hydrogen.

In another embodiment the invention relates to compounds of formula (I), in which $R^{11}$ represents a group selected from hydrogen, $C_1$-$C_6$-alkyl-, $C_3$-$C_7$-cycloalkyl-, heterocyclyl-, phenyl or heteroaryl
  wherein said $C_1$-$C_6$-alkyl, $C_3$-$C_7$-cycloalkyl-, heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^{11}$ represents a group selected from hydrogen, $C_1$-$C_6$-alkyl-.

In another embodiment the invention relates to compounds of formula (I), in which $R^{11}$ represents methyl.

In a preferred embodiment the invention relates to compounds of formula (I), in which $R^{10}$ represents hydrogen and in which $R^{11}$ represents methyl.

It is to be understood that the present invention relates to any sub-combination within any embodiment of the present invention of compounds of formula (I), supra.

More particularly still, the present invention covers compounds of formula (I) which are disclosed in the Example section of this text, infra.

Very specially preferred are combinations of two or more of the abovementioned preferred embodiments.

In particular, preferred subjects of the present invention are the compounds selected from:

(rac)-Ethyl[(3-{[5-fluoro-4-(4-fluoro-2-methoxyphenyl)pyrimidin-2-yl]amino}benzyl)(methyl)oxido-$\lambda^6$-sulfanylidene]carbamate (rac)-5-Fluoro-4-(4-fluoro-2-methoxyphenyl)-N-{3-[(S-methylsulfonimidoyl)methyl]phenyl}pyrimidin-2-amine (rac)-Ethyl{[3-({4-[2-(benzyloxy)-4-fluorophenyl]-5-fluoropyrimidin-2-yl}amino)benzyl](methyl)-oxido-$\lambda^6$-sulfanylidene}carbamate (rac)-4-[2-(Benzyloxy)-4-fluorophenyl]-5-fluoro-N-{3-[(S-methylsulfonimidoyl)methyl]phenyl}-pyrimidin-2-amine (rac)-Ethyl[(3-{[4-(3,4-dihydro-2H-chromen-8-yl)-5-fluoropyrimidin-2-yl]amino}benzyl)(methyl)oxido-$\lambda^6$-sulfanylidene]carbamate (rac)-4-(3,4-dihydro-2H-chromen-8-yl)-5-fluoro-N-{3-[(S-methylsulfonimidoyl)methyl]phenyl}-pyrimidin-2-amine (rac)-{[3-({4-[2-(Benzyloxy)-4-fluorophenyl]-5-fluoropyrimidin-2-yl}amino)benzyl](methyl)oxido-$\lambda^6$-sulfanylidene}cyanamide (rac)-1-[(3-{[5-Fluoro-4-(4-fluoro-2-methoxyphenyl)pyrimidin-2-yl]amino}benzyl)(methyl)oxido-$\lambda^6$-sulfanylidene]-3-methylurea (rac)-Ethyl[(3-fluoro-5-{[5-fluoro-4-(4-fluoro-2-methoxyphenyl)pyrimidin-2-yl]amino}benzyl)-(methyl)oxido-$\lambda^6$-sulfanylidene]carbamate (rac)-5-Fluoro-4-(4-fluoro-2-methoxyphenyl)-N-{3-fluoro-5-[(S-methylsulfonimidoyl)methyl]phenyl}-pyrimidin-2-amine 5-Fluoro-4-(4-fluoro-2-methoxyphenyl)-N-{3-[(S-methylsulfonimidoyl)methyl]phenyl}pyrimidin-2-amine; enantiomer 1

5-Fluoro-4-(4-fluoro-2-methoxyphenyl)-N-{3-[(S-methylsulfonimidoyl)methyl]phenyl}pyrimidin-2-amine; enantiomer 2

4-[2-(Benzyloxy)-4-fluorophenyl]-5-fluoro-N-{3-[(S-methylsulfonimidoyl)methyl]phenyl}pyrimidin-2-amine; enantiomer 1

4-[2-(Benzyloxy)-4-fluorophenyl]-5-fluoro-N-{3-[(S-methylsulfonimidoyl)methyl]phenyl}pyrimidin-2-amine; enantiomer 2

5-Fluoro-4-(4-fluoro-2-methoxyphenyl)-N-{3-fluoro-5-[(S-methylsulfonimidoyl)methyl]phenyl}-pyrimidin-2-amine; enantiomer 1

5-Fluoro-4-(4-fluoro-2-methoxyphenyl)-N-{3-fluoro-5-[(S-methylsulfonimidoyl)methyl]phenyl}-pyrimidin-2-amine; enantiomer 2

(rac)-[(3-{[5-Fluoro-4-(4-fluoro-2-methoxyphenyl)pyrimidin-2-yl]amino}benzyl)(methyl)oxido-$\lambda^6$-sulfanylidene]cyanamide

[(3-{[5-Fluoro-4-(4-fluoro-2-methoxyphenyl)pyrimidin-2-yl]amino}benzyl)(methyl)oxido-$\lambda^6$-sulfanylidene]cyanamide; enantiomer 1

[(3-{[5-Fluoro-4-(4-fluoro-2-methoxyphenyl)pyrimidin-2-yl]amino}benzyl)(methyl)oxido-$\lambda^6$-sulfanylidene]cyanamide; enantiomer 2

(rac)-[Ethyl(3-{[5-fluoro-4-(4-fluoro-2-methoxyphenyl)pyrimidin-2-yl]amino}benzyl)oxido-$\lambda^6$-sulfanylidene]cyanamide rac)-N-{3-[(S-Ethylsulfonimidoyl)methyl]phenyl}-5-fluoro-4-(4-fluoro-2-methoxyphenyl)pyrimidin-2-amine N-{3-[(S-Ethylsulfonimidoyl)methyl]phenyl}-5-fluoro-4-(4-fluoro-2-methoxyphenyl)pyrimidin-2-amine; enantiomer 1

N-{3-[(S-Ethylsulfonimidoyl)methyl]phenyl}-5-fluoro-4-(4-fluoro-2-methoxyphenyl)pyrimidin-2-amine; enantiomer 2

(rac)-[(2,3-Difluoro-5-{[5-fluoro-4-(4-fluoro-2-methoxyphenyl)pyrimidin-2-yl]amino}benzyl)-(methyl)oxido-$\lambda^6$-sulfanylidene]cyanamide (rac)-N-{3,4-Difluoro-5-[(S-methylsulfonimidoyl)methyl]phenyl}-5-fluoro-4-(4-fluoro-2-methoxy-phenyl)pyrimidin-2-amine N-{3,4-Difluoro-5-[(S-methylsulfonimidoyl)methyl]phenyl}-5-fluoro-4-(4-fluoro-2-methoxyphenyl)-pyrimidin-2-amine; enantiomer 1

N-{3,4-Difluoro-5-[(S-methylsulfonimidoyl)methyl]phenyl}-5-fluoro-4-(4-fluoro-2-methoxyphenyl)-pyrimidin-2-amine; enantiomer 2

(rac)-[(3-Bromo-5-{[5-fluoro-4-(4-fluoro-2-methoxyphenyl)pyrimidin-2-yl]amino}benzyl)(methyl)-oxido-$\lambda^6$-sulfanylidene]cyanamide (rac)-N-{3-Bromo-5-[(S-methylsulfonimidoyl)methyl]phenyl}-5-fluoro-4-(4-fluoro-2-methoxy-phenyl)pyrimidin-2-amine N-{3-Bromo-5-[(S-methylsulfonimidoyl)methyl]phenyl}-5-fluoro-4-(4-fluoro-2-methoxyphenyl)-pyrimidin-2-amine; enantiomer 1

N-{3-Bromo-5-[(S-methylsulfonimidoyl)methyl]phenyl}-5-fluoro-4-(4-fluoro-2-methoxyphenyl)-pyrimidin-2-amine; enantiomer 2

(rac)-[(3-{[5-Fluoro-4-(4-fluoro-2-methoxyphenyl)pyrimidin-2-yl]amino}-5-methoxybenzyl)(methyl)-oxido-$\lambda^6$-sulfanylidene]cyanamide (rac)-5-Fluoro-4-(4-fluoro-2-methoxyphenyl)-N-{3-methoxy-5-[(S-methylsulfonimidoyl)methyl]-phenyl}pyrimidin-2-amine 5-Fluoro-4-(4-fluoro-2-methoxyphenyl)-N-{3-methoxy-5-[(S-methylsulfonimidoyl)methyl]phenyl}-pyrimidin-2-amine; enantiomer 1

5-Fluoro-4-(4-fluoro-2-methoxyphenyl)-N-{3-methoxy-5-[(S-methylsulfonimidoyl)methyl]phenyl}-pyrimidin-2-amine; enantiomer 2

(rac)-[(3-{[4-(2-Ethoxy-4-fluorophenyl)-5-fluoropyrimidin-2-yl]amino}-5-fluorobenzyl)(methyl)oxido-$\lambda^6$-sulfanylidene]cyanamide (rac)-4-(2-Ethoxy-4-fluorophenyl)-5-fluoro-N-{3-fluoro-5-[(S-methylsulfonimidoyl)methyl]phenyl}-pyrimidin-2-amine 4-(2-Ethoxy-4-fluorophenyl)-5-fluoro-N-{3-fluoro-5-[(S-methylsulfonimidoyl)methyl]phenyl}-pyrimidin-2-amine; enantiomer 1

4-(2-Ethoxy-4-fluorophenyl)-5-fluoro-N-{3-fluoro-5-[(S-methylsulfonimidoyl)methyl]phenyl}-pyrimidin-2-amine; enantiomer 2

(rac)-{[3-{[5-Fluoro-4-(4-fluoro-2-methoxyphenyl)pyrimidin-2-yl]amino}-5-(trifluoromethyl)-benzyl](methyl)oxido-$\lambda^6$-sulfanylidene}cyanamide (rac)-5-Fluoro-4-(4-fluoro-2-methoxyphenyl)-N-{3-[(S-methylsulfonimidoyl)methyl]-5-(trifluoro-methyl)phenyl}pyrimidin-2-amine (rac)-[Ethyl(3-fluoro-5-{[5-fluoro-4-(4-fluoro-2-methoxyphenyl)pyrimidin-2-yl]amino}benzyl)oxido-$\lambda^6$-sulfanylidene]cyanamide (rac)-N-{3-[(S-Ethylsulfonimidoyl)methyl]-5-fluorophenyl}-5-fluoro-4-(4-fluoro-2-methoxyphenyl)-pyrimidin-2-amine N-{3-[(S-Ethylsulfonimidoyl)methyl]-5-fluorophenyl}-5-fluoro-4-(4-fluoro-2-methoxyphenyl)-pyrimidin-2-amine; enantiomer 1

N-{3-[(S-Ethylsulfonimidoyl)methyl]-5-fluorophenyl}-5-fluoro-4-(4-fluoro-2-methoxyphenyl)-pyrimidin-2-amine; enantiomer 2

(rac)-{[3-{[5-Fluoro-4-(4-fluoro-2-methoxyphenyl)pyrimidin-2-yl]amino}-5-(pentafluoroethyl)-benzyl](methyl)oxido-λ⁶-sulfanylidene}cyanamide
(rac)-5-Fluoro-4-(4-fluoro-2-methoxyphenyl)-N-{3-[(S-methylsulfonimidoyl)methyl]-5-(pentafluoro-ethyl)phenyl}pyrimidin-2-amine
(rac)-[Cyclopropyl(3-{[5-fluoro-4-(4-fluoro-2-methoxyphenyl)pyrimidin-2-yl]amino}benzyl)oxido-λ⁶-sulfanylidene]cyanamide
(rac)-N-{3-[(S-Cyclopropylsulfonimidoyl)methyl]phenyl}-5-fluoro-4-(4-fluoro-2-methoxyphenyl)-pyrimidin-2-amine
(rac)-[Cyclopropyl(3-fluoro-5-{[5-fluoro-4-(4-fluoro-2-methoxyphenyl)pyrimidin-2-yl]amino}-benzyl)oxido-λ⁶-sulfanylidene]cyanamide
(rac)-N-{3-[(S-Cyclopropylsulfonimidoyl)methyl]-5-fluorophenyl}-5-fluoro-4-(4-fluoro-2-methoxy-phenyl)pyrimidin-2-amine
N-{3-[(S-Cyclopropylsulfonimidoyl)methyl]-5-fluorophenyl}-5-fluoro-4-(4-fluoro-2-methoxy-phenyl)pyrimidin-2-amine; enantiomer 1
N-{3-[(S-Cyclopropylsulfonimidoyl)methyl]-5-fluorophenyl}-5-fluoro-4-(4-fluoro-2-methoxy-phenyl)pyrimidin-2-amine; enantiomer 2
(rac)-Ethyl[(3-{[4-(2,3-dihydro-1-benzofuran-7-yl)-5-fluoropyrimidin-2-yl]amino}benzyl)(methyl)-oxido-λ⁶-sulfanylidene]carbamate
(rac)-5-Fluoro-4-{4-fluoro-2-[(4-fluorobenzyl)oxy]phenyl}-N-{3-[(S-methylsulfonimidoyl)methyl]-phenyl}pyrimidin-2-amine
(rac)-[(3-Chloro-5-{[5-fluoro-4-(4-fluoro-2-methoxyphenyl)pyrimidin-2-yl]amino}benzyl)(methyl)-oxido-λ⁶-sulfanylidene]cyanamide
(rac)-N-{3-Chloro-5-[(S-methylsulfonimidoyl)methyl]phenyl}-5-fluoro-4-(4-fluoro-2-methoxy-phenyl)pyrimidin-2-amine
(rac)-[(3-{[5-Fluoro-4-(4-fluoro-2-methoxyphenyl)pyrimidin-2-yl]amino}-5-methylbenzyl)(methyl)-oxido-λ⁶-sulfanylidene]cyanamide
(rac)-5-Fluoro-4-(4-fluoro-2-methoxyphenyl)-N-{3-methyl-5-[(S-methylsulfonimidoyl)methyl]-phenyl}pyrimidin-2-amine
(rac)-{[3-{[5-Fluoro-4-(4-fluoro-2-methoxyphenyl)pyrimidin-2-yl]amino}-5-(pentafluoro-λ⁶-sulfanyl)benzyl](methyl)oxido-λ⁶-sulfanylidene}cyanamide
(rac)-5-Fluoro-4-(4-fluoro-2-methoxyphenyl)-N-{3-[(S-methylsulfonimidoyl)methyl]-5-(pentafluoro-λ⁶-sulfanyl)phenyl}pyrimidin-2-amine
5-Fluoro-4-(4-fluoro-2-methoxyphenyl)-N-{3-[(S-methylsulfonimidoyl)methyl]-5-(pentafluoro-λ⁶-sulfanyl)phenyl}pyrimidin-2-amine; enantiomer 1
5-Fluoro-4-(4-fluoro-2-methoxyphenyl)-N-{3-[(S-methylsulfonimidoyl)methyl]-5-(pentafluoro-λ⁶-sulfanyl)phenyl}pyrimidin-2-amine; enantiomer 2
2-Methoxyethyl[(3-fluoro-5-{[5-fluoro-4-(4-fluoro-2-methoxyphenyl)pyrimidin-2-yl]amino}benzyl)-(methyl)oxido-λ⁶-sulfanylidene]carbamate; single enantiomer or their enantiomers, diastereomers, salts, solvates or salts of solvates.

The above mentioned definitions of radicals which have been detailed in general terms or in preferred ranges also apply to the end products of the formula (I) and, analogously, to the starting materials or intermediates required in each case for the preparation.

The invention furthermore relates to a process for the preparation of the compounds of formula (I) according to the invention, in which N-unprotected sulfoximines of formula (6) are reacted to give N-functionalized sulfoximines of formula (I).

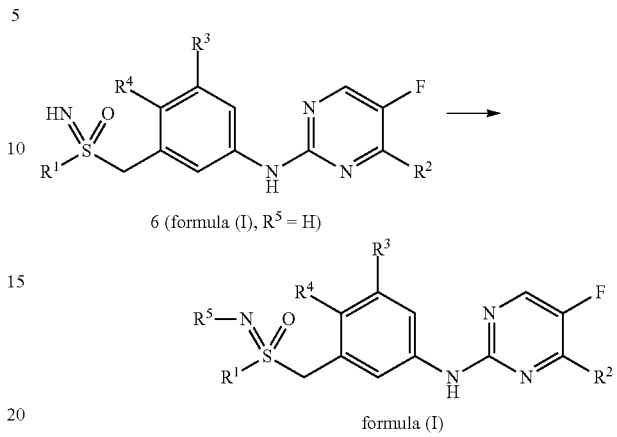

6 (formula (I), R⁵ = H)

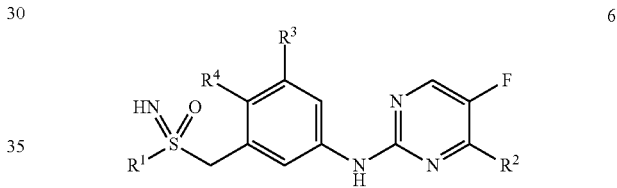

formula (I)

The present invention therefore relates to a method for the preparation of the compounds of formula (I), in which R⁵ is not a hydrogen atom, according to the invention, in which method the nitrogen of the sulfoximine group of a compound of formula (6)

6 in which $R^1$, $R^2$, $R^3$, $R^4$, $R^6$, $R^7$, $R^8$, $R^9$, $R^{10}$ and $R^{11}$ are as defined for the compound of general formula (I) according to the invention, is functionalized according to methods known in the art, thus providing a compound of general formula (I) according to the invention, in which $R^5$ is not hydrogen, and the resulting compounds are optionally, if appropriate, converted with the corresponding (i) solvents and/or (ii) bases or acids to the solvates, salts and/or solvates of the salts thereof.

There are multiple methods for the preparation of N-functionalized sulfoximines by functionalization of the nitrogen of the sulfoximine group:

Alkylation: see for example: a) U. Lücking et al, US 2007/0232632; b) C. R. Johnson, J. Org. Chem. 1993, 58, 1922; c) C. Bolm et al, Synthesis 2009, 10, 1601.

Acylation: see for example: a) C. Bolm et al, Chem. Europ. J. 2004, 10, 2942; b) C. Bolm et al, Synthesis 2002, 7, 879; c) C. Bolm et al, Chem. Europ. J. 2001, 7, 1118.

Arylation: see for example: a) C. Bolm et al, Tet. Lett. 1998, 39, 5731; b) C. Bolm et al., J. Org. Chem. 2000, 65, 169; c) C. Bolm et al, Synthesis 2000, 7, 911; d) C. Bolm et al, J. Org. Chem. 2005, 70, 2346; e) U. Lücking et al, WO2007/71455.

Reaction with isocyanates: see for example: a) V. J. Bauer et al, J. Org. Chem. 1966, 31, 3440; b) C. R. Johnson et al, J. Am. Chem. Soc. 1970, 92, 6594; c) S. Allenmark et al, Acta Chem. Scand. Ser. B 1983, 325; d) U. Lücking et al, US2007/0191393.

Reaction with sulfonylchlorides: see for example: a) D. J. Cram et al, J. Am. Chem. Soc. 1970, 92, 7369; b) C. R. Johnson et al, J. Org. Chem. 1978, 43, 4136; c) A. C. Barnes, J. Med. Chem. 1979, 22, 418; d) D. Craig et al, Tet. 1995, 51, 6071; e) U. Lücking et al, US2007/191393.

Reaction with chloroformiates: see for example: a) P. B. Kirby et al, DE2129678; b) D. J. Cram et al, J. Am. Chem. Soc. 1974, 96, 2183; c) P. Stoss et al, Chem. Ber. 1978, 111, 1453; d) U. Lücking et al, WO2005/37800.

N-unprotected sulfoximines of formula (6) can be prepared by deprotection of N-protected sulfoximines of formula (5). Preferred is the use of sodium ethanolate in ethanol at 60° C. (see for example: U. Lücking et al, WO2005/37800).

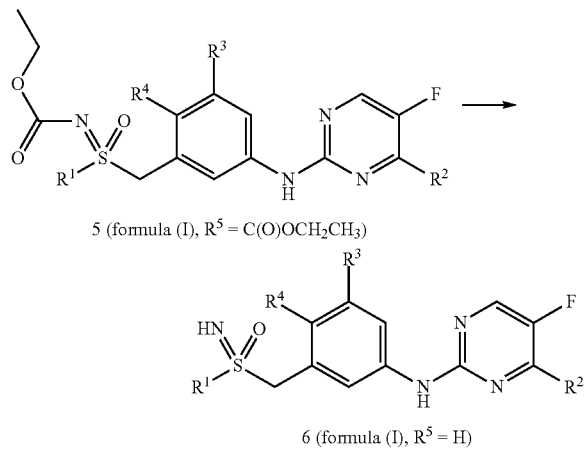

The invention therefore furthermore relates to a method for the preparation of the compounds of formula (I) according to the present invention, in which $R^5$ is a hydrogen atom (identical to the N-unprotected sulfoximines of formula (6) shown above), according to the invention, in which method the —C(O)O-ethyl group of an N-protected compound of formula (5)

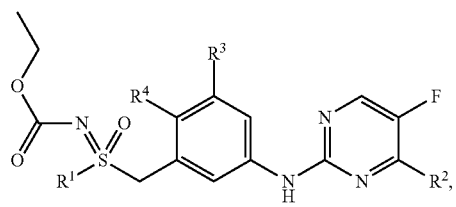

in which $R^1$, $R^2$, $R^3$, $R^4$, $R^6$, $R^7$, $R^8$, $R^9$, $R^{10}$ and $R^{11}$ are as defined for the compound of general formula (I) according to the present invention, is deprotected according to methods known in the art, thus providing a compound of general formula (I) according to the invention, in which $R^5$ is a hydrogen atom, and the resulting compounds (the N-unprotected sulfoximines of formula (6) shown above) are optionally, if appropriate, reacted with the corresponding (i) solvents and/or (ii) bases or acids to the solvates, salts and/or solvates of the salts thereof.

The present invention further concerns compounds of general formula (5)

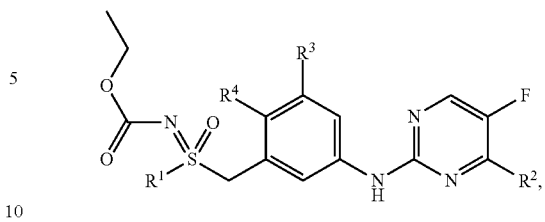

in which $R^1$, $R^2$, $R^3$, $R^4$, $R^6$, $R^7$, $R^8$, $R^9$, $R^{10}$ and $R^{11}$ are as defined for the compounds of the present invention according to general formula (I).

The present invention further relates to compounds of general formula (6)

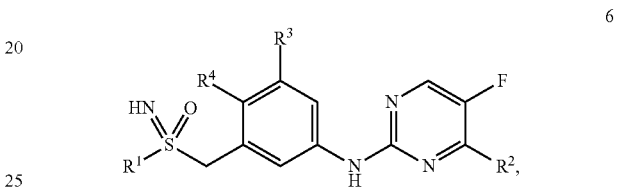

in which $R^1$, $R^2$, $R^3$, $R^4$, $R^6$, $R^7$, $R^8$, $R^9$, $R^{10}$ and $R^{11}$ are as defined for the compounds of the present invention according to general formula (I).

The invention furthermore relates to a method for the preparation of the compounds of general formula (I) according to the present invention, in which $R^5$ is —C(O)O-Ethyl (identical to the N-protected sulfoximines of formula (5) shown above), in which method a compound of formula (3),

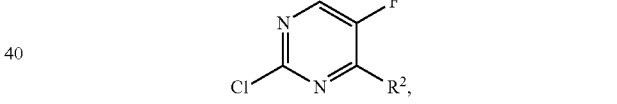

in which $R^2$ is as defined for the compound of general formula (I) according to the invention, is reacted with a compound of formula (4)

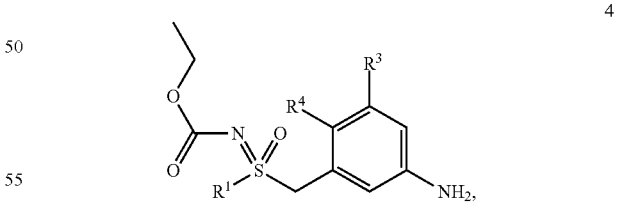

in which $R^1$, $R^3$ and $R^4$ are as defined for the compound of general formula (I) according to the invention, thus providing a compound of general formula (I) according to the invention, in which $R^5$ is —C(O)O-Ethyl, and the resulting compounds (see N-protected sulfoximines of formula (5) shown above) are optionally, if appropriate, converted with the corresponding (i) solvents and/or (ii) bases or acids to the solvates, salts and/or solvates of the salts thereof.

The cross-coupling reaction of a compound of formula (3) with a compound of formula (4) can be achieved by a Palladium-catalyzed C—N cross-coupling reaction (for a review on C—N cross-coupling reactions see for example: a) L. Jiang, S. L. Buchwald in 'Metal-Catalyzed Cross-Coupling Reactions', 2$^{nd}$ ed.: A. de Meijere, F. Diederich, Eds.: Wiley-VCH: Weinheim, Germany, 2004).

Preferred is the use of suitable palladium precatalysts based upon biarylmonphosphines that are easily activated and ensure the formation of the active mono-ligated Pd(0) complex (see for examples a) S. L. Buchwald et al, J. Am. Chem. Soc. 2008, 130, 6686; b) S. L. Buchwald et al, J. Am. Chem. Soc. 2008, 130, 13552). The reactions are run in the presence of a weak base at elevated temperatures (see for example: a) S. L: Buchwald et al, Tet. Lett. 2009, 50, 3672). Most preferred is the herein described use of chloro(2-dicyclohexylphosphino-2',4',6'-tri-iso-propyl-1,1'-biphenyl) [2-(2-aminoethyl)phenyl]palladium(II) methyl-tert-butylether adduct, 2-dicyclohexylphosphino-2',4',6'-triisopropylbiphenyl and potassium phosphate in toluene and 1-methylpyrrolidin-2-one. The reactions are preferably run under argon for 3 hours at 130° C. in a microwave oven. Most preferred is also the herein described use of chloro(2-dicyclohexylphosphino-2', 4',6'-tri-iso-propyl-1,1'-biphenyl)[2-(2-aminoethyl)phenyl]palladium(II) methyl-tert-butylether adduct, 2-dicyclohexylphosphino-2',4',6'-triisopropylbiphenyl and potassium phosphate in toluene and 1-methylpyrrolidin-2-one. The reactions are preferably run under argon for 3 hours at 130° C. in a microwave oven or in an oil bath.

Anilines of formula (4) can be prepared by the following processes: Reaction of suitable benzylchlorides or -bromides of formula (7) with suitable thiols of formula (8) under basic conditions yields the corresponding thioethers of formula (9) (see for example: Sammond et al, Bioorg. Med. Chem. Lett. 2005, 15, 3519).

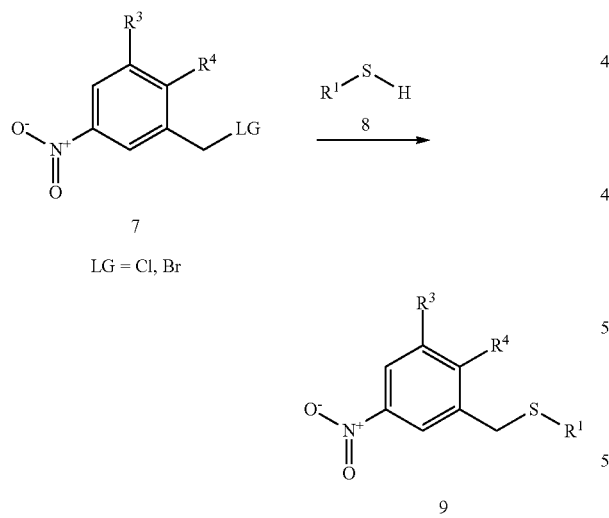

Oxidation of thioethers of formula (9) gives the corresponding sulfoxides of formula (10). The oxidation can be performed analogously to known processes (see for example: (a) M. H. Ali et al, Synthesis 1997, 764; (b) M. C. Carreno, Chem. Rev. 1995, 95, 1717; (c) I. Patel et al, Org. Proc. Res. Dev. 2002, 6, 225; (d) N. Khiar et al, Chem. Rev. 2003, 103, 3651). Preferred is the herein described use of periodic acid and iron(III)chloride.

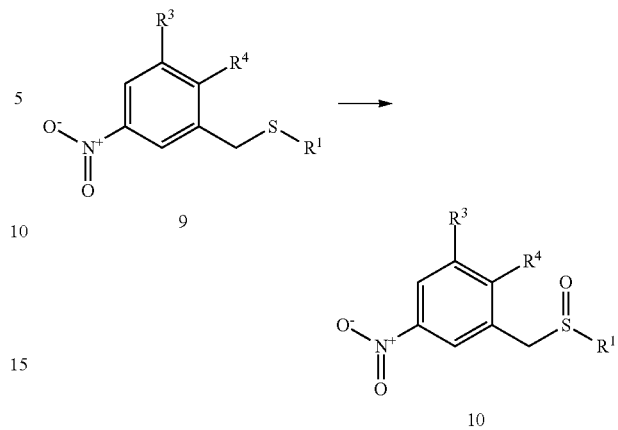

Rhodium-catalyzed imination of the sulfoxides of formula (10) followed by deprotection gives the corresponding N-unprotected sulfoximines of formula (11) (see for example: Bolm et al, Org. Lett. 2004, 6, 1305).

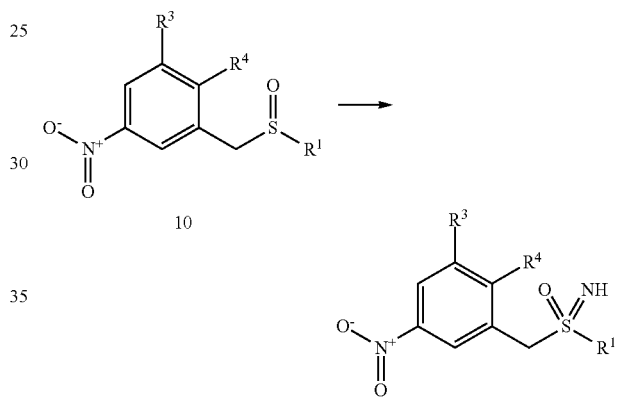

Introduction of a suitable protecting group leads to N-protected sulfoximines of formula (12) (see for example: Lücking et al. WO 2005/0378001.

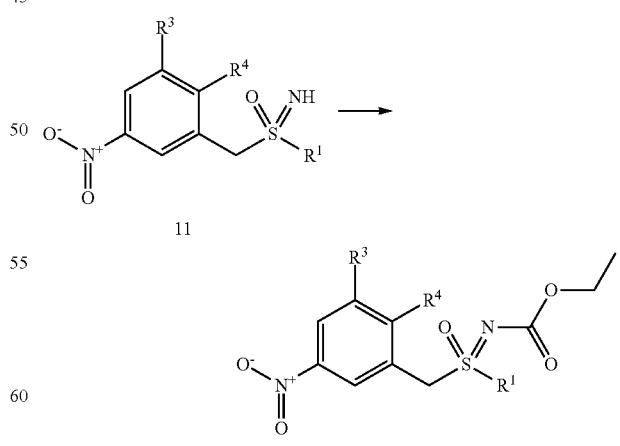

Reduction of the nitro group finally gives the desired anilines of formula (4). The reduction can be prepared analogously to known processes (see for example: (a) Sammond et al; Bioorg. Med. Chem. Lett. 2005, 15, 3519; (b) R. C. Larock, Comprehensive Organic Transformations, VCH, New York, 1989, 411-415).

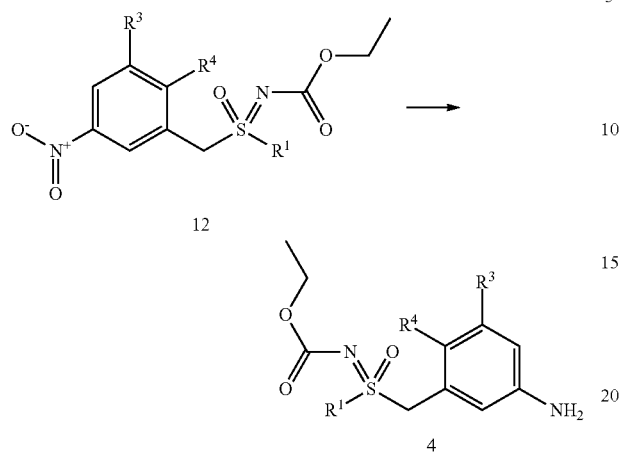

Compounds of formula (3) can be prepared by Palladium-catalysed coupling reactions of 2,4-dichloro-5-fluoro-pyrimidine (1) and compounds of formula (2) (scheme 1).

Compounds of general formula (2) can be prepared analogously to known processes (review: D. G. Hall, Boronic Acids, 2005 WILEY-VCH Verlag GmbH & Co. KGaA, Weinheim, ISBN 3-527-30991-8 and references cited herein). Further, a wide variety of compounds of general formula (2) are commercially available.

The coupling reaction of 2,4-dichloro-5-fluoro-pyrimidine with compounds of formula (2) is catalyzed by Pd catalysts, e.g. by Pd(0) catalysts or by Pd(II) catalysts. Examples for Pd(0) catalysts are tetrakis(triphenylphosphine)palladium(0) [Pd(PPh$_3$)$_4$] or tris(dibenzylideneacetone)di-palladium(0) [Pd$_2$(dba)$_3$], examples for Pd(II) catalysts dichlorobis(triphenylphosphine)-palladium(II) [Pd(PPh$_3$)$_2$Cl$_2$], palladium(II) acetate and triphenylphosphine or [1,1'-bis(diphenylphosphino)ferrocene]palladium dichloride [Pd(dppf)Cl$_2$] (review: D. G. Hall, Boronic Acids, 2005 WILEY-VCH Verlag GmbH & Co. KGaA, Weinheim, ISBN 3-527-30991-8 and references cited therein).

This reaction is preferably carried out in aprotic or protic solvents, preferably in a mixture of aprotic and protic solvents, more preferably in solvents like, for example, 1,2-dimethoxyethane, dioxane, dimethlyformamid, tetrahydrofuran, or isopropanol with water (review: D. G. Hall, Boronic Acids, 2005 WILEY-VCH Verlag GmbH & Co. KGaA, Weinheim, ISBN 3-527-30991-8 and references cited therein).

Preferably the reaction is carried out in the presence of a suitable base, such as for example aqueous potassium carbonate, aqueous sodium bicarbonate or aqueous potassium phosphate (review: D. G. Hall, Boronic Acids, 2005 WILEY-VCH Verlag GmbH & Co. KGaA, Weinheim, ISBN 3-527-30991-8 and references cited therein).

The reaction is performed at temperatures ranging from room temperature (=20° C.) to the boiling point of the solvent. Further on, the reaction can be performed at temperatures above the boiling point using pressure tubes and a microwave oven. (review: D. G. Hall, Boronic Acids, 2005 WILEY-VCH Verlag GmbH & Co. KGaA, Weinheim, ISBN 3-527-30991-8 and references cited therein).

The reaction is preferably completed after 1 to 36 hours of reaction time.

The invention furthermore relates to a method for the preparation of the compounds of formula (I) according to the present invention, in which $R^5$ is a cyano group (identical to the N-cyanosulfoximines of formula (16)),

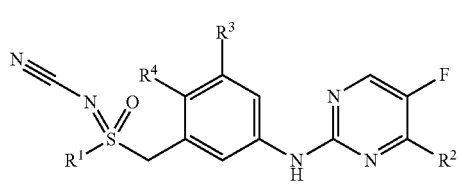

in which method a compound of formula (15)

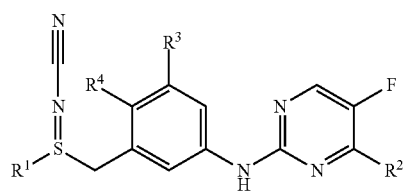

in which $R^1$, $R^2$, $R^3$, $R^4$, $R^6$, $R^7$, $R^8$, $R^9$, $R^{10}$ and $R^{11}$ are as defined for the compound of formula (I) according to the present invention, is oxidized according to methods known in the art, thus providing a compound of general formula (I) according to the invention, in which $R^5$ is a cyano group, and the resulting compounds (the N-cyanosulfoximines of formula (16) as shown above) are optionally, if appropriate, reacted with the corresponding (i) solvents and/or (ii) bases or acids to the solvates, salts and/or solvates of the salts thereof.

There are multiple methods for the oxidation of N-cyanosulfilimines of formula (15) to N-cyanosulfoximines of formula (16):

a) C. Bolm et al, Org. Lett. 2007, 9, 3809 b) J. E. G. Kemp et al, Tet. Lett. 1979, 39, 3785 c) M. R. Loso et al, US patent publication US2007/0203191 d) J. M. Babcock, US patent publication US2009/0023782.

The present invention relates to compounds of general formula (16)

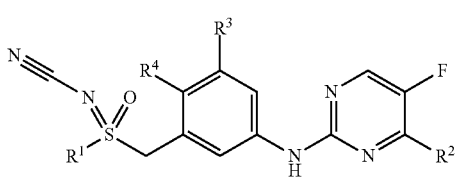

in which $R^1$, $R^2$, $R^3$, $R^4$, $R^6$, $R^7$, $R^8$, $R^9$, $R^{10}$ and $R^{11}$ are as defined for the compounds of the present invention according to general formula (I).

The invention furthermore relates to a method for the preparation of the compounds of formula (15) according to the present invention,

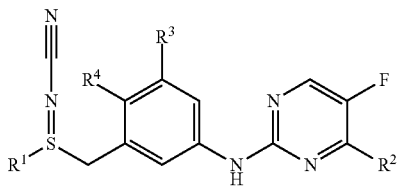

in which method a compound of formula (14)

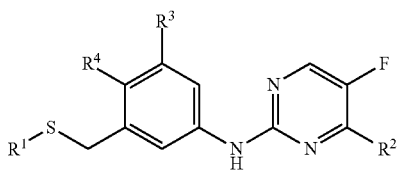

in which $R^1$, $R^2$, $R^3$, $R^4$, $R^6$, $R^7$, $R^8$, $R^9$, $R^{10}$ and $R^{11}$ are as defined for the compound of formula (I) according to the present invention, is subject to imination of the sulfide according to methods known in the art, thus providing a compound of formula (15) and the resulting compounds are optionally, if appropriate, reacted with the corresponding (i) solvents and/or (ii) bases or acids to the solvates, salts and/or solvates of the salts thereof.

There are multiple methods for the imination of sulfides of formula (14) to compounds of formula (15):
a) C. Bolm et al, Org. Lett. 2007, 9, 3809,
b) C. Bolm et al, Bioorg. Med. Chem. Lett. 2011, 21, 4888.
c) J. M. Babcock, US patent publication US2009/0023782.

The preparation of compounds of general formula (14) is described below in context of the description of synthesis Scheme 2.

In another embodiment the present invention concerns compounds of general formula (4)

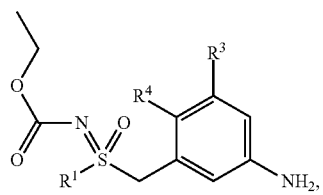

wherein $R^1$, $R^3$ and $R^4$ are as defined for the compound of general formula (I) according to the invention.

In another embodiment the present invention concerns compounds of general formula (11)

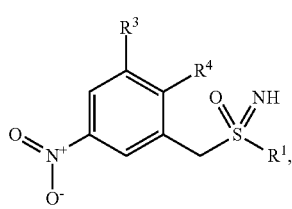

wherein $R^1$, $R^3$ and $R^4$ are as defined for the compound of general formula (I) according to the invention.

In another embodiment the present invention concerns compounds of general formula (12)

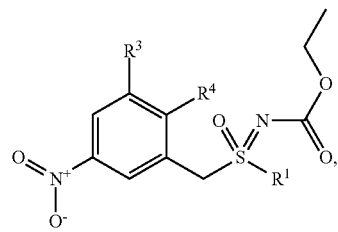

wherein $R^1$, $R^3$ and $R^4$ are as defined for the compound of general formula (I) according to the invention.

The compounds according to the invention show a valuable pharmacological and pharmacokinetic spectrum of action which could not have been predicted.

They are therefore suitable for use as medicaments for the treatment and/or prophylaxis of disorders in humans and animals.

Within the scope of the present invention, the term "treatment" includes prophylaxis.

The pharmaceutical activity of the compounds according to the invention can be explained by their action as inhibitors of CDK9. Thus, the compounds according to the general formula (I) as well as pharmaceutically acceptable salts thereof are used as inhibitors for CDK9.

Furthermore, the compounds according to the invention show a particularly high potency (demonstrated by a low $IC_{50}$ value in the CDK9/CycT1 assay) for inhibiting CDK9 activity.

In context of the present invention, the $IC_{50}$ value with respect to CDK9 can be determined by the methods described in the method section below. Preferably, it is determined according to Method 1a. ("CDK9/CycT1 kinase assay") described in the Materials and Method section below.

Surprisingly it turned out that the compounds according to the general formula (I) as well as pharmaceutically acceptable salts thereof selectively inhibit CDK9 in comparison to other cyclin-dependent protein kinases, preferably in comparison to CDK2. Thus, the compounds according to the general formula (I) as well as pharmaceutically acceptable salts thereof are preferably used as selective inhibitors for CDK9.

Compounds of the present invention according to general formula (I) show a significantly stronger CDK9 than CDK2 inhibition.

In context of the present invention, the $IC_{50}$ value with respect to CDK2 can be determined by the methods described in the method section below. Preferably, it is determined according to Method 2. ("CDK2/CycE kinase assay") described in the Materials and Method section below.

Further, as compared to the CDK9 inhibitors described in the prior art, preferred compounds of the present invention according to general formula (I) show a surprisingly high potency for inhibiting CDK9 activity at high ATP concentrations, which is demonstrated by their low $IC_{50}$ value in the CDK9/CycT1 high ATP kinase assay. Thus, these compounds have a lower probability to be competed out of the ATP-binding pocket of CDK9/CycT1 kinase due to the high intracellular ATP concentration (R. Copeland et al. (2006), Nature Reviews Drug Discovery 5, 730-739). According to this property the compounds of the present invention are particularly able to inhibit CDK9/CycT1 within cells for a longer period of time as compared to classical ATP competitive kinase inhibitors. This increases the anti-tumor cell efficacy at pharmacokinetic clearance-mediated declining serum concentrations of the inhibitor after dosing of a patient or an animal.

In context of the present invention, the $IC_{50}$ value with respect to CDK9 at high ATP concentrations can be determined by the methods described in the method section below. Preferably, it is determined according to Method 1b ("CDK9/CycT1 high ATP kinase assay"). described in the Materials and Method section below.

Further, preferred compounds of the present invention according to formula (I) surprisingly show an increased solubility in water at pH 6.5 compared to the compounds described in the prior art.

In context of the present invention the solubility in water at pH 6.5 is preferably determined according to Method 4. ("Equilibrium Shake Flask Solubility Assay") described in the Materials and Method section below.

Further, preferred compounds of the present invention according to formula (I) mediate a surprisingly strong antiproliferative activity in tumor cell lines such as HeLa. In context of the present invention, the $IC_{50}$ values of the compounds with respect to this cell line is preferably determined according to Method 3. ("Proliferation Assay") described in the Materials and Method section below.

Further, preferred compounds of the present invention according to formula (I) show no significant inhibition of carbonic anhydrase-1 or -2 ($IC_{50}$ values of more than 10 µM) and therefore show an improved side effect profile as compared to those CDK inhibitors described in the prior art containing a sulfonamide group, which inhibit carbonic anhydrase-1 or -2. In context of the present invention, the carbonic anhydrase-1 and -2 inhibition is preferably determined according to Method 5. ("Carbonic anhydrase Assay") described in the Materials and Method section below.

A further subject matter of the present invention is the use of the compounds of general formula (I) according to the invention for the treatment and/or prophylaxis of disorders, preferably of disorders relating to or mediated by CDK9 activity, in particular of hyper-proliferative disorders, virally induced infectious diseases and/or of cardiovascular diseases, more preferably of hyper-proliferative disorders.

The compounds of the present invention may be used to inhibit the activity or expression of CDK9. Therefore, the compounds of formula (I) are expected to be valuable as therapeutic agents. Accordingly, in another embodiment, the present invention provides a method of treating disorders relating to or mediated by CDK9 activity in a patient in need of such treatment, comprising administering to the patient an effective amount of a compound of formula (I) as defined above. In certain embodiments, the disorders relating to CDK9 activity are hyper-proliferative disorders, virally induced infectious diseases and/or cardiovascular diseases, more preferably hyper-proliferative disorders, particularly cancer.

The term "treating" or "treatment" as stated throughout this document is used conventionally, e.g., the management or care of a subject for the purpose of combating, alleviating, reducing, relieving, improving the condition of a disease or disorder, such as a carcinoma.

The term "subject" or "patient" includes organisms which are capable of suffering from a cell proliferative disorder or a disorder associated with reduced or insufficient programmed cell death (apoptosis) or who could otherwise benefit from the administration of a compound of the invention, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

The term "disorders relating to or mediated by CDK9" shall include diseases associated with or implicating CDK9 activity, for example the hyperactivity of CDK9, and conditions that accompany with these diseases. Examples of "disorders relating to or mediated by CDK9" include disorders resulting from increased CDK9 activity due to mutations in genes regulating CDK9 activity such as LARP7, HEXIM1/2 or 7sk snRNA, or disorders resulting from increased CDK9 activity due to activation of the CDK9/cyclinT/RNApolymerase II complex by viral proteins such as HIV-TAT or HTLV-TAX or disorders resulting from increased CDK9 activity due to activation of mitogenic signaling pathways.

The term "hyperactivity of CDK9" refers to increased enzymatic activity of CDK9 as compared to normal non-diseased cells, or it refers to increased CDK9 activity leading to unwanted cell proliferation, or to reduced or insufficient programmed cell death (apoptosis), or mutations leading to constitutive activation of CDK9.

The term "hyper-proliferative disorder" includes disorders involving the undesired or uncontrolled proliferation of a cell and it includes disorders involving reduced or insufficient programmed cell death (apoptosis). The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, hydrate or solvate thereof which is effective to treat or prevent the disorder.

Hyper-proliferative disorders in the context of this invention include, but are not limited to, e.g., psoriasis, keloids and other hyperplasias affecting the skin, endometriosis, skeletal disorders, angiogenic or blood vessel proliferative disorders, pulmonary hypertension, fibrotic disorders, mesangial cell proliferative disorders, colonic polyps, polycystic kidney disease, benign prostate hyperplasia (BPH), and solid tumors, such as cancers of the breast, respiratory tract, brain, reproductive organs, digestive tract, urinary tract, eye, liver, skin, head and neck, thyroid, parathyroid, and their distant metastases. Those disorders also include lymphomas, sarcomas and leukemias.

Examples of breast cancer include, but are not limited to invasive ductal carcinoma, invasive lobular carcinoma, ductal carcinoma in situ, and lobular carcinoma in situ, canine or feline mammary carcinoma.

Examples of cancers of the respiratory tract include, but are not limited to small-cell and non-small-cell lung carcinoma, as well as bronchial adenoma, pleuropulmonary blastoma, and mesothelioma. Examples of brain cancers include, but are not limited to brain stem and hypothalamic glioma, cerebellar and cerebral astrocytoma, glioblastoma, medulloblastoma, ependymoma, as well as neuroectodermal and pineal tumor.

Tumors of the male reproductive organs include, but are not limited to prostate and testicular cancer.

Tumors of the female reproductive organs include, but are not limited to endometrial, cervical, ovarian, vaginal and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers. Anal gland adenocarcinomas, mast cell tumors.

Tumors of the urinary tract include, but are not limited to bladder, penile, kidney, renal pelvis, ureter, urethral, and hereditary and sporadic papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer. mast cell tumors.

Head-and-neck cancers include, but are not limited to laryngeal, hypopharyngeal, nasopharyngeal, oropharyngeal cancer, lip and oral cavity cancer, and squamous cell cancer. Oral melanoma. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma. Malignant histiocytosis, fibrosarcoma, hemangiosarcoma, hemangiopericytoma, leiomyosarcoma.

Leukemias include, but are not limited to acute myeloid leukemia, acute lymphoblastic leukemia, chronic lymphocytic leukemia, chronic myelogenous leukemia, and hairy cell leukemia.

Fibrotic proliferative disorders, i.e. the abnormal formation of extracellular matrices, that may be treated with the compounds and methods of the present invention include lung fibrosis, atherosclerosis, restenosis, hepatic cirrhosis, and mesangial cell proliferative disorders, including renal diseases such as glomerulonephritis, diabetic nephropathy, malignant nephrosclerosis, thrombotic microangiopathy syndromes, transplant rejection, and glomerulopathies.

Other conditions in humans or other mammals that may be treated by administering a compound of the present invention include tumor growth, retinopathy, including diabetic retinopathy, ischemic retinal-vein occlusion, retinopathy of prematurity and age-related macular degeneration, rheumatoid arthritis, psoriasis, and bullous disorders associated with subepidermal blister formation, including bullous pemphigoid, erythema multiforme and dermatitis herpetiformis.

The compounds of the present invention may also be used to prevent and treat diseases of the airways and the lung, diseases of the gastrointestinal tract as well as diseases of the bladder and bile duct. The disorders mentioned above have been well characterized in humans, but also exist with a similar etiology in other animals, including mammals, and can be treated by administering pharmaceutical compositions of the present invention.

In a further aspect of the present invention, the compounds according to the invention are used in a method for preventing and/or treating infectious diseases, in particular virally induced infectious diseases. The virally induced infectious diseases, including opportunistic diseases, are caused by retroviruses, hepadnaviruses, herpesviruses, flaviviridae, and/or adenoviruses. In a further preferred embodiment of this method, the retroviruses are selected from lentiviruses or oncoretroviruses, wherein the lentivirus is selected from the group comprising: HIV-1, HIV-2, FIV, BIV, SIVs, SHIV, CAEV, VMV or EIAV, preferably HIV-1 or HIV-2 and wherein the oncoretrovirus is selected from the group consisting of: HTLV-I, HTLV-II or BLV. In a further preferred embodiment of this method, the hepadnavirus is selected from HBV, GSHV or WHV, preferably HBV, the herpesivirus is selected from the group comprising: HSV I, HSV II, EBV, VZV, HCMV or HHV 8, preferably HCMV and the flaviviridae is selected from HCV, West nile or Yellow Fever.

The compounds according to general formula (I) are also useful for prophylaxis and/or treatment of cardiovascular diseases such as cardiac hypertrophy, adult congenital heart disease, aneurysm, stable angina, unstable angina, angina pectoris, angioneurotic edema, aortic valve stenosis, aortic aneurysm, arrhythmia, arrhythmogenic right ventricular dysplasia, arteriosclerosis, arteriovenous malformations, atrial fibrillation, Behcet syndrome, bradycardia, cardiac tamponade, cardiomegaly, congestive cardiomyopathy, hypertrophic cardiomyopathy, restrictive cardiomyopathy, cardiovascular disease prevention, carotid stenosis, cerebral hemorrhage, Churg-Strauss syndrome, diabetes, Ebstein's Anomaly, Eisenmenger complex, cholesterol embolism, bacterial endocarditis, fibromuscular dysplasia, congenital heart defects, heart diseases, congestive heart failure, heart valve diseases, heart attack, epidural hematoma, hematoma, subdural, Hippel-Lindau disease, hyperemia, hypertension, pulmonary hypertension, hypertrophic growth, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, long QT syndrome mitral valve prolapse, moyamoya disease, mucocutaneous lymph node syndrome, myocardial infarction, myocardial ischemia, myocarditis, pericarditis, peripheral vascular diseases, phlebitis, polyarteritis nodosa, pulmonary atresia, Raynaud disease, restenosis, Sneddon syndrome, stenosis, superior vena cava syndrome, syndrome X, tachycardia, Takayasu's arteritis, hereditary hemorrhagic telangiectasia, telangiectasis, temporal arteritis, tetralogy of fallot, thromboangiitis obliterans, thrombosis, thromboembolism, tricuspid atresia, varicose veins, vascular diseases, vasculitis, vasospasm, ventricular fibrillation, Williams syndrome, peripheral vascular disease, varicose veins and leg ulcers, deep vein thrombosis, Wolff-Parkinson-White syndrome.

Preferred are cardiac hypertrophy, adult congenital heart disease, aneurysms, angina, angina pectoris, arrhythmias, cardiovascular disease prevention, cardiomyopathies, congestive heart failure, myocardial infarction, pulmonary hypertension, hypertrophic growth, restenosis, stenosis, thrombosis and arteriosclerosis.

A further subject matter of the present invention is the use of the compounds of general formula (I) according to the invention for the treatment and/or prophylaxis of disorders, in particular of the disorders mentioned above.

A further subject matter of the present invention are the compounds according to the invention for use in a method for the treatment and/or prophylaxis of the disorders mentioned above.

A preferred subject matter of the present invention are the compounds according to the invention for the use in a method for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas or ovarian carcinomas.

A further subject matter of the present invention is the use of the compounds according to the invention in the manufacture of a medicament for the treatment and/or prophylaxis of disorders, in particular the disorders mentioned above.

A preferred subject matter of the present invention is the use of the compounds according to the invention in the manufacture of a medicament for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas or ovarian carcinomas.

A further subject matter of the present invention is a method for the treatment and/or prophylaxis of disorders, in particular the disorders mentioned above, using an effective amount of the compounds according to the invention.

A preferred subject matter of the present invention is a method for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas or ovarian carcinomas.

Another aspect of the present invention relates to pharmaceutical combinations comprising a compound of general formula (I) according to the invention in combination with at least one or more further active ingredients.

As used herein the term "pharmaceutical combination" refers to a combination of at least one compound of general formula (I) according to the invention as active ingredient together with at least one other active ingredient with or without further ingredients, carrier, diluents and/or solvents.

Another aspect of the present invention relates to pharmaceutical compositions comprising a compound of general formula (I) according to the invention in combination with an inert, nontoxic, pharmaceutically suitable adjuvant.

As used herein the term "pharmaceutical composition" refers to a galenic formulation of at least one pharmaceutically active agent together with at least one further ingredient, carrier, diluent and/or solvent.

Another aspect of the present invention relates to the use of the pharmaceutical combinations and/or the pharmaceutical compositions according to the invention for the treatment and/or prophylaxis of disorders, in particular of the disorders mentioned above.

Compounds of formula (I) may be administered as the sole pharmaceutical agent or in combination with one or more additional therapeutic agents where the combination causes no unacceptable adverse effects. This pharmaceutical combination includes administration of a single pharmaceutical dosage formulation which contains a compound of formula (I) and one or more additional therapeutic agents, as well as administration of the compound of formula (I) and each additional therapeutic agent in its own separate pharmaceutical dosage formulation. For example, a compound of formula (I) and a therapeutic agent may be administered to the patient together in a single oral dosage composition such as a tablet or capsule, or each agent may be administered in separate dosage formulations.

Where separate dosage formulations are used, the compound of formula (I) and one or more additional therapeutic agents may be administered at essentially the same time (e.g., concurrently) or at separately staggered times (e.g., sequentially).

In particular, the compounds of the present invention may be used in fixed or separate combination with other anti-tumor agents such as alkylating agents, anti-metabolites, plant-derived anti-tumor agents, hormonal therapy agents, topoisomerase inhibitors, camptothecin derivatives, kinase inhibitors, targeted drugs, antibodies, interferons and/or biological response modifiers, anti-angiogenic compounds, and other anti-tumor drugs. In this regard, the following is a non-limiting list of examples of secondary agents that may be used in combination with the compounds of the present invention:

Alkylating agents include, but are not limited to, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, and mitolactol; platinum-coordinated alkylating compounds include, but are not limited to, cisplatin, carboplatin, eptaplatin, lobaplatin, nedaplatin, oxaliplatin, and satraplatin;

Anti-metabolites include, but are not limited to, methotrexate, 6-mercaptopurine riboside, mercaptopurine, 5-fluorouracil alone or in combination with leucovorin, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosfite, disodium premetrexed, pentostatin, pelitrexol, raltitrexed, triapine, trimetrexate, vidarabine, vincristine, and vinorelbine;

Hormonal therapy agents include, but are not limited to, exemestane, Lupron, anastrozole, doxercalciferol, fadrozole, formestane, 11-beta hydroxysteroid dehydrogenase 1 inhibitors, 17-alpha hydroxylase/17,20 lyase inhibitors such as abiraterone acetate, 5-alpha reductase inhibitors such as finasteride and epristeride, anti-estrogens such as tamoxifen citrate and fulvestrant, Trelstar, toremifene, raloxifene, lasofoxifene, letrozole, anti-androgens such as bicalutamide, flutamide, mifepristone, nilutamide, Casodex, and anti-progesterones and combinations thereof;

Plant-derived anti-tumor substances include, e.g., those selected from mitotic inhibitors, for example epothilones such as sagopilone, ixabepilone and epothilone B, vinblastine, vinflunine, docetaxel, and paclitaxel;

Cytotoxic topoisomerase inhibiting agents include, but are not limited to, aclarubicin, doxorubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide, and combinations thereof;

Immunologicals include interferons such as interferon alpha, interferon alpha-2a, interferon alpha-2b, interferon beta, interferon gamma-1a and interferon gamma-nl, and other immune enhancing agents such as L19-IL2 and other IL2 derivatives, filgrastim, lentinan, sizofilan, TheraCys, ubenimex, aldesleukin, alemtuzumab, BAM-002, dacarbazine, daclizumab, denileukin, gemtuzumab, ozogamicin, ibritumomab, imiquimod, lenograstim, lentinan, melanoma vaccine (Corixa), molgramostim, sargramostim, tasonermin, tecleukin, thymalasin, tositumomab, Vimlizin, epratuzumab, mitumomab, oregovomab, pemtumomab, and Provenge; Merial melanoma vaccine Biological response modifiers are agents that modify defense mechanisms of living organisms or biological responses such as survival, growth or differentiation of tissue cells to direct them to have anti-tumor activity; such agents include, e.g., krestin, lentinan, sizofuran, picibanil, ProMune, and ubenimex;

Anti-angiogenic compounds include, but are not limited to, acitretin, aflibercept, angiostatin, aplidine, asentar, axitinib, recentin, bevacizumab, brivanib alaninat, cilengtide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, and vitaxin;

Antibodies include, but are not limited to, trastuzumab, cetuximab, bevacizumab, rituximab, ticilimumab, ipilimumab, lumiliximab, catumaxomab, atacicept, oregovomab, and alemtuzumab;

VEGF inhibitors such as, e.g., sorafenib, DAST, bevacizumab, sunitinib, recentin, axitinib, aflibercept, telatinib, brivanib alaninate, vatalanib, pazopanib, and ranibizumab; Palladia EGFR (HER1) inhibitors such as, e.g., cetuximab, panitumumab, vectibix, gefitinib, erlotinib, and Zactima;

HER2 inhibitors such as, e.g., lapatinib, tratuzumab, and pertuzumab;

mTOR inhibitors such as, e.g., temsirolimus, sirolimus/Rapamycin, and everolimus;

c-Met inhibitors;

PI3K and AKT inhibitors;

CDK inhibitors such as roscovitine and flavopiridol;

Spindle assembly checkpoints inhibitors and targeted antimitotic agents such as PLK inhibitors, Aurora inhibitors (e.g. Hesperadin), checkpoint kinase inhibitors, and KSP inhibitors;

HDAC inhibitors such as, e.g., panobinostat, vorinostat, MS275, belinostat, and LBH589;

HSP90 and HSP70 inhibitors;

Proteasome inhibitors such as bortezomib and carfilzomib;

Serine/threonine kinase inhibitors including MEK inhibitors (such as e.g. RDEA 119) and Raf inhibitors such as sorafenib;

Farnesyl transferase inhibitors such as, e.g., tipifarnib;

Tyrosine kinase inhibitors including, e.g., dasatinib, nilotibib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab, pertuzumab, and c-Kit inhibitors; Palladia, masitinib Vitamin D receptor agonists;

Bcl-2 protein inhibitors such as obatoclax, oblimersen sodium, and gossypol;

Cluster of differentiation 20 receptor antagonists such as, e.g., rituximab;

Ribonucleotide reductase inhibitors such as, e.g., gemcitabine;

Tumor necrosis apoptosis inducing ligand receptor 1 agonists such as, e.g., mapatumumab; 5-Hydroxytryptamine receptor antagonists such as, e.g., rEV598, xaliprode, palonosetron hydro-chloride, granisetron, Zindol, and AB-1001;

Integrin inhibitors including alpha5-beta1 integrin inhibitors such as, e.g., E7820, JSM 6425, volociximab, and endostatin;

Androgen receptor antagonists including, e.g., nandrolone decanoate, fluoxymesterone, Android, Prost-aid, andromustine, bicalutamide, flutamide, apo-cyproterone, apo-flutamide, chlormadinone acetate, Androcur, Tabi, cyproterone acetate, and nilutamide;

Aromatase inhibitors such as, e.g., anastrozole, letrozole, testolactone, exemestane, amino-glutethimide, and formestane;

Matrix metalloproteinase inhibitors;

Other anti-cancer agents including, e.g., alitretinoin, ampligen, atrasentan bexarotene, bortezomib, bosentan, calcitriol, exisulind, fotemustine, ibandronic acid, miltefosine, mitoxantrone, I-asparaginase, procarbazine, dacarbazine, hydroxycarbamide, pegaspargase, pentostatin, tazaroten, velcade, gallium nitrate, canfosfamide, darinaparsin, and tretinoin.

The compounds of the present invention may also be employed in cancer treatment in conjunction with radiation therapy and/or surgical intervention.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone, (2) provide for the administration of lesser amounts of the administered chemotherapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (7) provide a longer time for tumor progression, and/or (8) yield efficacy and tolerability results at least as good as those of the agents used alone, compared to known instances where other cancer agent combinations produce antagonistic effects.

Furthermore, the compounds of formula (I) may be utilized, as such or in compositions, in research and diagnostics, or as analytical reference standards, and the like, which are well known in the art.

The compounds according to the invention can act systemically and/or locally. For this purpose, they can be administered in a suitable way, such as, for example, by the oral, parenteral, pulmonal, nasal, sublingual, lingual, buccal, rectal, dermal, transdermal, conjunctival or otic route, or as an implant or stent.

For these administration routes, it is possible to administer the compounds according to the invention in suitable application forms.

Suitable for oral administration are administration forms which work as described in the prior art and deliver the compounds according to the invention rapidly and/or in modified form, which comprise the compounds according to the invention in crystalline and/or amorphous and/or dissolved form, such as, for example, tablets (coated or uncoated, for example tablets provided with enteric coatings or coatings whose dissolution is delayed or which are insoluble and which control the release of the compound according to the invention), tablets which rapidly decompose in the oral cavity, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (for example intravenously, intraarterially, intracardially, intraspinally or intralumbally) or with inclusion of absorption (for example intramuscularly, subcutaneously, intracutaneously, percutaneously or intraperitoneally). Administration forms suitable for parenteral administration are, inter alia, preparations for injection and infusion in the form of solutions, suspensions, emulsions, lyophilizates or sterile powders.

Examples suitable for the other administration routes are pharmaceutical forms for inhalation (inter alia powder inhalers, nebulizers), nasal drops/solutions/sprays; tablets to be administered lingually, sublingually or buccally, films/wafers or capsules, suppositories, preparations for the eyes or ears, vaginal capsules, aqueous suspensions (lotions, shaking mixtures), lipophilic suspensions, ointments, creams, transdermal therapeutic systems (such as plasters, for example), milk, pastes, foams, dusting powders, implants or stents.

The compounds according to the invention can be converted into the stated administration forms. This can take place in a manner known per se by mixing with inert, nontoxic, pharmaceutically suitable adjuvants. These adjuvants include, inter alia, carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides) and flavour- and/or odour-masking agents.

The present invention furthermore provides medicaments comprising at least one compound according to the invention, usually together with one or more inert, nontoxic, pharmaceutically suitable adjuvants, and their use for the purposes mentioned above.

When the compounds of the present invention are administered as pharmaceuticals, to humans or animals, they can be given per se or as a pharmaceutical composition containing, for example, 0.1% to 99.5% (more preferably 0.5% to 90%) of active ingredient in combination with one or more inert, nontoxic, pharmaceutically suitable adjuvants.

Regardless of the route of administration selected, the compounds of the invention of general formula (I) and/or the pharmaceutical composition of the present invention are formulated into pharmaceutically acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient without being toxic to the patient.

Materials and Methods:

The percentage data in the following tests and examples are percentages by weight unless otherwise indicated; parts are parts by weight. Solvent ratios, dilution ratios and concentration data of liquid/liquid solutions are in each case based on volume.

Examples were tested in selected biological assays one or more times. When tested more than once, data are reported as either average values or as median values, wherein
the average value, also referred to as the arithmetic mean value, represents the sum of the values obtained divided by the number of times tested, and
the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro pharmacological properties of the compounds can be determined according to the following assays and methods.

1a. CDK9/CycT1 Kinase Assay:

CDK9/CycT1-inhibitory activity of compounds of the present invention was quantified employing the CDK9/CycT1 TR-FRET assay as described in the following paragraphs:

Recombinant full-length His-tagged human CDK9 and CycT1, expressed in insect cells and purified by Ni-NTA affinity chromatography, were purchased from Invitrogen (Cat. No PV4131). As substrate for the kinase reaction biotinylated peptide biotin-Ttds-YISPLKSPYKISEG (C-terminus in amid form) was used which can be purchased e.g. form the company JERINI Peptide Technologies (Berlin, Germany) For the assay 50 nl of a 100 fold concentrated solution of the test compound in DMSO was pipetted into a black low volume 384 well microtiter plate (Greiner Bio-One, Frickenhausen, Germany), 2 µl of a solution of CDK9/CycT1 in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.67 µM=>final conc. in the 5 µl assay volume is 1 µM) in assay buffer and the resulting mixture was incubated for a reaction time of 25 min at 22° C. The concentration of CDK9/CycT1 was adjusted depending of the activity of the enzyme lot and was chosen appropriate to have the assay in the linear range, typical concentrations were in the range of 1 µg/ml. The reaction was stopped by the addition of 5 µl of a solution of TR-FRET detection reagents (0.2 µM streptavidine-XL665 [Cisbio Bioassays, Codolet, France] and 1 nM anti-RB(pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

1b. CDK9/CycT1 High ATP Kinase Assay

CDK9/CycT1-inhibitory activity of compounds of the present invention at a high ATP concentration after preincubation of enzyme and test compounds was quantified employing the CDK9/CycT1 TR-FRET assay as described in the following paragraphs.

Recombinant full-length His-tagged human CDK9 and CycT1, expressed in insect cells and purified by Ni-NTA affinity chromatography, were purchase from Invitrogen (Cat. No PV4131). As substrate for the kinase reaction biotinylated peptide biotin-Ttds-YISPLKSPYKISEG (C-terminus in amid form) was used which can be purchased e.g. form the company JERINI peptide technologies (Berlin, Germany) For the assay 50 nl of a 100 fold concentrated solution of the test compound in DMSO was pipetted into a black low volume 384 well microtiter plate (Greiner Bio-One, Frickenhausen, Germany), 2 µl of a solution of CDK9/CycT1 in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 3.3 mM=>final conc. in the 5 µL1 assay volume is 2 mM) and substrate (1.67 µM=>final conc. in the 5 µl assay volume is 1 µM) in assay buffer and the resulting mixture was incubated for a reaction time of 25 min at 22° C. The concentration of CDK9/CycT1 was adjusted depending of the activity of the enzyme lot and was chosen appropriate to have the assay in the linear range, typical concentrations were in the range of 0.5 µg/ml. The reaction was stopped by the addition of 5 µl of a solution of TR-FRET detection reagents (0.2 µM streptavidine-XL665 [Cisbio Bioassays, Codolet, France] and 1 nM anti-RB(pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

2. CDK2/CycE Kinase Assay:

CDK2/CycE-inhibitory activity of compounds of the present invention was quantified employing the CDK2/CycE TR-FRET assay as described in the following paragraphs:

Recombinant fusion proteins of GST and human CDK2 and of GST and human CycE, expressed in insect cells (Sf9) and purified by Glutathion-Sepharose affinity chromatography, were purchased from ProQinase GmbH (Freiburg, Germany). As substrate for the kinase reaction biotinylated peptide biotin-Ttds-YISPLKSPYKISEG (C-terminus in amid form) was used which can be purchased e.g. form the company JERINI Peptide Technologies (Berlin, Germany)

For the assay 50 nl of a 100 fold concentrated solution of the test compound in DMSO was pipetted into a black low volume 384 well microtiter plate (Greiner Bio-One, Frickenhausen, Germany), 2 µl of a solution of CDK2/CycE in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.25 µM=>final conc. in the 5 µl assay volume is 0.75 µM) in assay buffer and the resulting mixture was incubated for a reaction time of 25 min at 22° C. The concentration of CDK2/CycE was adjusted depending of the activity of the enzyme lot and was chosen appropriate to have the assay in the linear range, typical concentrations were in the range of 130 ng/ml. The reaction was stopped by the addition of 5 µl of a solution of TR-FRET detection reagents (0.2 µM streptavidine-XL665 [Cisbio Bioassays, Codolet, France] and 1 nM anti-RB(pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

3. Proliferation Assay:

Cultivated tumour cells (HeLa, human cervical tumour cells, ATCC CCL-2; NCI-H460, human non-small cell lung carcinoma cells, ATCC HTB-177; A2780, human ovarian carcinoma cells, ECACC #93112519; DU 145, hormone-independent human prostate carcinoma cells, ATCC HTB-81; HeLa-MaTu-ADR, multidrug-resistant human cervical carcinoma cells, EPO-GmbH Berlin; Caco-2, human colorectal carcinoma cells, ATCC HTB-37; B16F10, mouse melanoma cells, ATCC CRL-6475) were plated at a density of 5,000 cells/well (DU145, HeLa-MaTu-ADR), 3,000 cells/well (NCI-H460, HeLa), 2,500 cells/well (A2780), 1,500 cells/well (Caco-2), or 1,000 cells/well (B16F10) in a 96-well multititer plate in 200 µL of their respective growth medium supplemented 10% fetal calf serum. After 24 hours, the cells of one plate (zero-point plate) were stained with crystal violet (see below), while the medium of the other plates was replaced by fresh culture medium (200 µL1), to which the test substances were added in various concentrations (0 µM, as well as in the range of 0.001-10 µM; the final concentration of the solvent dimethyl sulfoxide was 0.5%). The cells were incubated for 4 days in the presence of test substances. Cell proliferation was determined by staining the cells with crystal violet: the cells were fixed by adding 20 µl/measuring point of an 11% glutaric aldehyde solution for 15 minutes at room temperature. After three washing cycles of the fixed cells with water, the plates were dried at room temperature. The cells were stained by adding 100 µl/measuring point of a 0.1% crystal violet solution (pH 3.0). After three washing cycles of the stained cells with water, the plates were dried at room temperature. The dye was dissolved by adding 100 µl/measuring point of a 10% acetic acid solution. The extinction was determined by photometry at a wavelength of 595 nm. The change of cell number, in percent, was calculated by normalization of the measured values to the extinction values of the zero-point plate (=0%) and the extinction of the untreated (0 µm) cells (=100%). The $IC_{50}$ values (inhibitory concentration at 50% of maximal effect) were determined by means of a 4 parameter fit.

4. Equilibrium Shake Flask Solubility Assay:

The thermodynamic solubility of compounds in water was determined by an equilibrium shake flask method (see for example: E. H. Kerns, L. Di: Drug-like Properties: Concepts, Structure Design and Methods, 276-286, Burlington, Mass., Academic Press, 2008). A saturated solution of the drug was prepared and the solution was mixed for 24 h to ensure that equilibrium was reached. The solution was centrifuged to remove the insoluble fraction and the concentration of the compound in solution was determined using a standard calibration curve. To prepare the sample, 2 mg solid compound was weighed in a 4 mL glass vial. 1 mL phosphate buffer pH 6.5 was added. The suspension was stirred for 24 hrs at room temperature. The solution was centrifuged afterwards. To prepare the sample for the standard calibration, 2 mg solid sample was dissolved in 30 mL acetonitrile. After sonification the solution was diluted with water to 50 mL. Sample and standards were quantified by HPLC with UV-detection. For each sample two injection volumes (5 and 50 µl) in triplicates were made. Three injection volumes (5 µl, 10 µl and 20 µl) were made for the standard.

Chromatographic Conditions:

| | |
|---|---|
| HPLC column: | Xterra MS C18 2.5 µm 4.6 × 30 mm |
| Injection volume: | Sample: 3 × 5 µl and 3 × 50 µl |
| | Standard: 5 µl, 10 µl, 20 µl |
| Flow: | 1.5 mL/min |
| Mobile phase: | acidic gradient: |
| | A: Water/0.01% TFA |
| | B: Acetonitrile/0.01% TFA |
| | 0 min → 95% A 5% B |
| | 0-3 min → 35% A 65% B, linear gradient |
| | 3-5 min → 35% A 65% B, isocratic |
| | 5-6 min → 95% A 5% B, isocratic |
| UV detector: | wavelength near the absorption maximum (between 200 and 400 nm) |

The areas of sample- and standard injections as well as the calculation of the solubility value (in mg/l) were determined by using HPLC software (Waters Empower 2 FR).

5. Carbonic Anhydrase Assay

The principle of the assay is based on the hydrolysis of 4-nitrophenyl acetate by carbonic anhydrases (Pocker & Stone, Biochemistry, 1967, 6, 668), with subsequent photometric determination of the dye product 4-nitrophenolate at 400 nm by means of a 96-channel spectral photometer.

2 µL of the test compounds, dissolved in DMSO (100-fold final concentration), in a concentration range of 0.03-10 µmol/L (final), was pipetted as quadruplicates into the wells of a 96-hole microtiter plate. Wells that contained the solvent without test compounds were used as reference values (1. Wells without carbonic anhydrase for correction of the non-enzymatic hydrolysis of the substrate, and 2. Wells with carbonic anhydrase for determining the activity of the non-inhibited enzyme). 188 µL of assay buffer (10 mmol/L of Tris/HCl, pH 7.4, 80 mmol/L of NaCl), with or without 3 units/well of carbonic anhydrase-1 [=human carbonic anhydrase-1 (Sigma, #C4396)] in order to determine carbonic anhydrase-1 inhibition or 3 units/well of carbonic anhydrase-2 [=human carbonic anhydrase-2 (Sigma, #C6165)] for measuring carbonic anhydrase-2 inhibition, was pipetted into the wells of the microtiter plate. The enzymatic reaction was started by the addition of 10 microL of the substrate solution (1 mmol/L of 4-nitrophenyl acetate (Fluka #4602), dissolved in anhydrous acetonitrile (final substrate concentration: 50 µmol/L). The plate was incubated at room temperature for 15 minutes. Absorption was measured by photometry at a wavelength of 400 nm. The enzyme inhibition was calculated after the measured values were normalized to the absorption of the reactions in the wells without enzyme (=100% inhibition) and to the absorption of reactions in the wells with non-inhibited enzyme (=0% inhibition). $IC_{50}$ values were determined by means of a 4 parameter fit using the company's own software.

PREPARATIVE EXAMPLES

Syntheses of Compounds

The syntheses of the inventive disubstituted 5-fluoro-pyrimidines according to the present invention are preferably carried out according to schemes 1 and 2 below:

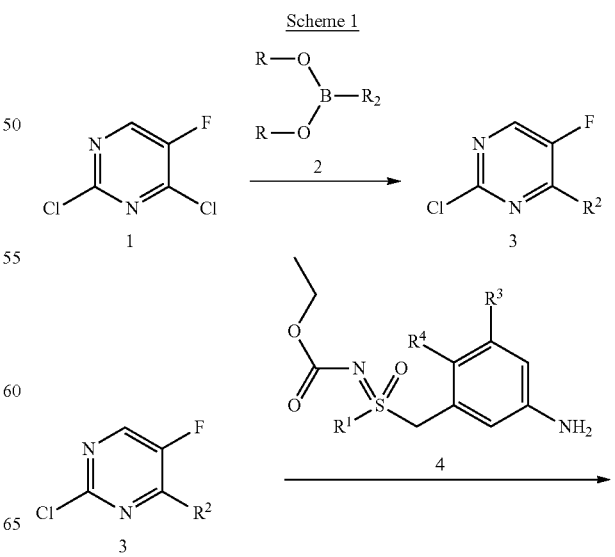

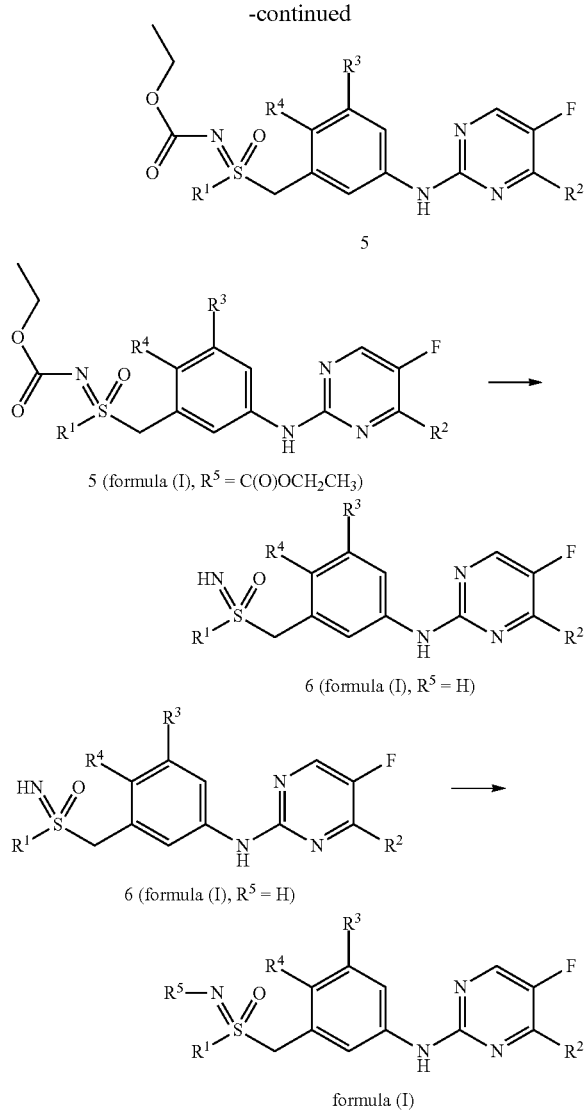

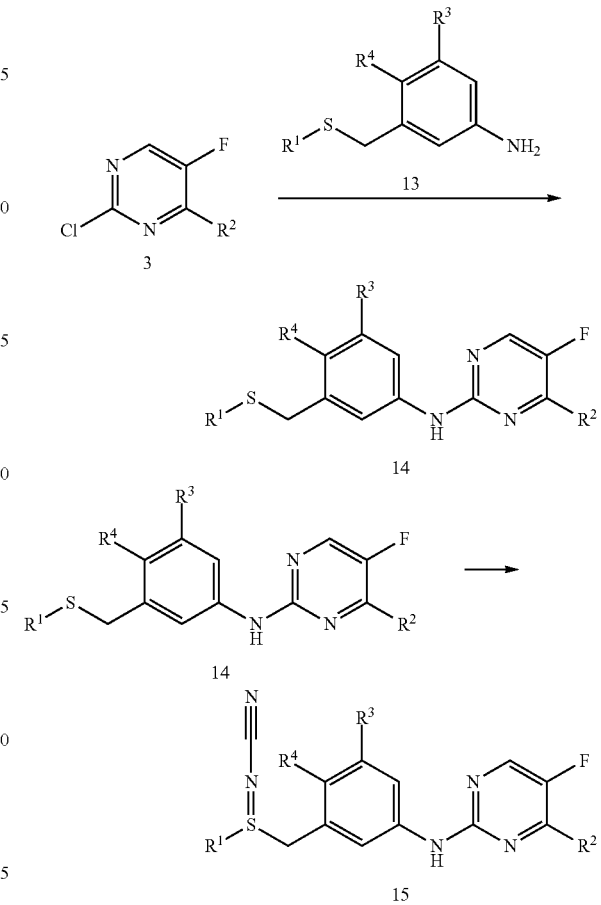

cross-coupling reactions (for a review on C—N cross-coupling reactions see for example: a) L. Jiang, S. L. Buchwald in 'Metal-Catalyzed Cross-Coupling Reactions', 2$^{nd}$ ed.: A. de Meijere, F. Diederich, Eds.: Wiley-VCH: Weinheim, Germany, 2004).

Preferred is the use of suitable palladium precatalysts based upon biarylmonphosphines that are easily activated and ensure the formation of the active mono-ligated Pd(0) complex (see for examples a) S. L. Buchwald et al, J. Am. Chem. Soc. 2008, 130, 6686; b) S. L. Buchwald et al, J. Am. Chem. Soc. 2008, 130, 13552). The reactions are run in the presence of a weak base at elevated temperatures (see for example: a) S. L: Buchwald et al, Tet. Lett. 2009, 50, 3672). Most preferred is the herein described use of chloro(2-dicyclohexylphosphino-2',4',6'-tri-iso-propyl-1,1'-biphenyl) [2-(2-aminoethyl)phenyl]palladium(II) methyl-tert-butylether adduct, 2-dicyclohexylphosphino-2',4',6'-triisopropylbiphenyl and potassium phosphate in toluene and 1-methylpyrrolidin-2-one. The reactions are preferably run under argon for 3 hours at 130° C. in a microwave oven or in an oil bath.

Deprotection of compounds of formula (5) gives the corresponding N-unprotected sulfoximines of formula (6). The deprotection is preferably carried out with sodium ethanolate in ethanol at 60° C.

N-unprotected sulfoximines of formula (6) may be reacted to to give N-functionalized derivatives of formula (I).

A synthesis route to N-cyanosulfoximines of formula (16) is shown in Scheme 2.

In the first step 2,4-dichloro-5-fluoropyrimidine (1) is reacted with a boronic acid derivative R$^2$—B(OR)$_2$ of formula (2) to give a compound of formula (3). The boronic acid derivative (2) may be a boronic acid (R═—H) or an ester of the boronic acid, e.g. its isopropyl ester (R═—CH(CH$_3$)$_2$), preferably an ester derived from pinacol in which the boronic acid intermediate forms a 2-aryl-4,4,5,5-tetramethyl-1,3,2-dioxaborolane (R—R═—C(CH$_3$)$_2$—C(CH$_3$)$_2$—).

The coupling reaction is catalyzed by Pd catalysts, e.g. by Pd(0) catalysts like tetrakis(triphenylphosphine)palladium (0) [Pd(PPh$_3$)$_4$], tris(dibenzylideneacetone)di-palladium(0) [Pd$_2$(dba)$_3$], or by Pd(II) catalysts like dichlorobis(triphenylphosphine)-palladium(II) [Pd(PPh$_3$)$_2$Cl$_2$], palladium(II) acetate and triphenylphosphine or by [1,1'-bis(diphenylphosphino)ferrocene]palladium dichloride [Pd(dppf)Cl$_2$].

The reaction is preferably carried out in a mixture of a solvent like 1,2-dimethoxyethane, dioxane, DMF, DME, THF, or isopropanol with water and in the presence of a base like aqueous potassium carbonate, aqueous sodium bicarbonate or potassium phosphate.

In the second step, a compound of formula (3) is reacted with a suitable aniline of formula (4) to give the corresponding cross-coupling product of formula (5). The compounds of formula (5) can be prepared by Palladium-catalyzed C—N

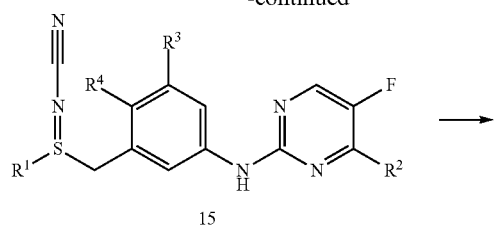

15

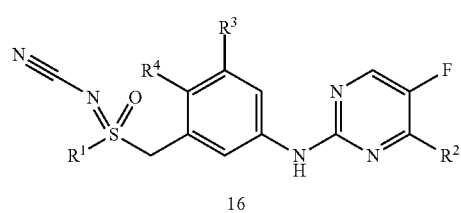

16

In the first step a compound of formula (3) is reacted with a suitable aniline of formula (13) to give a compound of formula (14).

This coupling reaction can be carried out in an alcohol like 1-butanol or in an inert solvent like DMF, THF, DME, dioxane or mixtures of such solvents in the presence of an acid like hydrogen chloride or 4-methylbenzenesulfonic acid. Preferably, the reaction is carried out at a elevated temperatures, for example 140° C.

Alternatively, Palladium-catalyzed C—N cross-coupling reactions as described above can be employed.

In the second step, a compound of formula (14) is reacted with cyanogen amine as a nitrogen source to give the corresponding N-cyanosulfilimine of formula (15). Preferably, the reaction is carried out using NBS and potassium tert-butoxide in methanol at room temperature (see for example: a) C. Bolm et al, Org. Lett. 2007, 9, 3809). Instead of NBS, iodine or iodobenzene diacetete (PhI(OAc)$_2$) can be employed (see for example: a) C. Bolm et al, Org. Lett. 2007, 9, 3809; b) C. Bolm et al, Bioorg. Med. Chem. Lett. 2011, 21, 4888; c) J. M. Babcock, US 2009/0023782). Most preferred is the use of iodobenzene diacetete.

Finally, the N-cyanosulfilimine of formula (15) is oxidized to the corresponding N-cyanosulfoximine of formula (16). The reaction is preferably carried out using mCPBA and potassium carbonate in ethanol at room temperature (see for example: a) C. Bolm et al, Org. Lett. 2007, 9, 3809). Alternatively, other oxidazing agents such as potassium peroxomonosulfate or sodium periodate/ruthenium trichloride can be employed (see for example: a) J. M. Babcock, US 2009/0023782). Most preferred is the use of potassium permanganate in acetone.

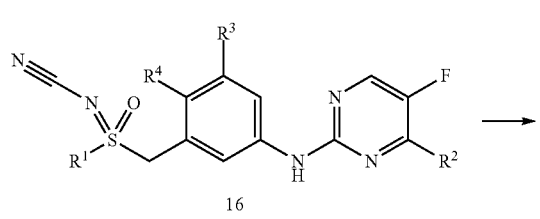

16

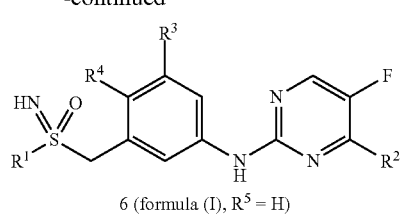

6 (formula (I), R$^5$ = H)

N-cyanosulfoximines of formula (16) can be converted to the corresponding N-unprotected sulfoximines of formula (6). The reaction is preferably carried out using trifluoroacetic anhydride (TFAA) in DCM followed by the reaction with potassium carbonate in methanol (see for example: a) C. Bolm et al, Org. Lett. 2007, 9, 3809).

A synthesis route to N-unprotected sulfoximines of formula (21) is shown in Scheme 3.

Scheme 3

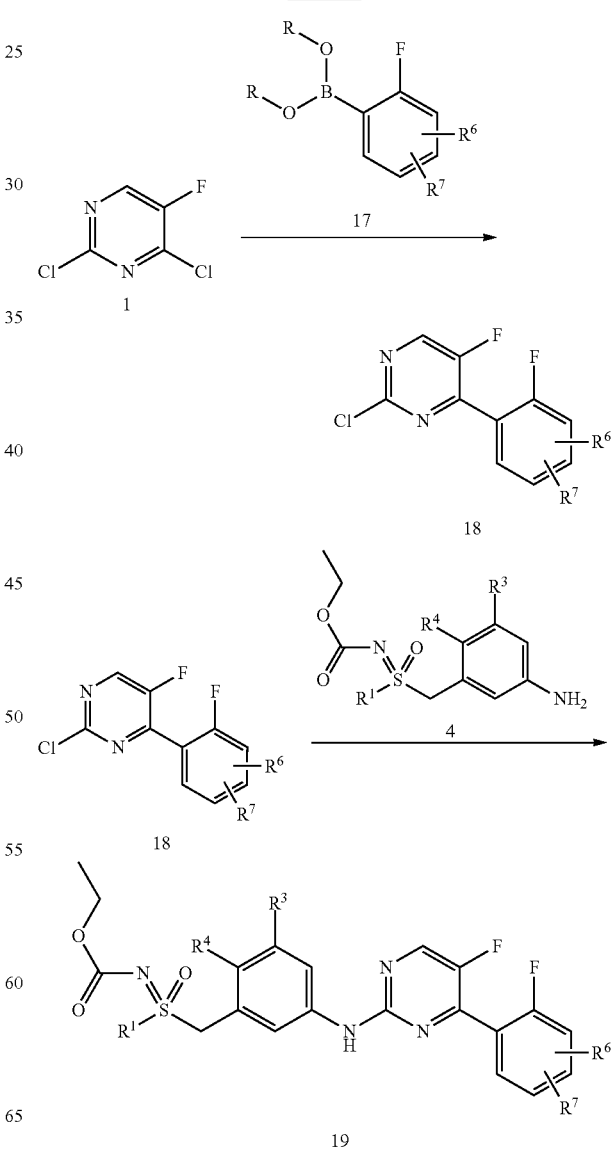

-continued

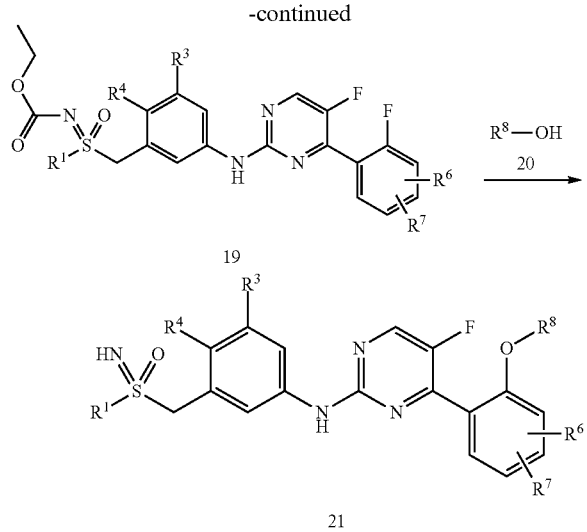

In the first step 2,4-dichloro-5-fluoropyrimidine (1) is reacted with a boronic acid derivative of formula (17) to give a compound of formula (18). The boronic acid derivative (17) may be a boronic acid (R=—H) or an ester of the boronic acid, e.g. its isopropyl ester (R=—CH(CH$_3$)$_2$), preferably an ester derived from pinacol in which the boronic acid intermediate forms a 2-aryl-4,4,5,5-tetramethyl-1,3,2-dioxaborolane (R—R=—C(CH$_3$)$_2$—C(CH$_3$)$_2$—). The coupling reaction is catalyzed by Pd catalysts, e.g. by Pd(0) catalysts like tetrakis(triphenylphosphine)palladium(0) [Pd(PPh$_3$)$_4$], tris(dibenzylideneacetone)di-palladium(0) [Pd$_2$(dba)$_3$], or by Pd(II) catalysts like dichlorobis(triphenylphosphine)-palladium(II) [Pd(PPh$_3$)$_2$Cl$_2$], palladium(II) acetate and triphenylphosphine or by [1,1'-bis(diphenylphosphino)ferrocene]palladium dichloride [Pd(dppf)C12]. The reaction is preferably carried out in a mixture of a solvent like 1,2-dimethoxyethane, dioxane, DMF, DME, THF, or isopropanol with water and in the presence of a base like aqueous potassium carbonate, aqueous sodium bicarbonate or potassium phosphate.

In the second step, a compound of formula (18) is reacted with a suitable aniline of formula (4) to give the corresponding cross-coupling product of formula (19). The compounds of formula (19) can be prepared by Palladium-catalyzed C—N cross-coupling reactions (for a review on C—N cross-coupling reactions see for example: a) L. Jiang, S. L. Buchwald in 'Metal-Catalyzed Cross-Coupling Reactions', 2$^{nd}$ ed.: A. de Meijere, F. Diederich, Eds.: Wiley-VCH: Weinheim, Germany, 2004). Preferred is the use of suitable palladium precatalysts based upon biarylmonphosphines that are easily activated and ensure the formation of the active monoligated Pd(0) complex (see for examples a) S. L. Buchwald et al, J. Am. Chem. Soc. 2008, 130, 6686; b) S. L. Buchwald et al, J. Am. Chem. Soc. 2008, 130, 13552). The reactions are run in the presence of a weak base at elevated temperatures (see for example: a) S. L: Buchwald et al, Tet. Lett. 2009, 50, 3672). Most preferred is the herein described use of chloro(2-dicyclohexylphosphino-2',4',6'-tri-iso-propyl-1,1'-biphenyl)[2-(2-aminoethyl)phenyl]palladium(II) methyl-tert-butylether adduct, 2-dicyclohexylphosphino-2',4',6'-triisopropylbiphenyl and potassium phosphate in toluene and 1-methylpyrrolidin-2-one. The reactions are preferably run under argon for 3 hours at 130° C. in a microwave oven or in an oil bath.

In the third step the ortho-flourine substituent in 4-position of the compound of formula (19) is replaced by a suitable alkoxy group —OR$^8$. The reaction is preferably carried out by adding at least two equivalents of sodium hydride to a solution of compound (19) in the respective alcohol (20) at 60° C. to give the desired N-unprotected sulfoximines of formula (21).

Preparation of Compounds:

Abbreviations used in the description of the chemistry and in the Examples that follow are:

CDCl$_3$ (deuterated chloroform); cHex (cyclohexane); d (doublet); DCM (dichloromethane); DIPEA (di-iso-propyl-ethylamine); DME (1,2-dimethoxyethane), DMF (dimethylformamide); DMSO (dimethyl sulfoxide); eq (equivalent); ES (electrospray); EtOAc (ethyl acetate); EtOH (ethanol); iPrOH (iso-propanol); mCPBA (meta-chloroperoxybenzoic acid), MeCN (acetonitrile), MeOH (methanol); MS (mass spectrometry); NBS (N-bromosuccinimide), NMR (nuclear magnetic resonance); p (pentet); Pd(dppf)C12 ([1,1'-bis(diphenylphosphino)ferrocene]dichloro palladium(II) complex with dichloromethane); iPrOH (iso-propanol); q (quartet); RT (room temperature); s (singlet); sat. aq. (saturated aqueous); SiO$_2$ (silica gel); TFA (trifluoroacetic acid); TFAA (trifluoroacetic anhydride), THF (tetrahydrofuran); tr (triplet).

The IUPAC names of the examples were generated using the program 'ACD/Name batch version 12.01' from ACD LABS.

Example 1

(rac)-Ethyl[(3-{[5-fluoro-4-(4-fluoro-2-methoxyphenyl)pyrimidin-2-yl]amino}benzyl)(methyl)-oxido-λ$^6$-sulfanylidene]carbamate

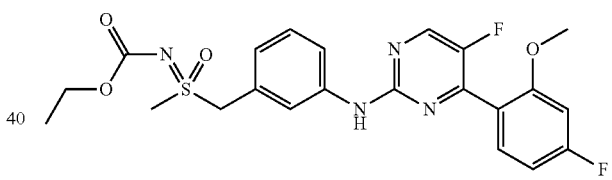

Preparation of Intermediate 1.1

1-[(Methylsulfanyl)methyl]-3-nitrobenzene

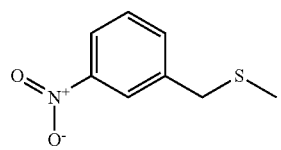

Sodium methanethiolate (13.5 g; 192 mmol) was added in two portions to a stirred solution of 1-(chloromethyl)-3-nitrobenzene (30.0 g; 175 mmol; Aldrich Chemical Company Inc.) in ethanol (360 mL) at −15° C. The cold bath was removed and the batch was stirred at room temperature for 3 hours. The batch was diluted with saturated aqueous sodium chloride solution and extracted with ethyl acetate (2×). The combined organic phases were washed with water, dried (sodium sulfate), filtered and concentrated to give the desired product (32.2 g) that was used without further purification.

¹H NMR (400 MHz, CDCl₃, 300K) δ=8.18 (m, 1H), 8.11 (m, 1H), 7.66 (m, 1H), 7.50 (m, 1H), 3.75 (s, 2H), 2.01 (s, 3H).

Preparation of Intermediate 1.2

(rac)-1-[(Methylsulfinyl)methyl]-3-nitrobenzene

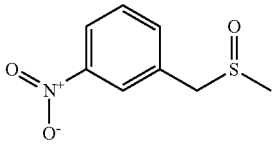

Iron(III)chloride (0.55 g; 3.4 mmol) was added to a solution of 1-[(methylsulfanyl)methyl]-3-nitrobenzene (21.6 g; 117.9 mmol) in MeCN (280 mL) and the batch was stirred at room temperature for 10 minutes. Periodic acid (28.8 g; 126.1 mmol) was added under stirring in one portion and the temperature was kept below 30° C. by cooling. The batch was stirred at room temperature for 90 minutes before it was added to a stirred solution of sodium thiosulfate pentahydrate (163 g; 660 mmol) in ice water (1500 mL). The batch was saturated with solid sodium chloride and extracted with THF (2×).

The combined organic phases were washed with saturated aqueous sodium chloride solution, dried (sodium sulfate), filtered and concentrated. The residue was purified by chromatography (DCM/ethanol 95:5) to give the desired product (16.6 g; 83.1 mmol).

¹H NMR (400 MHz, CDCl₃, 300K) δ=8.21 (m, 1H), 8.17 (m, 1H), 7.67 (m, 1H), 7.58 (m, 1H), 4.10 (d, 1H), 3.97 (d, 1H), 2.53 (s, 3H).

Preparation of Intermediate 1.3

(rac)-2,2,2-Trifluoro-N-[methyl(3-nitrobenzyl)oxido-λ⁶-sulfanylidene]acetamide

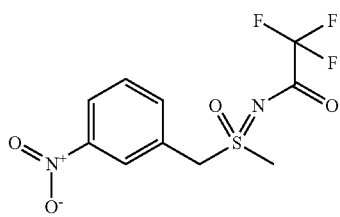 [SMILES: CS(=O)(Cc1cccc([N+](=O)[O-])c1)=NC(=O)C(F)(F)F]

To a suspension of (rac)-1-[(methylsulfinyl)methyl]-3-nitrobenzene (16.6 g; 83.1 mmol), trifluoroacetamide (18.8 g; 166.1 mmol), magnesium oxide (13.4 g; 332.3 mmol) and rhodium(II)-acetate dimer (1.7 g; 8.3 mmol) in DCM (2290 mL) was added iodobenzene diacetate (40.1 g; 124.6 mmol) at room temperature. The batch was stirred for 16 hours at room temperature, filtered and concentrated. The residue was purified by chromatography (DCM/ethanol 97:3) to give the desired product (25.6 g; 82.4 mmol).

¹H NMR (400 MHz, CDCl₃, 300K) δ=8.36 (m, 1H), 8.31 (m, 1H), 7.80 (m, 1H), 7.69 (m, 1H), 4.91 (d, 1H), 4.79 (d, 1H), 3.28 (s, 3H).

Preparation of Intermediate 1.4

(rac)-1-[(S-Methylsulfonimidoyl)methyl]-3-nitrobenzene

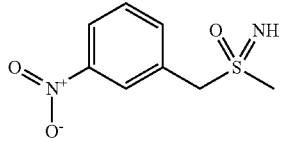

Potassium carbonate (56.9 g; 411.8 mmol) was added to a solution of (rac)-2,2,2-trifluoro-N-[methyl(3-nitrobenzyl)oxido-λ⁶-sulfanylidene]acetamide (25.6 g; 82.4 mmol) in MeOH (1768 mL) at room temperature. The batch was stirred for 1 hour at room temperature before it was diluted with ethyl acetate and saturated aqueous sodium chloride solution. After extraction with ethyl acetate (2×) the combined organic phases were dried (sodium sulfate), filtered and concentrated to give the desired product (13.9 g; 65.1 mmol).

¹H NMR (400 MHz, CDCl₃, 300K) δ=8.29 (m, 2H), 7.79 (m, 1H), 7.63 (m, 1H), 4.47 (d, 1H), 4.34 (d, 1H), 2.99 (s, 3H), 2.66 (br, 1H).

Preparation of Intermediate 1.5

(rac)-Ethyl[methyl(3-nitrobenzyl)oxido-λ⁶-sulfanylidene]carbamate

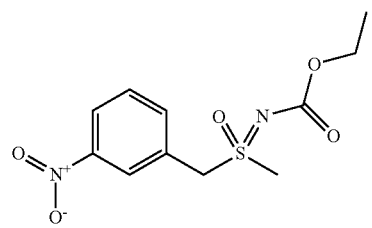 [SMILES: CCOC(=O)N=S(C)(=O)Cc1cccc([N+](=O)[O-])c1]

Ethyl chlorocarbonate (8.1 mL; 84.6 mmol) was added dropwise to a stirred solution of (rac)-1-[(S-methylsulfonimidoyl)methyl]-3-nitrobenzene (13.9 g; 65.1 mmol) in pyridine (615 mL) at 0° C. The batch was slowly warmed to room temperature. After 24 hours the batch was concentrated and the residue was dissolved in ethyl acetate and washed with saturated aqueous sodium chloride solution. The organic phase was filtered using a Whatman filter and concentrated to give the desired product (19.7 g) that was used without further purification.

¹H NMR (400 MHz, CDCl₃, 300K) δ=8.30 (m, 2H), 7.81 (m, 1H), 7.64 (m, 1H), 4.88 (d, 1H), 4.79 (d, 1H), 4.18 (q, 2H), 3.07 (s, 3H), 1.31 (tr, 3H).

Preparation of Intermediate 1.6

(rac)-Ethyl[(3-aminobenzyl)(methyl)oxido-λ⁶-sulfanylidene]carbamate

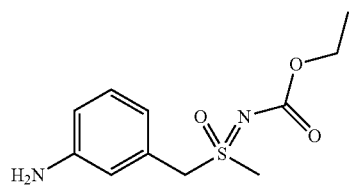 [SMILES: CCOC(=O)N=S(C)(=O)Cc1cccc(N)c1]

Titanium(III)chloride solution (about 15% in about 10% hydrochloric acid, 118 mL; Merck Schuchardt OHG) was added to a stirred solution of (rac)-ethyl[methyl(3-nitrobenzyl)oxido-λ$^6$-sulfanylidene]carbamate (5.0 g; 17.5 mmol) in THF (220 mL) at room temperature. The batch was stirred for 18 hours. By adding 2N sodium hydroxide solution the pH value of the reaction mixture, that was cooled with an ice bath, was raised to 8. The batch was saturated with solid sodium chloride and extracted with ethyl acetate (3×). The combined organic phases were washed with saturated aqueous sodium chloride solution, dried (sodium sulfate), filtered and concentrated to give the desired product (4.2 g) that was used without further purification.

$^1$H NMR (400 MHz, d$_6$-DMSO, 300K) δ=7.00 (m, 1H), 6.53 (m, 3H), 5.18 (br, 2H), 4.62 (s, 2H), 3.95 (m, 2H), 3.08 (s, 3H). 1.13 (tr, 3H).

Preparation of Intermediate 1.7

2-Chloro-5-fluoro-4-(4-fluoro-2-methoxyphenyl)pyrimidine

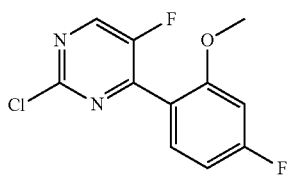 [SMILES: COc1cc(F)ccc1-c1nc(Cl)ncc1F]

A batch with 2,4-dichloro-5-fluoropyrimidine (200 mg; 1.20 mmol; Aldrich Chemical Company Inc.), (4-fluoro-2-methoxyphenyl)boronic acid (224 mg; 1.31 mmol; Aldrich Chemical Company Inc.) and tetrakis(triphenylphosphin)palladium(0) (138 mg; 0.12 mmol) in 1,2-dimethoxyethane (3.6 ml) and 2M solution of potassium carbonate (1.8 ml) was degassed using argon. The batch was stirred under argon for 16 hours at 90° C. After cooling the batch was diluted with ethyl acetate and washed with saturated aqueous sodium chloride solution. The organic phase was filtered using a Whatman filter and concentrated. The residue was purified by column chromatography (hexane/ethyl acetate 1:1) to give the desired product (106 mg; 0.41 mmol).

$^1$H NMR (400 MHz, CDCl$_3$, 300K) δ=8.47 (m, 1H), 7.51 (m, 1H), 6.82 (m, 1H), 6.73 (m, 1H), 3.85 (s, 3H).

Preparation of End Product:

A batch with (rac)-ethyl[(3-aminobenzyl)(methyl)oxido-λ$^6$-sulfanylidene]carbamate (346 mg; 1.35 mmol), 2-chloro-5-fluoro-4-(4-fluoro-2-methoxyphenyl)pyrimidine (450 mg; 1.75 mmol), chloro(2-dicyclohexylphosphino-2',4',6'-tri-isopropyl-1,1'-biphenyl)[2-(2-aminoethyl)phenyl]palladium(II) methyl-tert-butylether adduct (84 mg; 0.10 mmol; ABCR GmbH & CO. KG), 2-dicyclohexylphosphino-2',4',6'-triisopropylbiphenyl (48 mg; 0.10 mmol; Aldrich Chemical Company Inc.) and potassium phosphate (1431 mg; 6.7 mmol) in toluene (18.0 ml) and 1-methylpyrrolidin-2-one (2.4 ml) was degassed using argon. The batch was stirred under argon for 3 hours at 130° C. in a microwave oven. After cooling, the batch was diluted with saturated aqueous sodium chloride solution and extracted with ethyl acetate (2×). The combined organic phases were filtered using a Whatman filter and concentrated. The residue was purified by chromatography (DCM/EtOH 95:5) to give the desired product (208 mg; 0.44 mmol).

$^1$H NMR (400 MHz, CDCl$_3$, 300K) δ=8.30 (m, 1H), 7.86 (br, 1H), 7.56 (m, 1H), 7.47 (m, 1H), 7.36 (m, 1H), 7.24 (br, 1H), 7.06 (m, 1H), 6.82 (m, 1H), 6.75 (m, 1H), 4.71 (s, 2H), 4.17 (q, 2H), 3.86 (s, 3H), 2.96 (s, 3H), 1.31 (tr, 3H).

Example 2

(rac)-5-Fluoro-4-(4-fluoro-2-methoxyphenyl)-N-{3-[(S-methylsulfonimidoyl)methyl]phenyl}-pyrimidin-2-amine

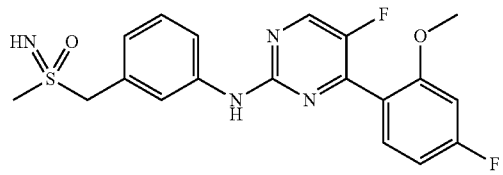 [SMILES: COc1cc(F)ccc1-c1nc(Nc2cccc(CS(C)(=N)=O)c2)ncc1F]

A freshly prepared 1.5M solution of sodium ethanolate in EtOH (0.37 mL; 0.56 mmol) was added under argon to a solution of (rac)-ethyl[(3-{[5-fluoro-4-(4-fluoro-2-methoxyphenyl)pyrimidin-2-yl]-amino}benzyl)(methyl)oxido-λ$^6$-sulfanylidene]carbamate (53 mg; 0.11 mmol) in EtOH (1.0 mL). The batch was stirred at 60° C. for 5 hours. After cooling the batch was diluted with saturated aqueous sodium chloride solution and extracted with ethyl acetate (3×). The combined organic phases were filtered using a Whatman filter and concentrated. The residue was purified by chromatography (DCM/EtOH 95:5) to give the desired product (33 mg; 0.08 mmol).

$^1$H NMR (400 MHz, CDCl$_3$, 300K) δ=8.30 (m, 1H), 7.78 (br, 1H), 7.59 (m, 1H), 7.48 (m, 1H), 7.35 (m, 1H), 7.24 (s, 1H), 7.05 (m, 1H), 6.81 (m, 1H), 6.75 (m, 1H), 4.37 (d, 1H), 4.25 (d, 1H), 3.86 (s, 3H), 2.92 (s, 3H), 2.65 (br, 1H).

Example 3

(rac)-Ethyl{[3-({4-[2-(benzyloxy)-4-fluorophenyl]-5-fluoropyrimidin-2-yl}amino)benzyl](methyl)-oxido-λ$^6$-sulfanylidene}carbamate

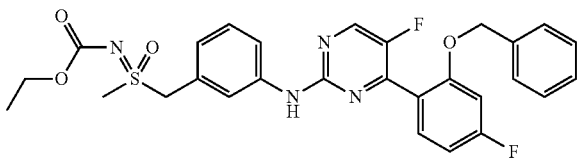 [SMILES: CCOC(=O)N=S(C)(=O)Cc1cccc(Nc2ncc(F)c(-c3ccc(F)cc3OCc3ccccc3)n2)c1]

Preparation of Intermediate 3.1

4-[2-(Benzyloxy)-4-fluorophenyl]-2-chloro-5-fluoropyrimidine

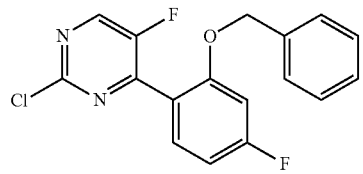 [SMILES: Fc1ccc(-c2nc(Cl)ncc2F)c(OCc2ccccc2)c1]

Intermediate 3.1 was prepared under similar conditions as described in the preparation of Intermediate 1.7 using 2,4- dichloro-5-fluoropyrimidine (Aldrich Chemical Company Inc.) and [2-(benzyloxy)-4-fluorophenyl]boronic acid (ABCR GmbH & CO. KG). The batch was purified by column chromatography (hexane/ethyl acetate 1:1).

$^1$H NMR (400 MHz, CDCl$_3$, 300K) δ=8.44 (m, 1H), 7.54 (m, 1H), 7.35 (m, 5H), 6.83 (m 1H), 6.79 (m, 1H), 5.11 (s, 2H).

Preparation of End Product:

Example 3 was prepared under similar conditions as described in the preparation of Example 1 using 4-[2-(benzyloxy)-4-fluorophenyl]-2-chloro-5-fluoropyrimidine and (rac)-ethyl[(3-aminobenzyl)(methyl)-oxido-λ$^6$-sulfanylidene]carbamate. The batch was purified by column chromatography (hexane/ethyl acetate 1:4).

$^1$H NMR (400 MHz, CDCl$_3$, 300K) δ=8.29 (m, 1H), 7.85 (br, 1H), 7.51 (m, 2H), 7.33 (m, 6H), 7.23 (s, 1H), 7.05 (m, 1H), 6.81 (m, 2H), 5.12 (s, 2H), 4.69 (s, 2H), 4.16 (q, 2H), 2.95 (s, 3H), 1.30 (tr, 3H).

Example 4

(rac)-4-[2-(Benzyloxy)-4-fluorophenyl]-5-fluoro-N-{3-[(S-methylsulfonimidoyl)methyl]phenyl}-pyrimidin-2-amine

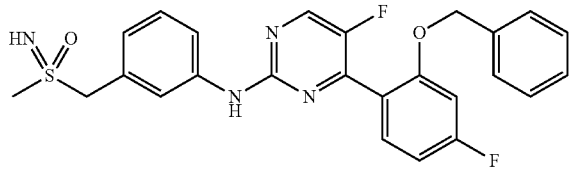 [SMILES: CS(=N)(=O)Cc1cccc(Nc2ncc(F)c(-c3ccc(F)cc3OCc3ccccc3)n2)c1]

Example 4 was prepared under similar conditions as described in the preparation of Example 2 using (rac)-ethyl{[3-({4-[2-(benzyloxy)-4-fluorophenyl]-5-fluoropyrimidin-2-yl}amino)benzyl](methyl)oxido-λ$^6$-sulfanylidene}carbamate. The batch was purified by column chromatography (DCM/EtOH 9:1).

$^1$H NMR (400 MHz, CDCl$_3$, 300K) δ=8.29 (m, 1H), 7.78 (br, 1H), 7.58 (m, 1H), 7.51 (m, 1H), 7.32 (m, 6H), 7.19 (s, 1H), 7.05 (m, 1H), 6.81 (m, 2H), 5.13 (s, 2H), 4.35 (d, 1H), 4.24 (d, 1H), 2.91 (s, 3H), 2.66 (br, 1H).

Example 5

(rac)-Ethyl[(3-{[4-(3,4-dihydro-2H-chromen-8-yl)-5-fluoropyrimidin-2-yl]amino}benzyl)(methyl)-oxido-λ$^6$-sulfanylidene]carbamate

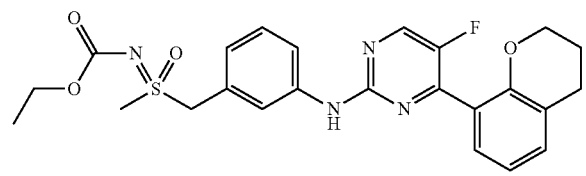 [SMILES: CCOC(=O)N=S(C)(=O)Cc1cccc(Nc2ncc(F)c(-c3cccc4c3OCCC4)n2)c1]

Preparation of Intermediate 5.1

2-Chloro-4-(3,4-dihydro-2H-chromen-8-yl)-5-fluoropyrimidine

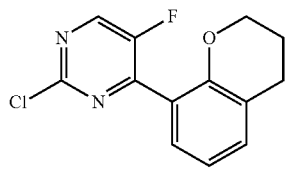 [SMILES: Fc1cnc(Cl)nc1-c1cccc2c1OCCC2]

A batch with 2,4-dichloro-5-fluoropyrimidine (565 mg; 3.28 mmol; Aldrich Chemical Company Inc.), 3,4-dihydro-2H-chromen-8-ylboronic acid (643 mg; 3.61 mmol; Parkway Scientific LLC) and bis(triphenylphosphine)palladium(II) chloride (230 mg; 0.33 mmol; Aldrich Chemical Company Inc.) in 1,2-dimethoxyethane (5.4 ml) and 2M solution of potassium carbonate (4.9 ml) was degassed using argon. The batch was stirred under argon for 16 hours at 90° C. After cooling the batch was diluted with ethyl acetate and washed with saturated aqueous sodium chloride solution. The organic phase was dried (sodium sulfate), filtered and concentrated. The residue was purified by chromatography (hexane/ethyl acetate 2%-20%) to give the desired product (701 mg; 2.57 mmol).

$^1$H NMR (400 MHz, CDCl$_3$, 300K) δ=8.44 (m, 1H), 7.31 (m, 1H), 7.21 (m, 1H), 6.97 (m, 1H), 4.20 (tr, 2H), 2.86 (tr, 2H), 2.04 (m, 2H).

Preparation of end product

Example 5 was prepared under similar conditions as described in the preparation of Example 1 using 2-chloro-4-(3,4-dihydro-2H-chromen-8-yl)-5-fluoropyrimidine and (rac)-ethyl[(3-aminobenzyl)(methyl)-oxido-λ$^6$-sulfanylidene]carbamate. The batch was purified by preparative HPLC.

| System: | Waters Autopurificationsystem: Pump 2545, Sample Manager 2767, CFO, DAD 2996, ELSD 2424, SQD 3001 |
|---|---|
| Column: | XBrigde C18 5 µm 100 × 30 mm |
| Solvent: | A = H$_2$O + 0.1% HCOOH |
| | B = MeCN |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO or DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.29 (m, 1H), 7.87 (br, 1H), 7.53 (m, 1H), 7.35 (m, 1H), 7.27 (m, 1H), 7.25 (m,

1H), 7.18 (m, 1H), 7.06 (m, 1H), 6.96 (m, 1H), 4.71 (s, 2H), 4.21 (m, 2H), 4.17 (q, 2H), 2.94 (s, 3H), 2.88 (tr, 2H), 2.05 (m, 2H), 1.31 (tr, 3H).

Example 6

(rac)-4-(3,4-Dihydro-2H-chromen-8-yl)-5-fluoro-N-{3-[(S-methylsulfonimidoyl)methyl]phenyl}-pyrimidin-2-amine

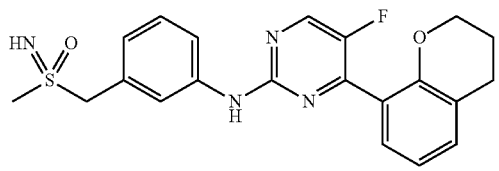 [SMILES: CS(=N)(=O)Cc1cccc(Nc2ncc(F)c(-c3cccc4c3OCCC4)n2)c1]

Example 6 was prepared under similar conditions as described in the preparation of Example 2 using (rac)-ethyl [(3-{[4-(3,4-dihydro-2H-chromen-8-yl)-5-fluoropyrimidin-2-yl]amino}benzyl)(methyl)oxido-λ⁶-sulfanylidene]carbamate. The batch was purified by preparative HPLC.

| System: | Waters Autopurificationsystem: Pump 2545, Sample Manager 2767, CFO, DAD 2996, ELSD 2424, SQD 3001 |
|---|---|
| Column: | XBrigde C18 5 μm 100 × 30 mm |
| Solvent: | A = H₂O + 0.1% HCOOH |
| | B = MeCN |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO or DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl₃, 300K) δ=8.28 (m, 1H), 7.80 (br, 1H), 7.59 (m, 1H), 7.34 (m, 1H), 7.28 (m, 2H), 7.18 (m, 1H), 7.04 (m, 1H), 6.96 (m, 1H), 4.35 (d, 1H), 4.23 (m, 3H), 2.90 (s, 3H), 2.87 (tr, 2H), 2.05 (m, 2H).

Example 7

(rac)-{[3-({4-[2-(Benzyloxy)-4-fluorophenyl]-5-fluoropyrimidin-2-yl}amino)benzyl](methyl)oxido-λ⁶-sulfanylidene}cyanamide

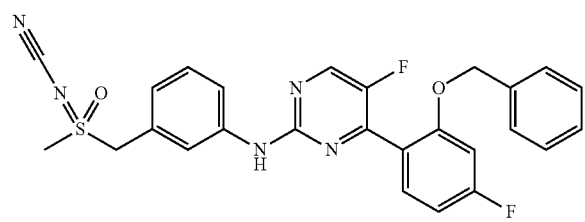 [SMILES: CS(=O)(Cc1cccc(Nc2ncc(F)c(-c3ccc(F)cc3OCc3ccccc3)n2)c1)=NC#N]

Preparation of Intermediate 7.1

4-[2-(Benzyloxy)-4-fluorophenyl]-5-fluoro-N-{3-[(methylsulfanyl)methyl]phenyl}pyrimidin-2-amine

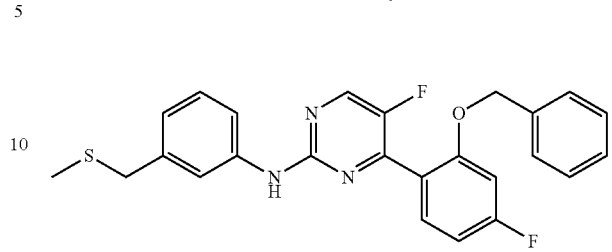

A 4N solution of hydrogen chloride in dioxane (0.34 mL; 1.35 mmol) was added to a stirred solution of 4-[2-(benzyloxy)-4-fluorophenyl]-2-chloro-5-fluoropyrimidine (450 mg; 1.35 mmol) and 3-[(methylsulfanyl)methyl]aniline (311 mg; 2.03 mmol) in 1-butanol (3.00 mL). The batch was stirred at 140° C. for 16 hours. After cooling the batch was diluted with ethyl acetate and washed with aqueous sodium bicarbonate solution and saturated aqueous sodium chloride solution. The organic phase was filtered using a Whatman filter and concentrated. The residue was purified by preparative HPLC to give the desired product (167 mg; 0.37 mmol).

| System: | Waters Autopurificationsystem: Pump 2545, Sample Manager 2767, CFO, DAD 2996, ELSD 2424, SQD 3001 |
|---|---|
| Column: | XBrigde C18 5 μm 100 × 30 mm |
| Solvent: | A = H₂O + 0.1% HCOOH |
| | B = MeCN |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO or DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl₃, 300K) δ=8.29 (m, 1H), 7.60 (br, 1H), 7.52 (m, 2H), 7.30 (m, 6H), 7.14 (s, 1H), 6.96 (m, 1H), 6.80 (m, 2H), 5.12 (s, 2H), 3.67 (s, 2H), 2.00 (s, 3H).

Preparation of End Product:

2-Bromo-1H-isoindole-1,3(2H)-dione (22.0 mg; 0.12 mmol) was added to a solution of 4-[2-(benzyloxy)-4-fluorophenyl]-5-fluoro-N-{3-[(methylsulfanyl)methyl]phenyl}pyrimidin-2-amine (37.0 mg; 0.08 mmol), cyanamide (4.5 mg; 0.11 mmol) and potassium 2-methylpropan-2-olate (11.1 mg; 0.10 mmol) in MeOH (0.44 mL) at RT. The batch was stirred for 4 hours before it was diluted with DCM and aqueous sodium thiosulfate solution. The batch was extracted with DCM (2×). The combined organic phases were filtered using a Whatman filter and concentrated to give crude (rac)-[[3-({4-[2-(benzyloxy)-4-fluorophenyl]-5-fluoropyrimidin-2-yl}amino)benzyl](methyl)-λ⁴-sulfanylidene]-cyanamide that was used without further purification.

The residue was taken up in EtOH (1.30 mL) and the resulting solution was cooled to 0° C. Potassium carbonate (55.9 mg; 0.40 mmol) and 3-chlorobenzenecarboperoxoic acid (49.9 mg; 0.20 mmol) were added to the stirred solution. The ice bath was removed and the batch was slowly warmed to room temperature. After 5 hours, the batch was diluted with DCM and saturated aqueous sodium chloride solution. The organic phases was filtered using a Whatman filter and concentrated. The residue was purified by preparative HPLC to give the desired product.

| | |
|---|---|
| System: | Waters Autopurificationsystem: Pump 254, Sample Manager 2767, CFO, DAD 2996, ELSD 2424, SQD 3100 |
| Column: | XBrigde C18 5 μm 100 × 30 mm |
| Solvent: | A = H$_2$O + 0.2% Vol. NH$_3$ (99%) |
| | B = Acetonitril |
| Gradient: | 0-1 min 30% B, 1-8 min 30-80% B |
| Flow: | 50 mL/min |
| Temperatuer: | RT |
| Detection: | DAD scan range 210-400 nm |
| | MS ESI+, ESI−, scan range 160-1000 m/z |
| | ELSD |
| Retention: | 7.0-7.2 min |
| MS(ES+): | m/z = 505 |

$^1$H NMR (400 MHz, CDCl$_3$, 300K) δ=8.32 (m, 1H), 7.96 (br, 1H), 7.51 (m, 2H), 7.35 (m, 7H), 7.06 (m, 1H), 6.82 (m, 2H), 5.13 (s, 2H), 4.57 (s, 2H), 2.97 (s, 3H).

Example 8

(rac)-1-[(3-{[5-Fluoro-4-(4-fluoro-2-methoxyphenyl)pyrimidin-2-yl]amino}benzyl)(methyl)oxido-λ$^6$-sulfanylidene]-3-methylurea

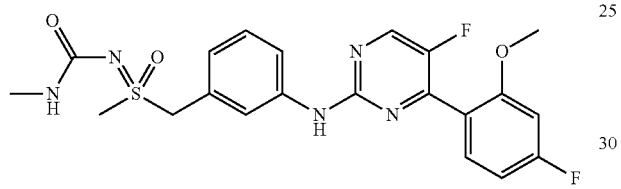

Isocyanatomethane (7.3 μL; 0.12 mmol) was added to a solution of (rac)-5-fluoro-4-(4-fluoro-2-methoxyphenyl)-N-{3-[(S-methylsulfonimidoyl)methyl]phenyl}pyrimidin-2-amine (50 mg; 0.12 mmol) in DMF (2.0 mL) and triethylamine (17.2 μL; 0.12 mmol) at RT. The batch was stirred for 17 hours at RT. The batch was diluted with saturated aqueous sodium chloride solution and extracted with ethyl acetate (2×). The combined organic phases were filtered using a Whatman filter and concentrated. The residue was purified by chromatography (DCM/EtOH 95:5) to give the desired product (24 mg; 0.05 mmol).

$^1$H NMR (400 MHz, CDCl$_3$, 300K) δ=8.30 (m, 1H), 7.78 (m, 1H), 7.62 (m, 1H), 7.48 (m, 1H), 7.34 (m, 1H), 7.28 (br, 1H), 7.06 (m, 1H), 6.82 (m, 1H), 6.75 (m, 1H), 4.96 (m, 1H), 4.82 (d, 1H), 4.58 (d, 1H), 3.86 (s, 3H), 2.98 (m, 3H), 2.78 (d, 3H).

Example 9

(rac)-Ethyl[(3-fluoro-5-{[5-fluoro-4-(4-fluoro-2-methoxyphenyl)pyrimidin-2-yl]amino}benzyl)-(methyl)oxido-λ$^6$-sulfanylidene]carbamate

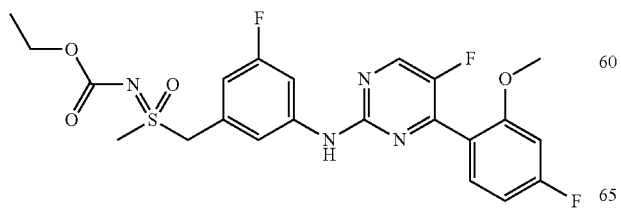

Preparation of Intermediate 9.1

1-Fluoro-3-[(methylsulfanyl)methyl]-5-nitrobenzene

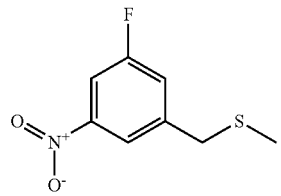

Intermediate 9.1 was prepared under similar conditions as described in the preparation of Intermediate 1.1 using 1-(chloromethyl)-3-fluoro-5-nitrobenzene (Hansa Fine Chemicals GmbH).

$^1$H NMR (400 MHz, CDCl$_3$, 300K) δ=8.00 (m, 1H), 7.82 (m, 1H), 7.44 (m, 1H), 3.74 (s, 2H), 2.03 (s, 3H).

Preparation of Intermediate 9.2

(rac)-1-Fluoro-3-[(methylsulfinyl)methyl]-5-nitrobenzene

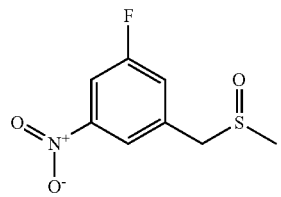

Intermediate 9.2 was prepared under similar conditions as described in the preparation of Intermediate 1.2 using 1-fluoro-3-[(methylsulfanyl)methyl]-5-nitrobenzene.

$^1$H NMR (400 MHz, d$_6$-DMSO, 300K) δ=8.06 (m, 2H), 7.63 (m, 1H), 4.32 (d, 1H), 4.08 (d, 1H), 2.45 (s, 3H).

Preparation of Intermediate 9.3: (rac)-2,2,2-trifluoro-N-[(3-fluoro-5-nitrobenzyl)(methyl)oxido-λ$^6$-sulfanylidene]acetamide

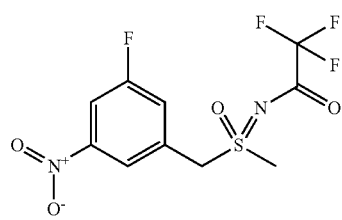 [SMILES: CS(=O)(Cc1cc(F)cc([N+](=O)[O-])c1)=NC(=O)C(F)(F)F]

Intermediate 9.3 was prepared under similar conditions as described in the preparation of Intermediate 1.3 using (rac)-1-fluoro-3-[(methylsulfinyl)methyl]-5-nitrobenzene.

$^1$H NMR (400 MHz, CDCl$_3$, 300K) δ=8.13 (m, 1H) 8.07 (m, 1H), 7.56 (m, 1H), 4.92 (d, 1H), 4.76 (d, 1H), 3.33 (s, 3H).

Preparation of Intermediate 9.4

(rac)-1-Fluoro-3-[(S-methylsulfonimidoyl)methyl]-5-nitrobenzene

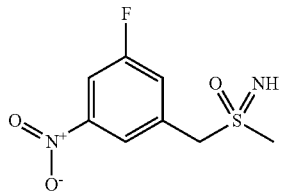

Intermediate 9.4 was prepared under similar conditions as described in the preparation of Intermediate 1.4 using (rac)-2,2,2-trifluoro-N-[(3-fluoro-5-nitrobenzyl)(methyl)oxido-$\lambda^6$-sulfanylidene]acetamide.

$^1$H NMR (400 MHz, CDCl$_3$, 300K) δ=8.19 (m, 1H), 8.08 (m, 1H), 7.76 (m, 1H), 4.60 (d, 1H), 4.49 (d, 1H), 3.85 (s, 1H), 2.79 (s, 3H).

Preparation of Intermediate 9.5

(rac)-Ethyl[(3-fluoro-5-nitrobenzyl)(methyl)oxido-$\lambda^6$-sulfanylidene]carbamate

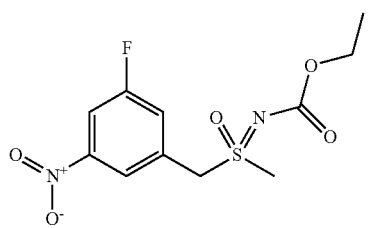 [SMILES: CCOC(=O)N=S(C)(=O)Cc1cc(F)cc([N+](=O)[O-])c1]

Intermediate 9.5 was prepared under similar conditions as described in the preparation of Intermediate 1.5 using (rac)-1-fluoro-3-[(S-methylsulfonimidoyl)methyl]-5-nitrobenzene.

$^1$H NMR (400 MHz, CDCl$_3$, 300K) δ=8.11 (m, 1H), 8.02 (m, 1H), 7.57 (m, 1H), 4.90 (d, 1H), 4.759 (d, 1H), 4.18 (q, 2H), 3.12 (s, 3H), 1.31 (tr, 3H).

Preparation of Intermediate 9.6

(rac)-Ethyl[(3-amino-5-fluorobenzyl)(methyl)oxido-$\lambda^6$-sulfanylidene]carbamate

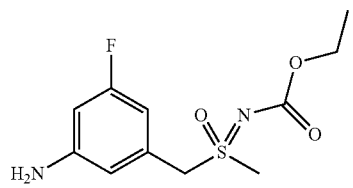 [SMILES: CCOC(=O)N=S(C)(=O)Cc1cc(N)cc(F)c1]

Intermediate 9.6 was prepared under similar conditions as described in the preparation of Intermediate 1.6 using (rac)-ethyl[(3-fluoro-5-nitrobenzyl)(methyl)oxido-$\lambda^6$-sulfanylidene]carbamate.

$^1$H NMR (400 MHz, CDCl$_3$, 300K) δ=6.49 (m, 3H), 4.58 (m, 2H), 4.17 (q, 2H), 3.91 (s, 2H), 3.00 (s, 3H), 1.31 (tr, 3H).

Preparation of End Product:

Example 9 was prepared under similar conditions as described in the preparation of Example 1 using 2-chloro-5-fluoro-4-(4-fluoro-2-methoxyphenyl)pyrimidine and (rac)-ethyl[(3-amino-5-fluorobenzyl)-(methyl)oxido-$\lambda^6$-sulfanylidene]carbamate. The batch was purified by chromatography (DCM/EtOH 95:5).

$^1$H NMR (400 MHz, CDCl$_3$, 300K) δ=8.34 (m, 1H), 7.69 (m, 1H), 7.47 (m, 1H), 7.35 (m, 2H), 6.78 (m, 3H), 4.68 (m, 2H), 4.17 (q, 2H), 3.87 (s, 3H), 3.00 (s, 3H), 1.31 (tr, 3H).

Example 10

(rac)-5-Fluoro-4-(4-fluoro-2-methoxyphenyl)-N-{3-fluoro-5-[(S-methylsulfonimidoyl)methyl]-phenyl}pyrimidin-2-amine

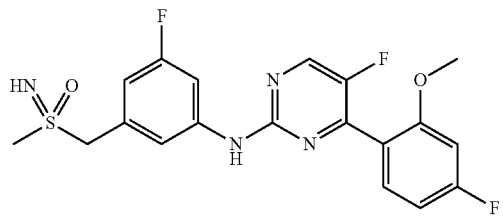

Example 10 was prepared under similar conditions as described in the preparation of Example 2 using (rac)-ethyl [(3-fluoro-5-{[5-fluoro-4-(4-fluoro-2-methoxyphenyl)pyrimidin-2-yl]amino}benzyl)(methyl)-oxido-$\lambda^6$-sulfanylidene]carbamate. The batch was purified by chromatography (DCM/EtOH 9:1).

$^1$H NMR (400 MHz, CDCl$_3$, 300K) δ=8.32 (m, 1H), 7.73 (m, 1H), 7.47 (m, 1H), 7.37 (br, 1H), 7.29 (br, 1H), 6.78 (m, 3H), 4.33 (d, 1H), 4.20 (d, 1H), 3.87 (s, 3H), 2.95 (s, 3H), 2.72 (s, 1H).

Example 11 and 12

Enantiomers of 5-fluoro-4-(4-fluoro-2-methoxyphenyl)-N-{3-[(S-methylsulfonimidoyl)methyl] phenyl}pyrimidin-2-amine

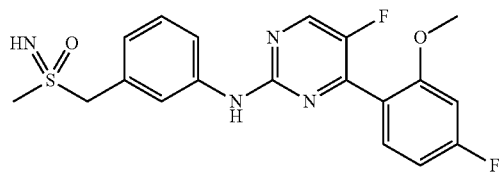 [SMILES: COc1cc(F)ccc1-c1nc(Nc2cccc(CS(C)(=N)=O)c2)ncc1F]

(rac)-5-Fluoro-4-(4-fluoro-2-methoxyphenyl)-N-{3-[(S-methylsulfonimidoyl)methyl]phenyl}pyrimidin-2-amine was separated into the enantiomers by preparative HPLC.

| System: | Dionex: Pump P 580, Gilson: Liquid Handler 215, Knauer: UV-Detektor K-2501 |
|---|---|
| Column: | Chiralcel OJ-H 5 µm 250 × 20 mm |
| Solvent: | EtOH/MeOH 50:50 (v/v) |
| Flow: | 15 mL/min |
| Temperature: | RT |
| Solution: | 35 mg/2.6 mL EtOH/MeOH 1:1 |
| Injection: | 2 × 1.3 mL |
| Detection: | UV 280 nm |

-continued

| | Retention time in min | purity in % |
|---|---|---|
| Example 11 Enantiomer 1 | 9.4-10.6 | 99.9 |
| Example 12 Enantiomer 2 | 10.6-12.6 | 97.5 |

Example 13 and 14

Enantiomers of 4-[2-(Benzyloxy)-4-fluorophenyl]-5-fluoro-N-{3-[(S-methylsulfonimidoyl)methyl]phenyl}-pyrimidin-2-amine

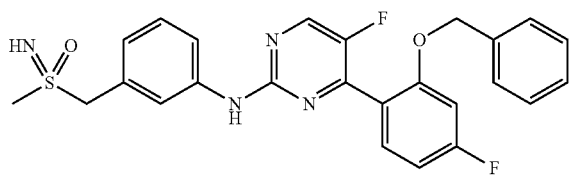 [SMILES: CS(=N)(=O)Cc1cccc(Nc2ncc(F)c(-c3ccc(F)cc3OCc3ccccc3)n2)c1]

(rac)-4-[2-(benzyloxy)-4-fluorophenyl]-5-fluoro-N-{3-[(S-methylsulfonimidoyl)methyl]phenyl}-pyrimidin-2-amine was separated into the enantiomers by preparative HPLC.

| System: | Dionex: Pump P 580, Gilson: Liquid Handler 215, Knauer: UV-Detektor K-2501 |
|---|---|
| Column: | Chiralcel OJ-H 5 µm 250 × 20 mm |
| Solvent: | EtOH/MeOH 50:50 (v/v) |
| Flow: | 15 mL/min |
| Temperature: | RT |
| Solution: | 45 mg/3.0 mL |
| Injection: | 2 × 1.5 mL |
| Detection: | UV 280 nm |

| | Retention time in min | purity in % |
|---|---|---|
| Example 13 Enantiomer 1 | 12.5-17.5 | 99.8 |
| Example 14 Enantiomer 2 | 19.2-25.6 | 99.7 |

Example 15 and 16

Enantiomers of 5-fluoro-4-(4-fluoro-2-methoxyphenyl)-N-{3-fluoro-5-[(S-methylsulfonimidoyl)methyl]phenyl}-pyrimidin-2-amine

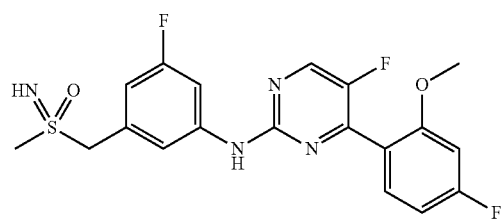 [SMILES: COc1cc(F)ccc1-c1nc(Nc2cc(F)cc(CS(C)(=N)=O)c2)ncc1F]

(rac)-5-Fluoro-4-(4-fluoro-2-methoxyphenyl)-N-{3-fluoro-5-[(S-methylsulfonimidoyl)methyl]phenyl}-pyrimidin-2-amine was separated into the enantiomers by preparative HPLC.

| System: | Dionex: Pump P 580, Gilson: Liquid Handler 215, Knauer: UV-Detektor K-2501 |
|---|---|
| Column: | Chiralpak IA 5 µm 250 × 30 mm |
| Solvent: | MeOH 100 (v/v) |
| Flow: | 50 mL/min |
| Temperature: | RT |
| Solution: | 1290 mg/8.0 mL DCM/MeOH |
| Injection: | 10 × 0.8 mL |
| Detection: | UV 280 nm |

| | Retention time in min | purity in % |
|---|---|---|
| Example 15 Enantiomer 1 | 7.4-11.2 | >99.9 |
| Example 16 Enantiomer 2 | 11.6-23.0 | 97.6 |

Example 17

(rac)-[(3-{[5-Fluoro-4-(4-fluoro-2-methoxyphenyl)pyrimidin-2-yl]amino}benzyl)(methyl)oxido-$\lambda^6$-sulfanylidene]cyanamide

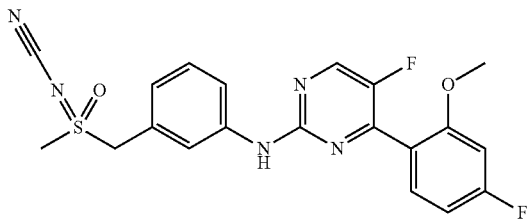

Preparation of Intermediate 17.1

5-Fluoro-4-(4-fluoro-2-methoxyphenyl)-N-{3-[(methylsulfanyl)methyl]phenyl}pyrimidin-2-amine

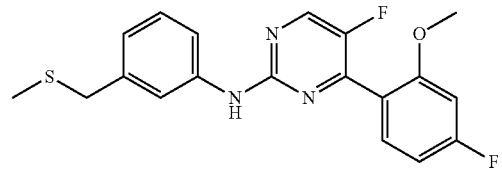 [SMILES: COc1cc(F)ccc1-c1nc(Nc2cccc(CSC)c2)ncc1F]

A 4N solution of hydrogen chloride in dioxane (0.61 mL; 2.45 mmol) was added to a stirred solution of 2-chloro-5-fluoro-4-(4-fluoro-2-methoxyphenyl)pyrimidine (630 mg; 2.45 mmol) and 3-[(methyl-sulfanyl)methyl]aniline (564 mg; 3.68 mmol) in 1-butanol (5.4 mL). The batch was stirred at 140° C. for 16 hours. After cooling the batch was diluted with ethyl acetate and washed with aqueous sodium bicarbonate solution and saturated aqueous sodium chloride solution. The organic phase was filtered using a Whatman filter and concentrated. The residue was purified by chromatography (hexane/ethyl acetate 2:1) to give the desired product (662 mg; 1.77 mmol).

¹H NMR (400 MHz, CDCl₃, 300K) δ=8.29 (m, 1H), 7.59 (m, 1H), 7.50 (m, 2H), 7.26 (m, 1H), 7.18 (br, 1H), 6.96 (m, 1H), 6.81 (m, 1H), 6.75 (m, 1H), 3.86 (s, 3H), 3.67 (s, 2H), 2.01 (s, 3H).

Preparation of Intermediate 17.2

[(3-{[5-Fluoro-4-(4-fluoro-2-methoxyphenyl)pyrimidin-2-yl]amino}benzyl)(methyl)-λ⁴-sulfanylidene]cyanamide

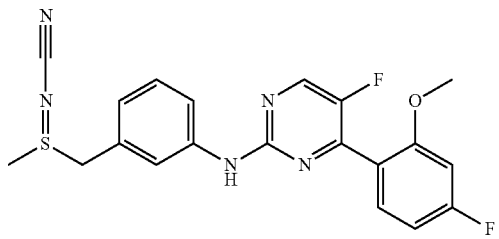 [SMILES: COc1cc(F)ccc1-c1nc(Nc2cccc(CS(C)=NC#N)c2)ncc1F]

Iodobenzene diacetete (626 mg; 1.94 mmol) was added to a stirred solution of 5-fluoro-4-(4-fluoro-2-methoxyphenyl)-N-{3-[(methylsulfanyl)methyl]phenyl}pyrimidin-2-amine (660 mg; 1.77 mmol) and cyanamide (149 mg; 3.53 mmol) in DCM (9.9 mL) at 0° C. The batch was stirred for 4 hours at this temperature before it was purified by chromatography (from hexane/ethyl acetate 1:1 to ethyl acetate) to give the pure product (670 mg; 1.62 mmol).

¹H NMR (400 MHz, CDCl₃, 300K) δ=8.32 (m, 1H), 7.86 (m, 1H), 7.48 (m, 2H), 7.35 (m, 1H), 7.28 (m, 1H), 6.97 (m, 1H), 6.82 (m, 1H), 6.76 (m, 1H), 4.42 (d, 1H), 4.19 (d, 1H), 3.87 (s, 3H), 2.71 (s, 3H).

Preparation of End Product:

DCM (8.1 mL) and ruthenium (III) chloride hydrate (55 mg; 0.24 mmol) were added to a stirred solution of sodium metaperiodate (1040 mg; 4.86 mmol) in water (6.3 mL) at RT. [(3-{[5-Fluoro-4-(4-fluoro-2-methoxyphenyl)pyrimidin-2-yl]amino}benzyl)(methyl)-λ⁴-sulfanylidene]cyanamide (670 mg; 1.62 mmol) dissolved in DCM (2.7 mL) was added dropwise over a period of 5 minutes. The mixture was stirred at RT overnight. Additional sodium metaperiodate (347 mg; 1.61 mmol) and ruthenium (III) chloride hydrate (18 mg; 0.08 mmol) were added to the mixture that was stirred for additional 20 hours. Finally, additional sodium metaperiodate (347 mg; 1.61 mmol) and ruthenium (III) chloride hydrate (18 mg; 0.08 mmol) were added to the mixture that was stirred for additional 20 hours. The batch was diluted with ethyl acetate and washed with saturated aqueous sodium chloride solution. The organic phase was filtered using a Whatman filter and concentrated. The residue was purified by chromatography (from hexane/ethyl acetate 7:1 to ethyl acetate) to give the pure product (120 mg; 0.28 mmol).

¹H NMR (400 MHz, CDCl₃, 300K) δ=8.33 (m, 1H), 7.98 (m, 1H), 7.54 (m, 1H), 7.47 (m, 1H), 7.40 (m, 1H), 7.31 (br, 1H), 7.07 (m, 1H), 6.82 (m, 1H), 6.76 (m, 1H), 4.59 (s, 2H), 3.87 (s, 3H), 3.00 (s, 3H).

Example 18 and 19

Enantiomers of [(3-{[5-fluoro-4-(4-fluoro-2-methoxyphenyl)pyrimidin-2-yl]amino}benzyl)(methyl)oxido-λ⁶-sulfanylidene]cyanamide

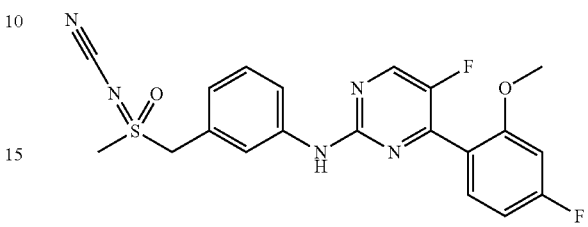

(rac)-[(3-{[5-Fluoro-4-(4-fluoro-2-methoxyphenyl)pyrimidin-2-yl]amino}benzyl)(methyl)oxido-λ⁶-sulfanylidene]cyanamide was separated into the enantiomers by preparative HPLC.

| System: | Dionex: Pump P 580, Gilson: Liquid Handler 215, Knauer: UV-Detektor K-2501 |
|---|---|
| Column: | Chiralpak IC 5 µm 250 × 30 mm |
| Solvent: | Hexane/EtOH 70:30 (v/v) |
| Flow: | 35 mL/min |
| Temperature: | RT |
| Solution: | 45 mg/1.5 mL EtOH/MeOH |
| Injection: | 2 × 0.75 mL |
| Detection: | UV 280 nm |

| | Retention time in min | purity in % |
|---|---|---|
| Example 18 Enantiomer 1 | 14.8-16.7 | 99.6 |
| Example 19 Enantiomer 2 | 16.7-18.5 | 96.9 |

Example 20

(rac)-[Ethyl(3-{[5-fluoro-4-(4-fluoro-2-methoxyphenyl)pyrimidin-2-yl]amino}benzyl)oxido-λ⁶-sulfanylidene]cyanamide

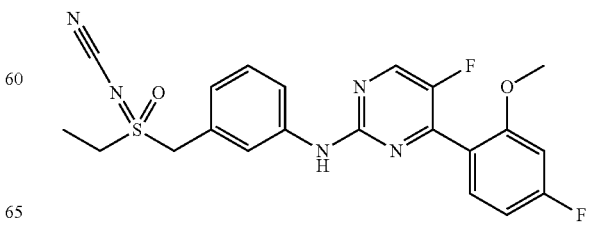

Preparation of Intermediate 20.1

N-{3-[(Ethylsulfanyl)methyl]phenyl}-5-fluoro-4-(4-fluoro-2-methoxyphenyl)pyrimidin-2-amine

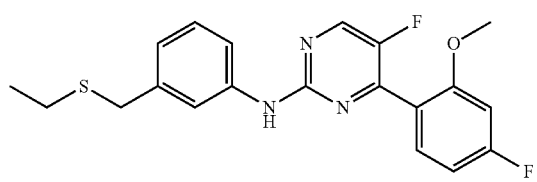 [SMILES: CCSCc1cccc(Nc2ncc(F)c(-c3ccc(F)cc3OC)n2)c1]

A mixture of 2-chloro-5-fluoro-4-(4-fluoro-2-methoxyphenyl)pyrimidine (750 mg; 2.92 mmol), 3-[(ethylsulfanyl)methyl]aniline (376 mg; 2.24 mmol), chloro(2-dicyclohexylphosphino-2',4',6'-tri-iso-propyl-1,1'-biphenyl)[2-(2-aminoethyl)phenyl]palladium(II) methyl-tert-butylether adduct (139 mg; 0.17 mmol; ABCR GmbH & CO. KG) and 2-(dicyclohexylphosphino)-2',4',6'-triisopropylbiphenyl (80 mg; 0.17 mmol; Aldrich Chemical Company Inc.) and potassium phosphate (2.39 g; 11.24 mmol) in toluene (15 ml) and NMP (3 mL) was stirred at 130° C. for 3 hours. After cooling, the batch was diluted with ethyl acetate and washed with aqueous sodium chloride solution. The organic phase was filtered using a Whatman filter and concentrated. The residue was purified by chromatography (hexane/ethyl acetate 2:1) to give the pure product (536 mg; 1.38 mmol).

$^1$H NMR (400 MHz, CDCl$_3$, 300K) δ=8.29 (m, 1H), 7.80 (m, 1H), 7.51 (m, 2H), 7.27 (m, 1H), 7.22 (m, 1H), 6.97 (m, 1H), 6.81 (m, 1H), 6.75 (m, 1H), 3.86 (s, 3H), 3.71 (s, 2H), 2.45 (q, 2H), 1.22 (tr, 3H). H)H

Preparation of Intermediate 20.2

(rac)-[Ethyl(3-{[5-fluoro-4-(4-fluoro-2-methoxyphenyl)pyrimidin-2-yl]amino}benzyl)-λ$^4$-sulfanylidene]cyanamide

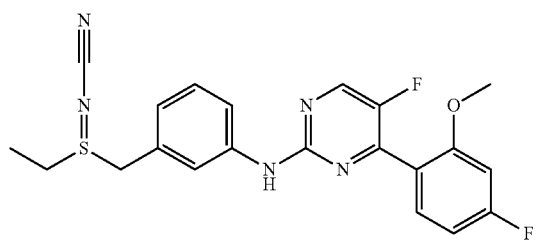 [SMILES: CCS(Cc1cccc(Nc2ncc(F)c(-c3ccc(F)cc3OC)n2)c1)=NC#N]

Intermediate 20.2 was prepared under similar conditions as described in the preparation of Intermediate 17.2 using N-{3-[(ethylsulfanyl)methyl]phenyl}-5-fluoro-4-(4-fluoro-2-methoxyphenyl)pyrimidin-2-amine. The batch was purified by chromatography (from hexane/ethyl acetate 1:1 to ethyl acetate).

$^1$H NMR (400 MHz, CDCl$_3$, 300K) δ=8.32 (m, 1H), 7.85 (m, 1H), 7.48 (m, 2H), 7.34 (m, 1H), 7.29 (br, 1H), 6.97 (m, 1H), 6.82 (m, 1H), 6.75 (m, 1H), 4.38 (d, 1H), 4.16 (d, 1H), 3.87 (s, 3H), 3.07 (m, 1H), 2.85 (m, 1H), 1.40 (tr, 3H).

Preparation of End Product:

Potassium permanganate (290 mg; 1.83 mmol) was added to a stirred solution of (rac)-[ethyl(3-{[5-fluoro-4-(4-fluoro-2-methoxyphenyl)pyrimidin-2-yl]amino}benzyl)-λ$^4$-sulfanylidene]cyanamide (392 mg; 0.92 mmol) in acetone (9.2 mL) at RT. The batch was stirred at 50° C. for one hour. The batch was concentrated and the residue was purified by chromatography (hexane/ethyl acetate 3:7) to give the desired product (258 mg; 0.58 mmol).

$^1$H NMR (400 MHz, CDCl$_3$, 300K) δ=8.32 (m, 1H), 7.98 (m, 1H), 7.49 (m, 2H), 7.38 (m, 1H), 7.31 (br, 1H), 7.06 (m, 1H), 6.82 (m, 1H), 6.75 (m, 1H), 4.57 (s, 2H), 3.86 (s, 3H), 3.12 (q, 2H), 1.40 (tr, 3H).

Example 21

(rac)-N-{3-[(S-Ethylsulfonimidoyl)methyl]phenyl}-5-fluoro-4-(4-fluoro-2-methoxyphenyl)-pyrimidin-2-amine

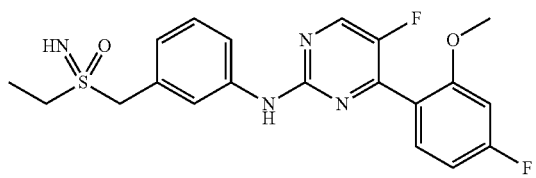 [SMILES: CCS(=N)(=O)Cc1cccc(Nc2ncc(F)c(-c3ccc(F)cc3OC)n2)c1]

To a stirring solution of (rac)-[ethyl(3-{[5-fluoro-4-(4-fluoro-2-methoxyphenyl)pyrimidin-2-yl]-amino}benzyl)oxido-λ$^6$-sulfanylidene]cyanamide (230 mg; 0.52 mmol) in DCM (23.1 mL) at 0° C., TFAA (0.55 mL; 3.89 mmol) was added. The mixture was allowed to react at RT for 2 hours. The reaction mixture was concentrated, taken up in MeOH (3.6 mL) and treated with potassium carbonate (358 mg; 2.58 mmol). The mixture was allowed to react at RT for 2 hours. The reaction mixture was diluted with ethyl acetate and THF and washed with saturated aqueous sodium chloride solution. The organic phase was filtered using a Whatman filter and concentrated. The residue was purified by chromatography (DCM/EtOH 4:1).

$^1$H NMR (400 MHz, CDCl$_3$, 300K) δ=8.30 (m, 1H), 7.78 (m, 1H), 7.60 (m, 1H), 7.49 (m, 1H), 7.35 (m, 1H), 7.24 (br, 1H), 7.05 (m, 1H), 6.81 (m, 1H), 6.75 (m, 1H), 4.31 (d, 1H), 4.17 (d, 1H), 3.86 (s, 3H), 3.02 (q, 2H), 1.40 (tr, 3H).

Example 22 and 23

Enantiomers of

N-{3-[(S-Ethylsulfonimidoyl)methyl]phenyl}-5-fluoro-4-(4-fluoro-2-methoxyphenyl)pyrimidin-2-amine

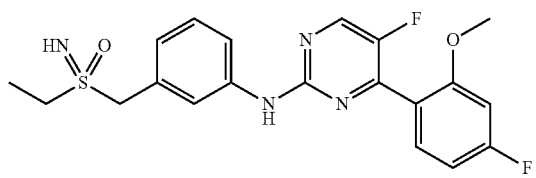 [SMILES: CCS(=N)(=O)Cc1cccc(Nc2ncc(F)c(-c3ccc(F)cc3OC)n2)c1]

(rac)-N-{3-[(S-Ethylsulfonimidoyl)methyl]phenyl}-5-fluoro-4-(4-fluoro-2-methoxyphenyl)pyrimidin-2-amine was separated into the enantiomers by preparative HPLC.

| System: | Dionex: Pump P 580, Gilson: Liquid Handler 215, Knauer: UV-Detektor K-2501 |
|---|---|
| Column: | Chiralpak IA 5 µm 250 × 30 mm |
| Solvent: | MeOH 100 (v/v) |
| Flow: | 50 mL/min |
| Temperature: | RT |
| Solution: | 190 mg/2 mL MeOH |
| Injection: | 4 × 0.5 mL |
| Detection: | UV 280 nm |

| | Retention time in min | purity in % |
|---|---|---|
| Example 22 Enantiomer 1 | 10.3-16.0 | 96.4 |
| Example 23 Enantiomer 2 | 16.0-24.5 | 95.9 |

Example 24

(rac)-[(2,3-Difluoro-5-{[5-fluoro-4-(4-fluoro-2-methoxyphenyl)pyrimidin-2-yl]amino}benzyl)-(methyl)oxido-λ⁶-sulfanylidene]cyanamide

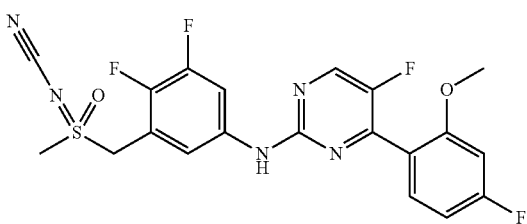 [SMILES: COc1cc(F)ccc1-c1nc(Nc2cc(F)c(F)c(CS(C)(=O)=NC#N)c2)ncc1F]

Preparation of Intermediate 24.1

(2,3-Difluoro-5-nitrophenyl)methanol

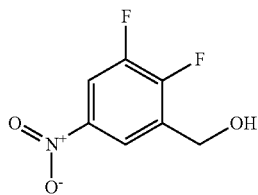 [SMILES: O=[N+]([O-])c1cc(F)c(F)c(CO)c1]

To a stirring solution of 2,3-difluoro-5-nitrobenzoic acid (Butt Park Ltd.; 9.00 g; 44.3 mmol) in THF at 0° C. was added a 1M solution of borane-tetrahydrofuran complex in THF (177.3 mL; 177.3 mmol). The mixture was allowed to react at RT overnight. Then, MeOH was cautiously added to the stirred mixture while cooling with an ice bath. The batch was diluted with ethyl acetate and washed with aqueous sodium hydroxide solution (1N) and saturated aqueous sodium chloride solution. The organic phase was dried (sodium sulfate), filtered and concentrated. The residue was purified by chromatography (hexane to hexane/ethyl acetate 1:2) to give the pure product (8.20 g; 43.4 mmol).

¹H NMR (400 MHz, CDCl₃, 300K) δ=8.26 (m, 1H), 8.03 (m, 1H), 4.89 (br, 2H), 2.13 (br, 1H).

Preparation of Intermediate 24.2

(5-Amino-2,3-difluorophenyl)methanol

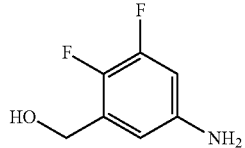

Intermediate 24.2 was prepared under similar conditions as described in the preparation of Intermediate 1.6 using (2,3-difluoro-5-nitrophenyl)methanol.

¹H NMR (400 MHz, CDCl₃, 300K) δ=6.47 (m, 1H), 6.42 (m, 1H), 4.69 (br, 2H).

Preparation of Intermediate 24.3

3,4-Difluoro-5-[(methylsulfanyl)methyl]aniline

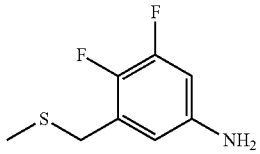

To a stirring solution of (5-amino-2,3-difluorophenyl)methanol (4.13 g; 25.9 mmol) in DCM (78 mL) and NMP (11 mL) at RT was added dropwise thionylchloride (4.7 mL; 64.9 mmol). The mixture was allowed to react at RT overnight. Then, the mixture was poured into aqueous sodium bicarbonate solution/saturated aqueous sodium chloride solution/ice. The batch was stirred for 2 hours before it was extracted with ethyl acetate (2×). The combined organic phases were filtered using a Whatman filter and concentrated to give crude 3-(chloromethyl)-4,5-difluoroaniline.

The residue was taken up in EtOH (75 mL) and sodium methanethiolate (3.61 g; 51.6 mmol) was added under stirring in three portions at 0° C. The cold bath was removed and the batch was stirred at RT overnight. The batch was diluted with saturated aqueous sodium chloride solution and extracted with ethyl acetate (2×). The combined organic phases were washed with water, filtered using a Whatman filter and concentrated. The residue was purified by chromatography (hexane to hexane/ethyl acetate 1:1) to give the desired product (1.27 g; 6.71 mmol).

¹H NMR (400 MHz, CDCl₃, 300K) δ=6.36 (m, 2H), 3.62 (br, 4H), 2.08 (s, 3H).

Preparation of Intermediate 24.4

N-{3,4-Difluoro-5-[(methylsulfanyl)methyl]phenyl}-5-fluoro-4-(4-fluoro-2-methoxyphenyl)-pyrimidin-2-amine

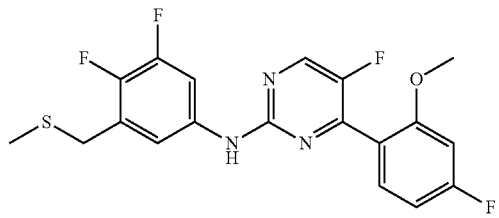 [SMILES: COc1cc(F)ccc1-c1nc(Nc2cc(F)c(F)c(CSC)c2)ncc1F]

Intermediate 24.4 was prepared under similar conditions as described in the preparation of Intermediate 20.1 using 2-chloro-5-fluoro-4-(4-fluoro-2-methoxyphenyl)pyrimidine and 3,4-difluoro-5-[(methyl-sulfanyl)methyl]aniline. The batch was purified by chromatography (hexane/ethyl acetate 3:2).

$^1$H NMR (400 MHz, CDCl$_3$, 300K) δ=8.30 (m, 1H), 7.72 (m, 1H), 7.48 (m, 1H), 7.14 (m, 2H), 6.78 (m, 2H), 3.87 (s, 3H), 3.70 (s, 2H), 2.06 (s, 3H).

Preparation of Intermediate 24.5

(rac)-[(2,3-Difluoro-5-{[5-fluoro-4-(4-fluoro-2-methoxyphenyl)pyrimidin-2-yl]amino}benzyl)(methyl)-λ$^4$-sulfanylidene]cyanamide

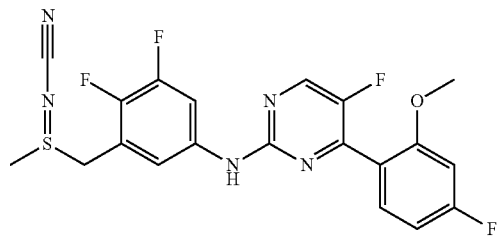 [SMILES: COc1cc(F)ccc1-c1nc(Nc2cc(F)c(F)c(CS(C)=NC#N)c2)ncc1F]

Intermediate 24.5 was prepared under similar conditions as described in the preparation of Intermediate 17.2 using N-{3,4-difluoro-5-[(methylsulfanyl)methyl]phenyl}-5-fluoro-4-(4-fluoro-2-methoxyphenyl)-pyrimidin-2-amine. The batch was purified by chromatography (DCM/EtOH 9:1).

$^1$H NMR (400 MHz, CDCl$_3$, 300K) δ=8.32 (m, 1H), 7.90 (m, 1H), 7.75 (br, 1H), 7.46 (m, 1H), 7.33 (m, 1H), 6.83 (m, 1H), 6.76 (m, 1H), 4.33 (m, 2H), 3.87 (s, 3H), 2.82 (s, 3H).
Preparation of End Product:

Example 24 was prepared under similar conditions as described in the preparation of Example 20 using (rac)-[(2,3-difluoro-5-{[5-fluoro-4-(4-fluoro-2-methoxyphenyl)pyrimidin-2-yl]amino}benzyl)(methyl)-λ$^4$-sulfanylidene]cyanamide. The batch was purified by chromatography (hexane/ethyl acetate 1:3).

$^1$H NMR (400 MHz, CDCl$_3$, 300K) δ=8.35 (m, 1H), 7.94 (m, 1H), 7.48 (m, 1H), 7.45 (m, 1H), 7.33 (br, 1H), 6.83 (m, 1H), 6.76 (m, 1H), 4.69 (m, 2H), 3.87 (s, 3H), 3.12 (s, 3H).

Example 25

(rac)-N-{3,4-Difluoro-5-[(S-methylsulfonimidoyl)methyl]phenyl}-5-fluoro-4-(4-fluoro-2-methoxyphenyl)pyrimidin-2-amine

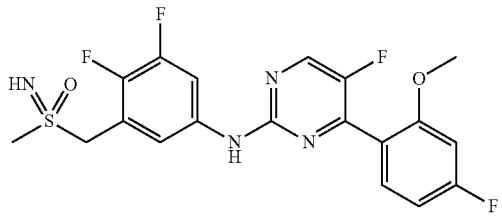 [SMILES: COc1cc(F)ccc1-c1nc(Nc2cc(F)c(F)c(CS(C)(=N)=O)c2)ncc1F]

Example 25 was prepared under similar conditions as described in the preparation of Example 21 using (rac)-[(2,3-difluoro-5-{[5-fluoro-4-(4-fluoro-2-methoxyphenyl)pyrimidin-2-yl]amino}benzyl)(methyl)-oxido-λ$^6$-sulfanylidene]cyanamide. The batch was purified by chromatography (DCM/EtOH 4:1).

$^1$H NMR (400 MHz, CDCl$_3$, 300K) δ=8.30 (m, 1H), 7.86 (m, 1H), 7.47 (m, 1H), 7.26 (m, 2H), 6.82 (m, 1H), 6.76 (m, 1H), 4.42 (d, 1H), 4.35 (d, 1H), 3.87 (s, 3H), 2.96 (s, 3H), 2.76 (s, 1H).

Example 26 and 27

Enantiomers of N-{3,4-Difluoro-5-[(S-methylsulfonimidoyl)methyl]phenyl}-5-fluoro-4-(4-fluoro-2-methoxyphenyl)-pyrimidin-2-amine

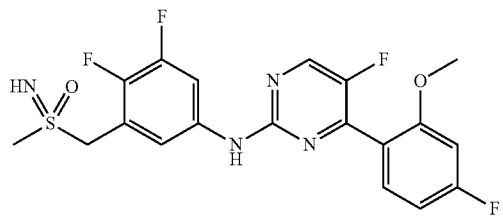 [SMILES: COc1cc(F)ccc1-c1nc(Nc2cc(F)c(F)c(CS(C)(=N)=O)c2)ncc1F]

(rac)-N-{3,4-Difluoro-5-[(S-methylsulfonimidoyl)methyl]phenyl}-5-fluoro-4-(4-fluoro-2-methoxy-phenyl)pyrimidin-2-amine was separated into the enantiomers by preparative HPLC:

| System: | Dionex: Pump P 580, Gilson: Liquid Handler 215, Knauer: UV-Detektor K-2501 |
|---|---|
| Column: | Chiralpak IA 5 μm 250 × 30 mm |
| Solvent: | EtOH/MeOH/Diethylamine 50:50:0.1 (v/v/v) |
| Flow: | 50 mL/min |
| Temperature: | RT |
| Solution: | 292 mg/5 mL EtOH/MeOH |
| Injection: | 10 × 0.5 mL |
| Detection: | UV 280 nm |

| | Retention time in min | purity in % |
|---|---|---|
| Example 26 Enantiomer 1 | 11.2-14.0 | >99.9 |
| Example 27 Enantiomer 2 | 14.0-16.5 | 96.1 |

Example 28

(rac)-[(3-Bromo-5-{[5-fluoro-4-(4-fluoro-2-methoxyphenyl)pyrimidin-2-yl]amino}benzyl)(methyl)-oxido-λ$^6$-sulfanylidene]cyanamide

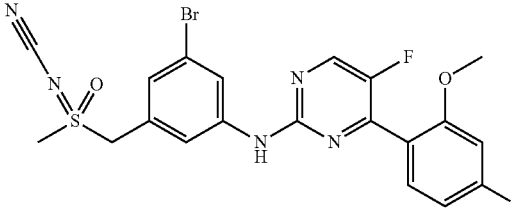

Preparation of Intermediate 28.1

Bis{3-bromo-5-[(methylsulfanyl)methyl]phenyl}diazene oxide

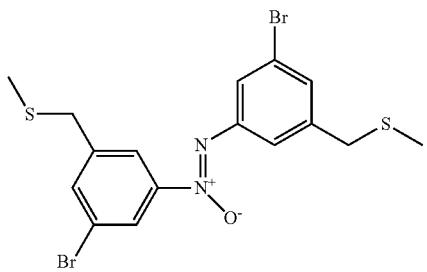

To a stirring solution of (3-bromo-5-nitrophenyl)methanol (5.00 g; 21.5 mmol; Biogene Organics Inc) in DCM (65 mL) and NMP (9 mL) at RT was added dropwise thionylchloride (3.9 mL; 53.9 mmol). The mixture was allowed to react at RT overnight. Then, the mixture was poured into aqueous sodium bicarbonate solution/saturated aqueous sodium chloride solution/ice. The batch was stirred for one hour before it was extracted with ethyl acetate (2×). The combined organic phases were filtered using a Whatman filter and concentrated to give crude 1-bromo-3-(chloromethyl)-5-nitrobenzene, that was used without further purification.

The residue was taken up in EtOH (85 mL) and sodium methanethiolate (4.04 g; 57.6 mmol) was added under stirring in three portions at 0° C. The cold bath was removed and the batch was stirred at room temperature overnight. Further sodium methanethiolate (2.03 g; 28.9 mmol) was added under stirring. After 4 hours, the batch was diluted with saturated aqueous sodium chloride solution and extracted with ethyl acetate (2×). The combined organic phases were dried (sodium sulfate), filtered and concentrated. The residue was purified by chromatography (hexane to hexane/ethyl acetate 4:1) to give the product (3.78 g; 7.94 mmol).

$^1$H NMR (400 MHz, CDCl$_3$, 300K) δ=8.35 (m, 1H), 8.32 (m, 1H), 8.19 (m, 1H), 7.99 (m, 1H), 7.69 (m, 1H), 7.53 (m, 1H), 3.73 (s, 2H), 3.70 (s, 2H), 2.04 (m, 6H).

Preparation of Intermediate 28.2

3-Bromo-5-[(methylsulfanyl)methyl]aniline

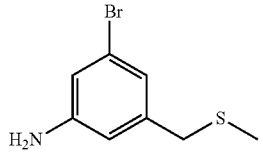

Hydrogen chloride (37.5%; 27.4 mL) was added dropwise over 4 hours to a refluxing mixture of bis{3-bromo-5-[(methylsulfanyl)methyl]phenyl}diazene oxide (3.65 g; 7.7 mmol) and iron powder (6.20 g; 110.9 mmol) in dioxane (60 mL). After cooling, the mixture was diluted with ethyl acetate and water. The mixture was basified using solid sodium bicarbonate and extracted with ethyl acetate (2×). The combined organic phases were washed with water, filtered using a Whatman filter and concentrated. The residue was purified by chromatography (hexane to hexane/ethyl acetate 1:1) to give the desired product (2.50 g; 10.77 mmol).

$^1$H NMR (400 MHz, CDCl$_3$, 300K) δ=6.82 (m, 1H), 6.71 (m, 1H), 6.56 (m 1H), 3.71 (br, 2H), 3.52 (s, 2H), 2.00 (s, 3H).

Preparation of Intermediate 28.3

N-{3-Bromo-5-[(methylsulfanyl)methyl]phenyl}-5-fluoro-4-(4-fluoro-2-methoxyphenyl)pyrimidin-2-amine

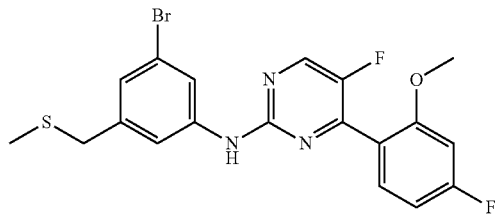

A 4N solution of hydrogen chloride in dioxane (0.54 mL; 2.15 mmol) was added to a stirred solution of 2-chloro-5-fluoro-4-(4-fluoro-2-methoxyphenyl)pyrimidine (553 mg; 2.15 mmol) and 3-bromo-5-[(methylsulfanyl)methyl]aniline (500 mg; 2.15 mmol) in 1-butanol (4.8 mL). The batch was stirred at 140° C. for 8 hours. After cooling the batch was diluted with ethyl acetate and washed with sodium bicarbonate and saturated aqueous sodium chloride solution. The organic phase was filtered using a Whatman filter and concentrated. The residue was purified by chromatography (hexane/ethyl acetate 4:1) to give the desired product (450 mg; 0.99 mmol).

$^1$H NMR (400 MHz, CDCl$_3$, 300K) δ=8.32 (m, 1H), 7.87 (m 1H), 7.50 (m, 1H), 7.42 (br, 1H), 7.17 (br, 1H), 7.10 (m, 1H), 6.81 (m, 1H), 6.76 (m, 1H), 3.87 (s, 3H), 3.61 (s, 2H), 2.01 (s, 3H).

Preparation of Intermediate 28.4

(rac)-[(3-Bromo-5-{[5-fluoro-4-(4-fluoro-2-methoxyphenyl)pyrimidin-2-yl]amino}benzyl)(methyl)-λ$^4$-sulfanylidene]cyanamide

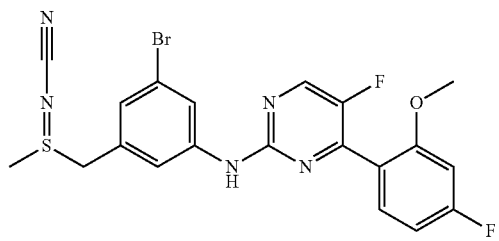 [SMILES: COc1cc(F)ccc1-c1nc(Nc2cc(Br)cc(CS(C)=NC#N)c2)ncc1F]

Intermediate 28.4 was prepared under similar conditions as described in the preparation of Intermediate 17.2 us in g N-{3-Bromo-5-[(methylsulfanyl)methyl]phenyl}-5-fluoro-4-(4-fluoro-2-methoxyphenyl)-pyrimidin-2-amine. The batch was purified by chromatography (ethyl acetate).

$^1$H NMR (400 MHz, CDCl$_3$, 300K) δ=8.35 (m, 1H), 7.89 (m, 1H), 7.68 (m, 1H), 7.48 (m, 1H), 7.30 (br, 1H), 7.10 (m, 1H), 6.83 (m, 1H), 6.77 (m, 1H), 4.36 (d, 1H), 4.11 (d, 1H), 3.87 (s, 3H), 2.75 (s, 3H).

Preparation of End Product:

Example 28 was prepared under similar conditions as described in the preparation of Example 20 using (rac)-[(3-Bromo-5-{[5-fluoro-4-(4-fluoro-2-methoxyphenyl)pyrimidin-2-yl]amino}benzyl)(methyl)-$\lambda^4$-sulfanylidene]cyanamide. The batch was purified by chromatography (hexane/ethyl acetate 3:1 to ethyl acetate).

$^1$H NMR (400 MHz, CDCl$_3$, 300K) δ=8.35 (m, 1H), 7.93 (m, 1H), 7.79 (m, 1H), 7.47 (m, 1H), 7.35 (br, 1H), 7.17 (m, 1H), 6.83 (m, 1H), 6.76 (m, 1H), 4.54 (m, 2H), 3.87 (s, 3H), 3.05 (s, 3H).

Example 29

(rac)-N-{3-Bromo-5-[(S-methylsulfonimidoyl)methyl]phenyl}-5-fluoro-4-(4-fluoro-2-methoxy-phenyl)pyrimidin-2-amine

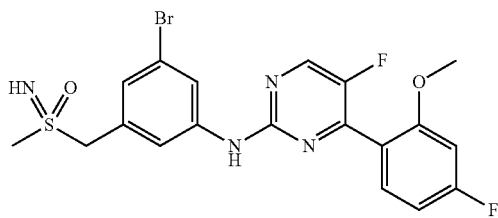

Example 29 was prepared under similar conditions as described in the preparation of Example 21 using (rac)-[(3-bromo-5-{[5-fluoro-4-(4-fluoro-2-methoxyphenyl)pyrimidin-2-yl]amino}benzyl)(methyl)-oxido-$\lambda^6$-sulfanylidene]cyanamide. The batch was purified by chromatography (DCM/EtOH 4:1). $^1$H NMR (400 MHz, CDCl$_3$, 300K) δ=8.32 (m, 1H), 7.98 (m, 1H), 7.60 (m, 1H), 7.48 (m, 1H), 7.23 (m, 1H), 7.18 (m, 1H), 6.81 (m, 1H), 6.76 (m, 1H), 4.31 (d, 1H), 4.18 (d, 1H), 3.87 (s, 3H), 2.94 (s, 3H), 2.71 (br, 1H).

Example 30 and 31

Enantiomers of N-{3-bromo-5-[(S-methylsulfonimidoyl)methyl]phenyl}-5-fluoro-4-(4-fluoro-2-methoxyphenyl)-pyrimidin-2-amine

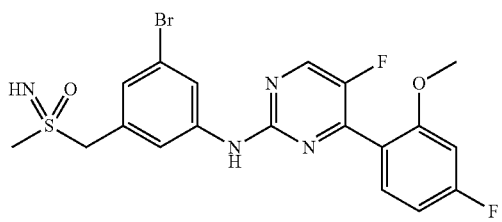 [SMILES: COc1cc(F)ccc1-c1nc(Nc2cc(Br)cc(CS(C)(=N)=O)c2)ncc1F]

(rac)-N-{3-Bromo-5-[(S-methylsulfonimidoyl)methyl]phenyl}-5-fluoro-4-(4-fluoro-2-methoxyphenyl)-pyrimidin-2-amine was separated into the enantiomers by preparative HPLC.

| System: | Agilent: Prep 1200, 2xPrep Pump G1361A, DLA G2258A, MWD G1365D, Prep FC G1364B |
|---|---|
| Column: | Chiralpak IC 5 µm 250 × 20 mm |
| Solvent: | Hexane/EtOH 85/15 (v/v) |
| Flow: | 40 mL/min |
| Temperature: | RT |
| Solution: | 52 mg/1.1 ml MeOH/DCM/DMF 1/1/1 |
| Injection: | 23 × 50 µl |
| Detection: | UV 280 nm |

| | Retention time in min | purity in % |
|---|---|---|
| Example 30 Enantiomer 1 | 8.8-9.9 | >99 |
| Example 31 Enantiomer 2 | 10.4-11.5 | 97.2 |

Example 32

(rac)-[(3-{[5-Fluoro-4-(4-fluoro-2-methoxyphenyl)pyrimidin-2-yl]amino}-5-methoxybenzyl)-(methyl)oxido-$\lambda^6$-sulfanylidene]cyanamide

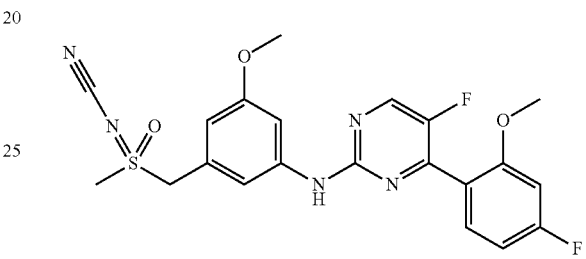

Preparation of Intermediate 32.1

Bis{3-methoxy-5-[(methylsulfanyl)methyl]phenyl}diazene oxide

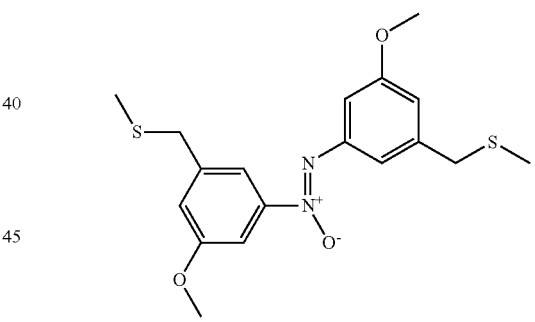

Sodium methanethiolate (2.58 g; 36.8 mmol) was added under stirring in three portions to a solution of 1-(chloromethyl)-3-methoxy-5-nitrobenzene (5.30 g; 26.3 mmol; FCH Group Company) in EtOH (60 mL) at 0° C. The cold bath was removed and the batch was stirred at room temperature overnight. Further sodium methanethiolate (0.92 g; 13.1 mmol) was added and the batch was stirred overnight. Further sodium methanethiolate (1.66 g; 23.6 mmol) was added and the batch was stirred overnight. The batch was diluted with saturated aqueous sodium chloride solution and extracted with ethyl acetate (2×). The combined organic phases were dried (sodium sulfate), filtered and concentrated. The residue was purified by chromatography (hexane to hexane/ethyl acetate 7:3) to give the product (2.9 g; 7.66 mmol).

$^1$H NMR (400 MHz, CDCl$_3$, 300K) δ=7.85 (m, 1H), 7.73 (m, 2H), 7.68 (m, 1H), 7.08 (m, 1H), 6.96 (m, 1H), 3.91 (s, 3H), 3.87 (s, 3H), 3.73 (s, 2H), 3.70 (s, 2H), 2.04 (s, 3H), 2.03 (s, 3H).

Preparation of Intermediate 32.2

3-Methoxy-5-[(methylsulfanyl)methyl]aniline

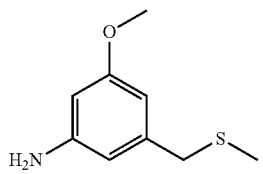

Intermediate 32.2 was prepared under similar conditions as described in the preparation of Intermediate 28.2 using bis{3-methoxy-5-[(methylsulfanyl)methyl]phenyl}diazene oxide. The residue was purified by chromatography (hexane to hexane/ethyl acetate 1:1) to give the desired product.

$^1$H NMR (400 MHz, CDCl$_3$, 300K) δ=6.28 (m, 2H), 6.12 (m, 1H), 3.76 (s, 3H), 3.66 (br, 2H), 3.55 (s, 2H), 2.02 (s, 3H).

Preparation of Intermediate 32.3

5-Fluoro-4-(4-fluoro-2-methoxyphenyl)-N-{3-methoxy-5-[(methylsulfanyl)methyl]phenyl}-pyrimidin-2-amine

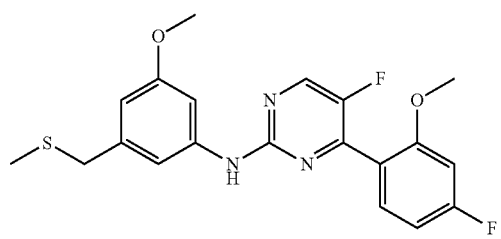 [SMILES: COc1cc(CSC)cc(Nc2ncc(F)c(-c3ccc(F)cc3OC)n2)c1]

Intermediate 32.3 was prepared under similar conditions as described in the preparation of Intermediate 20.1 using 2-chloro-5-fluoro-4-(4-fluoro-2-methoxyphenyl)pyrimidine and 3-methoxy-5-[(methyl-sulfanyl)methyl]aniline. The batch was purified by chromatography (hexane to hexane/ethyl acetate 7:3) to give the desired product.

$^1$H NMR (400 MHz, CDCl$_3$, 300K) δ=8.30 (m, 1H), 7.51 (m, 1H), 7.36 (m, 1H), 7.15 (br, 1H), 7.03 (m, 1H), 6.80 (m, 1H), 6.74 (m, 1H), 6.55 (m, 1H), 3.86 (s, 3H), 3.80 (s, 3H), 3.63 (s, 2H), 2.02 (s, 3H).

Preparation of Intermediate 32.4

(rac)-[(3-{[5-Fluoro-4-(4-fluoro-2-methoxyphenyl)pyrimidin-2-yl]amino}-5-methoxybenzyl)(methyl)-λ$^4$-sulfanylidene]cyanamide

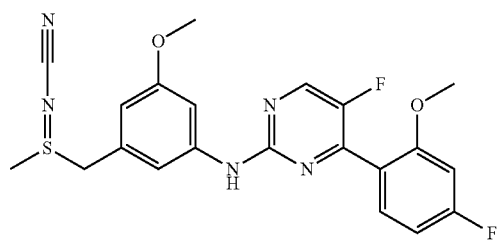 [SMILES: COc1cc(CS(C)=NC#N)cc(Nc2ncc(F)c(-c3ccc(F)cc3OC)n2)c1]

Intermediate 32.4 was prepared under similar conditions as described in the preparation of Intermediate 17.2 using 5-fluoro-4-(4-fluoro-2-methoxyphenyl)-N-{3-methoxy-5-[(methylsulfanyl)methyl]phenyl}-pyrimidin-2-amine. The batch was purified by chromatography (DCM/EtOH 9:1).

$^1$H NMR (400 MHz, CDCl$_3$, 300K) δ=8.32 (m, 1H), 7.47 (m, 1H), 7.33 (m, 1H), 7.25 (m, 2H), 6.82 (m, 1H), 6.75 (m, 1H), 6.52 (m, 1H), 4.37 (d, 1H), 4.13 (d, 1H), 3.86 (s, 3H), 3.81 (s, 3H), 2.71 (s, 3H).

Preparation of End Product:

Example 32 was prepared under similar conditions as described in the preparation of Example 20 using (rac)-[(3-{[5-fluoro-4-(4-fluoro-2-methoxyphenyl)pyrimidin-2-yl]amino}-5-methoxybenzyl)(methyl)-λ$^4$-sulfanylidene]cyanamide. The batch was purified by chromatography (DCM/EtOH 95:5).

$^1$H NMR (400 MHz, d$_6$-DMSO, 300K) δ=9.92 (m, 1H), 8.53 (m, 1H), 7.53 (m, 2H), 7.34 (m, 1H), 7.09 (m, 1H), 6.92 (m, 1H), 6.62 (m, 1H), 4.87 (m, 2H), 3.80 (s, 3H), 3.70 (s, 3H), 3.31 (s, 3H).

Example 33

(rac)-5-Fluoro-4-(4-fluoro-2-methoxyphenyl)-N-{3-methoxy-5-[(S-methylsulfonimidoyl)methyl]-phenyl}pyrimidin-2-amine

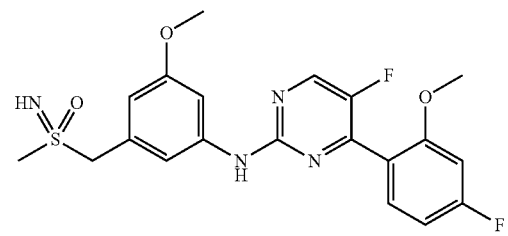 [SMILES: COc1cc(CS(C)(=N)=O)cc(Nc2ncc(F)c(-c3ccc(F)cc3OC)n2)c1]

Example 33 was prepared under similar conditions as described in the preparation of Example 21 using (rac)-[(3-{[5-fluoro-4-(4-fluoro-2-methoxyphenyl)pyrimidin-2-yl]amino}-5-methoxybenzyl)(methyl)-oxido-λ$^6$-sulfanylidene]cyanamide. The batch was purified by preparative HPLC.

| System: | Waters Autopurificationsystem: Pump 2545, Sample Manager 2767, CFO, DAD 2996, ELSD 2424, SQD 3001 |
|---|---|
| Column: | XBrigde C18 5 µm 100 × 30 mm |
| Solvent: | A = H$_2$O + 0.1% HCOOH |
|  | B = MeCN |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 ml DMSO or DMF |
| Injektion: | 1 × 2.5 mL |
| Detection: | DAD scan range 210-400 nm |
|  | MS ESI+, ESI−, scan range 160-1000 m/z |

$^1$H NMR (400 MHz, CDCl$_3$, 300K) δ=8.29 (m, 1H), 7.49 (m, 1H), 7.44 (m, 1H), 7.27 (m, 1H), 7.19 (m, 1H), 6.79 (m,

1H), 6.74 (m, 1H), 6.60 (m, 1H), 4.32 (d, 1H), 4.19 (d, 1H), 3.86 (s, 3H), 3.81 (s, 3H), 2.93 (s, 3H), 2.71 (br, 1H).

Example 34 and 35

Enantiomers of 5-fluoro-4-(4-fluoro-2-methoxyphenyl)-N-{3-methoxy-5-[(S-methylsulfonimidoyl)methyl]phenyl}-pyrimidin-2-amine

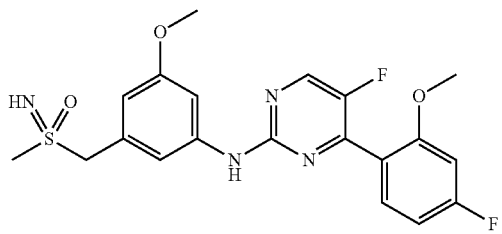 [SMILES: COc1cc(CS(C)(=N)=O)cc(Nc2ncc(F)c(-c3ccc(F)cc3OC)n2)c1]

(rac)-5-Fluoro-4-(4-fluoro-2-methoxyphenyl)-N-{3-methoxy-5-[(S-methylsulfonimidoyl)methyl]-phenyl}pyrimidin-2-amine was separated into the enantiomers by preparative HPLC.

| System: | Agilent: Prep 1200, 2xPrep Pump G1361A, DLA G2258A, MWD G1365D, Prep FC G1364B |
| --- | --- |
| Column: | Chiralpak IC 5 µm 250 × 20 mm |
| Solvent: | Hexane/EtOH 70:30 (v/v) |
| Flow: | 30 mL/min |
| Temperature: | RT |
| Solution: | 23 mg/700 µL MeOH/DCM |
| Injection: | 7 × 100 µl |
| Detection: | UV 280 nm |

| | Retention time in min | purity in % |
| --- | --- | --- |
| Example 34 Enantiomer 1 | 8.5-9.5 | >99 |
| Example 35 Enantiomer 2 | 9.7-11.0 | 96.1 |

Example 36

(rac)-[(3-{[4-(2-Ethoxy-4-fluorophenyl)-5-fluoropyrimidin-2-yl]amino}-5-fluorobenzyl)(methyl)-oxido-λ⁶-sulfanylidene]cyanamide

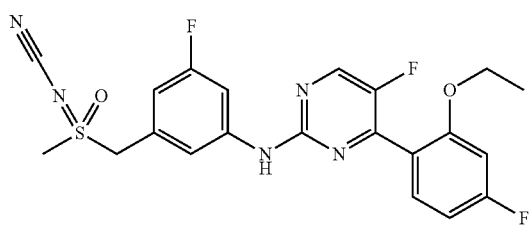 [SMILES: CCOc1cc(F)ccc1-c1nc(Nc2cc(F)cc(CS(C)(=O)=NC#N)c2)ncc1F]

Preparation of Intermediate 36.1

2-Chloro-4-(2-ethoxy-4-fluorophenyl'-5-fluoropyrimidine

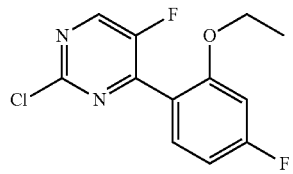 [SMILES: CCOc1cc(F)ccc1-c1nc(Cl)ncc1F]

Under argon, a mixture of 2,4-dichloro-5-fluoropyrimidine (4.13 g; 24.71 mmol), (2-ethoxy-4-fluoro-phenyl)boronic acid (5.00 g; 27.18 mmol; Aldrich Chemical Company Inc.) and [1,1'-bis-(diphenylphosphino)ferrocene]dichloropalladium(II) (2.01 g; 2.47 mmol; Aldrich Chemical Company Inc.) in a 2M solution of potassium carbonate (37 mL) and 1,2-dimethoxyethane (74 mL) was stirred for 150 minutes at 90° C. After cooling, the batch was diluted with ethyl acetate and washed with diluted aqueous sodium chloride solution. The organic phase was filtered using a Whatman filter and concentrated. The residue was purified by chromatography (hexane/ethyl acetate 4:1) to give the desired product (3.97 g; 14.67 mmol).

$^1$H NMR (400 MHz, CDCl$_3$, 300K) δ=8.46 (m, 1H), 7.52 (m, 1H), 6.80 (m, 1H), 6.71 (m, 1H), 4.08 (q, 2H), 1.36 (tr, 3H).

Preparation of Intermediate 36.2

4-(2-Ethoxy-4-fluorophenyl)-5-fluoro-N-{3-fluoro-5-[(methylsulfanyl)methyl]phenyl}pyrimidin-2-amine

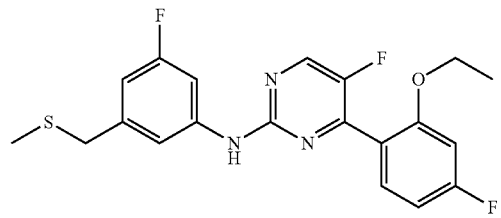 [SMILES: CCOc1cc(F)ccc1-c1nc(Nc2cc(F)cc(CSC)c2)ncc1F]

Intermediate 36.2 was prepared under similar conditions as described in the preparation of Intermediate 20.1 using 2-chloro-4-(2-ethoxy-4-fluorophenyl)-5-fluoropyrimidine and 3-fluoro-5-[(methylsulfanyl)-methyl]aniline. The residue was purified by chromatography (hexane to hexane/ethyl acetate 7:3) to give the desired product.

$^1$H NMR (400 MHz, CDCl$_3$, 300K) δ=8.31 (m, 1H), 7.62 (m, 1H), 7.51 (m, 1H), 7.37 (br, 1H), 7.15 (m, 1H), 6.79 (m, 1H), 6.71 (m, 2H), 4.10 (q, 2H), 3.63 (s, 2H), 2.01 (s, 3H), 1.37 (q, 3H).

Preparation of Intermediate 36.3

(rac)-[(3-{[4-(2-Ethoxy-4-fluorophenyl)-5-fluoropyrimidin-2-yl]amino}-5-fluorobenzyl)(methyl)-λ⁴-sulfanylidene]cyanamide

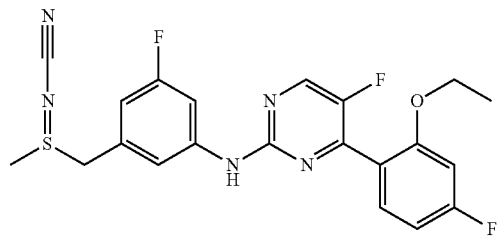 [SMILES: CCOc1cc(F)ccc1-c1nc(Nc2cc(F)cc(CS(C)=NC#N)c2)ncc1F]

Intermediate 36.3 was prepared under similar conditions as described in the preparation of Intermediate 17.2 using 4-(2-ethoxy-4-fluorophenyl)-5-fluoro-N-{3-fluoro-5-[(methylsulfanyl)methyl]-phenyl}-pyrimidin-2-amine. The batch was purified by chromatography (ethyl acetate).

$^1$H NMR (400 MHz, CDCl$_3$, 300K) δ=8.34 (m, 1H), 7.65 (m, 1H), 7.48 (m, 1H), 7.44 (br, 1H), 7.38 (m, 1H), 6.80 (m, 1H), 6.73 (m 1H), 6.71 (m, 1H), 4.37 (d, 1H), 4.11 (m, 3H), 2.76 (s, 3H), 1.37 (tr, 3H).

Preparation of End Product:

Example 36 was prepared under similar conditions as described in the preparation of Example 20 using (rac)-[(3-{[4-(2-Ethoxy-4-fluorophenyl)-5-fluoropyrimidin-2-yl]amino}-5-fluorobenzyl)(methyl)-λ⁴-sulfanylidene]cyanamide. The batch was purified by chromatography (hexane to hexane/ethyl acetate 3:7).

$^1$H NMR (400 MHz, CDCl$_3$, 300K) δ=8.34 (m, 1H), 7.68 (m, 1H), 7.48 (m, 3H), 6.78 (m, 3H), 4.57 (m, 2H), 4.10 (q, 2H), 3.05 (s, 3H), 1.37 (tr, 3H).

Example 37

(rac)-4-(2-Ethoxy-4-fluorophenyl)-5-fluoro-N-{3-fluoro-5-[(S-methylsulfonimidoyl)methyl]-phenyl}pyrimidin-2-amine

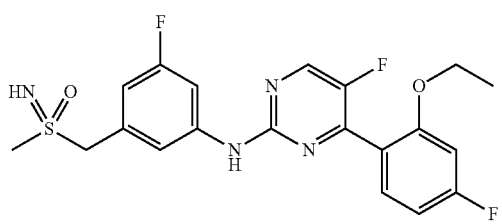 [SMILES: CCOc1cc(F)ccc1-c1nc(Nc2cc(F)cc(CS(C)(=N)=O)c2)ncc1F]

Example 37 was prepared under similar conditions as described in the preparation of Example 21 using (rac)-[(3-{[4-(2-Ethoxy-4-fluorophenyl)-5-fluoropyrimidin-2-yl]amino}-5-fluorobenzyl)(methyl)oxido-λ⁶-sulfanylidene]cyanamide. The batch was purified by preparative HPLC.

| System: | Waters Autopurificationsystem: Pump 254, Sample Manager 2767, CFO, DAD 2996, ELSD 2424, SQD 3100 |
|---|---|
| Column: | XBrigde C18 5 µm 100 × 30 mm |
| Solvent: | A = H$_2$O + 0.1% HCOOH |
| | B = MeCN |
| Gradient: | 0-8 min 30%-70% B |
| Flow: | 50 mL/min |
| Temperature: | RT |
| Solution: | 470 mg/7 mL DMSO |
| Injection: | 7 × 1 mL |
| Detection: | DAD scan range 210-400 nm |
| | MS ESI+, ESI−, scan range 160-1000 m/z |
| | ELSD |
| Retention: | 5.6-6.2 min |
| MS(ES+): | m/z = 436 |

$^1$H NMR (400 MHz, CDCl$_3$, 300K) δ=8.32 (m, 1H), 7.73 (m, 1H), 7.48 (m, 1H), 7.32 (m, 2H), 6.77 (m, 3H), 4.35 (d, 1H), 4.22 (d, 1H), 4.09 (q, 2H), 2.96 (s, 3H), 1.37 (tr, 3H).

Example 38 and 39

Enantiomers of 4-(2-ethoxy-4-fluorophenyl)-5-fluoro-N-{3-fluoro-5-[(S-methylsulfonimidoyl)methyl]phenyl}pyrimidin-2-amine

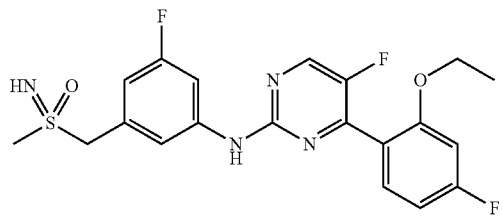 [SMILES: CCOc1cc(F)ccc1-c1nc(Nc2cc(F)cc(CS(C)(=N)=O)c2)ncc1F]

(rac)-4-(2-Ethoxy-4-fluorophenyl)-5-fluoro-N-{3-fluoro-5-[(S-methylsulfonimidoyl)methyl]phenyl}-pyrimidin-2-amine was separated into the enantiomers by preparative HPLC.

| System: | Agilent: Prep 1200, 2xPrep Pump G1361A, DLA G2258A, MWD G1365D, Prep FC G1364B |
|---|---|
| Column: | Chiralpak IA 5 µm 250 × 20 mm |
| Solvent: | Hexane/EtOH 70/30 (v/v) |
| Flow: | 30 mL/min |
| Temperature: | RT |
| Solution: | 220 mg/2.5 ml DMSO |
| Injection: | 10 × 200 µl; 5 × 100 µl |
| Detection: | UV 254 nm |

| | Retention time in min | purity in % |
|---|---|---|
| Example 38 Enantiomer 1 | 11.0-13.3 | >99 |
| Example 39 Enantiomer 2 | 13.9-17.5 | 99 |

Example 40

(rac)-{[3-{[5-Fluoro-4-(4-fluoro-2-methoxyphenyl)pyrimidin-2-yl]amino}-5-(trifluoromethyl)-benzyl](methyl)oxido-λ⁶-sulfanylidene}cyanamide

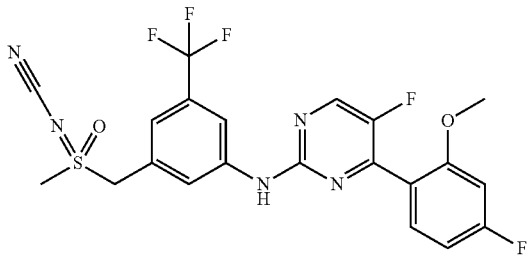 [SMILES: COc1cc(F)ccc1-c1nc(Nc2cc(CS(C)(=O)=NC#N)cc(C(F)(F)F)c2)ncc1F]

Preparation of Intermediate 40.1 tert-Butyl {3-[(methylsulfanyl)methyl]-5-(trifluoromethyl)phenyl}carbamate

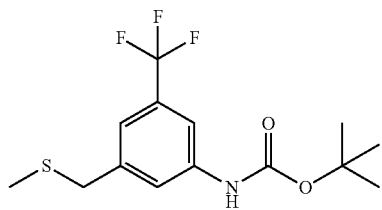 [SMILES: CSCc1cc(NC(=O)OC(C)(C)C)cc(C(F)(F)F)c1]

Intermediate 40.1 was prepared under similar conditions as described in the preparation of Intermediate 1.1 using (tert-butyl[3-(chloromethyl)-5-(trifluoromethyl)phenyl]carbamate (Enamine). The desired product was obtained by recrystallization from hexane.

$^{1}$H NMR (400 MHz, CDCl$_{3}$, 300K) δ=7.57 (s, 1H), 7.51 (s, 1H), 7.23 (s, 1H), 6.59 (s, 1H), 3.67 (s, 2H), 2.00 (s, 3H), 1.53 (s, 9H).

Preparation of Intermediate 40.2

3-[(Methylsulfanyl)methyl]-5-(trifluoromethyl)aniline

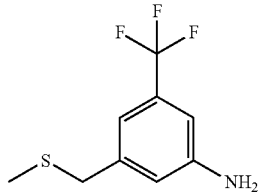

TFA (2.5 ml) was added to a stirred solution of tert-butyl {3-[(methylsulfanyl)methyl]-5-(tri-fluoromethyl)phenyl}carbamate (502 mg; 1.56 mmol) in DCM (5 mL) at 0° C. The ice bath was removed and the mixture was stirred for 45 min at RT. The batch was concentrated and saturated aqueous sodium bicarbonate solution was added. The batch was extracted with ethyl acetate (2×). The combined organic phases were dried (sodium sulfate), filtered and concentrated to give the crude product (336 mg), that was used without further purification.

$^{1}$H NMR (400 MHz, CDCl$_{3}$, 300K) δ=6.92 (s, 1H), 6.80 (s, 1H), 6.78 (s, 1H), 3.83 (br, 2H), 3.61 (s, 3H), 2.01 (s, 2H).

Preparation of Intermediate 40.3

5-Fluoro-4-(4-fluoro-2-methoxyphenyl)-N-{3-[(methylsulfanyl)methyl]-5-(trifluoromethyl)phenyl}-pyrimidin-2-amine

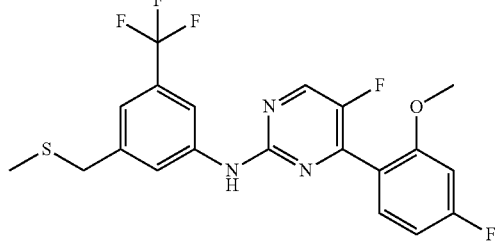

Intermediate 40.3 was prepared under similar conditions as described in the preparation of Intermediate 20.1 using 2-chloro-5-fluoro-4-(4-fluoro-2-methoxyphenyl)pyrimidine and 3-[(methylsulfanyl)methyl]-5-(trifluoromethyl)aniline. The residue was purified by chromatography (hexane to hexane/ethyl acetate 15%) to give the desired product.

$^{1}$H NMR (400 MHz, CDCl$_{3}$, 300K) δ=8.33 (m, 1H), 7.98 (br, 1H), 7.68 (s, 1H), 7.51 (m, 1H), 7.27 (m, 1H), 7.20 (s, 1H), 6.82 (m, 1H), 6.75 (m, 1H), 3.86 (s, 3H), 3.69 (s, 2H), 2.01 (s, 3H).

Preparation of Intermediate 40.4

(rac)-{[3-{[5-Fluoro-4-(4-fluoro-2-methoxyphenyl)pyrimidin-2-yl]amino}-5-(trifluoromethyl)-benzyl](methyl)-λ⁴-sulfanylidene}cyanamide

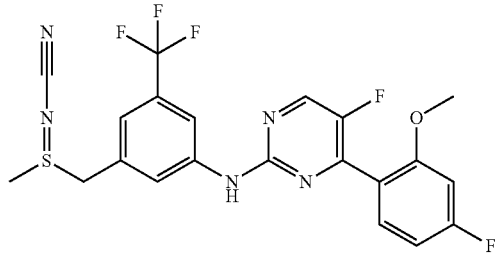 [SMILES: COc1cc(F)ccc1-c1nc(Nc2cc(CS(C)=NC#N)cc(C(F)(F)F)c2)ncc1F]

Intermediate 40.4 was prepared under similar conditions as described in the preparation of Intermediate 17.2 using 5-fluoro-4-(4-fluoro-2-methoxyphenyl)-N-{3-[(methylsulfanyl)methyl]-5-(trifluoromethyl)-phenyl}pyrimidin-2-amine. The batch was purified by chromatography (DCM/EtOH 9:1).

$^{1}$H NMR (400 MHz, CDCl$_{3}$, 300K) δ=8.35 (m, 1H), 8.09 (m, 1H), 8.04 (s, 1H), 7.92 (s, 1H), 7.48 (m, 1H), 7.19 (s, 1H), 6.83 (m, 1H), 6.76 (m, 1H), 4.43 (d, 1H), 4.21 (d, 1H), 3.87 (s, 3H), 2.78 (s, 3H),

Preparation of End Product:

Example 40 was prepared under similar conditions as described in the preparation of Example 20 using (rac)-{[3-{[5-Fluoro-4-(4-fluoro-2-methoxyphenyl)pyrimidin-2-yl]amino}-5-(trifluoromethyl)benzyl]-(methyl)-$\lambda^4$-sulfanylidene}cyanamide. The batch was purified by chromatography (hexane/ethyl acetate 9:1 to ethyl acetate).

$^1$H NMR (400 MHz, CDCl$_3$, 300K) δ=8.37 (m, 1H), 8.06 (m, 2H), 7.47 (m, 2H), 7.26 (m, 1H), 6.83 (m, 1H), 6.77 (m, 1H), 4.63 (m, 2H), 3.87 (s, 3H), 3.06 (s, 3H).

Example 41

(rac)-5-Fluoro-4-(4-fluoro-2-methoxyphenyl)-N-[3-[(S-methylsulfonimidoyl)methyl]-5-(trifluoro-methyl)phenyl]pyrimidin-2-amine

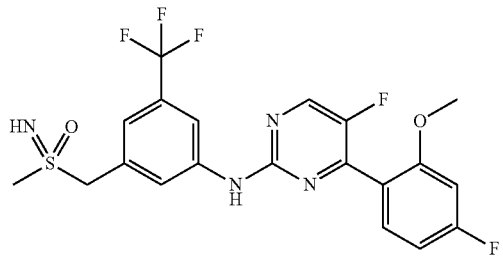 [SMILES: COc1cc(F)ccc1-c1nc(Nc2cc(CS(C)(=N)=O)cc(C(F)(F)F)c2)ncc1F]

Example 41 was prepared under similar conditions as described in the preparation of Example 21 using (rac)-{[3-{[5-fluoro-4-(4-fluoro-2-methoxyphenyl)pyrimidin-2-yl]amino}-5-(trifluoromethyl)benzyl]-(methyl)oxido-$\lambda^6$-sulfanylidene}cyanamide. The batch was purified chromatography (DCM/EtOH 95:5).

$^1$H NMR (400 MHz, CDCl$_3$, 300K) δ=8.32 (m, 1H), 8.11 (s, 1H), 7.85 (s, 1H), 7.47 (m, 2H), 7.27 (m, 1H), 6.81 (m, 1H), 6.76 (m, 1H), 4.39 (d, 1H), 4.26 (d, 1H), 3.86 (s, 3H), 2.96 (s, 3H), 2.75 (br, 1H).

Example 42

(rac)-[Ethyl(3-fluoro-5-{[5-fluoro-4-(4-fluoro-2-methoxyphenyl)pyrimidin-2-yl]amino}benzyl)-oxido-$\lambda^6$-sulfanylidene]cyanamide

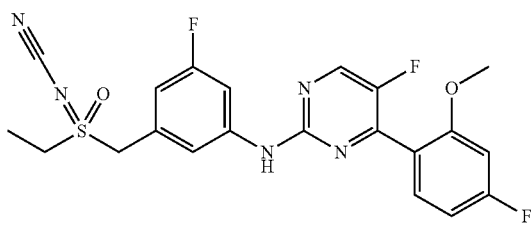

Preparation of Intermediate 42.1

1-[(Ethylsulfanyl)methyl]-3-fluoro-5-nitrobenzene

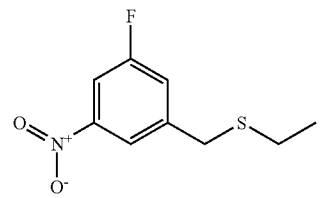

Intermediate 42.1 was prepared under similar conditions as described in the preparation of Intermediate 9.1 using 1-(chloromethyl)-3-fluoro-5-nitrobenzene (Hansa Fine Chemicals GmbH) and sodium ethanethiolate.

$^1$H NMR (400 MHz, CDCl$_3$, 300K) δ=8.04 (m, 1H), 7.84 (m, 1H), 7.47 (m, 1H), 3.81 (s, 2H), 2.49 (q, 2H), 1.29 (tr, 3H).

Preparation of Intermediate 42.2

3-[(Ethylsulfanyl)methyl]-5-fluoroaniline

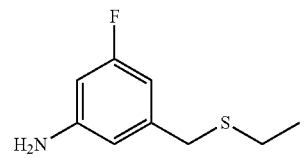

Intermediate 42.2 was prepared under similar conditions as described in the preparation of Intermediate 1.6 using 1-[(ethylsulfanyl)methyl]-3-fluoro-5-nitrobenzene.

$^1$H NMR (400 MHz, CDCl$_3$, 300K) δ=6.42 (m, 2H), 6.27 (m, 1H), 3.78 (br, 2H), 3.59 (s, 2H), 2.45 (q, 2H), 1.23 (tr, 3H).

Preparation of Intermediate 42.3

N-{3-[(Ethylsulfanyl)methyl]-5-fluorophenyl}-5-fluoro-4-(4-fluoro-2-methoxyphenyl)pyrimidin-2-amine

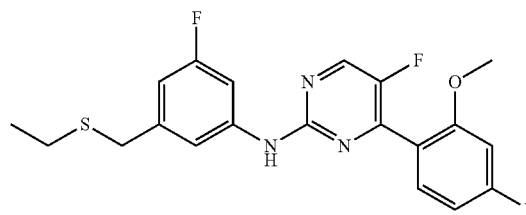

Intermediate 42.3 was prepared under similar conditions as described in the preparation of Intermediate 20.1 using 2-chloro-5-fluoro-4-(4-fluoro-2-methoxyphenyl)pyrimidine and 3-[(ethylsulfanyl)methyl]-5-fluoroaniline. The batch was purified by chromatography (hexane to hexane/ethyl acetate 30%) to give the desired product.

¹H NMR (400 MHz, CDCl₃, 300K) δ=8.32 (m, 1H), 7.61 (m, 1H), 7.49 (m, 1H), 7.30 (m, 1H), 7.13 (s, 1H), 6.74 (m, 3H), 3.86 (s, 3H), 3.66 (s, 2H), 2.45 (q, 2H), 1.22 (q, 3H).

Preparation of Intermediate 42.4

(rac)-[Ethyl(3-fluoro-5-{[5-fluoro-4-(4-fluoro-2-methoxyphenyl)pyrimidin-2-yl]amino}benzyl)-λ⁴-sulfanylidene]cyanamide

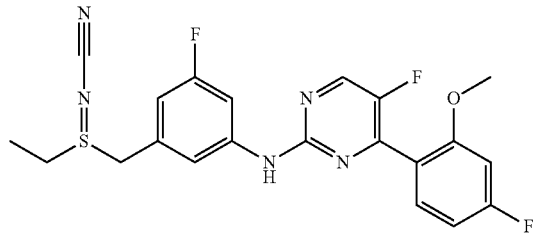 [SMILES: CCS(Cc1cc(F)cc(Nc2ncc(F)c(-c3ccc(F)cc3OC)n2)c1)=NC#N]

Intermediate 42.4 was prepared under similar conditions as described in the preparation of Intermediate 17.2 using N-{3-[(ethylsulfanyl)methyl]-5-fluorophenyl}-5-fluoro-4-(4-fluoro-2-methoxy-phenyl)pyrimidin-2-amine. The batch was purified by chromatography (hexane/ethyl acetate 25% to ethyl acetate).

¹H NMR (400 MHz, CDCl₃, 300K) δ=8.33 (m, 1H), 7.70 (m, 2H), 7.47 (m, 1H), 7.34 (m, 1H), 6.75 (m, 3H), 4.31 (d, 1H), 4.11 (d, 1H), 3.86 (s, 3H), 3.09 (m, 1H), 2.91 (m, 1H), 1.42 (tr, 3H).

Preparation of End Product:

Example 42 was prepared under similar conditions as described in the preparation of Example 20 using (rac)-[ethyl(3-fluoro-5-{[5-fluoro-4-(4-fluoro-2-methoxyphenyl)pyrimidin-2-yl]amino}benzyl)-λ⁴-sulfanylidene]cyanamide. The batch was purified by chromatography (hexane/ethyl acetate 20% to ethyl acetate).

¹H NMR (400 MHz, CDCl₃, 300K) δ=8.35 (m, 1H), 7.68 (m, 1H), 7.46 (m, 3H), 6.80 (m, 3H), 4.53 (m, 2H), 3.87 (s, 3H), 3.16 (q, 2H), 1.44 (tr, 3H).

Example 43

(rac)-N-{3-[(S-Ethylsulfonimidoyl)methyl]-5-fluorophenyl}-5-fluoro-4-(4-fluoro-2-methoxyphenyl)-pyrimidin-2-amine

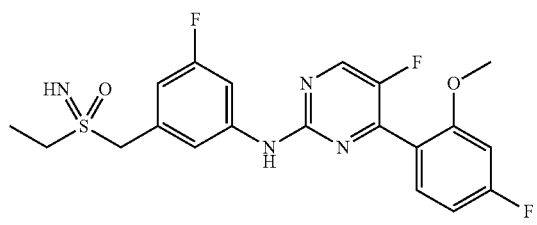 [SMILES: CCS(=N)(=O)Cc1cc(F)cc(Nc2ncc(F)c(-c3ccc(F)cc3OC)n2)c1]

Example 43 was prepared under similar conditions as described in the preparation of Example 21 using (rac)-[ethyl(3-fluoro-5-{[5-fluoro-4-(4-fluoro-2-methoxyphenyl)pyrimidin-2-yl]amino}benzyl)oxido-λ⁶-sulfanylidene]cyanamide. The batch was purified chromatography (DCM/EtOH 9:1).

¹H NMR (400 MHz, CDCl₃, 300K) δ=8.32 (m, 1H), 7.74 (m, 1H), 7.48 (m, 1H), 7.37 (s, 1H), 7.28 (m, 1H), 6.79 (m, 3H), 4.28 (d, 1H), 4.13 (d, 1H), 3.87 (s, 3H), 3.05 (q, 2H), 1.42 (tr, 3H).

Example 44 and 45

Enantiomers of N-{3-[(S-ethylsulfonimidoyl)methyl]-5-fluorophenyl}-5-fluoro-4-(4-fluoro-2-methoxyphenyl)-pyrimidin-2-amine

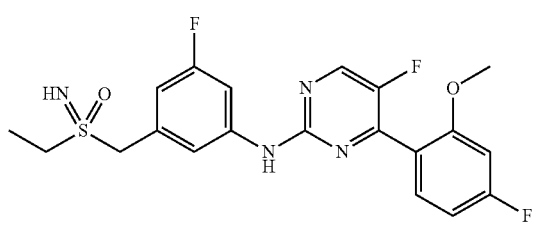 [SMILES: CCS(=N)(=O)Cc1cc(F)cc(Nc2ncc(F)c(-c3ccc(F)cc3OC)n2)c1]

(rac)-N-{3-[(S-Ethylsulfonimidoyl)methyl]-5-fluorophenyl}-5-fluoro-4-(4-fluoro-2-methoxyphenyl)-pyrimidin-2-amine was separated into the enantiomers by preparative HPLC.

| System: | Agilent: Prep 1200, 2xPrep Pump G1361A, DLA G2258A, MWD G1365D, Prep FC G1364B |
|---|---|
| Column: | Chiralpak ID 5 μm 250 × 20 mm |
| Solvent: | Hexane/EtOH 75:25 (v/v) |
| Flow: | 40 mL/min |
| Temperature: | RT |
| Solution: | 690 mg/3 mL MeOH + 0.3 ml DMSO |
| Injection: | 17 × 0.2 mL |
| Detection: | UV 220 nm |

| | Retention time in min | purity in % |
|---|---|---|
| Example 44 Enantiomer 1 | 5.4-6.4 | >99 |
| Example 45 Enantiomer 2 | 6.6-8.6 | 97.1 |

Example 46

(rac)-{[3-{[5-Fluoro-4-(4-fluoro-2-methoxyphenyl)pyrimidin-2-yl]amino}-5-(pentafluoroethyl)-benzyl](methyl)oxido-λ⁶-sulfanylidene}cyanamide

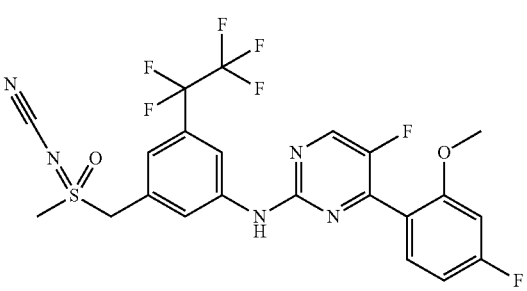 [SMILES: COc1cc(F)ccc1-c1nc(Nc2cc(CS(C)(=O)=NC#N)cc(C(F)(F)C(F)(F)F)c2)ncc1F]

Preparation of Intermediate 46.1

[3-Nitro-5-(pentafluoroethyl)phenyl]methanol

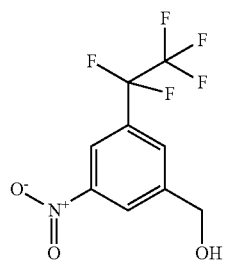 [SMILES: O=[N+]([O-])c1cc(CO)cc(C(F)(F)C(F)(F)F)c1]

Intermediate 46.1 was prepared under similar conditions as described in the preparation of Intermediate 24.1 using 3-nitro-5-(pentafluoroethyl)benzoic acid (Manchester Organics Limited).
$^1$H NMR (400 MHz, CDCl$_3$, 300K) δ=8.46 (s, 1H), 8.37 (s, 1H), 7.95 (s, 1H), 4.92 (s, 2H), 2.22 (br, 1H).

Preparation of Intermediate 46.2

[3-Amino-5-(pentafluoroethyl)phenyl]methanol

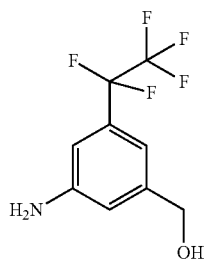

Intermediate 46.2 was prepared under similar conditions as described in the preparation of Intermediate 1.6 using [3-nitro-5-(pentafluoroethyl)phenyl]methanol.
$^1$H NMR (400 MHz, CDCl$_3$, 300K) δ=6.94 (s, 1H), 6.86 (s, 1H), 6.79 (s, 1H), 4.66 (s, 2H), 3.84 (br, 2H).

Preparation of Intermediate 46.3

[3-{[5-Fluoro-4-(4-fluoro-2-methoxyphenyl)pyrimidin-2-yl]amino}-5-(pentafluoroethyl)phenyl]-methanol

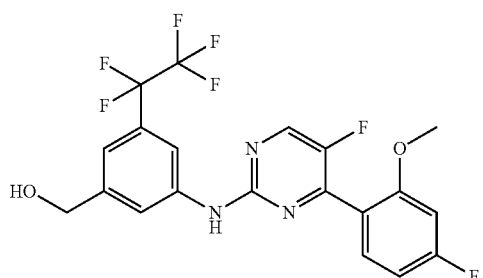

Intermediate 46.3 was prepared under similar conditions as described in the preparation of Intermediate 20.1 using 2-chloro-5-fluoro-4-(4-fluoro-2-methoxyphenyl)pyrimidine and [3-amino-5-(pentafluoro-ethyl)phenyl]methanol. The residue was purified by chromatography (hexane/ethyl acetate 6:4) to give the desired product.
$^1$H NMR (400 MHz, CDCl$_3$, 300K) δ=8.33 (m, 1H), 7.98 (s, 1H), 7.76 (s, 1H), 7.50 (m, 1H), 7.43 (br, 1H), 7.23 (s, 1H), 6.81 (m, 1H), 6.75 (m, 1H), 4.76 (s, 2H), 3.86 (s, 3H),

Preparation of Intermediate 46.4

5-Fluoro-4-(4-fluoro-2-methoxyphenyl)-N-{3-[(methylsulfanyl)methyl]-5-(pentafluoroethyl)-phenyl}pyrimidin-2-amine

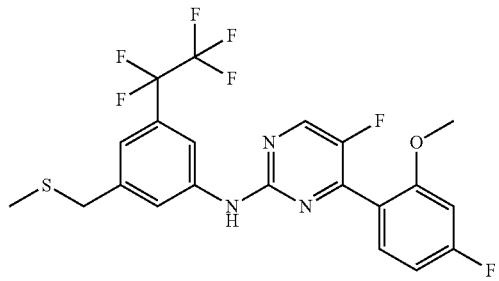 [SMILES: COc1cc(F)ccc1-c1nc(Nc2cc(CSC)cc(C(F)(F)C(F)(F)F)c2)ncc1F]

Intermediate 46.4 was prepared under similar conditions as described in the preparation of Intermediate 24.3 using [3-{[5-fluoro-4-(4-fluoro-2-methoxyphenyl)pyrimidin-2-yl]amino}-5-(pentafluoroethyl)-phenyl]methanol. The residue was purified by chromatography (hexane/ethyl acetate 2:1) to give the desired product.
$^1$H NMR (400 MHz, CDCl$_3$, 300K) δ=8.33 (m, 1H), 7.94 (s, 1H), 7.72 (s, 1H), 7.51 (m, 1H), 7.43 (s, 1H), 7.16 (s, 1H), 6.81 (m, 1H), 6.75 (m, 1H), 3.86 (s, 3H), 3.70 (s, 2H), 2.00 (s, 3H).

Preparation of Intermediate 46.5

(rac)-{[3-{[5-Fluoro-4-(4-fluoro-2-methoxyphenyl)pyrimidin-2-yl]amino}-5-(pentafluoroethyl)-benzyl](methyl)-λ$^4$-sulfanylidene}cyanamide

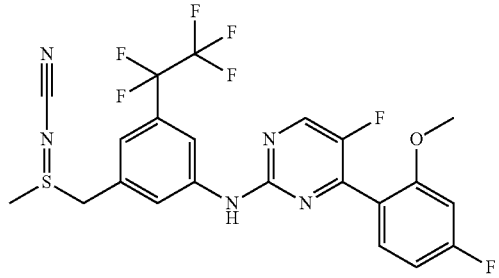 [SMILES: COc1cc(F)ccc1-c1nc(Nc2cc(CS(C)=NC#N)cc(C(F)(F)C(F)(F)F)c2)ncc1F]

Intermediate 46.5 was prepared under similar conditions as described in the preparation of Intermediate 17.2 using 5-Fluoro-4-(4-fluoro-2-methoxyphenyl)-N-{3-[(methylsulfanyl)methyl]-5-(pentafluoroethyl)-phenyl}pyrimidin-2-amine. The batch was purified by chromatography (DCM/EtOH 95:5).

¹H NMR (400 MHz, CDCl₃, 300K) δ=8.40 (m, 1H), 8.08 (s, 1H), 7.99 (m, 1H), 7.72 (m, 1H), 7.52 (m, 1H), 7.20 (s, 1H), 6.86 (m, 1H), 6.80 (m, 1H), 4.48 (d, 1H), 4.26 (d, 1H), 3.90 (s, 3H), 2.92 (s, 3H).

Preparation of End Product:

Example 46 was prepared under similar conditions as described in the preparation of Example 20 using (rac)-{[3-{[5-fluoro-4-(4-fluoro-2-methoxyphenyl)pyrimidin-2-yl]amino}-5-(pentafluoroethyl)benzyl]-(methyl)-λ⁴-sulfanylidene}cyanamide. The batch was purified by chromatography (DCM/EtOH 95:5).

¹H NMR (400 MHz, CDCl₃, 300K) δ=8.37 (m, 1H), 8.10 (s, 1H), 8.02 (s, 1H), 7.48 (m, 2H), 7.22 (s, 1H), 6.82 (m, 1H), 6.76 (m, 1H), 4.64 (m, 2H), 3.86 (s, 3H), 3.05 (s, 3H).

Example 47

(rac)-5-Fluoro-4-(4-fluoro-2-methoxyphenyl)-N-[3-[(S-methylsulfonimidoyl)methyl]-5-(pentafluoroethyl)phenyl]pyrimidin-2-amine

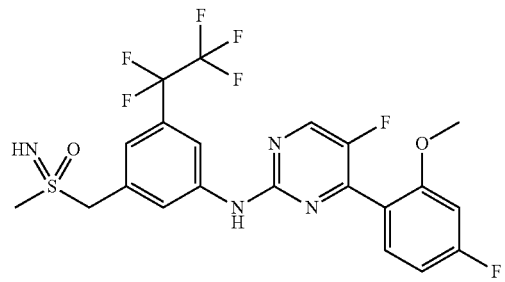 [SMILES: COc1cc(F)ccc1-c1nc(Nc2cc(CS(C)(=N)=O)cc(C(F)(F)C(F)(F)F)c2)ncc1F]

Example 47 was prepared under similar conditions as described in the preparation of Example 21 using (rac)-{[3-{[5-fluoro-4-(4-fluoro-2-methoxyphenyl)pyrimidin-2-yl]amino}-5-(pentafluoroethyl)benzyl]-(methyl)oxido-λ⁶-sulfanylidene}cyanamide. The batch was purified by preparative HPLC.

| System: | Waters Autopurificationsystem: Pump 254, Sample Manager 2767, CFO, DAD 2996, ELSD 2424, SQD 3100 |
|---|---|
| Column: | XBrigde C18 5 μm 100 × 30 mm |
| Solvent: | A = H₂O + 0.1% Vol. HCOOH (99%) |
|  | B = MeCN |
| Gradient: | 0-8 min 30-100% B |
| Flow: | 50 mL/min |
| Temperature: | RT |
| Solution: | 258 mg/3 mL DMSO/MeOH 1:1 |
| Injection: | 3 × 1 mL |
| Detection: | DAD scan range 210-400 nm |
|  | MS ESI+, ESI−, scan range 160-1000 m/z |
|  | ELSD |
| Retention: | 4.8-5.1 min |
| MS(ES+): | m/z = 522 |

¹H NMR (400 MHz, d₆-DMSO, 300K) δ=10.20 (s, 1H), 8.62 (m, 1H), 8.20 (s, 1H), 7.99 (s, 1H), 7.55 (m, 1H), 7.33 (s, 1H), 7.13 (m, 1H), 6.95 (m, 1H), 4.45 (m, 2H), 3.84 (s, 3H), 3.66 (s, 1H), 2.80 (s, 3H).

Example 48

(rac)-[Cyclopropyl(3-{[5-fluoro-4-(4-fluoro-2-methoxyphenyl)pyrimidin-2-yl]amino}benzyl)oxido-λ⁶-sulfanylidene]cyanamide

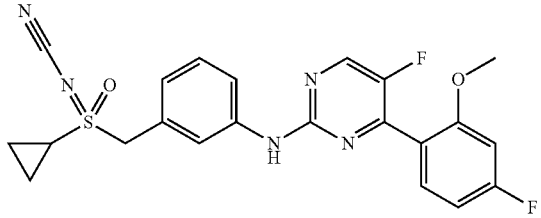 [SMILES: COc1cc(F)ccc1-c1nc(Nc2cccc(CS(=O)(=NC#N)C3CC3)c2)ncc1F]

Preparation of Intermediate 48.1

1-[(Cyclopropylsulfanyl)methyl]-3-nitrobenzene

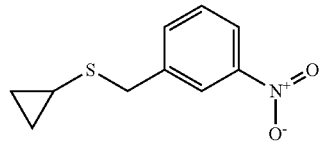 [SMILES: O=[N+]([O-])c1cccc(CSC2CC2)c1]

Sulfur (0.91 g; 27.5 mmol) was added portions wise to a stirred 0.5M solution of bromo-(cyclopropyl)magnesium in THF (50.0 ml; 25.0 mmol). The batch was stirred at 50° C. for 1 hour and then cooled to 0° C. Lithium tetrahydridoaluminate(1-) (522 mg; 13.8 mmol) was cautiously added under stirring. The batch was stirred for 30 minutes at 50° C. and cooled to 0° C. again. Water (2 ml) was cautiously added under stirring. Finally, sulfuric acid (5%; 100 ml) was cautiously added and the batch was stirred for 10 minutes. The organic phase was separated and the aqueous phase was extracted with diethyl ether (2×). The combined organic phases were washed with saturated aqueous ammonium chloride solution (2×), aqueous sodium bicarbonate solution (5%, 2×), water (2×) and saturated aqueous sodium chloride solution (2×). The organic phase was dried (magnesium sulfate) and filtered before it was slowly added to a stirred batch of 1-(chloromethyl)-3-nitrobenzene (2.15 g; 12.5 mmol) and potassium carbonate (2.59 g; 18.8 mmol) in DMF (40 ml). The batch was stirred at 85° C. overnight. After cooling, the batch was filtered over celite and concentrated in vacuo. The residue was taken up in ethyl acetate and washed with water (2×) and saturated aqueous sodium chloride solution (2×). The organic phase was dried (sodium sulfate), filtered and concentrated. The residue was purified by chromatography (hexane/ethyl acetate 8:2) to give the desired product (2.38 g; 11.4 mmol).

¹H NMR (400 MHz, d₆-DMSO, 300K) δ=8.16 (m, 1H), 8.06 (m, 1H), 7.75 (m, 1H), 7.56 (m, 1H), 3.90 (s, 2H), 1.72 (m, 1H), 0.77 (m, 2H), 0.39 (m, 2H).

Preparation of Intermediate 48.2

3-[(Cyclopropylsulfanyl)methyl]aniline

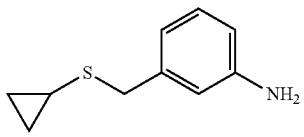 [SMILES: Nc1cccc(CSC2CC2)c1]

Intermediate 48.2 was prepared under similar conditions as described in the preparation of Intermediate 1.6 using 1-[(cyclopropylsulfanyl)methyl]-3-nitrobenzene.

$^1$H NMR (400 MHz, d$_6$-DMSO, 300K) δ=6.89 (m, 1H), 6.49 (m, 1H), 6.38 (m, 2H), 4.96 (s, 2H), 3.56 (s, 2H), 1.75 (m, 1H), 0.78 (m, 2H), 0.42 (m, 2H).

Preparation of Intermediate 48.3

N-{3-[(Cyclopropylsulfanyl)methyl]phenyl}-5-fluoro-4-(4-fluoro-2-methoxyphenyl)pyrimidin-2-amine

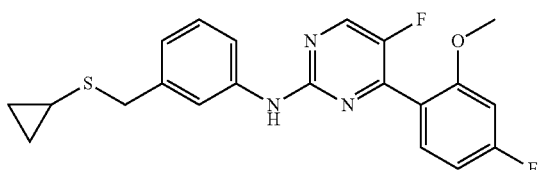

Intermediate 48.3 was prepared under similar conditions as described in the preparation of Intermediate 20.1 using 2-chloro-5-fluoro-4-(4-fluoro-2-methoxyphenyl)pyrimidine and 3-[(cyclopropylsulfanyl)-methyl]aniline. The batch was purified by chromatography (hexane/ethyl acetate 30%) to give the desired product.

$^1$H NMR (400 MHz, d$_6$-DMSO, 300K) δ=9.71 (s, 1H), 8.51 (m, 1H), 7.70 (m, 1H), 7.54 (m, 1H), 7.49 (m, 1H), 7.16 (m, 1H), 7.09 (m, 1H), 6.91 (m, 1H), 6.85 (m, 1H), 3.80 (s, 3H), 3.68 (s, 2H), 1.74 (m, 1H), 0.74 (m, 2H), 0.41 (m, 2H).

Preparation of Intermediate 48.4

(rac)-[Cyclopropyl(3-{[5-fluoro-4-(4-fluoro-2-methoxyphenyl)pyrimidin-2-yl]amino}benzyl)-λ$^4$-sulfanylidene]cyanamide

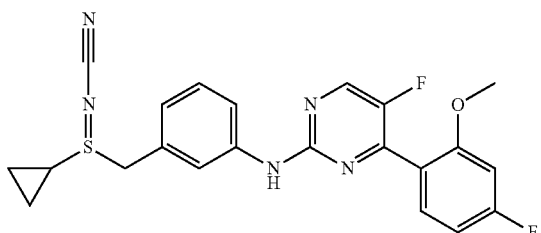

Intermediate 48.4 was prepared under similar conditions as described in the preparation of Intermediate 17.2 using N-{3-[(cyclopropylsulfanyl)methyl]phenyl}-5-fluoro-4-(4-fluoro-2-methoxyphenyl)-pyrimidin-2-amine. The batch was purified by chromatography (hexane/ethyl acetate 25% to ethyl acetate).

$^1$H NMR (400 MHz, d$_6$-DMSO, 300K) δ=9.86 (s, 1H), 8.52 (m, 1H), 7.82 (m, 1H), 7.68 (m, 1H), 7.53 (m, 1H), 7.27 (m, 1H), 7.09 (m, 1H), 7.01 (m, 1H), 6.92 (m, 1H), 4.49 (d, 1H), 4.35 (d, 1H), 3.80 (s, 3H), 2.68 (m, 1H), 1.04 (m, 3H), 0.81 (m, 1H).

Preparation of End Product:

Example 48 was prepared under similar conditions as described in the preparation of Example 20 using (rac)-[Cyclopropyl(3-{[5-fluoro-4-(4-fluoro-2-methoxyphenyl)pyrimidin-2-yl]amino}benzyl)-λ$^4$-sulfanylidene]cyanamide. The batch was purified by chromatography (hexane/ethyl acetate 12% to ethyl acetate).

$^1$H NMR (400 MHz, d$_6$-DMSO, 300K) δ=9.89 (s, 1H), 8.52 (m, 1H), 7.85 (m, 1H), 7.74 (m, 1H), 7.52 (m, 1H), 7.29 (m, 1H), 7.09 (m, 1H), 7.02 (m, 1H), 6.91 (m, 1H), 4.96 (d, 1H), 4.89 (d, 1H), 3.80 (s, 3H), 2.91 (m, 1H), 1.12 (m, 3H), 0.86 (m, 1H).

Example 49

(rac)-N-{3-[(S-Cyclopropylsulfonimidoyl)methyl]phenyl}-5-fluoro-4-(4-fluoro-2-methoxyphenyl)-pyrimidin-2-amine

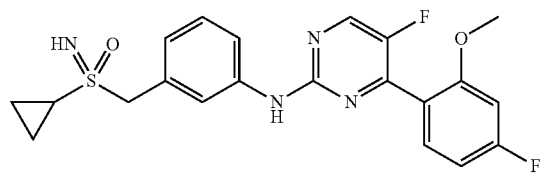 [SMILES: COc1cc(F)ccc1-c1nc(Nc2cccc(CS(=N)(=O)C3CC3)c2)ncc1F]

Example 49 was prepared under similar conditions as described in the preparation of Example 21 using (rac)-[Cyclopropyl(3-{[5-fluoro-4-(4-fluoro-2-methoxyphenyl)pyrimidin-2-yl]amino}benzyl)oxido-λ$^6$-sulfanylidene]cyanamide. The batch was purified by chromatography (hexane/ethyl acetate 25% to ethyl acetate).

$^1$H NMR (400 MHz, d$_6$-DMSO, 300K) δ=9.77 (s, 1H), 8.51 (m, 1H), 7.75 (m, 1H), 7.66 (m, 1H), 7.51 (m, 1H), 7.22 (m, 1H), 7.09 (m, 1H), 6.96 (m, 1H), 6.91 (m, 1H), 4.25 (d, 1H), 4.19 (d, 1H), 3.80 (s, 3H), 3.42 (s, 1H), 2.30 (m, 1H), 0.88 (m, 1H), 0.75 (m, 3H).

Example 50

(rac)-[Cyclopropyl(3-fluoro-5-{[5-fluoro-4-(4-fluoro-2-methoxyphenyl)pyrimidin-2-yl]amino}-benzyl)oxido-λ$^6$-sulfanylidene]cyanamide

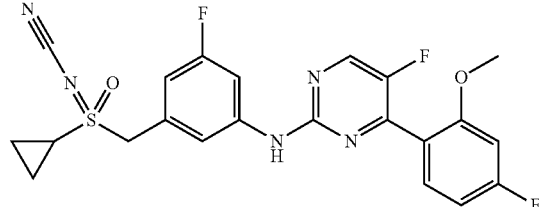

Preparation of Intermediate 50.1

1-[(Cyclopropylsulfanyl)methyl]-3-fluoro-5-nitrobenzene

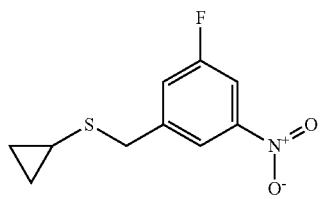 [SMILES: O=[N+]([O-])c1cc(F)cc(CSC2CC2)c1]

Intermediate 50.1 was prepared under similar conditions as described in the preparation of Intermediate 48.1 using 1-(chloromethyl)-3-fluoro-5-nitrobenzene (Hansa Fine Chemicals GmbH). The batch was purified by chromatography (hexane/ethyl acetate 4:1).

$^1$H NMR (400 MHz, CDCl$_3$, 300K) δ=8.02 (m, 1H), 7.81 (m, 1H), 7.42 (m, 1H), 3.81 (s, 2H), 1.74 (m, 1H), 0.86 (m, 2H), 0.55 (m, 2H).

Preparation of Intermediate 50.2

3-[(Cyclopropylsulfanyl)methyl]-5-fluoroaniline

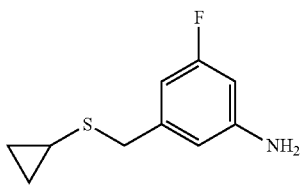 [SMILES: Nc1cc(F)cc(CSC2CC2)c1]

Intermediate 50.2 was prepared under similar conditions as described in the preparation of Intermediate 1.6 using 1-[(cyclopropylsulfanyl)methyl]-3-fluoro-5-nitrobenzene.

$^1$H NMR (400 MHz, CDCl$_3$, 300K) δ=6.43 (m, 2H), 6.25 (m, 1H), 3.74 (br, 2H), 3.63 (s, 2H), 1.79 (m, 1H), 0.82 (m, 2H), 0.54 (m, 2H).

Preparation of Intermediate 50.3

N-{3-[(Cyclopropylsulfanyl)methyl]-5-fluorophenyl}-5-fluoro-4-(4-fluoro-2-methoxyphenyl)-pyrimidin-2-amine

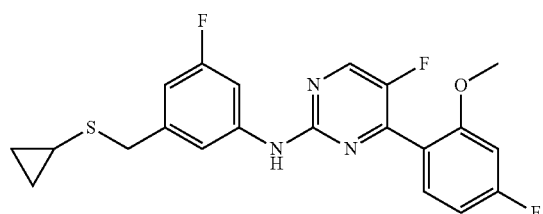

Intermediate 50.3 was prepared under similar conditions as described in the preparation of Intermediate 20.1 using 2-chloro-5-fluoro-4-(4-fluoro-2-methoxyphenyl)pyrimidine and 3-[(cyclopropylsulfanyl)-methyl]-5-fluoroaniline. The batch was purified by chromatography (hexane to hexane/ethyl acetate 50%) to give the desired product.

$^1$H NMR (400 MHz, CDCl$_3$, 300K) δ=8.34 (m, 1H), 7.63 (m, 1H), 7.52 (m, 1H), 7.23 (s, 1H), 7.17 (m, 1H), 6.84 (m, 1H), 6.78 (m, 1H), 6.73 (m, 1H), 3.89 (s, 3H), 3.74 (s, 2H), 1.81 (m, 1H), 0.83 (m, 2H), 0.57 (m, 2H).

Preparation of Intermediate 50.4

(rac)-[Cyclopropyl(3-fluoro-5-{[5-fluoro-4-(4-fluoro-2-methoxyphenyl)pyrimidin-2-yl]amino}-benzyl)-λ$^4$-sulfanylidene]cyanamide

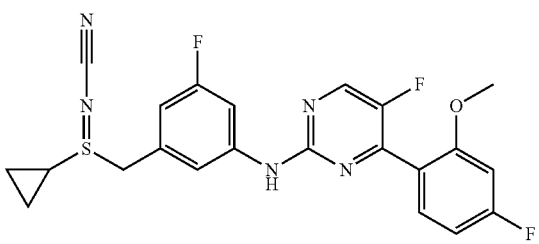 [SMILES: COc1cc(F)ccc1-c1nc(Nc2cc(F)cc(CS(=NC#N)C3CC3)c2)ncc1F]

Intermediate 50.4 was prepared under similar conditions as described in the preparation of Intermediate 17.2 using N-{3-[(cyclopropylsulfanyl)methyl]-5-fluorophenyl}-5-fluoro-4-(4-fluoro-2-methoxyphenyl)-pyrimidin-2-amine. The batch was purified by chromatography (ethyl acetate).

$^1$H NMR (400 MHz, CDCl$_3$, 300K) δ=8.34 (m, 1H), 7.65 (m, 1H), 7.48 (m, 1H), 7.39 (s, 1H), 7.34 (br, 1H), 6.83 (m, 1H), 6.78 (m, 1H), 6.71 (m, 1H), 4.43 (d, 1H), 4.22 (d, 1H), 3.87 (s, 3H), 2.48 (m, 1H), 1.28 (m, 2H), 1.14 (m, 2H).

Preparation of End Product

Example 50 was prepared under similar conditions as described in the preparation of Example 20 using (rac)-[cyclopropyl(3-fluoro-5-{[5-fluoro-4-(4-fluoro-2-methoxyphenyl)pyrimidin-2-yl]amino}benzyl)-λ$^4$-sulfanylidene]cyanamide. The batch was purified by chromatography (hexane to hexane/ethyl acetate 70%).

$^1$H NMR (400 MHz, d$_6$-DMSO, 300K) δ=8.34 (m, 1H), 7.70 (m, 1H), 7.49 (m, 2H), 7.32 (br, 1H), 6.79 (m, 3H), 4.56 (d, 1H), 4.48 (d, 1H), 3.87 (s, 3H), 2.39 (m, 1H), 1.19 (m, 4H).

Example 51

(rac)-N-{3-[(S-Cyclopropylsulfonimidoyl)methyl]-5-fluorophenyl}-5-fluoro-4-(4-fluoro-2-methoxy-phenyl)pyrimidin-2-amine

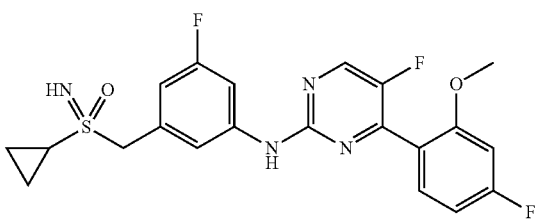 [SMILES: COc1cc(F)ccc1-c1nc(Nc2cc(F)cc(CS(=N)(=O)C3CC3)c2)ncc1F]

Example 51 was prepared under similar conditions as described in the preparation of Example 21 using (rac)-[cyclopropyl(3-fluoro-5-{[5-fluoro-4-(4-fluoro-2-methoxyphenyl)pyrimidin-2-yl]amino}benzyl)-oxido-λ⁶-sulfanylidene]cyanamide. The batch was purified chromatography (DCM to DCM/EtOH 4:1).

¹H NMR (400 MHz, CDCl₃, 300K) δ=8.32 (m, 1H), 7.73 (m, 1H), 7.49 (m, 1H), 7.31 (s, 1H), 7.27 (m, 1H), 6.79 (m, 3H), 4.30 (d, 1H), 4.20 (d, 1H), 3.87 (s, 3H), 2.38 (m, 1H), 1.16 (m, 2H), 0.97 (m, 2H).

Example 52 and 53

Enantiomers of N-{3-[(S-cyclopropylsulfonimidoyl)methyl]-5-fluorophenyl}-5-fluoro-4-(4-fluoro-2-methoxy-phenyl)pyrimidin-2-amine

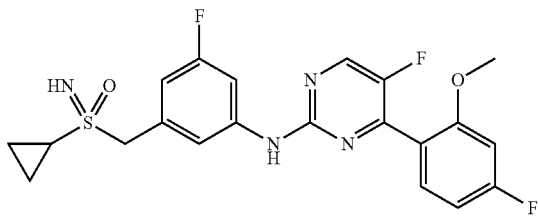 [SMILES: COc1cc(F)ccc1-c1nc(Nc2cc(F)cc(CS(=N)(=O)C3CC3)c2)ncc1F]

(rac)-N-{3-[(S-cyclopropylsulfonimidoyl)methyl]-5-fluorophenyl}-5-fluoro-4-(4-fluoro-2-methoxy-phenyl)pyrimidin-2-amine was separated into the enantiomers by preparative HPLC.

| System: | Sepiatec: Prep SFC100, |
|---|---|
| Column: | Chiralpak ID 5 μm 250 × 20 mm |
| Solvent: | CO₂/MeOH 70:30 |
| Flow: | 80 mL/min |
| Pressure (outlet): | 150 bar |
| Temperature: | 40° C. |
| Solution: | 132 mg/2.5 mL MeOH/DCM 1:1 |
| Injection: | 5 × 0.5 mL |
| Detection: | UV 254 nm |

| | Retention time in min | purity in % |
|---|---|---|
| Example 52 Enantiomer 1 | 3.10-3.75 | >99 |
| Example 53 Enantiomer 2 | 3.80-4.75 | 95.3 |

Example 54

(rac)-Ethyl[(3-{[4-(2,3-dihydro-1-benzofuran-7-yl)-5-fluoropyrimidin-2-yl]amino}benzyl)(methyl)-oxido-λ⁶-sulfanylidene]carbamate

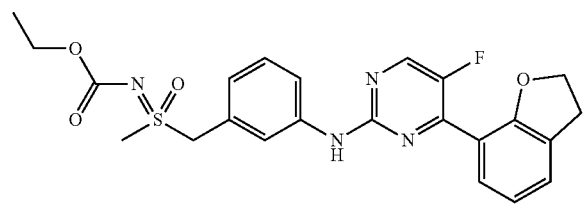 [SMILES: CCOC(=O)N=S(C)(=O)Cc1cccc(Nc2ncc(F)c(-c3cccc4c3OCC4)n2)c1]

Preparation of Intermediate 54.1

2-Chloro-4-(2,3-dihydro-1-benzofuran-7-yl)-5-fluoropyrimidine

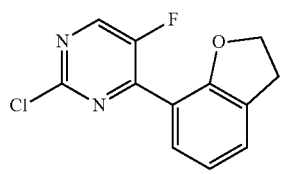 [SMILES: Fc1cnc(Cl)nc1-c1cccc2c1OCC2]

Intermediate 54.1 was prepared under similar conditions as described in the preparation of Intermediate 36.1 using 2,4-dichloro-5-fluoropyrimidine and 2,3-dihydro-1-benzofuran-7-ylboronic acid (Combi-Blocks Inc.).

¹H NMR (400 MHz, d₆-DMSO, 300K) δ=8.88 (m, 1H), 7.43 (m, 1H), 7.34 (m, 1H), 6.98 (m, 1H), 4.58 (tr, 2H), 3.24 (tr, 2H).

Preparation of End Product

Example 54 was prepared under similar conditions as described in the preparation of Example 1 using 2-chloro-4-(2,3-dihydro-1-benzofuran-7-yl)-5-fluoropyrimidine and (rac)-ethyl[(3-aminobenzyl)-(methyl)oxido-λ⁶-sulfanylidene]carbamate. The batch was purified preparative HPLC.

| System: | Waters Autopurificationsystem: Pump 2545, Sample Manager 2767, CFO, DAD 2996, ELSD 2424, SQD 3001 |
|---|---|
| Column: | XBrigde C18 5 μm 100 × 30 mm |
| Solvent: | A = H₂O + 0.1% HCOOH |
| | B = MeCN |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO or DMF |
| Injektion: | 1 × 2.5 mL |
| Detection: | DAD scan range 210-400 nm |
| | MS ESI+, ESI−, scan range 160-1000 m/z |

¹H NMR (400 MHz, d₆-DMSO, 300K) δ=9.84 (s, 1H), 8.53 (m, 1H), 7.77 (m, 2H), 7.36 (m, 2H), 7.28 (m, 1H), 6.98 (m, 2H), 4.77 (s, 2H), 4.57 (m, 2H), 3.93 (m, 2H), 3.24 (m, 2H), 3.11 (s, 3H), 1.10 (tr, 3H).

Example 55

(rac)-5-Fluoro-4-[4-fluoro-2-[(4-fluorobenzyl)oxy]phenyl]-N-[3-{(S-methylsulfonimidoyl)methyl]-phenyl}pyrimidin-2-amine

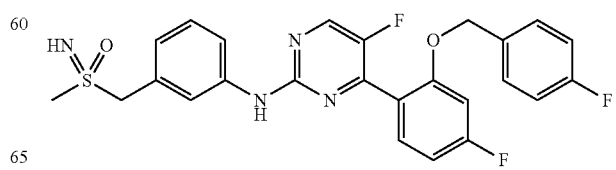

Preparation of Intermediate 55.1

2-Chloro-4-(2,4-difluorophenyl)-5-fluoropyrimidine

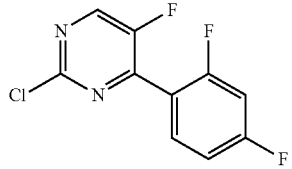 [SMILES: Fc1ccc(-c2nc(Cl)ncc2F)c(F)c1]

Intermediate 55.1 was prepared under similar conditions as described in the preparation of Intermediate 36.1 using 2,4-dichloro-5-fluoropyrimidine and (2,4-difluorophenyl)boronic acid (ABCR GmbH & CO. KG).
$^1$H NMR (400 MHz, CDCl$_3$, 300K) δ=8.56 (m, 1H), 7.73 (m, 1H), 7.07 (m, 1H), 6.95 (m, 1H).

Preparation of Intermediate 55.2

(rac)-Ethyl[(3-{[4-(2,4-difluorophenyl)-5-fluoropyrimidin-2-yl]amino}benzyl)(methyl)oxido-λ$^6$-sulfanylidene]carbamate

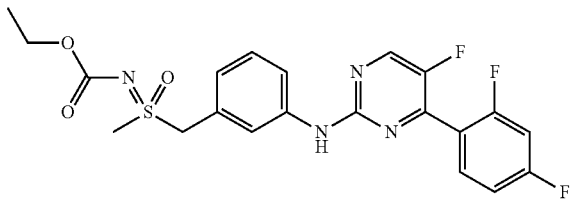 [SMILES: CCOC(=O)N=S(C)(=O)Cc1cccc(Nc2ncc(F)c(-c3ccc(F)cc3F)n2)c1]

Intermediate 55.2 was prepared under similar conditions as described in the preparation of Example 1 using 2-chloro-4-(2,4-difluorophenyl)-5-fluoropyrimidine and (rac)-ethyl[(3-aminobenzyl)(methyl)-oxido-λ$^6$-sulfanylidene]carbamate. The batch was purified chromatography (DCM/EtOH 95:5).
$^1$H NMR (400 MHz, CDCl$_3$, 300K) δ=8.39 (m, 1H), 7.90 (br, 1H), 7.72 (m, 1H), 7.56 (m, 1H), 7.37 (m, 1H), 7.31 (s, 1H), 7.07 (m, 2H), 6.98 (m, 1H), 4.71 (m, 2H), 4.17 (q, 2H), 2.98 (s, 3H), 1.31 (q, 3H), Preparation of End Product Sodium hydride (60%; 34.4 mg; 0.86 mmol) was added under stirring to a solution of (rac)-ethyl[(3-{[4-(2,4-difluorophenyl)-5-fluoropyrimidin-2-yl]amino}benzyl)(methyl)oxido-λ$^6$-sulfanylidene]carbamate (100.0 mg; 0.22 mmol) in (4-fluorophenyl)methanol (0.5 ml; ABCR GmbH & CO. KG) at room temperature. The batch was stirred under argon at 70° C. for 19 hours before additional sodium hydride (60%; 17.2 mg; 0.43 mmol) was added. After 6 hours, additional sodium hydride (60%; 34.4 mg; 0.86 mmol) was added and the batch was stirred for 16 hours. After cooling, the batch was diluted with DCM and saturated aqueous sodium chloride solution. The organic phase was filtered using a Whatman filter and concentrated. The desired product (6.4 mg; 0.01 mmol) was isolated by preparative HPLC.

| | |
|---|---|
| System: | Waters Autopurificationsystem: Pump 254, Sample Manager 2767, CFO, DAD 2996, SQD 3100 |
| Column: | XBrigde C18 5 μm 100 × 30 mm |
| Solvent: | A = H$_2$O + 0.2% NH$_3$ (32%) |
| | B = MeCN |
| Gradient: | 0-8 min 30-70% B |
| Flow: | 50 mL/min |
| Temperature: | RT |
| Solution: | 346 mg/4 mL DMF/MeOH 1 + 1 |
| Injection: | 5 × 0.8 mL |
| Detection: | DAD scan range 210-400 nm |
| | MS ESI+, ESI−, scan range 160-1000 m/z |
| Retention: | 5.58-5.93 min |
| MS(ES+): | m/z = 498 |

$^1$H NMR (400 MHz, CDCl$_3$, 300K) δ=8.28 (m, 1H), 7.78 (m, 1H), 7.58 (m, 1H), 7.52 (m, 1H), 7.32 (m, 3H), 7.20 (s, 1H), 7.04 (m, 3H), 6.84 (m, 1H), 6.76 (m, 1H), 5.07 (s, 2H), 4.35 (d, 1H), 4.23 (d, 1H), 2.91 (s, 3H), 2.66 (br, 1H).

Example 56

(rac)-[(3-Chloro-5-{[5-fluoro-4-(4-fluoro-2-methoxyphenyl)pyrimidin-2-yl]amino}benzyl)(methyl)-oxido-λ$^6$-sulfanylidene]cyanamide

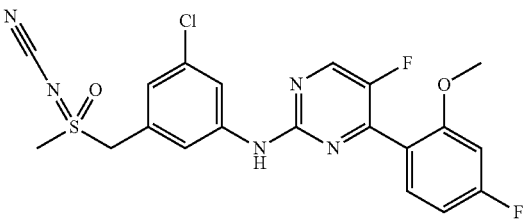

Preparation of Intermediate 56.1

(3-Chloro-5-nitrophenyl)methanol

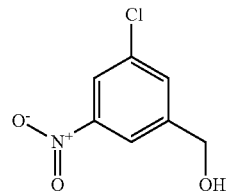 [SMILES: O=[N+]([O-])c1cc(Cl)cc(CO)c1]

Intermediate 56.1 was prepared under similar conditions as described in the preparation of Intermediate 24.1 using 3-chloro-5-nitrobenzoic acid (ABCR GmbH & CO. KG).
$^1$H NMR (400 MHz, CDCl$_3$, 300K) δ=8.13 (m, 2H), 7.71 (s, 1H), 4.81 (m, 2H), 2.00 (br, 1H).

Preparation of Intermediate 56.2

1-Chloro-3-(chloromethyl)-5-nitrobenzene

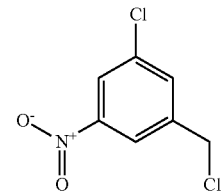 [SMILES: O=[N+]([O-])c1cc(Cl)cc(CCl)c1]

Intermediate 56.2 was prepared under similar conditions as described in the preparation of Intermediate 24.3 using (3-chloro-5-nitrophenyl)methanol.

¹H NMR (400 MHz, CDCl₃, 300K) δ=8.17 (m, 2H), 7.72 (s, 1H), 4.62 (s, 2H).

Preparation of Intermediate 56.3

1-Chloro-3-[(methylsulfanyl)methyl]-5-nitrobenzene

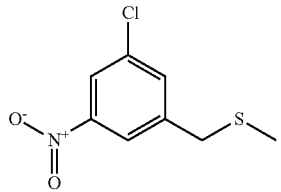

Intermediate 56.3 was prepared under similar conditions as described in the preparation of Intermediate 1.1 using 1-chloro-3-(chloromethyl)-5-nitrobenzene.
¹H NMR (400 MHz, CDCl₃, 300K) δ=8.11 (m, 1H), 8.08 (s, 1H), 7.66 (s, 1H), 3.72 (m, 2H), 2.03 (s, 3H).

Preparation of Intermediate 56.4

3-Chloro-5-[(methylsulfanyl)methyl]aniline

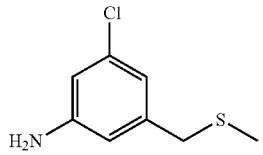

Intermediate 56.4 was prepared under similar conditions as described in the preparation of Intermediate 1.6 using 1-chloro-3-[(methylsulfanyl)methyl]-5-nitrobenzene.
¹H NMR (400 MHz, CDCl₃, 300K) δ=6.68 (m, 1H), 6.56 (m, 1H), 6.52 (m, 1H), 3.73 (br, 2H), 3.53 (s, 2H), 2.01 (s, 3H).

Preparation of Intermediate 56.5

N-{3-Chloro-5-[(methylsulfanyl)methyl]phenyl}-5-fluoro-4-(4-fluoro-2-methoxyphenyl)pyrimidin-2-amine

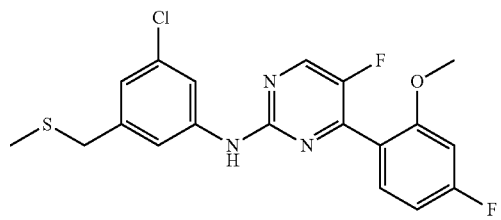

Intermediate 56.5 was prepared under similar conditions as described in the preparation of Intermediate 28.3 using 2-chloro-5-fluoro-4-(4-fluoro-2-methoxyphenyl)pyrimidine and 3-chloro-5-[(methylsulfanyl)-methyl]aniline. The batch was purified by chromatography (hexane to hexane/ethyl acetate 30%) to give the desired product.

¹H NMR (400 MHz, CDCl₃, 300K) δ=8.32 (m, 1H), 7.75 (m, 1H), 7.49 (m, 1H), 7.35 (s, 1H), 7.18 (s, 1H), 6.95 (s, 1H), 6.79 (m, 2H), 3.87 (s, 3H), 3.61 (s, 2H), 2.01 (s, 3H).

Preparation of Intermediate 56.6

(rac)-[(3-Chloro-5-{[5-fluoro-4-(4-fluoro-2-methoxyphenyl)pyrimidin-2-yl]amino}benzyl)(methyl)-λ⁴-sulfanylidene]cyanamide

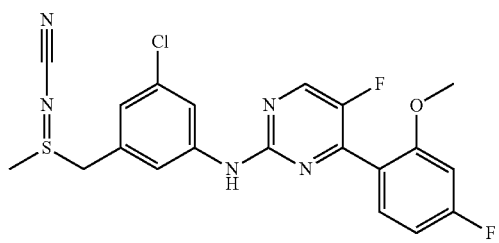 [SMILES: COc1cc(F)ccc1-c1nc(Nc2cc(Cl)cc(CS(C)=NC#N)c2)ncc1F]

Intermediate 56.6 was prepared under similar conditions as described in the preparation of Intermediate 17.2 using N-{3-chloro-5-[(methylsulfanyl)methyl]phenyl}-5-fluoro-4-(4-fluoro-2-methoxyphenyl)-pyrimidin-2-amine. The batch was purified by chromatography (ethyl acetate).
¹H NMR (400 MHz, CDCl₃, 300K) δ=8.35 (m, 1H), 7.76 (m, 1H), 7.61 (m, 1H), 7.47 (m 1H), 7.32 (s, 1H), 6.95 (m, 1H), 6.83 (m, 1H), 6.77 (m, 1H), 4.36 (d, 1H), 4.12 (d, 1H), 3.87 (s, 3H), 2.75 (s, 3H).

Preparation of End Product:

Example 56 was prepared under similar conditions as described in the preparation of Example 20 using (rac)-[(3-Chloro-5-{[5-fluoro-4-(4-fluoro-2-methoxyphenyl)pyrimidin-2-yl]amino}benzyl)(methyl)-λ⁴-sulfanylidene]cyanamide. The batch was purified by chromatography (hexane/ethyl acetate 20% to ethyl acetate).
¹H NMR (400 MHz, CDCl₃, 300K) δ=8.35 (m, 1H), 7.79 (m, 1H), 7.73 (br, 1H), 7.47 (m, 1H), 7.35 (s, 1H), 7.02 (br, 1H), 6.82 (m, 1H), 6.76 (m, 1H), 4.55 (m, 2H), 3.87 (s, 3H), 3.05 (s, 3H).

Example 57

(rac)-N-{3-Chloro-5-[(S-methylsulfonimidoyl)methyl]phenyl}-5-fluoro-4-(4-fluoro-2-methoxy-phenyl)pyrimidin-2-amine

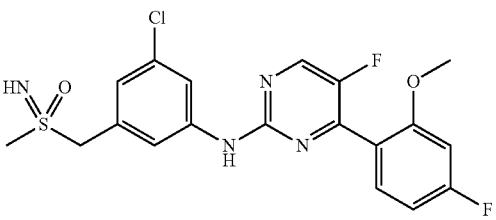

Example 57 was prepared under similar conditions as described in the preparation of Example 21 using (rac)-[(3-chloro-5-{[5-fluoro-4-(4-fluoro-2-methoxyphenyl)pyrimidin-2-yl]amino}benzyl)(methyl)-oxido-λ⁶-sulfanylidene]cyanamide. The batch was purified by chromatography (DCM to DCM/EtOH 4:1).

¹H NMR (400 MHz, CDCl₃, 300K) δ=8.32 (m, 1H), 7.85 (m, 1H), 7.54 (m, 1H), 7.48 (m, 1H), 7.18 (s, 1H), 7.03 (m, 1H), 6.79 (m, 2H), 4.31 (d, 1H), 4.19 (d, 1H), 3.87 (s, 3H), 2.94 (s, 3H).

Example 58

(rac)-[(3-{[5-Fluoro-4-(4-fluoro-2-methoxyphenyl)pyrimidin-2-yl]amino}-5-methylbenzyl)(methyl)-oxido-λ⁶-sulfanylidene]cyanamide

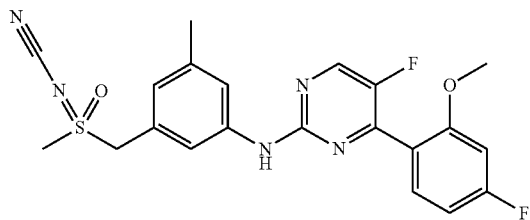 [SMILES: COc1cc(F)ccc1-c1nc(Nc2cc(C)cc(CS(C)(=O)=NC#N)c2)ncc1F]

Preparation of Intermediate 58.1

3-(Chloromethyl)-5-methylaniline

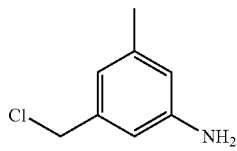

To a stirred solution of 3-amino-5-methyl-benzyl alcohol (6.32 g; 42.8 mmol; GL Syntech LLC, Hatfield, Pa.) in DCM (140 mL) at 0° C. was added dropwise thionylchloride (9.4 mL; 128 mmol). The mixture was allowed to react at room temperature overnight. Then, the mixture was concentrated under reduced pressure. The resulting material was dissolved in DCM again and evaporated to dryness to give crude 3-(chloromethyl)-5-methylaniline (9.5 g).

Preparation of Intermediate 58.2

3-Methyl-5-[(methylsulfanyl)methyl]aniline

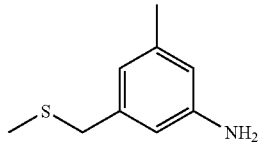

Intermediate 58.2 was prepared under similar conditions as described in the preparation of Intermediate 1.1 using 3-(chloromethyl)-5-methylaniline.

¹H NMR (300 MHz, d₆-DMSO, 300K) δ=6.30 (m, 1H), 6.24 (m, 2H), 4.95 (s, 2H), 3.47 (s, 2H), 2.12 (s, 3H), 1.94 (s, 3H).

Preparation of Intermediate 58.3

5-Fluoro-4-(4-fluoro-2-methoxyphenyl)-N-{3-methyl-5-[(methylsulfanyl)methyl]phenyl}pyrimidin-2-amine

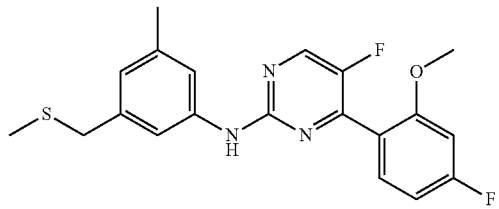 [SMILES: COc1cc(F)ccc1-c1nc(Nc2cc(C)cc(CSC)c2)ncc1F]

Intermediate 58.3 was prepared under similar conditions as described in the preparation of Intermediate 20.1 using 2-chloro-5-fluoro-4-(4-fluoro-2-methoxyphenyl)pyrimidine and 3-methyl-5-[(methyl-sulfanyl)methyl]aniline. The batch was purified by chromatography (hexane/ethyl acetate 5% to 32%) to give the desired product.

¹H NMR (400 MHz, d₆-DMSO, 300K) δ=9.67 (s, 1H), 8.54 (d, 1H), 7.53 (m, 2H), 7.41 (s, 1H), 7.12 (dd, 1H), 6.95 (td, 1H), 6.70 (s, 1H), 3.84 (s, 3H), 3.59 (s, 2H), 2.24 (s, 3H), 1.95 (s, 3H).

Preparation of Intermediate 58.4 rac-(3-{[5-fluoro-4-(4-fluoro-2-methoxyphenyl)pyrimidin-2-yl]amino}-5-methylbenzyl)(methyl)-λ⁴-sulfanylidene]cyanamide

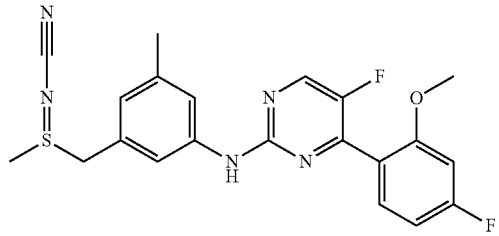 [SMILES: COc1cc(F)ccc1-c1nc(Nc2cc(C)cc(CS(C)=NC#N)c2)ncc1F]

Intermediate 58.4 was prepared under similar conditions as described in the preparation of Intermediate 17.2 using 5-fluoro-4-(4-fluoro-2-methoxyphenyl)-N-{3-methyl-5-[(methylsulfanyl)methyl]phenyl}-pyrimidin-2-amine. The batch was purified by chromatography (hexane/ethyl acetate 25% to ethyl acetate).

¹H NMR (400 MHz, d₆-DMSO, 300K) δ=9.84 (s, 1H), 8.55 (d, 1H), 7.63 (s, 1H), 7.56 (m, 2H), 7.12 (dd, 1H), 6.96 (td, 1H), 6.82 (s, 1H), 4.39 (d, 1H), 4.20 (d, 1H), 3.84 (s, 3H), 2.83 (s, 3H), 2.28 (s, 3H).

Preparation of End Product:

Example 58 was prepared under similar conditions as described in the preparation of Example 20 using rac-(3-{[5-fluoro-4-(4-fluoro-2-methoxyphenyl)pyrimidin-2-yl]amino}-5-methylbenzyl)(methyl)-λ⁴-sulfanylidene]cyanamide. The batch was purified by chromatography (hexane/ethyl acetate).

¹H NMR (400 MHz, DMSO-d₆, 300K) δ=9.87 (s, 1H), 8.55 (d, 1H), 7.68 (s, 1H), 7.55 (m, 2H), 7.12 (dd, 1H), 6.95 (td, 1H), 6.86 (s, 1H), 4.89 (m, 2H), 3.84 (s, 3H), 3.34 (s, 3H), 2.29 (s, 3H).

Example 59

(rac)-5-Fluoro-4-(4-fluoro-2-methoxyphenyl)-N-{3-methyl-5-[(S-methylsulfonimidoyl)methyl]-phenyl}pyrimidin-2-amine

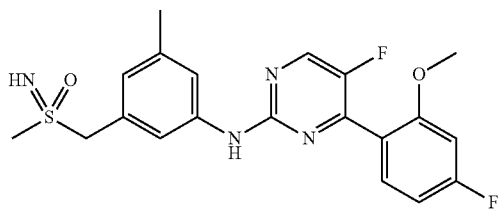 [SMILES: COc1cc(F)ccc1-c1nc(Nc2cc(C)cc(CS(C)(=N)=O)c2)ncc1F]

Example 59 was prepared under similar conditions as described in the preparation of Example 21 using (rac)-[(3-{[5-fluoro-4-(4-fluoro-2-methoxyphenyl)pyrimidin-2-yl]amino}-5-methylbenzyl)(methyl)-oxido-$\lambda^6$-sulfanylidene]cyanamide. The batch was purified by chromatography (ethyl acetate).

$^1$H NMR (500 MHz, $d_6$-DMSO, 300K) δ=9.73 (s, 1H), 8.54 (d, 1H), 7.57 (s, 1H), 7.54 (dd, 1H), 7.49 (s, 1H), 7.12 (dd, 1H), 6.95 (td, 1H), 6.82 (s, 1H), 4.25 (m, 2H), 3.84 (s, 3H), 3.51 (s, 1H), 2.78 (s, 3H), 2.27 (s, 3H).

Example 60

(rac)-{[3-{[5-Fluoro-4-(4-fluoro-2-methoxyphenyl)pyrimidin-2-yl]amino}-5-(pentafluoro-$\lambda^6$-sulfanyl)benzyl](methyl)oxido-$\lambda$6-sulfanylidene}cyanamide

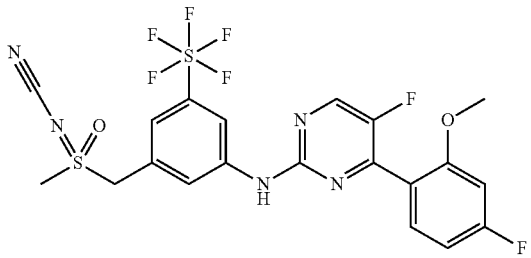 [SMILES: COc1cc(F)ccc1-c1nc(Nc2cc(CS(C)(=O)=NC#N)cc(S(F)(F)(F)(F)F)c2)ncc1F]

Preparation of Intermediate 60.1

3-Nitro-5-(pentafluoro-$\lambda^6$-sulfanyl)benzoic acid

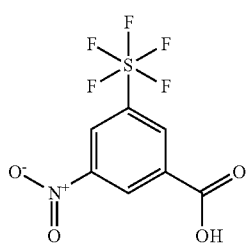 [SMILES: O=C(O)c1cc([N+](=O)[O-])cc(S(F)(F)(F)(F)F)c1]

Nitric acid (100%; 4.1 mL) was added dropwise over 30 minutes to a stirred solution of 3-(pentafluoro-$\lambda^6$-sulfanyl)benzoic acid (5.1 g; 20.6 mmol; ABCR GmbH & CO. KG) in sulfuric acid (17.0 mL) at 0° C. The ice bath was removed and the mixture was stirred for 88 hours at room temperature. The batch was cautiously added to ice. The precipitate was separated, washed with water and finally taken up in ethyl acetate. The organic solution was washed with water, filtered using a Whatman filter and concentrated to give the desired product (4.4 g; 15.0 mmol).

$^1$H NMR (400 MHz, CDCl$_3$, 300K) δ=9.12 (s, 1H), 8.90 (m, 1H), 8.83 (m, 1H).

Preparation of Intermediate 60.2

[3-Nitro-5-(pentafluoro-$\lambda^6$-sulfanyl)phenyl]methanol

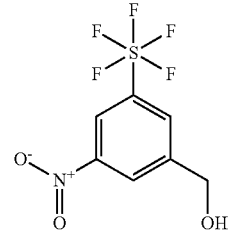 [SMILES: O=[N+]([O-])c1cc(CO)cc(S(F)(F)(F)(F)F)c1]

Intermediate 60.2 was prepared under similar conditions as described in the preparation of Intermediate 24.1 using 3-nitro-5-(pentafluoro-$\lambda^6$-sulfanyl)benzoic acid.

$^1$H NMR (400 MHz, CDCl$_3$, 300K) δ=8.54 (s, 1H), 8.42 (s, 1H), 8.12 (s, 1H), 4.92 (d, 2), 2.19 (tr, 1H).

Preparation of Intermediate 60.3

[3-Nitro-5-(pentafluoro-$\lambda^6$-sulfanyl)phenyl]methanol

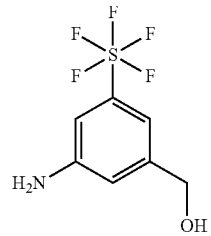

Intermediate 60.3 was prepared under similar conditions as described in the preparation of Intermediate 1.6 using [3-nitro-5-(pentafluoro-$\lambda^6$-sulfanyl)phenyl]methanol.

$^1$H NMR (400 MHz, CDCl$_3$, 300K) δ=7.11 (s, 1H), 6.96 (m, 1H), 6.81 (s, 1H), 4.66 (br, 2H), 3.89 (br, 2H).

Preparation of Intermediate 60.4

[3-{[5-Fluoro-4-(4-fluoro-2-methoxyphenyl)pyrimidin-2-yl]amino}-5-(pentafluoro-$\lambda^6$-sulfanyl)-phenyl]methanol

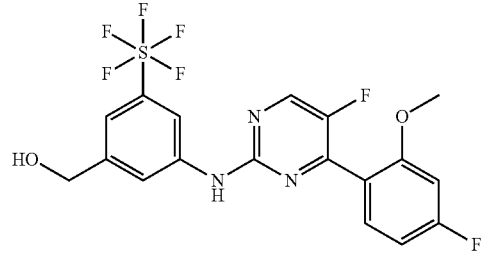 [SMILES: COc1cc(F)ccc1-c1nc(Nc2cc(CO)cc(S(F)(F)(F)(F)F)c2)ncc1F]

Intermediate 60.4 was prepared under similar conditions as described in the preparation of Intermediate 20.1 using 2-chloro-5-fluoro-4-(4-fluoro-2-methoxyphenyl)pyrimidine and [3-nitro-5-(pentafluoro-λ⁶-sulfanyl)phenyl]methanol. The batch was purified by chromatography (DCM/EtOH 9:1) to give the desired product.

¹H NMR (400 MHz, CDCl₃, 300K) δ=8.34 (m, 1H), 8.28 (m, 1H), 7.64 (s, 1H), 7.51 (m, 1H), 7.41 (m, 2H), 6.82 (m, 1H), 6.76 (m, 1H), 4.75 (s, 2H), 3.87 (s, 3H).

Preparation of Intermediate 60.5

5-Fluoro-4-(4-fluoro-2-methoxyphenyl)-N-{3-[(methylsulfanyl)methyl]-5-(pentafluoro-λ⁶-sulfanyl)phenyl}pyrimidin-2-amine

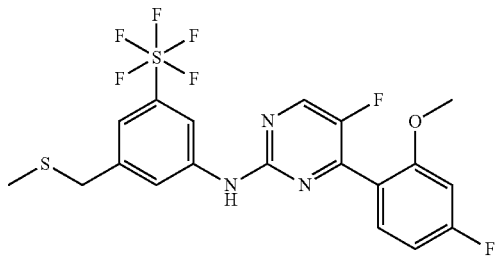 [SMILES: COc1cc(F)ccc1-c1nc(Nc2cc(CSC)cc(S(F)(F)(F)(F)F)c2)ncc1F]

Intermediate 60.5 was prepared under similar conditions as described in the preparation of Intermediate 24.3 using [3-{[5-fluoro-4-(4-fluoro-2-methoxyphenyl)pyrimidin-2-yl]amino}-5-(pentafluoro-λ⁶-sulfanyl)phenyl]methanol. The batch was purified by chromatography (hexane/ethyl acetate 4:1) to give the desired product.

¹H NMR (400 MHz, CDCl₃, 300K) δ=8.34 (m, 1H), 8.23 (m, 1H), 7.61 (s, 1H), 7.52 (m, 1H), 7.33 (s, 1H), 7.28 (s, 1H), 6.82 (m, 1H), 6.76 (m, 1H), 3.86 (s, 3H), 3.69 (s, 2H), 2.02 (s, 3H).

Preparation of Intermediate 60.6

(rac)-{[3-{[5-fluoro-4-(4-fluoro-2-methoxyphenyl)pyrimidin-2-yl]amino}-5-(pentafluoro-λ⁶-sulfanyl)benzyl](methyl)-λ⁴-sulfanylidene}cyanamide

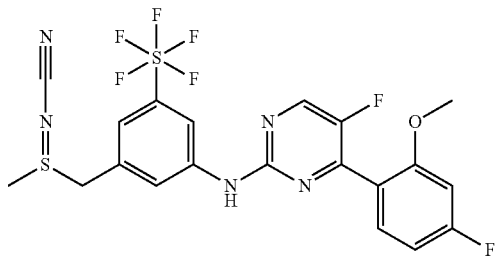 [SMILES: COc1cc(F)ccc1-c1nc(Nc2cc(CS(C)=NC#N)cc(S(F)(F)(F)(F)F)c2)ncc1F]

Intermediate 60.6 was prepared under similar conditions as described in the preparation of Intermediate 17.2 using 5-fluoro-4-(4-fluoro-2-methoxyphenyl)-N-{3-[(methylsulfanyl)methyl]-5-(pentafluoro-λ⁶-sulfanyl)phenyl}pyrimidin-2-amine. The batch was purified by chromatography (DCM/EtOH 95:5).

¹H NMR (400 MHz, CDCl₃, 300K) δ=8.41 (m, 1H), 8.35 (m, 1H), 7.79 (m, 2H), 7.48 (m, 1H), 7.32 (s 1H), 6.82 (m 1H), 6.75 (m, 1H), 4.40 (d, 1H), 4.21 (d, 1H), 3.85 (s, 3H), 2.80 (s, 3H).

Preparation of End Product:

Example 60 was prepared under similar conditions as described in the preparation of Example 20 using (rac)-{[3-{[5-fluoro-4-(4-fluoro-2-methoxyphenyl)pyrimidin-2-yl]amino}-5-(pentafluoro-λ⁶-sulfanyl)-benzyl](methyl)-λ⁴-sulfanylidene}cyanamide. The batch was purified by chromatography (DCM/EtOH 95:5).

¹H NMR (400 MHz, CDCl₃, 300K) δ=8.37 (m, 1H), 8.34 (m, 1H), 7.96 (s, 1H), 7.53 (s, 1H), 7.49 (m, 1H), 7.39 (m, 1H), 6.83 (m, 1H), 6.76 (m, 1H), 4.63 (m, 2H), 3.86 (s, 3H), 3.09 (s, 3H).

Example 61

(rac)-5-Fluoro-4-(4-fluoro-2-methoxyphenyl)-N-{3-[(S-methylsulfonimidoyl)methyl]-5-(pentafluoro-λ⁶-sulfanyl)phenyl}pyrimidin-2-amine

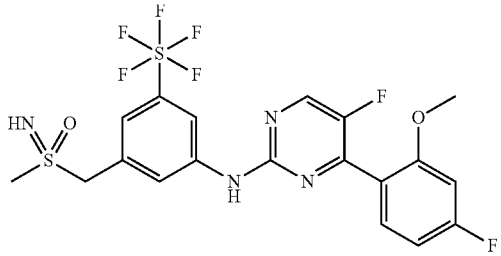

Example 61 was prepared under similar conditions as described in the preparation of Example 21 using (rac)-{[3-{[5-fluoro-4-(4-fluoro-2-methoxyphenyl)pyrimidin-2-yl]amino}-5-(pentafluoro-λ⁶-sulfanyl)-benzyl](methyl)oxido-λ⁶-sulfanylidene}cyanamide. The batch was purified by chromatography (DCM/EtOH 9:1).

¹H NMR (400 MHz, CDCl₃, 300K) δ=8.39 (m, 1H), 8.32 (m, 1H), 7.75 (s, 1H), 7.48 (m, 2H), 7.38 (s, 1H), 6.80 (m, 1H), 6.75 (m, 1H), 4.39 (d, 1H), 4.26 (d, 1H), 3.86 (s, 3H), 2.98 (s, 3H), 2.82 (br, 1H).

Example 62 and 63

Enantiomers of 5-Fluoro-4-(4-fluoro-2-methoxyphenyl)-N-[3-[(S-methylsulfonimidoyl)methyl]-5-(pentafluoro-λ⁶-sulfanyl)phenyl]pyrimidin-2-amine

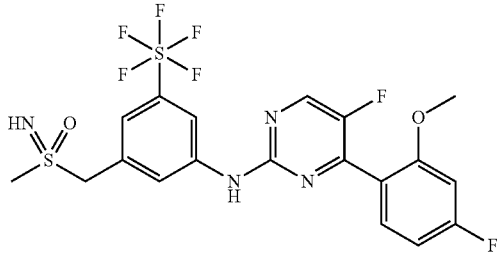

(rac)-5-Fluoro-4-(4-fluoro-2-methoxyphenyl)-N-{3-[(S-methylsulfonimidoyl)methyl]-5-(pentafluoro-λ⁶-sulfanyl)phenyl}pyrimidin-2-amine was separated into the enantiomers by preparative HPLC.

| | | |
|---|---|---|
| System: | Agilent: Prep 1200, 2xPrep Pump G1361A, DLA G2258A, MWD G1365D, Prep FC G1364B | |
| Column: | Chiralpak OJ-H 5 µm 250 × 20 mm | |
| Solvent: | EtOH/MeOH 50/50 (v/v) | |
| Flow: | 25 mL/min | |
| Temperature: | RT | |
| Solution: | 106 mg/2.6 ml MeOH | |
| Injection: | 13 × 200 µl | |
| Detection: | UV 280 nm | |

| | Retention time in min | purity in % |
|---|---|---|
| Example 62 Enantiomer 1 | 4.5-5.8 | >99 |
| Example 63 Enantiomer 2 | 6.5-8.5 | >99 |

Example 64

2-Methoxyethyl[(3-fluoro-5-{[5-fluoro-4-(4-fluoro-2-methoxyphenyl)pyrimidin-2-yl]amino}-benzyl)(methyl)oxido-$\lambda^6$-sulfanylidene]carbamate, single enantiomer

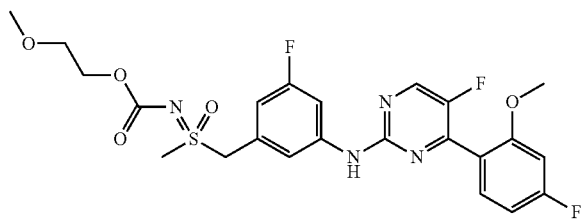 [SMILES: COCCOC(=O)N=S(C)(=O)Cc1cc(F)cc(Nc2ncc(F)c(-c3ccc(F)cc3OC)n2)c1]

2-Methoxyethyl carbonochloridate (18 µL; 0.15 mmol; Sigma-Aldrich Corporation) was added dropwise to a stirred solution of 5-fluoro-4-(4-fluoro-2-methoxyphenyl)-N-{3-fluoro-5-[(S-methyl-sulfonimidoyl)methyl]phenyl}pyrimidin-2-amine (Example 15; 50.0 mg; 0.12 mmol) in pyridine (1.1 mL) at 0° C. The mixture was stirred at RT for 24 hours before the batch was concentrated. Ethyl acetate and aqueous sodium chloride solution were added. The batch was extracted with ethyl acetate (2×). The combined organic phases were filtered using a Whatman filter and concentrated. The residue was purified by preparative HPLC.

| | |
|---|---|
| System: | Waters Autopurificationsystem: Pump 2545, Sample Manager 2767, CFO, DAD 2996, ELSD 2424, SQD 3001 |
| Column: | XBrigde C18 5 µm 100 × 30 mm |
| Solvent: | A = H$_2$O + 0.1% HCOOH |
| | B = MeCN |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO or DMF |
| Injektion: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.33 (m, 1H), 7.78 (m, 1H), 7.48 (m, 2H), 7.31 (s, 1H), 6.82 (m, 1H), 6.76 (m, 2H), 4.76 (d, 1H), 4.64 (d, 1H), 4.34 (m, 1H), 4.24 (m, 1H), 3.87 (s, 3H), 3.67 (tr, 2H), 3.42 (s, 3H), 2.99 (s, 3H).

The following Table 1 provides an overview on the compounds described in the example section:

TABLE 1

| Example No. | Structure | Name of compound |
|---|---|---|
| 1 | 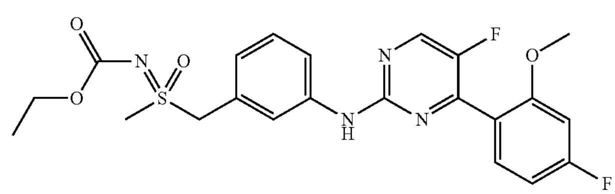 [SMILES: CCOC(=O)N=S(C)(=O)Cc1cccc(Nc2ncc(F)c(-c3ccc(F)cc3OC)n2)c1] | (rac)-Ethyl[(3-{[5-fluoro-4-(4-fluoro-2-methoxyphenyl)pyrimidin-2-yl]amino}benzyl)(methyl)oxido-$\lambda^6$-sulfanylidene]carbamate |
| 2 | 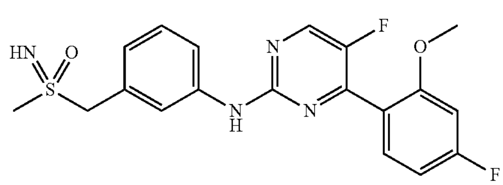 [SMILES: COc1cc(F)ccc1-c1nc(Nc2cccc(CS(C)(=N)=O)c2)ncc1F] | (rac)-5-Fluoro-4-(4-fluoro-2-methoxyphenyl)-N-{3-[(S-methyl-sulfonimidoyl)methyl]phenyl}pyrimidin-2-amine |
| 3 | 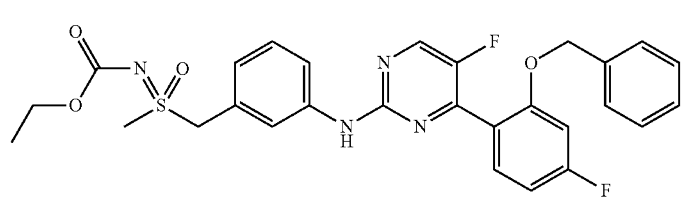 [SMILES: CCOC(=O)N=S(C)(=O)Cc1cccc(Nc2ncc(F)c(-c3ccc(F)cc3OCc3ccccc3)n2)c1] | (rac)-Ethyl{[3-({4-[2-(benzyloxy)-4-fluorophenyl]-5-fluoropyrimidin-2-yl}amino)benzyl](methyl)oxido-$\lambda^6$-sulfanylidene}carbamate |

TABLE 1-continued

| Example No. | Structure | Name of compound |
|---|---|---|
| 4 | 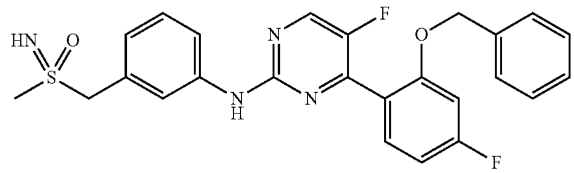 [SMILES: CS(=N)(=O)Cc1cccc(Nc2ncc(F)c(-c3ccc(F)cc3OCc3ccccc3)n2)c1] | (rac)-4-[2-(Benzyloxy)-4-fluorophenyl]-5-fluoro-N-{3-[(S-methylsulfonimidoyl)methyl]phenyl}pyrimidin-2-amine |
| 5 | 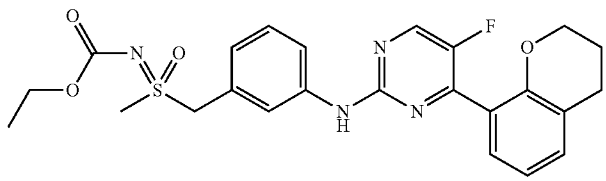 [SMILES: CCOC(=O)N=S(C)(=O)Cc1cccc(Nc2ncc(F)c(-c3cccc4c3OCCC4)n2)c1] | (rac)-Ethyl[(3-{[4-(3,4-dihydro-2H-chromen-8-yl)-5-fluoropyrimidin-2-yl]amino}benzyl)(methyl)oxido-λ$^6$-sulfanylidene]carbamate |
| 6 | 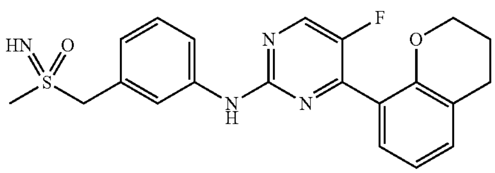 [SMILES: CS(=N)(=O)Cc1cccc(Nc2ncc(F)c(-c3cccc4c3OCCC4)n2)c1] | (rac)-4-(3,4-dihydro-2H-chromen-8-yl)-5-fluoro-N-{3-[(S-methylsulfonimidoyl)methyl]phenyl}pyrimidin-2-amine |
| 7 | 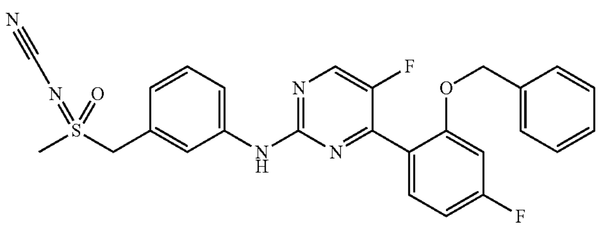 [SMILES: CS(=O)(Cc1cccc(Nc2ncc(F)c(-c3ccc(F)cc3OCc3ccccc3)n2)c1)=NC#N] | (rac)-{[3-({4-[2-(Benzyloxy)-4-fluorophenyl]-5-fluoropyrimidin-2-yl}amino)benzyl](methyl)oxido-λ$^6$-sulfanylidene}cyanamide |
| 8 | 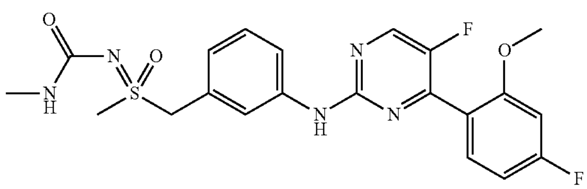 [SMILES: CNC(=O)N=S(C)(=O)Cc1cccc(Nc2ncc(F)c(-c3ccc(F)cc3OC)n2)c1] | (rac)-1-[(3-{[5-Fluoro-4-(4-fluoro-2-methoxyphenyl)pyrimidin-2-yl]amino}benzyl)(methyl)oxido-λ$^6$-sulfanylidene]-3-methylurea |
| 9 | 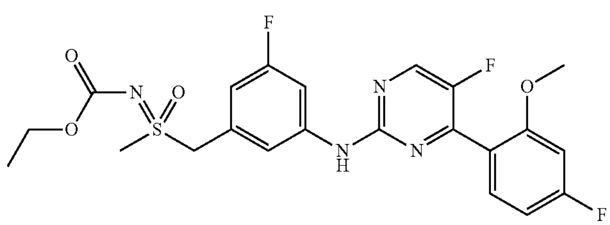 [SMILES: CCOC(=O)N=S(C)(=O)Cc1cc(F)cc(Nc2ncc(F)c(-c3ccc(F)cc3OC)n2)c1] | (rac)-Ethyl[(3-fluoro-5-{[5-fluoro-4-(4-fluoro-2-methoxyphenyl)pyrimidin-2-yl]amino}benzyl)(methyl)oxido-λ$^6$-sulfanylidene]carbamate |
| 10 | 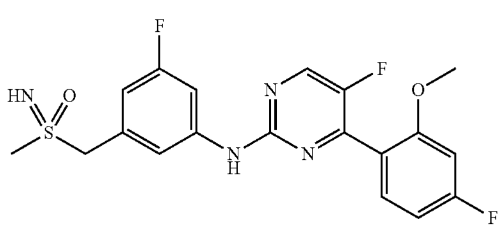 [SMILES: COc1cc(F)ccc1-c1nc(Nc2cc(F)cc(CS(C)(=N)=O)c2)ncc1F] | (rac)-5-Fluoro-4-(4-fluoro-2-methoxyphenyl)-N-{3-fluoro-5-[(S-methylsulfonimidoyl)methyl]phenyl}pyrimidin-2-amine |
| 11 | 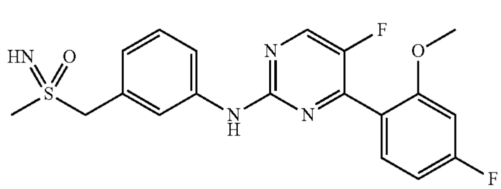 [SMILES: COc1cc(F)ccc1-c1nc(Nc2cccc(CS(C)(=N)=O)c2)ncc1F] | 5-Fluoro-4-(4-fluoro-2-methoxyphenyl)-N-{3-[(S-methylsulfonimidoyl)methyl]phenyl}pyrimidin-2-amine; enantiomer 1 |

TABLE 1-continued

| Example No. | Structure | Name of compound |
|---|---|---|
| 12 | 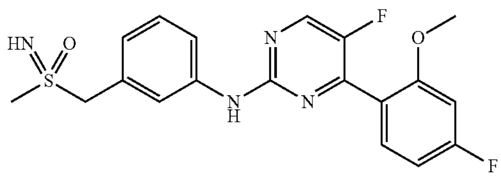 [SMILES: COc1cc(F)ccc1-c1nc(Nc2cccc(CS(C)(=N)=O)c2)ncc1F] | 5-Fluoro-4-(4-fluoro-2-methoxyphenyl)-N-(3-[(S-methylsulfonimidoyl)methyl]phenyl}pyrimidin-2-amine; enantiomer 2 |
| 13 | 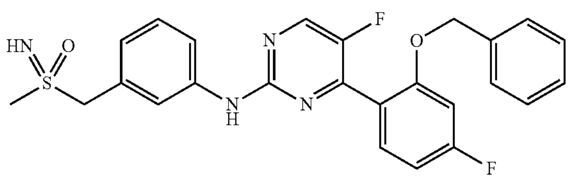 [SMILES: CS(=N)(=O)Cc1cccc(Nc2ncc(F)c(-c3ccc(F)cc3OCc3ccccc3)n2)c1] | 4-[2-(Benzyloxy)-4-fluorophenyl]-5-fluoro-N-{3-[(S-methylsulfonimidoyl)methyl]phenyl}pyrimidin-2-amine; enantiomer 1 |
| 14 | 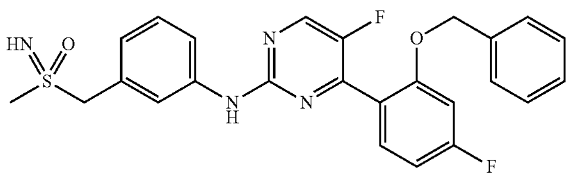 [SMILES: CS(=N)(=O)Cc1cccc(Nc2ncc(F)c(-c3ccc(F)cc3OCc3ccccc3)n2)c1] | 4-[2-(Benzyloxy)-4-fluorophenyl]-5-fluoro-N-{3-[(S-methylsulfonimidoyl)methyl]phenyl}pyrimidin-2-amine; enantiomer 2 |
| 15 | 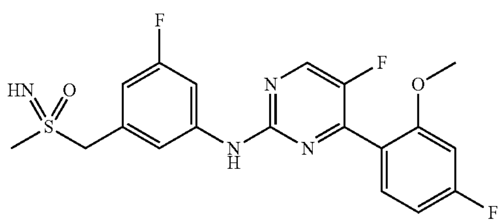 [SMILES: COc1cc(F)ccc1-c1nc(Nc2cc(F)cc(CS(C)(=N)=O)c2)ncc1F] | 5-Fluoro-4-(4-fluoro-2-methoxyphenyl)-N-{3-fluoro-5-[(S-methylsulfonimidoyl)methyl]phenyl}pyrimidin-2-amine; enantiomer 1 |
| 16 | 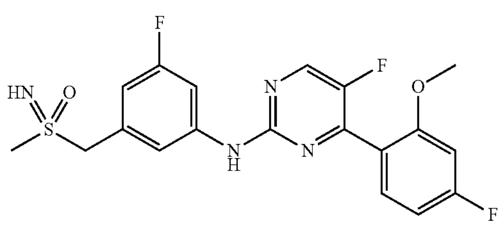 [SMILES: COc1cc(F)ccc1-c1nc(Nc2cc(F)cc(CS(C)(=N)=O)c2)ncc1F] | 5-Fluoro-4-(4-fluoro-2-methoxyphenyl)-N-{3-fluoro-5-[(S-methylsulfonimidoyl)methyl]phenyl}pyrimidin-2-amine; enantiomer 2 |
| 17 | 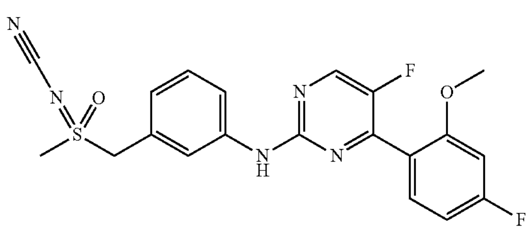 [SMILES: COc1cc(F)ccc1-c1nc(Nc2cccc(CS(C)(=O)=NC#N)c2)ncc1F] | (rac)-[(3-{[5-Fluoro-4-(4-fluoro-2-methoxyphenyl)pyrimidin-2-yl]amino}benzyl)(methyl)oxido-$\lambda^6$-sulfanylidene]cyanamide |
| 18 | 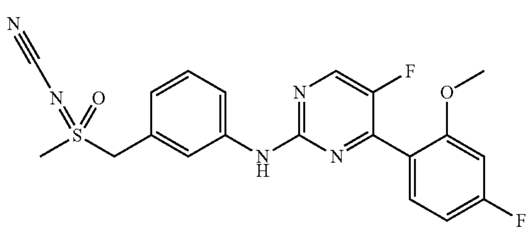 [SMILES: COc1cc(F)ccc1-c1nc(Nc2cccc(CS(C)(=O)=NC#N)c2)ncc1F] | [(3-{[5-Fluoro-4-(4-fluoro-2-methoxyphenyl)pyrimidin-2-yl]amino}benzyl)(methyl)oxido-$\lambda^6$-sulfanylidene]cyanamide; enantiomer 1 |

TABLE 1-continued

| Example No. | Structure | Name of compound |
|---|---|---|
| 19 | 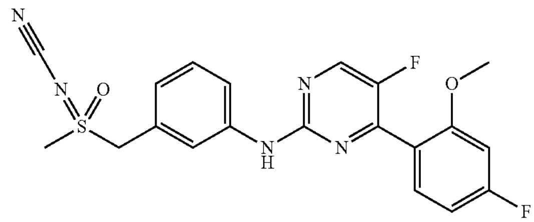 [SMILES: COc1cc(F)ccc1-c1nc(Nc2cccc(CS(C)(=O)=NC#N)c2)ncc1F] | [(3-{[5-Fluoro-4-(4-fluoro-2-methoxyphenyl)pyrimidin-2-yl]amino}benzyl)(methyl)oxido-$\lambda^6$-sulfanylidene]cyanamide; enantiomer 2 |
| 20 | 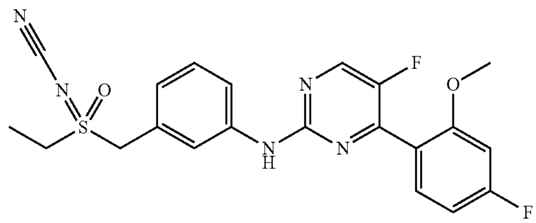 [SMILES: CCS(=O)(Cc1cccc(Nc2ncc(F)c(-c3ccc(F)cc3OC)n2)c1)=NC#N] | (rac)-[Ethyl(3-{[5-fluoro-4-(4-fluoro-2-methoxyphenyl)pyrimidin-2-yl]amino}benzyl)oxido-$\lambda^6$-sulfanylidene]cyanamide |
| 21 | 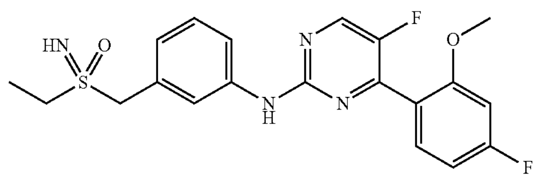 [SMILES: CCS(=N)(=O)Cc1cccc(Nc2ncc(F)c(-c3ccc(F)cc3OC)n2)c1] | (rac)-N-{3-[(S-Ethylsulfonimidoyl)methyl]phenyl}-5-fluoro-4-(4-fluoro-2-methoxyphenyl)pyrimidin-2-amine |
| 22 | 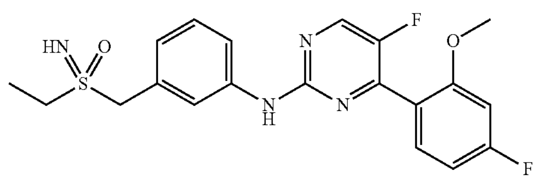 [SMILES: CCS(=N)(=O)Cc1cccc(Nc2ncc(F)c(-c3ccc(F)cc3OC)n2)c1] | N-{3-[(S-Ethylsulfonimidoyl)methyl]phenyl}-5-fluoro-4-(4-fluoro-2-methoxyphenyl)pyrimidin-2-amine; enantiomer 1 |
| 23 | 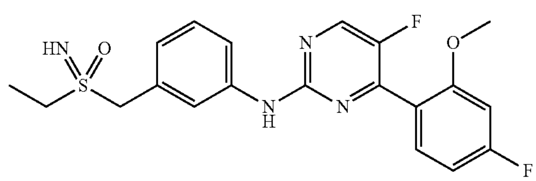 [SMILES: CCS(=N)(=O)Cc1cccc(Nc2ncc(F)c(-c3ccc(F)cc3OC)n2)c1] | N-{3-[(S-Ethylsulfonimidoyl)methyl]phenyl}-5-fluoro-4-(4-fluoro-2-methoxyphenyl)pyrimidin-2-amine; enantiomer 2 |
| 24 | 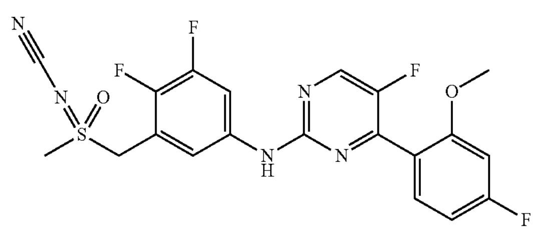 [SMILES: COc1cc(F)ccc1-c1nc(Nc2cc(F)c(F)c(CS(C)(=O)=NC#N)c2)ncc1F] | (rac)-[(2,3-Difluoro-5-{[5-fluoro-4-(4-fluoro-2-methoxyphenyl)pyrimidin-2-yl]amino}benzyl)(methyl)oxido-$\lambda^6$-sulfanylidene]cyanamide |
| 25 | 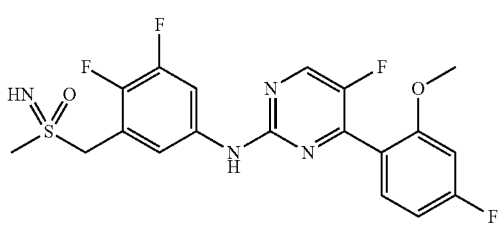 [SMILES: COc1cc(F)ccc1-c1nc(Nc2cc(F)c(F)c(CS(C)(=N)=O)c2)ncc1F] | (rac)-N-{3,4-Difluoro-5-[(S-methylsulfonimidoyl)methyl]phenyl}-5-fluoro-4-(4-fluoro-2-methoxyphenyl)pyrimidin-2-amine |

TABLE 1-continued

| Example No. | Structure | Name of compound |
|---|---|---|
| 26 | 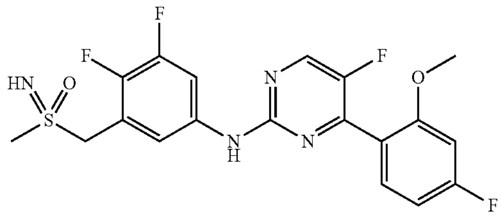 [SMILES: COc1cc(F)ccc1-c1nc(Nc2cc(F)c(F)c(CS(C)(=N)=O)c2)ncc1F] | N-{3,4-Difluoro-5-[(S-methylsulfonimidoyl)methyl]phenyl}-5-fluoro-4-(4-fluoro-2-methoxyphenyl)pyrimidin-2-amine; enantiomer 1 |
| 27 | 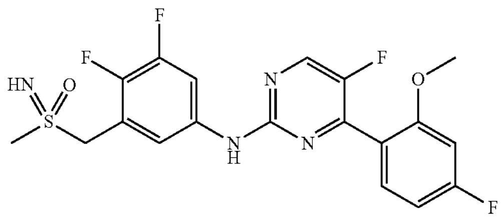 | N-{3,4-Difluoro-5-[(S-methylsulfonimidoyl)methyl]phenyl}-5-fluoro-4-(4-fluoro-2-methoxyphenyl)pyrimidin-2-amine; enantiomer 2 |
| 28 | 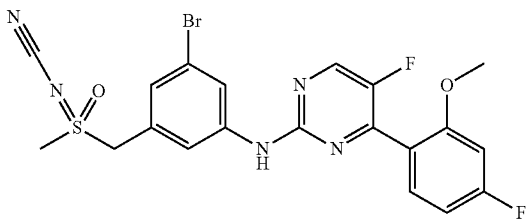 [SMILES: COc1cc(F)ccc1-c1nc(Nc2cc(Br)cc(CS(C)(=O)=NC#N)c2)ncc1F] | (rac)-[(3-Bromo-5-{[5-fluoro-4-(4-fluoro-2-methoxyphenyl)pyrimidin-2-yl]amino}benzyl)(methyl)oxido-$\lambda^6$-sulfanylidene]cyanamide |
| 29 | 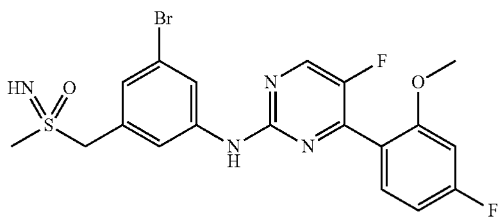 | (rac)-N-{3-Bromo-5-[(S-methylsulfonimidoyl)methyl]phenyl}-5-fluoro-4-(4-fluoro-2-methoxyphenyl)pyrimidin-2-amine |
| 30 | 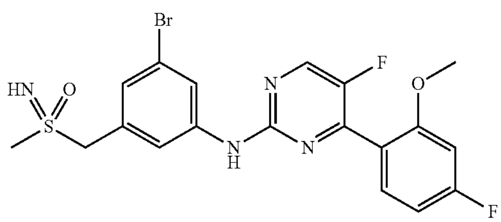 | N-{3-Bromo-5-[(S-methylsulfonimidoyl)methyl]phenyl}-5-fluoro-4-(4-fluoro-2-methoxyphenyl)pyrimidin-2-amine; enantiomer 1 |
| 31 | 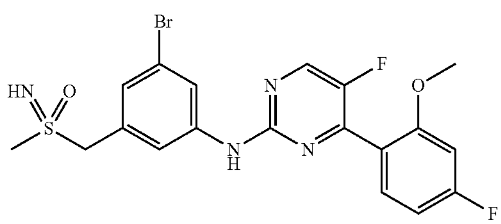 | N-{3-Bromo-5-[(S-methylsulfonimidoyl)methyl]phenyl}-5-fluoro-4-(4-fluoro-2-methoxyphenyl)pyrimidin-2-amine; enantiomer 2 |
| 32 | 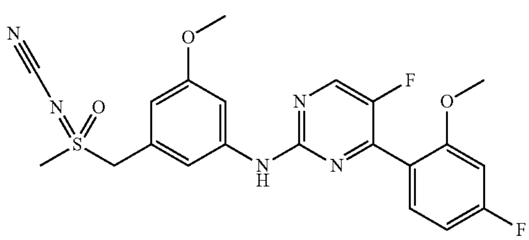 [SMILES: COc1cc(CS(C)(=O)=NC#N)cc(Nc2ncc(F)c(-c3ccc(F)cc3OC)n2)c1] | (rac)-[(3-{[5-Fluoro-4-(4-fluoro-2-methoxyphenyl)pyrimidin-2-yl]amino}-5-methoxybenzyl)(methyl)oxido-$\lambda^6$-sulfanylidene]cyanamide |

TABLE 1-continued

| Example No. | Structure | Name of compound |
|---|---|---|
| 33 | 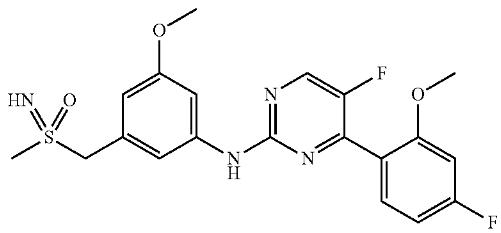 [SMILES: COc1cc(CS(C)(=N)=O)cc(Nc2ncc(F)c(-c3ccc(F)cc3OC)n2)c1] | (rac)-5-Fluoro-4-(4-fluoro-2-methoxyphenyl)-N-{3-methoxy-5-[(S-methylsulfonimidoyl)methyl]phenyl}pyrimidin-2-amine |
| 34 | 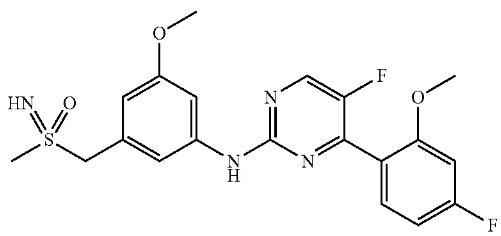 [SMILES: COc1cc(CS(C)(=N)=O)cc(Nc2ncc(F)c(-c3ccc(F)cc3OC)n2)c1] | 5-Fluoro-4-(4-fluoro-2-methoxyphenyl)-N-{3-methoxy-5-[(S-methylsulfonimidoyl)methyl]phenyl}pyrimidin-2-amine; enantiomer 1 |
| 35 | 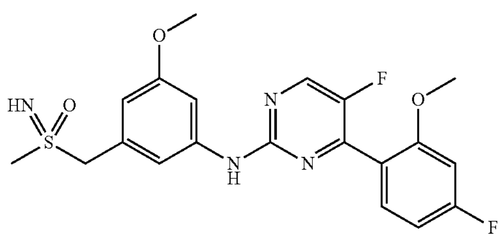 [SMILES: COc1cc(CS(C)(=N)=O)cc(Nc2ncc(F)c(-c3ccc(F)cc3OC)n2)c1] | 5-Fluoro-4-(4-fluoro-2-methoxyphenyl)-N-{3-methoxy-5-[(S-methylsulfonimidoyl)methyl]phenyl}pyrimidin-2-amine; enantiomer 2 |
| 36 | 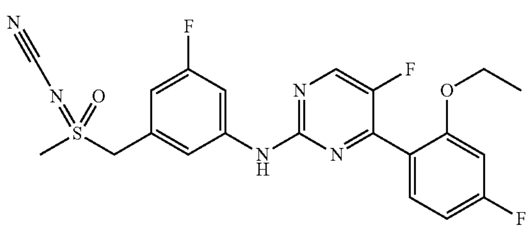 [SMILES: CCOc1cc(F)ccc1-c1nc(Nc2cc(F)cc(CS(C)(=O)=NC#N)c2)ncc1F] | (rac)-[(3-{[4-(2-Ethoxy-4-fluorophenyl)-5-fluoropyrimidin-2-yl]amino}-5-fluorobenzyl)(methyl)oxido-$\lambda^6$-sulfanylidene]cyanamide |
| 37 | 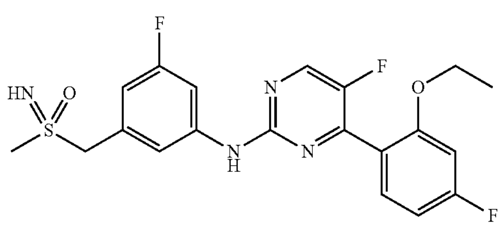 [SMILES: CCOc1cc(F)ccc1-c1nc(Nc2cc(F)cc(CS(C)(=N)=O)c2)ncc1F] | (rac)-4-(2-Ethoxy-4-fluorophenyl)-5-fluoro-N-{3-fluoro-5-[(S-methylsulfonimidoyl)methyl]phenyl}pyrimidin-2-amine |
| 38 | 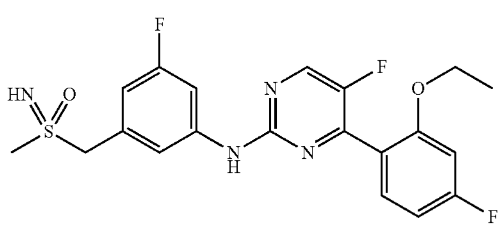 [SMILES: CCOc1cc(F)ccc1-c1nc(Nc2cc(F)cc(CS(C)(=N)=O)c2)ncc1F] | 4-(2-Ethoxy-4-fluorophenyl)-5-fluoro-N-{3-fluoro-5-[(S-methylsulfonimidoyl)methyl]phenyl}pyrimidin-2-amine; enantiomer 1 |

TABLE 1-continued

| Example No. | Structure | Name of compound |
|---|---|---|
| 39 | 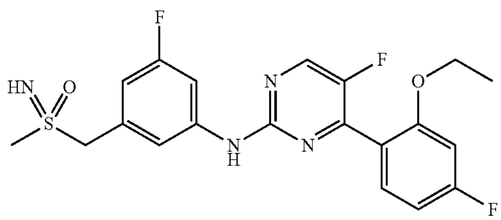 [SMILES: CCOc1cc(F)ccc1-c1nc(Nc2cc(F)cc(CS(C)(=N)=O)c2)ncc1F] | 4-(2-Ethoxy-4-fluorophenyl)-5-fluoro-N-{3-fluoro-5-[(S-methylsulfonimidoyl)methyl]phenyl}pyrimidin-2-amine; enantiomer 2 |
| 40 | 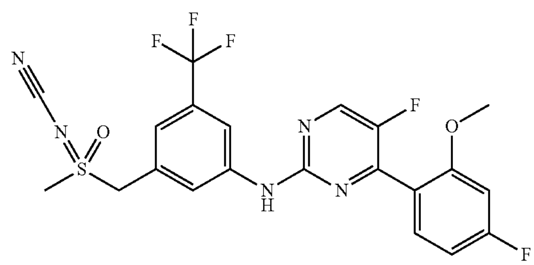 [SMILES: COc1cc(F)ccc1-c1nc(Nc2cc(CS(C)(=O)=NC#N)cc(C(F)(F)F)c2)ncc1F] | (rac)-{[3-{[5-Fluoro-4-(4-fluoro-2-methoxyphenyl)pyrimidin-2-yl]amino}-5-(trifluoromethyl)benzyl](methyl)oxido-$\lambda^6$-sulfanylidene}cyanamide |
| 41 | 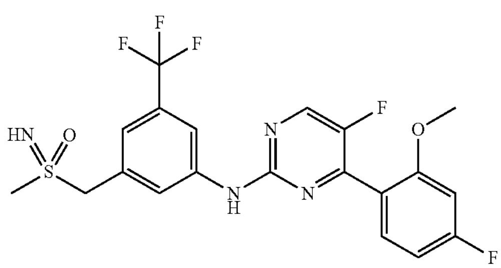 [SMILES: COc1cc(F)ccc1-c1nc(Nc2cc(CS(C)(=N)=O)cc(C(F)(F)F)c2)ncc1F] | (rac)-5-Fluoro-4-(4-fluoro-2-methoxyphenyl)-N-{3-[(S-methylsulfonimidoyl)methyl]-5-(trifluoromethyl)phenyl}pyrimidin-2-amine |
| 42 | 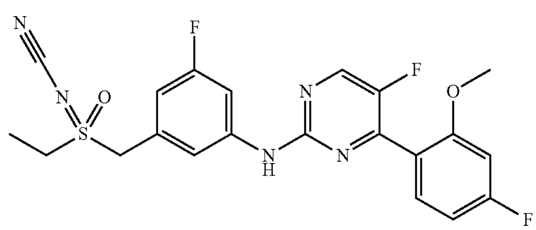 [SMILES: CCS(=O)(Cc1cc(F)cc(Nc2ncc(F)c(-c3ccc(F)cc3OC)n2)c1)=NC#N] | (rac)-[Ethyl(3-fluoro-5-{[5-fluoro-4-(4-fluoro-2-methoxyphenyl)pyrimidin-2-yl]amino}benzyl)oxido-$\lambda^6$-sulfanylidene]cyanamide |
| 43 | 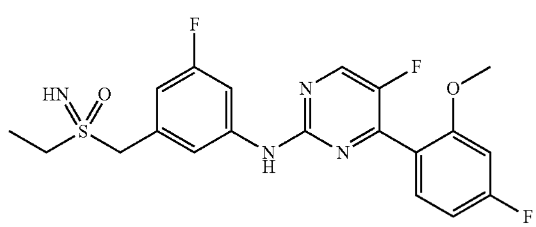 [SMILES: CCS(=N)(=O)Cc1cc(F)cc(Nc2ncc(F)c(-c3ccc(F)cc3OC)n2)c1] | (rac)-N-{3-[(S-Ethylsulfonimidoyl)methyl]-5-fluorophenyl}-5-fluoro-4-(4-fluoro-2-methoxyphenyl)pyrimidin-2-amine |
| 44 | 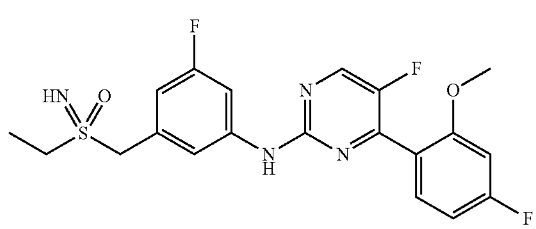 [SMILES: CCS(=N)(=O)Cc1cc(F)cc(Nc2ncc(F)c(-c3ccc(F)cc3OC)n2)c1] | N-{3-[(S-ethylsulfonimidoyl)methyl]-5-fluorophenyl}-5-fluoro-4-(4-fluoro-2-methoxyphenyl)pyrimidin-2-amine; enantiomer 1 |

TABLE 1-continued

| Example No. | Structure | Name of compound |
|---|---|---|
| 45 | 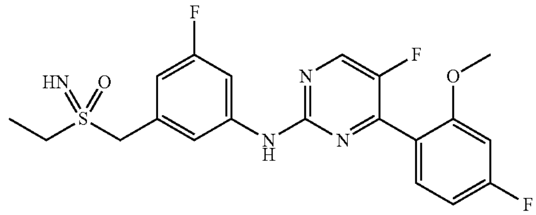 [SMILES: CCS(=N)(=O)Cc1cc(F)cc(Nc2ncc(F)c(-c3ccc(F)cc3OC)n2)c1] | N-{3-[(S-ethylsulfonimidoyl)methyl]-5-fluorophenyl}-5-fluoro-4-(4-fluoro-2-methoxyphenyl)pyrimidin-2-amine; enantiomer 2 |
| 46 | 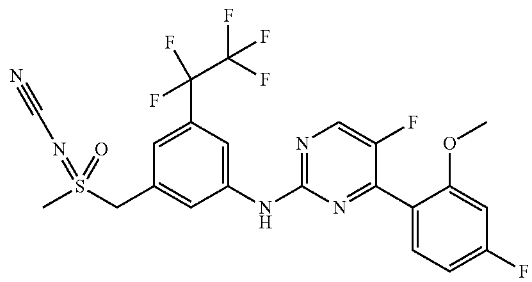 [SMILES: COc1cc(F)ccc1-c1nc(Nc2cc(CS(C)(=O)=NC#N)cc(C(F)(F)C(F)(F)F)c2)ncc1F] | (rac)-{[3-{[5-Fluoro-4-(4-fluoro-2-methoxyphenyl)pyrimidin-2-yl]amino}-5-(pentafluoroethyl)benzyl](methyl)oxido-$\lambda^6$-sulfanylidene}cyanamide |
| 47 | 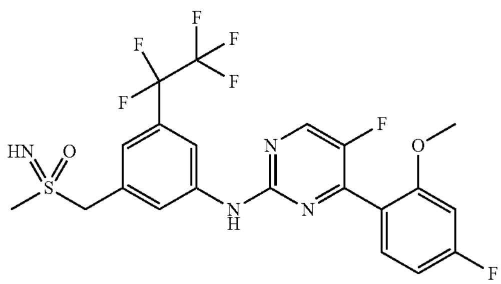 [SMILES: COc1cc(F)ccc1-c1nc(Nc2cc(CS(C)(=N)=O)cc(C(F)(F)C(F)(F)F)c2)ncc1F] | (rac)-5-Fluoro-4-(4-fluoro-2-methoxyphenyl)-N-{3-[(S-methylsulfonimidoyl)methyl]-5-(pentafluoroethyl)phenyl}pyrimidin-2-amine |
| 48 | 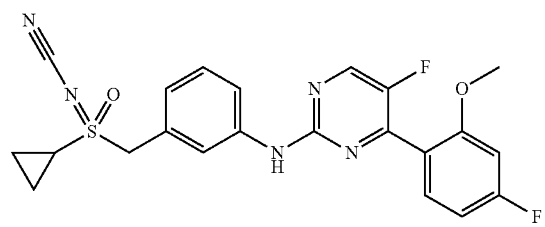 [SMILES: COc1cc(F)ccc1-c1nc(Nc2cccc(CS(=O)(=NC#N)C3CC3)c2)ncc1F] | (rac)-[Cyclopropyl(3-{[5-fluoro-4-(4-fluoro-2-methoxyphenyl)pyrimidin-2-yl]amino}benzyl)oxido-$\lambda^6$-sulfanylidene]cyanamide |
| 49 | 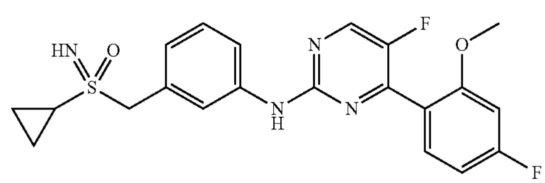 [SMILES: COc1cc(F)ccc1-c1nc(Nc2cccc(CS(=N)(=O)C3CC3)c2)ncc1F] | (rac)-N-{3-[(S-Cyclopropylsulfonimidoyl)methyl]phenyl}-5-fluoro-4-(4-fluoro-2-methoxyphenyl)pyrimidin-2-amine |
| 50 | 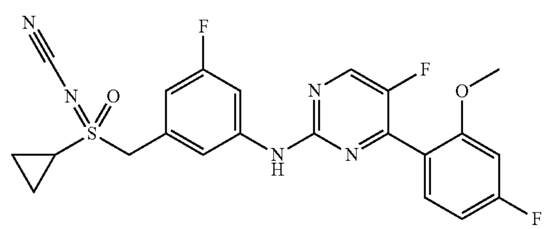 [SMILES: COc1cc(F)ccc1-c1nc(Nc2cc(F)cc(CS(=O)(=NC#N)C3CC3)c2)ncc1F] | (rac)-[Cyclopropyl(3-fluoro-5-{[5-fluoro-4-(4-fluoro-2-methoxyphenyl)pyrimidin-2-yl]amino}benzyl)oxido-$\lambda^6$-sulfanylidene]cyanamide |

TABLE 1-continued

| Example No. | Structure | Name of compound |
|---|---|---|
| 51 | 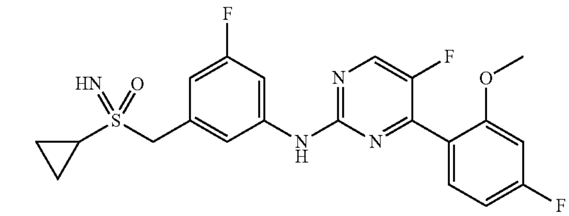 [SMILES: COc1cc(F)ccc1-c1nc(Nc2cc(F)cc(CS(=N)(=O)C3CC3)c2)ncc1F] | (rac)-N-{3-[(S-Cyclopropylsulfonimidoyl)methyl]-5-fluorophenyl}-5-fluoro-4-(4-fluoro-2-methoxyphenyl)pyrimidin-2-amine |
| 52 | 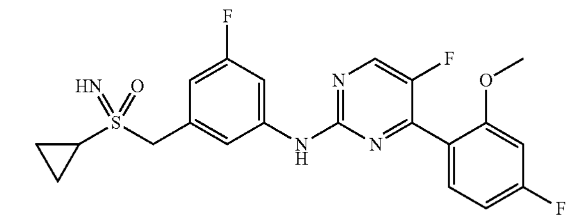 [SMILES: COc1cc(F)ccc1-c1nc(Nc2cc(F)cc(CS(=N)(=O)C3CC3)c2)ncc1F] | N-{3-[(S-Cyclopropylsulfonimidoyl)methyl]-5-fluorophenyl}-5-fluoro-4-(4-fluoro-2-methoxyphenyl)pyrimidin-2-amine; enantiomer 1 |
| 53 | 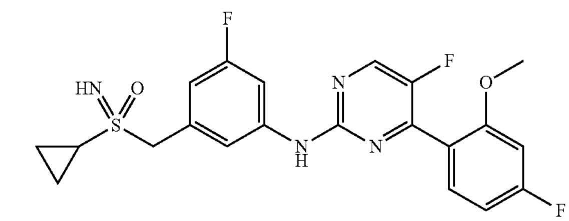 [SMILES: COc1cc(F)ccc1-c1nc(Nc2cc(F)cc(CS(=N)(=O)C3CC3)c2)ncc1F] | N-{3-[(S-Cyclopropylsulfonimidoyl)methyl]-5-fluorophenyl}-5-fluoro-4-(4-fluoro-2-methoxyphenyl)pyrimidin-2-amine; enantiomer 2 |
| 54 | 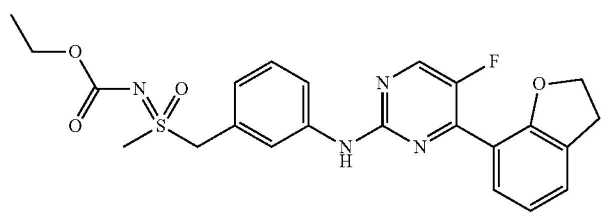 [SMILES: CCOC(=O)N=S(C)(=O)Cc1cccc(Nc2ncc(F)c(-c3cccc4c3OCC4)n2)c1] | (rac)-Ethyl[(3-{[4-(2,3-dihydro-1-benzofuran-7-yl)-5-fluoropyrimidin-2-yl]amino}benzyl)(methyl)oxido-$\lambda^6$-sulfanylidene]carbamate |
| 55 | 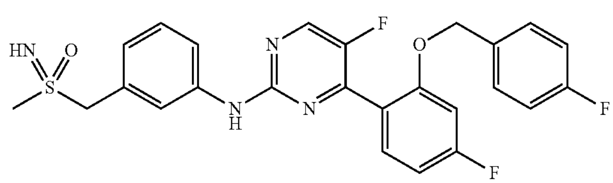 [SMILES: CS(=N)(=O)Cc1cccc(Nc2ncc(F)c(-c3ccc(F)cc3OCc3ccc(F)cc3)n2)c1] | (rac)-5-Fluoro-4-{4-fluoro-2-[(4-fluorobenzyl)oxy]phenyl}-N-{3-[(S-methylsulfonimidoyl)methyl]phenyl}pyrimidin-2-amine |
| 56 | 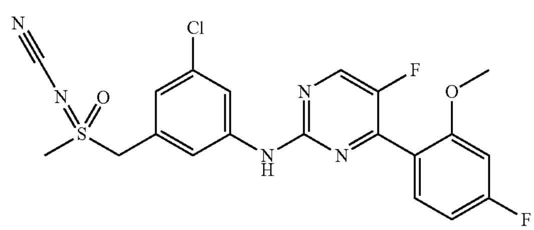 [SMILES: COc1cc(F)ccc1-c1nc(Nc2cc(Cl)cc(CS(C)(=O)=NC#N)c2)ncc1F] | (rac)-[(3-Chloro-5-{[5-fluoro-4-(4-fluoro-2-methoxyphenyl)pyrimidin-2-yl]amino}benzyl)(methyl)oxido-$\lambda^6$-sulfanylidene]cyanamide |
| 57 | 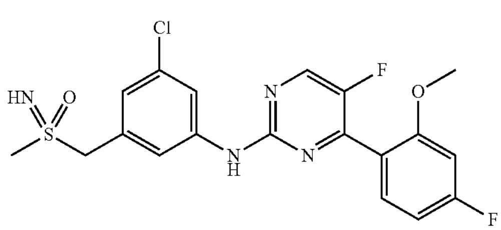 | (rac)-N-{3-Chloro-5-[(S-methylsulfonimidoyl)methyl]phenyl}-5-fluoro-4-(4-fluoro-2-methoxyphenyl)pyrimidin-2-amine |

TABLE 1-continued

| Example No. | Structure | Name of compound |
|---|---|---|
| 58 | 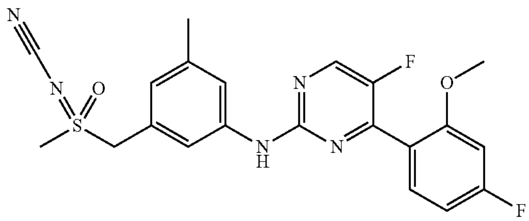 [SMILES: COc1cc(F)ccc1-c1nc(Nc2cc(C)cc(CS(C)(=O)=NC#N)c2)ncc1F] | (rac)-[(3-{[5-Fluoro-4-(4-fluoro-2-methoxyphenyl)pyrimidin-2-yl]amino}-5-methylbenzyl)(methyl)oxido-λ⁶-sulfanylidene]cyanamide |
| 59 | 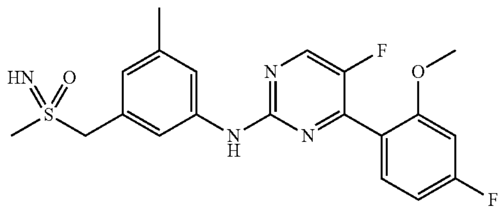 [SMILES: COc1cc(F)ccc1-c1nc(Nc2cc(C)cc(CS(C)(=N)=O)c2)ncc1F] | (rac)-5-Fluoro-4-(4-fluoro-2-methoxyphenyl)-N-{3-methyl-5-[(S-methylsulfonimidoyl)methyl]phenyl}pyrimidin-2-amine |
| 60 | 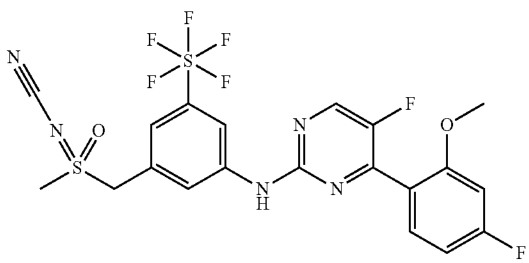 [SMILES: COc1cc(F)ccc1-c1nc(Nc2cc(CS(C)(=O)=NC#N)cc(S(F)(F)(F)(F)F)c2)ncc1F] | (rac)-{[3-{[5-Fluoro-4-(4-fluoro-2-methoxyphenyl)pyrimidin-2-yl]amino}-5-(pentafluoro-λ⁶-sulfanyl)benzyl](methyl)oxido-λ⁶-sulfanylidene}cyanamide |
| 61 | 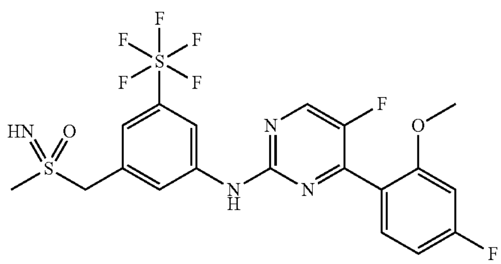 [SMILES: COc1cc(F)ccc1-c1nc(Nc2cc(CS(C)(=N)=O)cc(S(F)(F)(F)(F)F)c2)ncc1F] | (rac)-5-Fluoro-4-(4-fluoro-2-methoxyphenyl)-N-{3-[(S-methylsulfonimidoyl)methyl]-5-(pentafluoro-λ⁶-sulfanyl)phenyl}pyrimidin-2-amine |
| 62 | 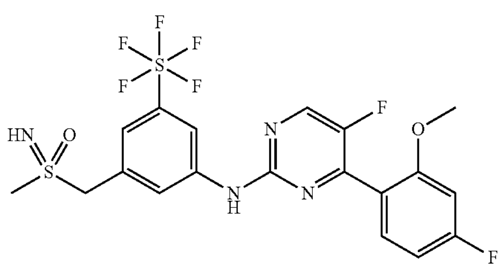 [SMILES: COc1cc(F)ccc1-c1nc(Nc2cc(CS(C)(=N)=O)cc(S(F)(F)(F)(F)F)c2)ncc1F] | 5-Fluoro-4-(4-fluoro-2-methoxyphenyl)-N-{3-[(S-methylsulfonimidoyl)methyl]-5-(pentafluoro-λ⁶-sulfanyl)phenyl}pyrimidin-2-amine; enantiomer 1 |
| 63 | 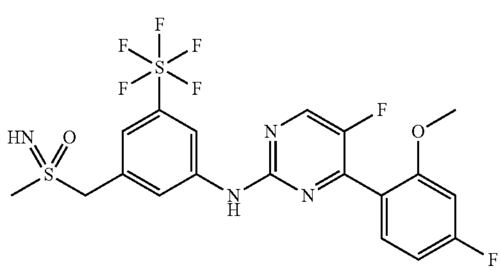 [SMILES: COc1cc(F)ccc1-c1nc(Nc2cc(CS(C)(=N)=O)cc(S(F)(F)(F)(F)F)c2)ncc1F] | 5-Fluoro-4-(4-fluoro-2-methoxyphenyl)-N-{3-[(S-methylsulfonimidoyl)methyl]-5-(pentafluoro-λ⁶-sulfanyl)phenyl}pyrimidin-2-amine; enantiomer 2 |

TABLE 1-continued

| Example No. | Structure | Name of compound |
|---|---|---|
| 64 | 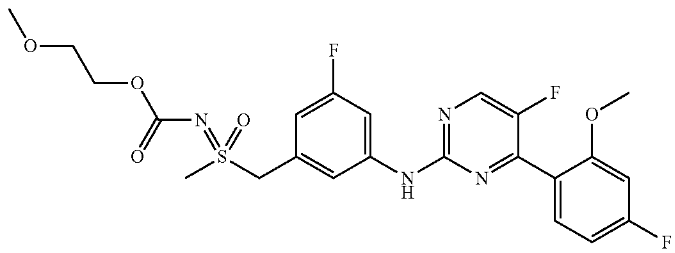 [SMILES: COCCOC(=O)N=S(C)(=O)Cc1cc(F)cc(Nc2ncc(F)c(-c3ccc(F)cc3OC)n2)c1] | 2-Methoxyethyl[(3-fluoro-5-{[5-fluoro-4-(4-fluoro-2-methoxyphenyl)pyrimidin-2-yl]amino}benzyl)(methyl)oxido-$\lambda^6$-sulfanylidene]carbamate; single enantiomer |

Results:

TABLE 2

Inhibition for CDK9 and CDK2 of compounds according to the present invention
The $IC_{50}$ (inhibitory concentration at 50% of maximal effect) values are indicated in nM, "n.t." means that the compounds have not been tested in this assay.

| ① | Name of compound | ② | ③ | ④ |
|---|---|---|---|---|
| 1 | (rac)-Ethyl[(3-{[5-fluoro-4-(4-fluoro-2-methoxyphenyl)-pyrimidin-2-yl]amino}benzyl)(methyl)oxido-$\lambda^6$-sulfanylidene]-carbamate | 8 nM | 780 nM | 38 nM |
| 2 | (rac)-5-Fluoro-4-(4-fluoro-2-methoxyphenyl)-N-{3-[(S-methyl-sulfonimidoyl)methyl]phenyl}pyrimidin-2-amine | 15 nM | 1100 nM | 248 nM |
| 3 | (rac)-Ethyl{[3-({4-[2-(benzyloxy)-4-fluorophenyl]-5-fluoro-pyrimidin-2-yl}amino)benzyl](methyl)oxido-$\lambda^6$-sulfanylidene}-carbamate | 9 nM | 1100 nM | 12 nM |
| 4 | (rac)-4-[2-(Benzyloxy)-4-fluorophenyl]-5-fluoro-N-{3-[(S-methylsulfonimidoyl)methyl]phenyl}pyrimidin-2-amine | 9 nM | 850 nM | 7 nM |
| 5 | (rac)-Ethyl[(3-{[4-(3,4-dihydro-2H-chromen-8-yl)-5-fluoro-pyrimidin-2-yl]amino}benzyl)(methyl)oxido-$\lambda^6$-sulfanylidene]-carbamate | 14 nM | 330 nM | 14 nM |
| 6 | (rac)-4-(3,4-dihydro-2H-chromen-8-yl)-5-fluoro-N-{3-[(S-methylsulfonimidoyl)methyl]phenyl}pyrimidin-2-amine | 8 nM | 270 nM | 67 nM |
| 7 | (rac)-{[3-({4-[2-(Benzyloxy)-4-fluorophenyl]-5-fluoro-pyrimidin-2-yl}amino)benzyl](methyl)oxido-$\lambda^6$-sulfanylidene}-cyanamide | 35 nM | 20000 nM | 25 nM |
| 8 | (rac)-1-[(3-{[5-Fluoro-4-(4-fluoro-2-methoxyphenyl)pyrimidin-2-yl]amino}benzyl)(methyl)oxido-$\lambda^6$-sulfanylidene]-3-methyl-urea | 7 nM | 430 nM | 23 nM |
| 9 | (rac)-Ethyl[(3-fluoro-5-{[5-fluoro-4-(4-fluoro-2-methoxy-phenyl)pyrimidin-2-yl]amino}benzyl)(methyl)oxido-$\lambda^6$-sulfanylidene]carbamate | 8 nM | 560 nM | 12 nM |
| 10 | (rac)-5-Fluoro-4-(4-fluoro-2-methoxyphenyl)-N-{3-fluoro-5-[(S-methylsulfonimidoyl)methyl]phenyl}pyrimidin-2-amine | 5 nM | 220 nM | 13 nM |
| 11 | 5-Fluoro-4-(4-fluoro-2-methoxyphenyl)-N-{3-[(S-methyl-sulfonimidoyl)methyl]phenyl}pyrimidin-2-amine; enantiomer 1 | 5 nM | 470 nM | 95 nM |
| 12 | 5-Fluoro-4-(4-fluoro-2-methoxyphenyl)-N-{3-[(S-methyl-sulfonimidoyl)methyl]phenyl}pyrimidin-2-amine; enantiomer 2 | 7 nM | 540 nM | 106 nM |
| 13 | 4-[2-(Benzyloxy)-4-fluorophenyl]-5-fluoro-N-{3-[(S-methyl-sulfonimidoyl)methyl]phenyl}pyrimidin-2-amine; enantiomer 1 | 8 nM | 280 nM | 2 nM |
| 14 | 4-[2-(Benzyloxy)-4-fluorophenyl]-5-fluoro-N-{3-[(S-methyl-sulfonimidoyl)methyl]phenyl}pyrimidin-2-amine; enantiomer 2 | 8 nM | 480 nM | 5 nM |
| 15 | 5-Fluoro-4-(4-fluoro-2-methoxyphenyl)-N-{3-fluoro-5-[(S-methylsulfonimidoyl)methyl]phenyl}pyrimidin-2-amine; enantiomer 1 | 6 nM | 320 nM | 27 nM |
| 16 | 5-Fluoro-4-(4-fluoro-2-methoxyphenyl)-N-{3-fluoro-5-[(S-methylsulfonimidoyl)methyl]phenyl}pyrimidin-2-amine; enantiomer 2 | 9 nM | 310 nM | 37 nM |
| 17 | (rac)-[(3-{[5-Fluoro-4-(4-fluoro-2-methoxyphenyl)pyrimidin-2-yl]amino}benzyl)(methyl)oxido-$\lambda^6$-sulfanylidene]cyanamide | 3 nM | 240 nM | 8 nM |
| 18 | [(3-{[5-Fluoro-4-(4-fluoro-2-methoxyphenyl)pyrimidin-2-yl]amino}benzyl)(methyl)oxido-$\lambda^6$-sulfanylidene]cyanamide; enantiomer 1 | 8 nM | 330 nM | 7 nM |
| 19 | [(3-{[5-Fluoro-4-(4-fluoro-2-methoxyphenyl)pyrimidin-2-yl]amino}benzyl)(methyl)oxido-$\lambda^6$-sulfanylidene]cyanamide; enantiomer 2 | 7 nM | 570 nM | 11 nM |
| 20 | (rac)-[Ethyl(3-{[5-fluoro-4-(4-fluoro-2-methoxyphenyl)-pyrimidin-2-yl]amino}benzyl)oxido-$\lambda^6$-sulfanylidene]cyan-amide | 2 nM | 170 nM | 9 nM |

TABLE 2-continued

Inhibition for CDK9 and CDK2 of compounds according to the present invention
The IC$_{50}$ (inhibitory concentration at 50% of maximal effect) values are indicated
in nM, "n.t." means that the compounds have not been tested in this assay.

| ① Name of compound | ② | ③ | ④ |
|---|---|---|---|
| 21 (rac)-N-{3-[(S-Ethylsulfonimidoyl)methyl]phenyl}-5-fluoro-4-(4-fluoro-2-methoxyphenyl)pyrimidin-2-amine | 5 nM | 380 nM | 135 nM |
| 22 N-{3-[(S-Ethylsulfonimidoyl)methyl]phenyl}-5-fluoro-4-(4-fluoro-2-methoxyphenyl)pyrimidin-2-amine; enantiomer 1 | 7 nM | 410 nM | 96 nM |
| 23 N-{3-[(S-Ethylsulfonimidoyl)methyl]phenyl}-5-fluoro-4-(4-fluoro-2-methoxyphenyl)pyrimidin-2-amine; enantiomer 2 | 7 nM | 350 nM | 125 nM |
| 24 (rac)-[(2,3-Difluoro-5-{[5-fluoro-4-(4-fluoro-2-methoxy-phenyl)pyrimidin-2-yl]amino}benzyl)(methyl)oxido-λ$^6$-sulfanylidene]cyanamide | 2 nM | 73 nM | 3 nM |
| 25 (rac)-N-{3,4-Difluoro-5-[(S-methylsulfonimidoyl)methyl]-phenyl}-5-fluoro-4-(4-fluoro-2-methoxyphenyl)pyrimidin-2-amine | 4 nM | 170 nM | 23 nM |
| 26 N-{3,4-Difluoro-5-[(S-methylsulfonimidoyl)methyl]phenyl}-5-fluoro-4-(4-fluoro-2-methoxyphenyl)pyrimidin-2-amine; enantiomer 1 | 6 nM | 210 nM | 34 nM |
| 27 N-{3,4-Difluoro-5-[(S-methylsulfonimidoyl)methyl]phenyl}-5-fluoro-4-(4-fluoro-2-methoxyphenyl)pyrimidin-2-amine; enantiomer 2 | 4 nM | 180 nM | 57 nM |
| 28 (rac)-[(3-Bromo-5-{[5-fluoro-4-(4-fluoro-2-methoxyphenyl)-pyrimidin-2-yl]amino}benzyl)(methyl)oxido-λ$^6$-sulfanylidene]-cyanamide | 4 nM | 120 nM | 2 nM |
| 29 (rac)-N-{3-Bromo-5-[(S-methylsulfonimidoyl)methyl]phenyl}-5-fluoro-4-(4-fluoro-2-methoxyphenyl)pyrimidin-2-amine | 2 nM | 86 nM | 2 nM |
| 30 N-{3-Bromo-5-[(S-methylsulfonimidoyl)methyl]phenyl}-5-fluoro-4-(4-fluoro-2-methoxyphenyl)pyrimidin-2-amine; enantiomer 1 | 3 nM | 110 nM | 2 nM |
| 31 N-{3-Bromo-5-[(S-methylsulfonimidoyl)methyl]phenyl}-5-fluoro-4-(4-fluoro-2-methoxyphenyl)pyrimidin-2-amine; enantiomer 2 | 4 nM | 120 nM | 3 nM |
| 32 (rac)-[(3-{[5-Fluoro-4-(4-fluoro-2-methoxyphenyl)pyrimidin-2-yl]amino}-5-methoxybenzyl)(methyl)oxido-λ$^6$-sulfanylidene]-cyanamide | 4 nM | 130 nM | 1 nM |
| 33 (rac)-5-Fluoro-4-(4-fluoro-2-methoxyphenyl)-N-{3-methoxy-5-[(S-methylsulfonimidoyl)methyl]phenyl}pyrimidin-2-amine | 3 nM | 150 nM | 5 nM |
| 34 5-Fluoro-4-(4-fluoro-2-methoxyphenyl)-N-{3-methoxy-5-[(S-methylsulfonimidoyl)methyl]phenyl}pyrimidin-2-amine; enantiomer 1 | 4 nM | 210 nM | 6 nM |
| 35 5-Fluoro-4-(4-fluoro-2-methoxyphenyl)-N-{3-methoxy-5-[(S-methylsulfonimidoyl)methyl]phenyl}pyrimidin-2-amine; enantiomer 2 | 4 nM | 190 nM | 6 nM |
| 36 (rac)-[(3-{[4-(2-Ethoxy-4-fluorophenyl)-5-fluoropyrimidin-2-yl]amino}-5-fluorobenzyl)(methyl)oxido-λ$^6$-sulfanylidene]-cyanamide | 5 nM | 290 nM | 8 nM |
| 37 (rac)-4-(2-Ethoxy-4-fluorophenyl)-5-fluoro-N-{3-fluoro-5-[(S-methylsulfonimidoyl)methyl]phenyl}pyrimidin-2-amine | 6 nM | 510 nM | 60 nM |
| 38 4-(2-Ethoxy-4-fluorophenyl)-5-fluoro-N-{3-fluoro-5-[(S-methylsulfonimidoyl)methyl]phenyl}pyrimidin-2-amine; enantiomer 1 | 4 nM | 260 nM | 29 nM |
| 39 4-(2-Ethoxy-4-fluorophenyl)-5-fluoro-N-{3-fluoro-5-[(S-methylsulfonimidoyl)methyl]phenyl}pyrimidin-2-amine; enantiomer 2 | 5 nM | 240 nM | 73 nM |
| 40 (rac)-{[3-{[5-Fluoro-4-(4-fluoro-2-methoxyphenyl)pyrimidin-2-yl]amino}-5-(trifluoromethyl)benzyl](methyl)oxido-λ$^6$-sulfanylidene}cyanamide | 4 nM | 200 nM | 4 nM |
| 41 (rac)-5-Fluoro-4-(4-fluoro-2-methoxyphenyl)-N-{3-[(S-methylsulfonimidoyl)methyl]-5-(trifluoromethyl)phenyl}-pyrimidin-2-amine | 2 nM | 180 nM | 3 nM |
| 42 (rac)-[Ethyl(3-fluoro-5-{[5-fluoro-4-(4-fluoro-2-methoxy-phenyl)pyrimidin-2-yl]amino}benzyl)oxido-λ$^6$-sulfanylidene]-cyanamide | 2 nM | 160 nM | n.t. |
| 43 (rac)-N-{3-[(S-Ethylsulfonimidoyl)methyl]-5-fluorophenyl}-5-fluoro-4-(4-fluoro-2-methoxyphenyl)pyrimidin-2-amine | 6 nM | 290 nM | 36 nM |
| 44 N-{3-[(S-ethylsulfonimidoyl)methyl]-5-fluorophenyl}-5-fluoro-4-(4-fluoro-2-methoxyphenyl)pyrimidin-2-amine; enantiomer 1 | 4 nM | 220 nM | 35 nM |
| 45 N-{3-[(S-ethylsulfonimidoyl)methyl]-5-fluorophenyl}-5-fluoro-4-(4-fluoro-2-methoxyphenyl)pyrimidin-2-amine; enantiomer 2 | 5 nM | 250 nM | 45 nM |
| 46 (rac)-{[3-{[5-Fluoro-4-(4-fluoro-2-methoxyphenyl)pyrimidin-2-yl]amino}-5-(pentafluoroethyl)benzyl](methyl)oxido-λ$^6$-sulfanylidene}cyanamide | 25 nM | 630 nM | 8 nM |
| 47 (rac)-5-Fluoro-4-(4-fluoro-2-methoxyphenyl)-N-{3-[(S-methyl-sulfonimidoyl)methyl]-5-(pentafluoroethyl)phenyl}pyrimidin-2-amine | 6 nM | 230 nM | 5 nM |

TABLE 2-continued

Inhibition for CDK9 and CDK2 of compounds according to the present invention
The IC$_{50}$ (inhibitory concentration at 50% of maximal effect) values are indicated
in nM, "n.t." means that the compounds have not been tested in this assay.

| ① Name of compound | ② | ③ | ④ |
|---|---|---|---|
| 48 (rac)-[Cyclopropyl(3-{[5-fluoro-4-(4-fluoro-2-methoxyphenyl)-pyrimidin-2-yl]amino}benzyl)oxido-λ$^6$-sulfanylidene]cyanamide | 2 nM | 220 nM | 5 nM |
| 49 (rac)-N-{3-[(S-Cyclopropylsulfonimidoyl)methyl]phenyl}-5-fluoro-4-(4-fluoro-2-methoxyphenyl)pyrimidin-2-amine | 14 nM | 410 nM | 279 nM |
| 50 (rac)-[Cyclopropyl(3-fluoro-5-{[5-fluoro-4-(4-fluoro-2-methoxyphenyl)pyrimidin-2-yl]amino}benzyl)oxido-λ$^6$-sulfanylidene]cyanamide | 6 nM | 250 nM | 4 nM |
| 51 (rac)-N-{3-[(S-Cyclopropylsulfonimidoyl)methyl]-5-fluorophenyl}-5-fluoro-4-(4-fluoro-2-methoxyphenyl)pyrimidin-2-amine | 9 nM | 410 nM | 104 nM |
| 52 N-{3-[(S-Cyclopropylsulfonimidoyl)methyl]-5-fluorophenyl}-5-fluoro-4-(4-fluoro-2-methoxyphenyl)pyrimidin-2-amine; enantiomer 1 | 9 nM | 580 nM | 110 nM |
| 53 N-{3-[(S-Cyclopropylsulfonimidoyl)methyl]-5-fluorophenyl}-5-fluoro-4-(4-fluoro-2-methoxyphenyl)pyrimidin-2-amine; enantiomer 2 | 7 nM | 380 nM | 51 nM |
| 54 (rac)-Ethyl[(3-{[4-(2,3-dihydro-1-benzofuran-7-yl)-5-fluoropyrimidin-2-yl]amino}benzyl)(methyl)oxido-λ$^6$-sulfanylidene]carbamate | 9 nM | 350 nM | 10 nM |
| 55 (rac)-5-Fluoro-4-{4-fluoro-2-[(4-fluorobenzyl)oxy]phenyl}-N-{3-[(S-methylsulfonimidoyl)methyl]phenyl}pyrimidin-2-amine | 5 nM | 770 nM | 4 nM |
| 56 (rac)-[(3-Chloro-5-{[5-fluoro-4-(4-fluoro-2-methoxyphenyl)-pyrimidin-2-yl]amino}benzyl)(methyl)oxido-λ$^6$-sulfanylidene]cyanamide | 4 nM | 160 nM | 2 nM |
| 57 (rac)-N-{3-Chloro-5-[(S-methylsulfonimidoyl)methyl]phenyl}-5-fluoro-4-(4-fluoro-2-methoxyphenyl)pyrimidin-2-amine | 5 nM | 180 nM | 7 nM |
| 58 (rac)-[(3-{[5-Fluoro-4-(4-fluoro-2-methoxyphenyl)pyrimidin-2-yl]amino}-5-methylbenzyl)(methyl)oxido-λ$^6$-sulfanylidene]cyanamide | 3 nM | 220 nM | 2 nM |
| 60 (rac)-{[3-{[5-Fluoro-4-(4-fluoro-2-methoxyphenyl)pyrimidin-2-yl]amino}-5-(pentafluoro-λ$^6$-sulfanyl)benzyl](methyl)oxido-λ$^6$-sulfanylidene}cyanamide | 6 nM | 320 nM | 12 nM |
| 61 (rac)-5-Fluoro-4-(4-fluoro-2-methoxyphenyl)-N-{3-[(S-methylsulfonimidoyl)methyl]-5-(pentafluoro-λ$^6$-sulfanyl)phenyl}-pyrimidin-2-amine | 6 nM | 290 nM | 6 nM |
| 62 5-Fluoro-4-(4-fluoro-2-methoxyphenyl)-N-{3-[(S-methylsulfonimidoyl)methyl]-5-(pentafluoro-λ$^6$-sulfanyl)phenyl}-pyrimidin-2-amine; enantiomer 1 | 5 nM | 170 nM | 5 nM |
| 63 5-Fluoro-4-(4-fluoro-2-methoxyphenyl)-N-{3-[(S-methylsulfonimidoyl)methyl]-5-(pentafluoro-λ$^6$-sulfanyl)phenyl}-pyrimidin-2-amine; enantiomer 2 | 3 nM | 200 nM | 3 nM |
| 64 2-Methoxyethyl[(3-fluoro-5-{[5-fluoro-4-(4-fluoro-2-methoxyphenyl)pyrimidin-2-yl]amino}benzyl)(methyl)oxido-λ$^6$-sulfanylidene]carbamate; single enantiomer | 3 nM | 330 nM | 3 nM |

①: Example Number
②: CDK9: CDK9/CycT1 kinase assay as described under Method 1a. of Materials and Methods
③: CDK2: CDK2/CycE kinase assay as described under Method 2. of Materials and Methods
④: high ATP CDK9: CDK9/CycT1 kinase assay as described under Method 1b. of Materials and Methods

TABLE 3

Inhibition of proliferation of HeLa, HeLa-MaTu-ADR, A2780, NCI-H460, DU145, Caco-2
and B16F10 cells by compounds according to the present invention, determined as described above
(Method 3. of Materials and Methods section). All IC$_{50}$ (inhibitory concentration at 50% of maximal
effect) values are indicated in nM, "n.t." means that the compounds have not been tested in this assay.

| ① Name of compound | ② | ③ | ④ | ⑤ | ⑥ | ⑦ | ⑧ |
|---|---|---|---|---|---|---|---|
| 1 (rac)-Ethyl[(3-{[5-fluoro-4-(4-fluoro-2-methoxyphenyl)pyrimidin-2-yl]amino}benzyl)(methyl)oxido-λ$^6$-sulfanylidene]carbamate | 280 | 350 | 390 | 420 | 470 | 480 | n.t. |
| 2 (rac)-5-Fluoro-4-(4-fluoro-2-methoxyphenyl)-N-{3-[(S-methylsulfonimidoyl)methyl]phenyl}pyrimidin-2-amine | 270 | 360 | 390 | 420 | 460 | 510 | 250 |
| 3 (rac)-Ethyl{[3-({4-[2-(benzyloxy)-4-fluorophenyl]-5-fluoropyrimidin-2-yl}amino)benzyl](methyl)oxido-λ$^6$-sulfanylidene}carbamate | 720 | 580 | 690 | 670 | 550 | 800 | n.t. |

TABLE 3-continued

Inhibition of proliferation of HeLa, HeLa-MaTu-ADR, A2780, NCI-H460, DU145, Caco-2 and B16F10 cells by compounds according to the present invention, determined as described above (Method 3. of Materials and Methods section). All $IC_{50}$ (inhibitory concentration at 50% of maximal effect) values are indicated in nM, "n.t." means that the compounds have not been tested in this assay.

| ① Name of compound | ② | ③ | ④ | ⑤ | ⑥ | ⑦ | ⑧ |
|---|---|---|---|---|---|---|---|
| 4 (rac)-4-[2-(Benzyloxy)-4-fluorophenyl]-5-fluoro-N-{3-[(S-methyl-sulfonimidoyl)methyl]phenyl}pyrimidin-2-amine | 320 | 330 | 400 | 420 | 470 | 390 | n.t. |
| 5 (rac)-Ethyl[(3-{[4-(3,4-dihydro-2H-chromen-8-yl)-5-fluoropyrimidin-2-yl]amino}benzyl)(methyl)oxido-λ⁶-sulfanylidene]carbamate | 490 | 390 | 600 | 540 | 560 | 920 | n.t. |
| 6 (rac)-4-(3,4-dihydro-2H-chromen-8-yl)-5-fluoro-N-{3-[(S-methyl-sulfonimidoyl)methyl]phenyl}pyrimidin-2-amine | 408 | 280 | 350 | 340 | 310 | 540 | n.t. |
| 7 (rac)-{[3-({4-[2-(Benzyloxy)-4-fluorophenyl]-5-fluoropyrimidin-2-yl}-amino)benzyl](methyl)oxido-λ⁶-sulfanylidene}cyanamide | 1160 | n.t. | n.t. | n.t. | n.t. | n.t. | n.t. |
| 8 (rac)-1-[(3-{[5-Fluoro-4-(4-fluoro-2-methoxyphenyl)pyrimidin-2-yl]-amino}benzyl)(methyl)oxido-λ⁶-sulfanylidene]-3-methylurea | 336 | 330 | 350 | 310 | 310 | 390 | 100 |
| 9 (rac)-Ethyl[(3-fluoro-5-{[5-fluoro-4-(4-fluoro-2-methoxyphenyl)pyrimidin-2-yl]amino}benzyl)(methyl)oxido-λ⁶-sulfanylidene]carbamate | 304 | 120 | 330 | 230 | 210 | 420 | n.t. |
| 10 (rac)-5-Fluoro-4-(4-fluoro-2-methoxyphenyl)-N-{3-fluoro-5-[(S-methyl-sulfonimidoyl)methyl]phenyl}pyrimidin-2-amine | 130 | 140 | 280 | 220 | 140 | 360 | 120 |
| 11 5-Fluoro-4-(4-fluoro-2-methoxyphenyl)-N-{3-[(S-methyl-sulfonimidoyl)methyl]phenyl}pyrimidin-2-amine; enantiomer 1 | 295 | 260 | 370 | 400 | 380 | 340 | 94 |
| 12 5-Fluoro-4-(4-fluoro-2-methoxyphenyl)-N-{3-[(S-methyl-sulfonimidoyl)methyl]phenyl}pyrimidin-2-amine; enantiomer 2 | 400 | 380 | 570 | 530 | 360 | 720 | 100 |
| 13 4-[2-(Benzyloxy)-4-fluorophenyl]-5-fluoro-N-{3-[(S-methyl-sulfonimidoyl)methyl]phenyl}pyrimidin-2-amine; enantiomer 1 | 305 | 210 | 350 | 340 | 230 | 310 | n.t. |
| 14 4-[2-(Benzyloxy)-4-fluorophenyl]-5-fluoro-N-{3-[(S-methyl-sulfonimidoyl)methyl]phenyl}pyrimidin-2-amine; enantiomer 2 | 325 | 320 | 360 | 380 | 260 | 30 | n.t. |
| 15 5-Fluoro-4-(4-fluoro-2-methoxyphenyl)-N-{3-fluoro-5-[(S-methyl-sulfonimidoyl)methyl]phenyl}pyrimidin-2-amine; enantiomer 1 | 320 | 240 | 180 | 230 | 220 | 260 | 64 |
| 16 5-Fluoro-4-(4-fluoro-2-methoxyphenyl)-N-{3-fluoro-5-[(S-methyl-sulfonimidoyl)methyl]phenyl}pyrimidin-2-amine; enantiomer 2 | 292 | 190 | 240 | 260 | 290 | 300 | 57 |
| 17 (rac)-[(3-{[5-Fluoro-4-(4-fluoro-2-methoxyphenyl)pyrimidin-2-yl]-amino}benzyl)(methyl)oxido-λ⁶-sulfanylidene]cyanamide | 310 | n.t. | n.t. | n.t. | n.t. | n.t. | 79 |
| 18 [(3-{[5-Fluoro-4-(4-fluoro-2-methoxyphenyl)pyrimidin-2-yl]amino}-benzyl)(methyl)oxido-λ⁶-sulfanylidene]cyanamide; enantiomer 1 | 420 | 120 | 150 | 110 | 170 | 140 | n.t. |
| 19 [(3-{[5-Fluoro-4-(4-fluoro-2-methoxyphenyl)pyrimidin-2-yl]amino}-benzyl)(methyl)oxido-λ⁶-sulfanylidene]cyanamide; enantiomer 2 | 280 | 150 | 170 | 150 | 200 | 280 | n.t. |
| 20 (rac)-[Ethyl(3-{[5-fluoro-4-(4-fluoro-2-methoxyphenyl)pyrimidin-2-yl]amino}benzyl)oxido-λ⁶-sulfanylidene]cyanamide | 111 | 100 | 150 | 170 | 130 | 200 | 72 |
| 21 (rac)-N-{3-[(S-Ethylsulfonimidoyl)methyl]phenyl}-5-fluoro-4-(4-fluoro-2-methoxyphenyl)pyrimidin-2-amine | 535 | n.t. | n.t. | n.t. | n.t. | n.t. | 290 |

TABLE 3-continued

Inhibition of proliferation of HeLa, HeLa-MaTu-ADR, A2780, NCI-H460, DU145, Caco-2 and B16F10 cells by compounds according to the present invention, determined as described above (Method 3. of Materials and Methods section). All $IC_{50}$ (inhibitory concentration at 50% of maximal effect) values are indicated in nM, "n.t." means that the compounds have not been tested in this assay.

| (1) Name of compound | (2) | (3) | (4) | (5) | (6) | (7) | (8) |
|---|---|---|---|---|---|---|---|
| 22 N-{3-[(S-Ethylsulfonimidoyl)methyl]phenyl}-5-fluoro-4-(4-fluoro-2-methoxyphenyl)pyrimidin-2-amine; enantiomer 1 | 976 | n.t. | n.t. | n.t. | n.t. | n.t. | n.t. |
| 23 N-{3-[(S-Ethylsulfonimidoyl)methyl]phenyl}-5-fluoro-4-(4-fluoro-2-methoxyphenyl)pyrimidin-2-amine; enantiomer 2 | 473 | 370 | 430 | 340 | 270 | 1200 | n.t. |
| 24 (rac)-[(2,3-Difluoro-5-{[5-fluoro-4-(4-fluoro-2-methoxyphenyl)pyrimidin-2-yl]amino}benzyl)(methyl)oxido-$\lambda^6$-sulfanylidene]cyanamide | 104 | 81 | 99 | 110 | 94 | 140 | 48 |
| 25 (rac)-N-{3,4-Difluoro-5-[(S-methylsulfonimidoyl)methyl]phenyl}-5-fluoro-4-(4-fluoro-2-methoxyphenyl)pyrimidin-2-amine | 355 | 140 | 330 | 340 | 200 | 370 | 140 |
| 26 N-{3,4-Difluoro-5-[(S-methylsulfonimidoyl)methyl]phenyl}-5-fluoro-4-(4-fluoro-2-methoxyphenyl)pyrimidin-2-amine; enantiomer 1 | 295 | n.t. | n.t. | n.t. | n.t. | n.t. | 150 |
| 27 N-{3,4-Difluoro-5-[(S-methylsulfonimidoyl)methyl]phenyl}-5-fluoro-4-(4-fluoro-2-methoxyphenyl)pyrimidin-2-amine; enantiomer 2 | 285 | 190 | 190 | 340 | 310 | 370 | 180 |
| 28 (rac)-[(3-Bromo-5-{[5-fluoro-4-(4-fluoro-2-methoxyphenyl)pyrimidin-2-yl]amino}benzyl)(methyl)oxido-$\lambda^6$-sulfanylidene]cyanamide | 103 | 58 | 110 | 62 | 83 | 110 | 32 |
| 29 (rac)-N-{3-Bromo-5-[(S-methylsulfonimidoyl)methyl]phenyl}-5-fluoro-4-(4-fluoro-2-methoxyphenyl)pyrimidin-2-amine | 107 | 74 | 130 | 100 | 74 | 130 | 47 |
| 30 N-{3-Bromo-5-[(S-methylsulfonimidoyl)methyl]phenyl}-5-fluoro-4-(4-fluoro-2-methoxyphenyl)pyrimidin-2-amine; enantiomer 1 | 145 | 110 | 98 | 130 | 120 | 150 | 62 |
| 31 N-{3-Bromo-5-[(S-methylsulfonimidoyl)methyl]phenyl}-5-fluoro-4-(4-fluoro-2-methoxyphenyl)pyrimidin-2-amine; enantiomer 2 | 169 | 59 | 90 | 120 | 98 | 130 | 1000 |
| 32 (rac)-[(3-{[5-Fluoro-4-(4-fluoro-2-methoxyphenyl)pyrimidin-2-yl]amino}-5-methoxybenzyl)(methyl)oxido-$\lambda^6$-sulfanylidene]cyanamide | 104 | 52 | 110 | 34 | 56 | 120 | 33 |
| 33 (rac)-5-Fluoro-4-(4-fluoro-2-methoxyphenyl)-N-{3-methoxy-5-[(S-methylsulfonimidoyl)methyl]phenyl}pyrimidin-2-amine | 137 | 82 | 130 | 150 | 67 | 150 | 62 |
| 34 5-Fluoro-4-(4-fluoro-2-methoxyphenyl)-N-{3-methoxy-5-[(S-methyl-sulfonimidoyl)methyl]phenyl}pyrimidin-2-amine; enantiomer 1 | 246 | 130 | 130 | 130 | 180 | 210 | n.t. |
| 35 5-Fluoro-4-(4-fluoro-2-methoxyphenyl)-N-{3-methoxy-5-[(S-methyl-sulfonimidoyl)methyl]phenyl}pyrimidin-2-amine; enantiomer 2 | 128 | 130 | 120 | 130 | 140 | 150 | 98 |
| 36 (rac)-[(3-{[4-(2-Ethoxy-4-fluorophenyl)-5-fluoropyrimidin-2-yl]amino}-5-fluorobenzyl)(methyl)oxido-$\lambda^6$-sulfanylidene]cyanamide | 245 | 200 | 210 | 300 | 290 | 330 | 150 |
| 37 (rac)-4-(2-Ethoxy-4-fluorophenyl)-5-fluoro-N-{3-fluoro-5-[(S-methyl-sulfonimidoyl)methyl]phenyl}pyrimidin-2-amine | 304 | 140 | 350 | 380 | 350 | 350 | 180 |

TABLE 3-continued

Inhibition of proliferation of HeLa, HeLa-MaTu-ADR, A2780, NCI-H460, DU145, Caco-2 and B16F10 cells by compounds according to the present invention, determined as described above (Method 3. of Materials and Methods section). All IC$_{50}$ (inhibitory concentration at 50% of maximal effect) values are indicated in nM, "n.t." means that the compounds have not been tested in this assay.

| ① Name of compound | ② | ③ | ④ | ⑤ | ⑥ | ⑦ | ⑧ |
|---|---|---|---|---|---|---|---|
| 38 4-(2-Ethoxy-4-fluorophenyl)-5-fluoro-N-{3-fluoro-5-[(S-methyl-sulfonimidoyl)methyl]phenyl}pyrimidin-2-amine; enantiomer 1 | 294 | n.t. | n.t. | n.t. | n.t. | n.t. | 200 |
| 39 4-(2-Ethoxy-4-fluorophenyl)-5-fluoro-N-{3-fluoro-5-[(S-methylsulfonimidoyl)methyl]phenyl}pyrimidin-2-amine; enantiomer 2 | 397 | n.t. | n.t. | n.t. | n.t. | n.t. | 200 |
| 40 (rac)-{[3-{[5-Fluoro-4-(4-fluoro-2-methoxyphenyl)pyrimidin-2-yl]amino}-5-(trifluoromethyl)benzyl](methyl)oxido-λ$^6$-sulfanylidene}cyanamide | 84 | 100 | 140 | 140 | 150 | 130 | 37 |
| 41 (rac)-5-Fluoro-4-(4-fluoro-2-methoxyphenyl)-N-{3-[(S-methyl-sulfonimidoyl)methyl]-5-(trifluoromethyl)phenyl}pyrimidin-2-amine | 102 | 110 | 120 | 150 | 150 | 220 | 42 |
| 42 (rac)-[Ethyl(3-fluoro-5-{[5-fluoro-4-(4-fluoro-2-methoxyphenyl)pyrimidin-2-yl]amino}benzyl)oxido-λ$^6$-sulfanylidene]cyanamide | 126 | 34 | 34 | 61 | 30 | 33 | 41 |
| 43 (rac)-N-{3-[(S-Ethylsulfonimidoyl)methyl]-5-fluorophenyl}-5-fluoro-4-(4-fluoro-2-methoxyphenyl)pyrimidin-2-amine | 269 | 200 | 200 | 290 | 240 | 320 | 150 |
| 44 N-{3-[(S-ethylsulfonimidoyl)methyl]-5-fluorophenyl}-5-fluoro-4-(4-fluoro-2-methoxyphenyl)pyrimidin-2-amine; enantiomer 1 | 297 | n.t. | n.t. | n.t. | n.t. | n.t. | 180 |
| 45 N-{3-[(S-ethylsulfonimidoyl)methyl]-5-fluorophenyl}-5-fluoro-4-(4-fluoro-2-methoxyphenyl)pyrimidin-2-amine; enantiomer 2 | 313 | n.t. | n.t. | n.t. | n.t. | n.t. | 97 |
| 46 (rac)-{[3-{[5-Fluoro-4-(4-fluoro-2-methoxyphenyl)pyrimidin-2-yl]amino}-5-(pentafluoroethyl)benzyl](methyl)oxido-λ$^6$-sulfanylidene}cyanamide | 899 | n.t. | n.t. | n.t. | n.t. | n.t. | n.t. |
| 47 (rac)-5-Fluoro-4-(4-fluoro-2-methoxyphenyl)-N-{3-[(S-methyl-sulfonimidoyl)methyl]-5-(pentafluoroethyl)phenyl}pyrimidin-2-amine | 115 | 110 | 100 | 200 | 130 | 270 | 100 |
| 48 (rac)-[Cyclopropyl(3-{[5-fluoro-4-(4-fluoro-2-methoxyphenyl)pyrimidin-2-yl]amino}benzyl)oxido-λ$^6$-sulfanylidene]cyanamide | 215 | 170 | 120 | 210 | 170 | 330 | 76 |
| 49 (rac)-N-{3-[(S-Cyclopropylsulfonimidoyl)methyl]phenyl}-5-fluoro-4-(4-fluoro-2-methoxyphenyl)pyrimidin-2-amine | 730 | n.t | n.t. | n.t. | n.t. | n.t. | n.t. |
| 50 (rac)-[Cyclopropyl(3-fluoro-5-{[5-fluoro-4-(4-fluoro-2-methoxyphenyl)pyrimidin-2-yl]amino}benzyl)oxido-λ$^6$-sulfanylidene]-cyanamide | 111 | 140 | 120 | 210 | 180 | 270 | 48 |
| 51 (rac)-N-{3-[(S-Cyclopropylsulfonimidoyl)methyl]-5-fluorophenyl}-5-fluoro-4-(4-fluoro-2-methoxyphenyl)pyrimidin-2-amine | 930 | n.t. | n.t. | n.t. | n.t. | n.t. | n.t. |
| 54 (rac)-Ethyl[(3-{[4-(2,3-dihydro-1-benzofuran-7-yl)-5-fluoropyrimidin-2-yl]amino}benzyl)(methyl)oxido-λ$^6$-sulfanylidene]carbamate | 787 | n.t. | n.t. | n.t. | n.t. | n.t. | n.t. |
| 55 (rac)-5-Fluoro-4-{4-fluoro-2-[(4-fluorobenzyl)oxy]phenyl}-N-{3-[(S-methylsulfonimidoyl)methyl]phenyl}pyrimidin-2-amine | 796 | n.t. | n.t. | n.t. | n.t. | n.t. | n.t. |
| 60 (rac)-{[3-{[5-Fluoro-4-(4-fluoro-2-methoxyphenyl)pyrimidin-2-yl]amino}-5-(pentafluoro-λ$^6$-sulfanyl)benzyl](methyl)oxido-λ$^6$-sulfanylidene}cyanamide | 96 | 68 | 66 | 92 | 91 | 120 | 38 |

TABLE 3-continued

Inhibition of proliferation of HeLa, HeLa-MaTu-ADR, A2780, NCI-H460, DU145, Caco-2 and B16F10 cells by compounds according to the present invention, determined as described above (Method 3. of Materials and Methods section). All IC$_{50}$ (inhibitory concentration at 50% of maximal effect) values are indicated in nM, "n.t." means that the compounds have not been tested in this assay.

| ① Name of compound | ② | ③ | ④ | ⑤ | ⑥ | ⑦ | ⑧ |
|---|---|---|---|---|---|---|---|
| 61 (rac)-5-Fluoro-4-(4-fluoro-2-methoxyphenyl)-N-{3-[(S-methylsulfonimidoyl)methyl]-5-(pentafluoro-λ$^6$-sulfanyl)phenyl}pyrimidin-2-amine | 441 | 37 | 41 | 110 | 57 | 130 | 83 |

①: Example Number
②: Inhibition of HeLa cell proliferation
③: Inhibition of HeLa-MaTu-ADR cell proliferation
④: Inhibition of H460 cell proliferation
⑤: Inhibition of DU145 cell proliferation
⑥: Inhibition of Caco-2 cell proliferation
⑦: Inhibition of B16F10 cell proliferation
⑧: Inhibition of A2780 cell proliferation

TABLE 4

Thermodynamic solubility of compounds according to the present invention in water at pH 6.5 as determined by the equilibrium shake flask method described under Method 4. of Materials and Methods.

| ① Name of compound | ② |
|---|---|
| 2 (rac)-5-Fluoro-4-(4-fluoro-2-methoxyphenyl)-N-{3-[(S-methylsulfonimidoyl)methyl]phenyl}pyrimidin-2-amine | 98 |
| 15 5-Fluoro-4-(4-fluoro-2-methoxyphenyl)-N-{3-fluoro-5-[(S-methylsulfonimidoyl)methyl]phenyl}pyrimidin-2-amine; enantiomer 1 | 16 |
| 16 5-Fluoro-4-(4-fluoro-2-methoxyphenyl)-N-{3-fluoro-5-[(S-methylsulfonimidoyl)methyl]phenyl}pyrimidin-2-amine; enantiomer 2 | 24 |

①: Example Number
②: Solubilty in mg/l.

TABLE 5

Inhibition of Carbonic anhydrase-1 and Carbonic anhydrase-2 as determined by the Carbonic anhydrase Assay described above

| ① Name of compound | ② | ③ |
|---|---|---|
| 11 5-Fluoro-4-(4-fluoro-2-methoxyphenyl)-N-{3-[(S-methylsulfonimidoyl)methyl]phenyl}pyrimidin-2-amine; enantiomer 1 | >10000 nM | >10000 nM |
| 16 5-Fluoro-4-(4-fluoro-2-methoxyphenyl)-N-{3-fluoro-5-(S-methylsulfonimidoyl)methyl]phenyl}pyrimidin-2-amine; enantiomer 2 | >10000 nM | >10000 nM |

①: Compound Number
②: Inhibition of Carbonic anhydrase-1: the IC$_{50}$ (inhibitory concentration at 50% of maximal effect) values are indicated in nM.
③ Inhibition of Carbonic anhydrase-2: the IC$_{50}$ (inhibitory concentration at 50% of maximal effect) values are indicated in nM.

The invention claimed is:
1. A compound of general formula (I)

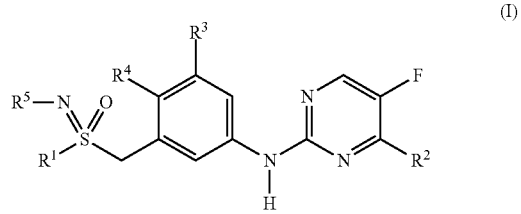

wherein
R$^1$ represents a group selected from the group consisting of C$_1$-C$_6$-alkyl-, C$_3$-C$_7$-cycloalkyl-, heterocyclyl-, phenyl, heteroraryl, phenyl-C$_1$-C$_3$-alkyl- and heteroaryl-C$_1$-C$_3$-alkyl-,
wherein said group is optionally substituted with one or two or three substituents, identically or differently, selected from the group consisting of hydroxy, cyano, halogen, halo-C$_1$-C$_3$-alkyl-, C$_1$-C$_6$-alkoxy-, C$_1$-C$_3$-fluoroalkoxy-, amino, alkylamino-, dialkylamino-, acetylamino-, N-methyl-N-acetylamino-, and cyclic amines;
R$^2$ represents a group selected from the group consisting of

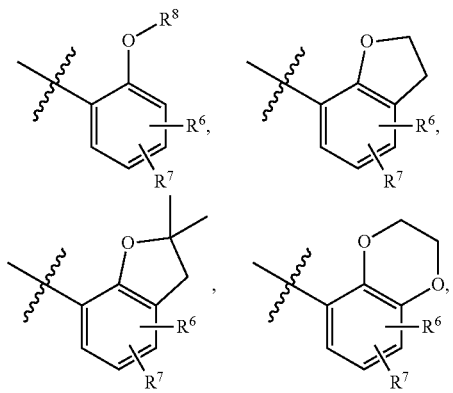

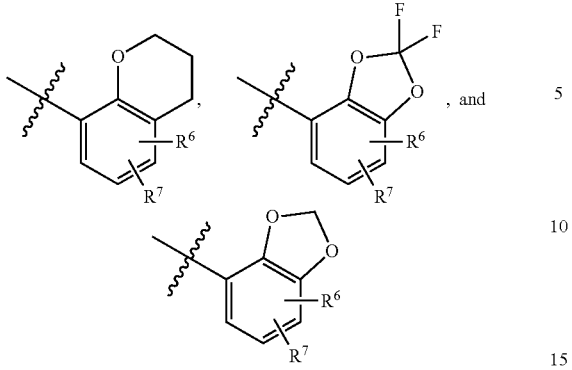

$R^3$, $R^4$ represent, independently from each other, a group selected from the group consisting of a hydrogen atom, halogen atom, cyano, —$SF_5$, $C_1$-$C_3$-alkyl-, $C_1$-$C_3$-alkoxy-, halo-$C_1$-$C_3$-alkyl-, and $C_1$-$C_3$-fluoroalkoxy-;

$R^5$ represents a group selected from the group consisting of a hydrogen atom, cyano, —$C(O)R^9$, —$C(O)OR^9$, —$S(O)_2R^9$, —$C(O)NR^{10}R^{11}$, $C_1$-$C_6$-alkyl-, $C_3$-$C_7$-cycloalkyl-, heterocyclyl-, phenyl, and heteroaryl wherein said $C_1$-$C_6$-alkyl, $C_3$-$C_7$-cycloalkyl-, heterocyclyl-, phenyl or heteroaryl group is optionally substituted with one, two or three substituents, identically or differently, selected from the group consisting of halogen, hydroxy, cyano, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, and $C_1$-$C_3$-fluoroalkoxy-;

$R^6$, $R^7$ represent, independently from each other, a group selected from the group consisting of a hydrogen atom, halogen atom, cyano, $C_1$-$C_3$-alkyl-, $C_1$-$C_3$-alkoxy-, halo-$C_1$-$C_3$-alkyl-, and $C_1$-$C_3$-fluoroalkoxy-;

$R^8$ represents a group selected from the group consisting of a) a $C_1$-$C_6$-alkyl group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, heterocyclyl-, phenyl, and heteroaryl, wherein said $C_3$-$C_7$-cycloalkyl-, heterocyclyl-, phenyl or heteroaryl group is optionally substituted with one, two or three substituents, identically or differently, selected from the group consisting of halogen, hydroxy, cyano, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, and $C_1$-$C_3$-fluoroalkoxy-;

b) a $C_3$-$C_6$-alkenyl group, which is optionally substituted with one or two or three substituents, identically or differently, selected from the group the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, heterocyclyl-, phenyl, and heteroaryl, wherein said $C_3$-$C_7$-cycloalkyl-, heterocyclyl-, phenyl or heteroaryl group is optionally substituted with one, two or three substituents, identically or differently, selected from the group consisting of halogen, hydroxy, cyano, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, and $C_1$-$C_3$-fluoroalkoxy-;

c) a $C_3$-$C_6$-alkynyl group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, heterocyclyl-, phenyl, and heteroaryl, wherein said $C_3$-$C_7$-cycloalkyl-, heterocyclyl-, phenyl or heteroaryl group is optionally substituted with one, two or three substituents, identically or differently, selected from the group consisting of halogen, hydroxy, cyano, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, and $C_1$-$C_3$-fluoroalkoxy-;

d) a $C_3$-$C_7$-cycloalkyl- group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, and $C_2$-$C_3$-alkynyl-;

e) a heterocyclyl-group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl, $C_1$-$C_3$-fluoroalkoxy-, $C_1$-$C_3$-alkoxy-, $C_2$-$C_3$-alkenyl-, and $C_2$-$C_3$-alkynyl-;

f) a phenyl group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, and $C_1$-$C_3$-alkoxy-;

g) a heteroaryl group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, and $C_1$-$C_3$-alkoxy-;

h) a phenyl-$C_1$-$C_3$-alkyl- group, which phenyl group is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, and $C_1$-$C_3$-alkoxy-;

i) a heteroaryl-$C_1$-$C_3$-alkyl- group, which heteroaryl group is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$ alkyl-, halo $C_1$-$C_3$-alkyl-, $C_1$-$C_3$-fluoroalkoxy-, and $C_1$-$C_3$-alkoxy-;

j) a $C_3$-$C_6$-cycloalkyl-$C_1$-$C_3$-alkyl- group, which $C_3$-$C_6$-cycloalkyl group is optionally substituted with one or two or three substituents, identically or differently, selected from the group consisting of halogen, $C_1$-$C_3$-alkyl-, $C_1$-$C_3$-alkoxy-, halo-$C_1$-$C_3$-alkyl-, and $C_1$-$C_3$-fluoroalkoxy-;

k) a heterocyclyl-$C_1$-$C_3$-alkyl- group, which heterocyclyl group is optionally substituted with one or two or three substituents, identically or differently, selected from the group consisting of halogen, $C_1$-$C_3$-alkyl-, $C_1$-$C_3$-alkoxy, halo-$C_1$-$C_3$-alkyl-, and $C_1$-$C_3$-fluoroalkoxy-;

l) phenyl-cyclopropyl- group, which phenyl group is optionally substituted with one or two or three substituents, identically or differently, selected from the group consisting of halogen, hydroxy, $NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, and $C_1$-$C_3$-alkoxy-; and m) a heteroaryl-cyclopropyl- group, which heteroaryl group is optionally substituted with one or two or three substituents, identically or differently, selected from the group consisting of halogen, hydroxy, $NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, and $C_1$-$C_3$-alkoxy-;

$R^9$ represents a group selected from the group consisting of $C_1$-$C_6$-alkyl-, $C_3$-$C_7$-cycloalkyl-, heterocyclyl-, phenyl, benzyl and heteroaryl wherein said group is optionally substituted with one, two or three substituents, identically or differently, selected from the group consisting of halogen, hydroxy, $C_1$-$C_3$ alkyl $C_1$-$C_3$-alkoxy-, amino, alkylamino-, dialkylamino-, acetylamino-, N-methyl-N-acetylamino-, cyclic amines, halo-$C_1$-$C_3$-alkyl-, and $C_1$-$C_3$-fluoroalkoxy-; and $R^{10}$, $R^{11}$ represent, independently from each other, a group selected from the group consisting of hydrogen, $C_1$-$C_6$-alkyl-, $C_3$-$C_7$-cycloalkyl-, heterocyclyl-, phenyl and heteroaryl wherein said $C_1$-$C_6$-alkyl-, $C_3$-$C_7$-cycloalkyl-, heterocyclyl-, phenyl or heteroaryl group is optionally substituted with one, two or three substituents, identically or differently, selected from the group consisting of halogen, hydroxy, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-C3-alkyl-, and $C_1$-$C_3$-fluoroalkoxy-;

or an enantiomer, diastereomer, salt, solvate or salt of a solvate thereof.

2. The compound of general formula (I) according to claim 1, wherein $R^3$ represents a group selected from the group consisting of a halogen atom, cyano, —$SF_5$, $C_1$-$C_3$-alkyl-, $C_1$-$C_3$-alkoxy-, halo-$C_1$-$C_3$-alkyl-, and $C_1$-$C_3$-fluoroalkoxy-; and $R^4$ represents hydrogen, or an enantiomer, diastereomer, salt, solvate or salt of a solvate thereof.

3. The compound of general formula (I) according to claim 1, wherein $R^1$ represents a group selected from the group consisting of $C_1$-$C_6$-alkyl-, $C_3$-$C_7$-cycloalkyl-, heterocyclyl-, phenyl, heteroaryl, phenyl-$C_1$-$C_3$-alkyl- and heteroaryl-$C_1$-$C_3$-alkyl-, wherein said group is optionally substituted with one or two or three substituents, identically or differently, selected from the group consisting of hydroxy, cyano, halogen, halo-$C_1$-$C_3$-alkyl-, $C_1$-$C_6$-alkoxy-, $C_1$-$C_3$-fluoroalkoxy-, amino, alkylamino-, dialkylamino-, acetylamino-, N-methyl-N-acetylamino-, and cyclic amines;

$R^2$ represents a group selected from the group consisting of

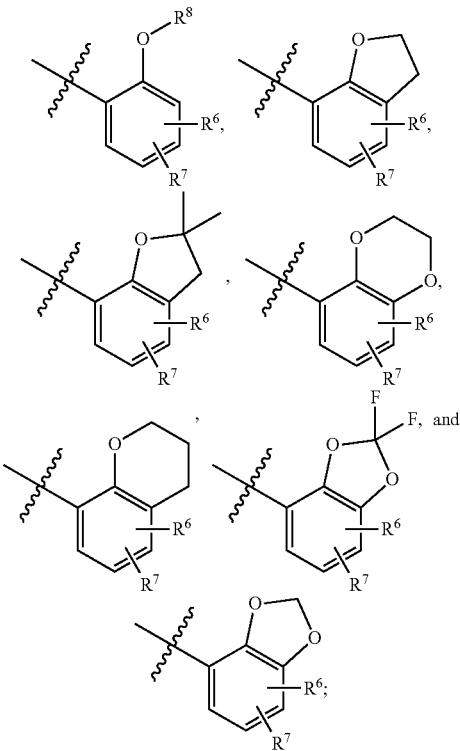

$R^3$, $R^4$ represent, independently from each other, a group selected from the group consisting of a hydrogen atom, fluoro atom, chloro atom, cyano, $C_1$-$C_3$-alkyl-, $C_1$-$C_3$-alkoxy-, halo-$C_1$-$C_3$-alkyl-, and $C_1$-$C_3$-fluoroalkoxy-;

$R^5$ represents a group selected from the group consisting of a hydrogen atom, cyano, —C(O)$R^9$, —C(O)O$R^9$, —S(O)$_2R^9$, —C(O)N$R^{10}R^{11}$, $C_1$-$C_6$-alkyl-, $C_3$-$C_7$-cycloalkyl-, heterocyclyl-, phenyl, and heteroaryl wherein said $C_1$-$C_6$-alkyl, $C_3$-$C_7$-cycloalkyl-, heterocyclyl-, phenyl or heteroaryl group is optionally substituted with one, two or three substituents, identically or differently, selected from the group consisting of halogen, hydroxy, cyano, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, and $C_1$-$C_3$-fluoroalkoxy-;

$R^6$, $R^7$ represent, independently from each other, a group selected from the group consisting of a hydrogen atom, fluoro atom, chloro atom, cyano, $C_1$-$C_3$-alkyl-, $C_1$-$C_3$-alkoxy-, halo-$C_1$-$C_3$-alkyl-, and $C_1$-$C_3$-fluoroalkoxy-;

$R^8$ represents a group selected from the group consisting of a) a $C_1$-$C_6$-alkyl group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$- alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, heterocyclyl-, phenyl, and heteroaryl, wherein said $C_3$-$C_7$-cycloalkyl-, heterocyclyl-, phenyl or heteroaryl group is optionally substituted with one, two or three substituents, identically or differently, selected from the group consisting of halogen, hydroxy, cyano, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, and $C_1$-$C_3$-fluoroalkoxy-;

b) a $C_3$-$C_7$-cycloalkyl- group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy, $C_2$-$C_3$-alkenyl-, and $C_2$-$C_3$-alkynyl-;

c) a heterocyclyl-group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, and $C_2$-$C_3$-alkynyl-;

d) a phenyl group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, and $C_1$-$C_3$-alkoxy-;

e) a heteroaryl group, which is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, and $C_1$-$C_3$-alkoxy-;

f) a phenyl-$C_1$-$C_3$-alkyl- group, which phenyl group is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, and $C_1$-C3-alkoxy-;

g) a heteroaryl-$C_1$-$C_3$-alkyl- group, which heteroaryl group is optionally substituted with one or two or three substituents, identically or differently, selected from the group consisting of halogen, hydroxy, amino, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, and $C_1$-$C_3$-alkoxy-;

h) a $C_3$-$C_6$-cycloalkyl-$C_1$-$C_3$-alkyl- group, which $C_3$-$C_6$-cycloalkyl group is optionally substituted with one or two or three substituents, identically or differently, selected from the group consisting of halogen, $C_1$-$C_3$-alkyl-, $C_1$-$C_3$-alkoxy-, halo-$C_1$-$C_3$-alkyl-, and $C_1$-$C_3$-fluoroalkoxy-;

i) a heterocyclyl-$C_1$-$C_3$-alkyl- group, which heterocyclyl group is optionally substituted with one or two or three substituents, identically or differently, selected from the group consisting of halogen, $C_1$-$C_3$-alkyl-, $C_1$-$C_3$ alkoxy halo-$C_1$-$C_3$-alkyl-, and $C_1$-$C_3$-fluoroalkoxy-;

j) phenyl-cyclopropyl- group, which phenyl group is optionally substituted with one or two or three substituents, identically or differently, selected from the group consisting of halogen, hydroxy, $NH_2$, alkylamino-, dialkylamino-, acetylamino-, N-methyl-N-acetylamino-, cyclic amines, cyano, $C_1$-$C_3$-alkyl-, $C_1$-$C_3$-alkoxy-, halo-$C_1$-$C_3$-alkyl-, $C_1$-$C_3$-fluoroalkoxy-, and $C_1$-$C_3$-alkoxy-; and k) a heteroaryl-cyclopropyl- group, which heteroaryl group is optionally substituted with one or two or three substituents, identically or differently, selected from the group consisting of halogen, hydroxy, $NH_2$, alkylamino-, acetylamino-, N-methyl-N-acetylamino-, cyclic amines, cyano, $C_1$-$C_3$-alkyl-, halo-$C_1$-C3-alkyl-, $C_1$-$C_3$-fluoroalkoxy-, and $C_1$-$C_3$-alkoxy-;

$R^9$ represents a group selected from the group consisting of $C_1$-$C_6$-alkyl-, $C_3$-$C_7$-cycloalkyl-, heterocyclyl-, phenyl, benzyl and heteroaryl wherein said group is optionally substituted with one, two or three substituents, identically or differently, selected from the group consisting of halogen, hydroxy, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, and $C_1$-$C_3$-fluoroalkoxy-; and $R^{10}$, $R^{11}$ represent, independently from each other, a group selected from the group consisting of hydrogen, $C_1$-$C_6$-alkyl-, $C_3$-$C_7$-cycloalkyl-, heterocyclyl-, phenyl and heteroaryl wherein said $C_1$-$C_6$-alkyl, $C_3$-$C_7$-cycloalkyl-, heterocyclyl-, phenyl or heteroaryl group is optionally substituted with one, two or three substituents, identically or differently, selected from the group consisting of halogen, hydroxy, $C_1$-$C_3$-alkyl-, $C_1$-$C_3$-alkoxy-, amino, alkylamino-, dialkylamino-, acetylamino-, N-methyl-N-acetylamino-, cyclic amines, halo-$C_1$-$C_3$-alkyl-, and $C_1$-$C_3$-fluoroalkoxy-;

or a salt, solvate or salt of a solvate thereof.

4. The compound of general formula (I) according to claim 1, wherein $R^1$ represents $C_1$-$C_6$-alkyl-, or $C_3$-$C_5$-cycloalkyl-, wherein said group is optionally substituted with one or two substituents, identically or differently, selected from the group consisting of hydroxy, $C_1$-$C_2$-alkoxy-, halo-$C_1$-$C_2$-alkyl-, and $C_1$-$C_2$-fluoroalkoxy-;

$R^2$ represents a group selected from the group consisting of

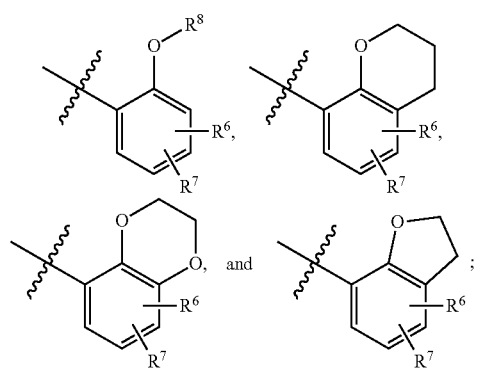

$R^3$ represents a hydrogen atom or fluoro atom;
$R^4$ represents a hydrogen atom or a fluoro atom;

$R^5$ represents a group selected from the group consisting of a hydrogen atom, cyano, —C(O)OR$^9$, and —C(O)NR$^{10}$R$^{11}$;

$R^6$, $R^7$ represent, independently from each other, a hydrogen atom, fluoro atom, or chloro atom;

$R^8$ represents a group selected from the group consisting of
a) a $C_1$-$C_6$-alkyl group, which is optionally substituted with one or two or three substituents, identically or differently, selected from the group consisting of halogen, hydroxy, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_3$-$C_7$-cycloalkyl-, heterocyclyl-, phenyl, and heteroaryl,
wherein said $C_3$-$C_7$-cycloalkyl-, heterocyclyl-, phenyl or heteroaryl group is optionally substituted with one, two or three substituents, identically or differently, selected from the group consisting of halogen, hydroxy, $C_1$-$C_3$-alkyl-, $C_1$-$C_3$-alkoxy-, dialkylamino-, acetylamino-, N-methyl-N-acetylamino-, cyclic amines, halo-$C_1$-$C_3$-alkyl-, and $C_1$-$C_3$-fluoroalkoxy-;
b) a phenyl-$C_1$-$C_3$-alkyl- group, which phenyl group is optionally substituted with one or two or three substituents, identically or differently, selected from the group consisting of halogen, hydroxy, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoro alkoxy-, and $C_1$-$C_3$-alkoxy-;
c) a heteroaryl-$C_1$-$C_3$-alkyl- group, which heteroaryl group is optionally substituted with one or two or three substituents, identically or differently, selected from the group consisting of halogen, hydroxy, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, and $C_1$-$C_3$-alkoxy-;
d) a $C_3$-$C_6$-cycloalkyl-$C_1$-$C_3$-alkyl- group, which $C_3$-$C_6$-cycloalkyl group is optionally substituted with one or two or three substituents, identically or differently, selected from the group consisting of halogen, $C_1$-$C_3$-alkyl-, $C_1$-$C_3$-alkoxy-, halo-$C_1$-$C_3$-alkyl-, and $C_1$-$C_3$-fluoroalkoxy-;
e) a heterocyclyl-$C_1$-$C_3$-alkyl- group, which heterocyclyl group is optionally substituted with one or two or three substituents, identically or differently, selected from the group consisting of halogen, $C_1$-$C_3$-alkyl-, $C_1$-$C_3$-alkoxy-, halo-$C_1$-$C_3$-alkyl-, and $C_1$-$C_3$-fluoro alkoxy-;
f) phenyl-cyclopropyl- group, which phenyl group is optionally substituted with one or two or three substituents, identically or differently, selected from the group consisting of halogen, hydroxy, —NH$_2$, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, and $C_1$-$C_3$-alkoxy-; and
g) a heteroaryl-cyclopropyl- group, which heteroaryl group is optionally substituted with one or two or three substituents, identically or differently, selected from the group consisting of halogen, hydroxy, —NH$_2$, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, and $C_1$-$C_3$-alkoxy-;

$R^9$ represents a $C_1$-$C_3$-alkyl group; and $R^{10}$, $R^{11}$ represent, independently from each other, hydrogen, or $C_1$-$C_2$-alkyl-;

or a salt, solvate or salt of a solvate thereof.

5. The compound of general formula (1) according to claim 1, wherein

R represents a $C_1$-$C_6$-alkyl-, or $C_3$-$C_5$-cycloalkyl- group, wherein said group is optionally substituted with one or two substituents, identically or differently, selected from the group consisting of $C_1$-$C_2$-alkoxy-, halo-$C_1$-$C_2$-alkyl-, and $C_1$-$C_2$-fluoroalkoxy-;

$R^2$ represents

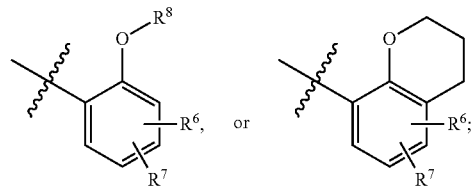

$R^3$ represents a hydrogen atom or a fluoro atom;

$R^4$ represents a hydrogen atom or a fluoro atom;

$R^5$ represents a hydrogen atom, cyano, —C(O)OR$^9$, or —C(O)NR$^{10}$R$^{11}$;

$R^6$, $R^7$ represent, independently from each other, a hydrogen atom, or fluoro atom;

$R^8$ represents a group selected from the group consisting of
a) a $C_1$-$C_3$-alkyl group, which is optionally substituted with one or two or three substituents, identically or differently, selected from the group consisting of halogen, cyano, and halo-$C_1$-$C_3$-alkyl-;
b) a phenyl-$C_1$-$C_3$-alkyl- group, which phenyl group is optionally substituted with one or two or three substituents, identically or differently, selected from the group consisting of halogen, cyano, $C_1$-$C_3$-alkyl-, halo-$C_1$-$C_3$-alkyl-, $C_1$-$C_3$-fluoroalkoxy-, and $C_1$-$C_3$-alkoxy-;
c) a heteroaryl-$C_1$-$C_3$-alkyl- group, which heteroaryl group is optionally substituted with one or two substituents, identically or differently, selected from the group consisting of halogen, cyano, $C_1$-$C_3$-alkyl-, halo-$C_1$-$C_3$-alkyl-, $C_1$-$C_3$-fluoroalkoxy-, and $C_1$-$C_3$-alkoxy-;
d) a $C_3$-$C_6$-cycloalkyl-$C_1$-$C_3$-alkyl- group, which $C_3$-$C_6$-cycloalkyl group is optionally substituted with one or two or three substituents, identically or differently, selected from the group consisting of halogen, $C_1$-$C_3$-alkyl-, C halo-$C_1$-$C_3$-alkyl-, and $C_1$-$C_3$-fluoroalkoxy-;
e) a heterocyclyl-$C_1$-$C_3$-alkyl- group, which heterocyclyl group is optionally substituted with one or two or three substituents, identically or differently, selected from the group consisting of halogen, $C_1$-$C_3$-alkyl-, $C_1$-$C_3$-alkoxy-, halo-$C_1$-$C_3$-alkyl-, and $C_1$-$C_3$-fluoroalkoxy-;
f) phenyl-cyclopropyl- group, which phenyl group is optionally substituted with one or two or three substituents, identically or differently, selected from the group consisting of halogen, cyano, $C_1$-$C_3$-alkyl-, halo-$C_1$-$C_3$-alkyl-, $C_1$-$C_3$-fluoroalkoxy-, and $C_1$-$C_3$-alkoxy-; and
g) a heteroaryl-cyclopropyl- group, which heteroaryl group is optionally substituted with one or two or three substituents, identically or differently, selected from the group consisting of halogen, cyano, $C_1$-$C_3$-alkyl-, halo-$C_1$-$C_3$-alkyl-, $C_1$-$C_3$-fluoroalkoxy-, and $C_1$-$C_3$-alkoxy-;

$R^9$ represents a $C_1$-$C_3$-alkyl group; and
$R^{10}$, $R^{11}$ represent, independently from each other, hydrogen, or $C_1$-$C_2$-alkyl-;
or a salt, solvate or salt of a solvate thereof.

6. The compound of general formula (1) according to claim 1, wherein
$R^1$ represents a $C_1$-$C_3$-alkyl- or cyclopropyl group;
$R^2$ represents

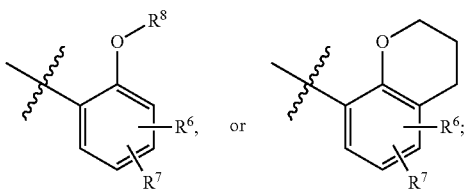

$R^3$ represents a hydrogen atom or fluoro atom;
$R^4$ represents a hydrogen atom or fluoro atom;
$R^5$ represents a hydrogen atom, cyano, —C(O)OR$^9$, or —C(O)NR$^{10}$R$^{11}$;
$R^6$, $R^7$ represent, independently from each other, a hydrogen atom, or fluoro atom;
$R^8$ represents
  a) a $C_1$-$C_3$-alkyl group; or
  b) a phenyl-$C_1$-$C_3$-alkyl- group, which phenyl group is optionally substituted with one or two, identically or differently, halogen atoms;
$R^9$ represents a $C_1$-$C_2$-alkyl group; and
$R^{10}$, $R^{11}$ represent, independently from each other, a hydrogen atom, or $C_1$-$C_2$-alkyl-;
or a salt, solvate or salt of a solvate thereof.

7. The compound of general formula (I) according to claim 1, wherein
$R^1$ represents $C_1$-$C_3$-alkyl- or cyclopropyl-,
$R^2$ represents

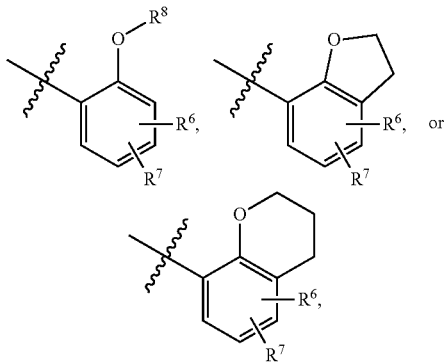

$R^3$, $R^4$ represent, independently from each other, a hydrogen atom, a fluoro, a chloro or a bromo atom, —SF$_5$, $C_1$-$C_3$-alkyl-, $C_1$-$C_2$-alkoxy- or CF$_3$—,
$R^5$ represents a hydrogen atom, cyano, —C(O)OR$^9$ or —C(O)NR$^{10}$R$^{11}$,
$R^6$, $R^7$ represent, independently from each other, a hydrogen atom or a fluoro atom,
$R^8$ represents
  a) a $C_1$-$C_3$-alkyl group, which is optionally substituted with fluorine, or
  b) a phenyl-C1-C2-alkyl- group, which phenyl group is optionally substituted with halogen, $R^9$ represents a $C_1$-$C_6$-alkyl-, which is optionally substituted with $C_1$-$C_3$-alkoxy, and
$R^{10}$, $R^{11}$ represent, independently from each other, hydrogen or a $C_1$-$C_6$-alkyl-,
or an enantiomer, diastereomer, salt, solvate or salt of a solvate thereof.

8. The compound of general formula (I) according to claim 1, wherein
$R^1$ represents a methyl group;
$R^2$ represents

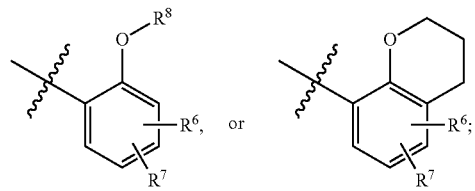

$R^3$ represents a hydrogen atom, or fluoro atom;
$R^4$ represents a hydrogen atom;
$R^5$ represents a hydrogen atom, cyano, —C(O)OR$^9$, or —C(O)NR$^{10}$R$^{11}$;
$R^6$, $R^7$ represent, independently from each other, a hydrogen atom, or fluoro atom;
$R^8$ represents
  a) a methyl group; or
  b) a benzyl group;
$R^9$ represents an ethyl group;
$R^{10}$ represents a hydrogen atom; and
$R^{11}$ represents a methyl group;
or a salt, solvate or salt of a solvate thereof.

9. The compound according to claim 1, which is selected from the group consisting of
(rac)-Ethyl[(3-{[5-fluoro-4-(4-fluoro-2-methoxyphenyl)pyrimidin-2-yl]amino}benzyl)(methyl) oxido sulfanylidene]carbamate;
(rac)-5-Fluoro-4-(4-fluoro-2-methoxyphenyl)-N-{3-[(S-methylsulfonimidoyl)methyl]phenyl}pyrimidin-2-amine;
(rac)-Ethyl {[3-({4-[2-(benzyloxy)-4-fluorophenyl]-5-fluoropyrimidin-2-yl}amino)benzyl](methyl)-oxido-$\lambda^6$-sulfanylidene}carbamate;
(rac)-4-[2-(Benzyloxy)-4-fluorophenyl]-5-fluoro-N-{3-[(S-methylsulfonimidoyl)methyl]phenyl}-pyrimidin-2-amine;
(rac)-Ethyl[(3-{[4-(3,4-dihydro-2H-chromen-8-yl)-5-fluoropyrimidin-2-yl]amino}benzyl)(methyl)-oxido-$\lambda^6$-sulfanylidene]carbamate;
(rac)-4-(3,4-dihydro-2H-chromen-8-yl)-5-fluoro-N-{3-[(S-methylsulfonimidoyl)methyl]phenyl}-pyrimidin-2-amine;
(rac)-{[3-({4-[2-(Benzyloxy)-4-fluorophenyl]-5-fluoropyrimidin-2-yl}amino)benzyl](methyl)oxido-$\lambda^6$-sulfanylidene}cyanamide;
(rac)-1-[(3-{[5-Fluoro-4-(4-fluoro-2-methoxyphenyl)pyrimidin-2-yl]amino}benzyl)(methyl)oxido-$\lambda^6$-sulfanylidene]-3-methylurea;
(rac)-Ethyl[(3-fluoro-5-{[5-fluoro-4-(4-fluoro-2-methoxyphenyl)pyrimidin-2-yl]amino}benzyl)-(methyl) oxido-sulfanylidene]carbamate;
(rac)-5-Fluoro-4-(4-fluoro-2-methoxyphenyl)-N-{3-fluoro-5-[(S-methylsulfonimidoyl)methyl]-phenyl}pyrimidin-2-amine;

5-Fluoro-4-(4-fluoro-2-methoxyphenyl)-N-{3-[(S-methylsulfonimidoyl)methyl]phenyl}pyrimidin-2-amine; enantiomer 1;
5-Fluoro-4-(4-fluoro-2-methoxyphenyl)-N-{3-[(S-methylsulfonimidoyl)methyl]phenyl}pyrimidin-2-amine; enantiomer 2;
4-[2-(Benzyloxy)-4-fluorophenyl]-5-fluoro-N-{3-[(S-methylsulfonimidoyl)methyl]phenyl}pyrimidin-2-amine; enantiomer 1;
4-[2-(Benzyloxy)-4-fluorophenyl]-5-fluoro-N-{3-[(S-methylsulfonimidoyl)methyl]phenyl}pyrimidin-2-amine; enantiomer 2;
5-Fluoro-4-(4-fluoro-2-methoxyphenyl)-N-{3-fluoro-5-[(S-methylsulfonimidoyl)methyl]phenyl}-pyrimidin-2-amine; enantiomer 1;
5-Fluoro-4-(4-fluoro-2-methoxyphenyl)-N-{3-fluoro-5-[(S-methylsulfonimidoyl)methyl]phenyl}-pyrimidin-2-amine; enantiomer 2;
(rac)-[(3-{[5-Fluoro-4-(4-fluoro-2-methoxyphenyl)pyrimidin-2-yl]amino}benzyl)(methyl)oxido-$\lambda^6$-sulfanylidene]cyanamide;
[(3-{[5-Fluoro-4-(4-fluoro-2-methoxyphenyl)pyrimidin-2-yl]amino}benzyl)(methyl)oxido-$\lambda^6$-sulfanylidene]cyanamide; enantiomer 1;
[(3-{[5-Fluoro-4-(4-fluoro-2-methoxyphenyl)pyrimidin-2-yl]amino}benzyl)(methyl)oxido-$\lambda^6$-sulfanylidene]cyanamide; enantiomer 2;
(rac)-[Ethyl(3-{[5-fluoro-4-(4-fluoro-2-methoxyphenyl)pyrimidin-2-yl]amino}benzyl)oxido-$\lambda^6$-sulfanylidene]cyanamide;
rac)-N-{3-[(S-Ethylsulfonimidoyl)methyl]phenyl}-5-fluoro-4-(4-fluoro-2-methoxyphenyl)pyrimidin-2-amine;
N-{3-[(S-Ethylsulfonimidoyl)methyl]phenyl}-5-fluoro-4-(4-fluoro-2-methoxyphenyl)pyrimidin-2-amine; enantiomer 1;
N-{3-[(S-Ethylsulfonimidoyl)methyl]phenyl}-5-fluoro-4-(4-fluoro-2-methoxyphenyl)pyrimidin-2-amine; enantiomer 2;
(rac)-[(2,3-Difluoro-5-{[5-fluoro-4-(4-fluoro-2-methoxyphenyl)pyrimidin-2-yl]amino}benzyl)-(methyl)oxido-$\lambda^6$-sulfanylidene]cyanamide;
(rac)-N-{3,4-Difluoro-5-[(S-methylsulfonimidoyl)methyl]phenyl}-5-fluoro-4-(4-fluoro-2-methoxy-phenyl)pyrimidin-2-amine;
N-{3,4-Difluoro-5-[(S-methylsulfonimidoyl)methyl]phenyl}-5-fluoro-4-(4-fluoro-2-methoxyphenyl)-pyrimidin-2-amine; enantiomer 1;
N-{3,4-Difluoro-5-[(S-methylsulfonimidoyl)methyl]phenyl}-5-fluoro-4-(4-fluoro-2-methoxyphenyl)-pyrimidin-2-amine; enantiomer 2;
(rac)-[(3-Bromo-5-{[5-fluoro-4-(4-fluoro-2-methoxyphenyl)pyrimidin-2-yl]amino}benzyl)(methyl)-oxido-$\lambda^6$-sulfanylidene]cyanamide;
(rac)-N-{3-Bromo-5-[(S-methylsulfonimidoyl)methyl]phenyl}-5-fluoro-4-(4-fluoro-2-methoxy-phenyl)pyrimidin-2-amine;
N-{3-Bromo-5-[(S-methylsulfonimidoyl)methyl]phenyl}-5-fluoro-4-(4-fluoro-2-methoxyphenyl)-pyrimidin-2-amine; enantiomer 1;
N-{3-Bromo-5-[(S-methylsulfonimidoyl)methyl]phenyl}-5-fluoro-4-(4-fluoro-2-methoxyphenyl)-pyrimidin-2-amine; enantiomer 2;
(rac)-[(3-{[5-Fluoro-4-(4-fluoro-2-methoxyphenyl)pyrimidin-2-yl]amino}-5-methoxybenzyl)(methyl)-oxido-$\lambda^6$-sulfanylidene]cyanamide;
(rac)-5-Fluoro-4-(4-fluoro-2-methoxyphenyl)-N-{3-methoxy-5-[(S-methylsulfonimidoyl)methyl]-phenyl}pyrimidin-2-amine;
5-Fluoro-4-(4-fluoro-2-methoxyphenyl)-N-{3-methoxy-5-[(S-methylsulfonimidoyl)methyl]phenyl}-pyrimidin-2-amine; enantiomer 1;
5-Fluoro-4-(4-fluoro-2-methoxyphenyl)-N-{3-methoxy-5-[(S-methylsulfonimidoyl)methyl]phenyl}-pyrimidin-2-amine; enantiomer 2;
(rac)-[(3-{[4-(2-Ethoxy-4-fluorophenyl)-5-fluoropyrimidin-2-yl]amino}-5-fluorobenzyl)(methyl)oxido-$\lambda^6$-sulfanylidene]cyanamide;
(rac)-4-(2-Ethoxy-4-fluorophenyl)-5-fluoro-N-{3-fluoro-5-[(S-methylsulfonimidoyl)methyl]phenyl}-pyrimidin-2-amine;
4-(2-Ethoxy-4-fluorophenyl)-5-fluoro-N-{3-fluoro-5-[(S-methylsulfonimidoyl)methyl]phenyl}-pyrimidin-2-amine; enantiomer 1;
4-(2-Ethoxy-4-fluorophenyl)-5-fluoro-N-{3-fluoro-5-[(S-methylsulfonimidoyl)methyl]phenyl}-pyrimidin-2-amine; enantiomer 2;
(rac)-{[3-{[5-Fluoro-4-(4-fluoro-2-methoxyphenyl)pyrimidin-2-yl]amino}-5-(trifluoromethyl)-benzyl](methyl) oxido-$\lambda^6$-sulfanylidene}cyanamide;
(rac)-5-Fluoro-4-(4-fluoro-2-methoxyphenyl)-N-{3-[(S-methylsulfonimidoyl)methyl]-5-(trifluoro-methyl) phenyl}pyrimidin-2-amine;
(rac)-[Ethyl(3-fluoro-5-{[5-fluoro-4-(4-fluoro-2-methoxyphenyl)pyrimidin-2-yl]amino}benzyl)oxido-$\lambda^6$-sulfanylidene]cyanamide;
(rac)-N-{3-[(S-Ethylsulfonimidoyl)methyl]-5-fluorophenyl}-5-fluoro-4-(4-fluoro-2-methoxyphenyl)-pyrimidin-2-amine;
N-{3-[(S-Ethylsulfonimidoyl)methyl]-5-fluorophenyl}-5-fluoro-4-(4-fluoro-2-methoxyphenyl)-pyrimidin-2-amine; enantiomer 1;
N-{3-[(S-Ethylsulfonimidoyl)methyl]-5-fluorophenyl}-5-fluoro-4-(4-fluoro-2-methoxyphenyl)-pyrimidin-2-amine; enantiomer 2;
(rac)-{[3-{[5-Fluoro-4-(4-fluoro-2-methoxyphenyl)pyrimidin-2-yl]amino}-5-(pentafluoroethyl)-benzyl](methyl)oxido-$\lambda^6$-sulfanylidene}cyanamide;
(rac)-5-Fluoro-4-(4-fluoro-2-methoxyphenyl)-N-{3-[(S-methylsulfonimidoyl)methyl]-5-(pentafluoro-ethyl) phenyl}pyrimidin-2-amine;
(rac)-[Cyclopropyl(3-{[5-fluoro-4-(4-fluoro-2-methoxyphenyl)pyrimidin-2-yl]amino}benzyl)oxido-$\lambda^6$-sulfanylidene]cyanamide;
(rac)-N-{3-[(S-Cyclopropylsulfonimidoyl)methyl]phenyl}-5-fluoro-4-(4-fluoro-2-methoxyphenyl)-pyrimidin-2-amine;
(rac)-[Cyclopropyl(3-fluoro-5-{[5-fluoro-4-(4-fluoro-2-methoxyphenyl)pyrimidin-2-yl]amino}-benzyl)oxido-$\lambda^6$-sulfanylidene]cyanamide;
(rac)-N-{3-[(S-Cyclopropylsulfonimidoyl)methyl]-5-fluorophenyl}-5-fluoro-4-(4-fluoro-2-methoxy-phenyl)pyrimidin-2-amine;
N-{3-[(S-Cyclopropylsulfonimidoyl)methyl]-5-fluorophenyl}-5-fluoro-4-(4-fluoro-2-methoxy-phenyl)pyrimidin-2-amine; enantiomer 1;
N-{3-[(S-Cyclopropylsulfonimidoyl)methyl]-5-fluorophenyl}-5-fluoro-4-(4-fluoro-2-methoxy-phenyl)pyrimidin-2-amine; enantiomer 2;
(rac)-Ethyl[(3-{[4-(2,3-dihydro-1-benzofuran-7-yl)-5-fluoropyrimidin-2-yl]amino}benzyl)(methyl)-oxido-$\lambda^6$-sulfanylidene]carbamate;

(rac)-5-Fluoro-4-{4-fluoro-2-[(4-fluorobenzyl)oxy]phenyl}-N-{3-[(S-methylsulfonimidoyl)methyl]phenyl}pyrimidin-2-amine;

(rac)-[(3-Chloro-5-{[5-fluoro-4-(4-fluoro-2-methoxyphenyl)pyrimidin-2-yl]amino}benzyl)(methyl)-oxido-$\lambda^6$-sulfanylidene]cyanamide;

(rac)-N-{3-Chloro-5-[(S-methylsulfonimidoyl)methyl]phenyl}-5-fluoro-4-(4-fluoro-2-methoxy-phenyl)pyrimidin-2-amine;

(rac)-[(3-{[5-Fluoro-4-(4-fluoro-2-methoxyphenyl)pyrimidin-2-yl]amino}-5-methylbenzyl)(methyl)-oxido-$\lambda^6$-sulfanylidene]cyanamide;

(rac)-5-Fluoro-4-(4-fluoro-2-methoxyphenyl)-N-{3-methyl-5-[(S-methylsulfonimidoyl)methyl]phenyl}pyrimidin-2-amine;

(rac)-{[3-{[5-Fluoro-4-(4-fluoro-2-methoxyphenyl)pyrimidin-2-yl]amino}-5-(pentafluoro-$\lambda^6$-sulfanyl)benzyl](methyl)oxido-$\lambda^6$-sulfanylidene}-cyanamide;

(rac)-5-Fluoro-4-(4-fluoro-2-methoxyphenyl)-N-{3-[(S-methylsulfonimidoyl)methyl]-5-(pentafluoro-$\lambda^6$-sulfanyl)phenyl}pyrimidin-2-amine;

5-Fluoro-4-(4-fluoro-2-methoxyphenyl)-N-{3-[(S-methylsulfonimidoyl)methyl]-5-(pentafluoro-$\lambda^6$-sulfanyl)phenyl}pyrimidin-2-amine; enantiomer 1;

5-Fluoro-4-(4-fluoro-2-methoxyphenyl)-N-{3-[(S-methylsulfonimidoyl)methyl]-5-(pentafluoro-$\lambda^6$-sulfanyl)phenyl}pyrimidin-2-amine; enantiomer 2; and 2-Methoxyethyl[(3-fluoro-5-{[5-fluoro-4-(4-fluoro-2-methoxyphenyl)pyrimidin-2-yl]amino}benzyl)-(methyl)oxido-$\lambda^6$-sulfanylidene]carbamate; single enantiomer, or a salt, solvate or salt of a solvate thereof.

10. A pharmaceutical combination comprising a compound according to claim 1 in combination with at least one or more further active ingredients.

11. A pharmaceutical composition comprising a compound according to claim 1 in combination with an inert, nontoxic, pharmaceutically suitable adjuvant.

12. A method for the treatment of a disease or disorder selected from the group consisting of lung carcinomas, prostate carcinomas, cervical carcinomas, colorectal carcinomas, melanomas and ovarian carcinomas comprising administering to a patient in need thereof a therapeutically effective amount of a compound according to claim 1.

13. The method according to claim 12, wherein the disease or disorder is mediated by CDK9.

\* \* \* \* \*